US007618819B2

(12) United States Patent
Kuehnle

(10) Patent No.: US 7,618,819 B2
(45) Date of Patent: Nov. 17, 2009

(54) USE OF PSEUDOGENE INSERTION SITES TO CREATE NOVEL TRAITS IN TRANSGENIC ORGANISMS

(75) Inventor: Adelheid R. Kuehnle, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 246 days.

(21) Appl. No.: 11/053,541

(22) Filed: Feb. 8, 2005

(65) Prior Publication Data

US 2005/0241017 A1 Oct. 27, 2005

Related U.S. Application Data

(60) Division of application No. 10/835,516, filed on Apr. 28, 2004, now Pat. No. 7,129,392, which is a continuation of application No. 09/918,740, filed on Jul. 31, 2001, now abandoned.

(60) Provisional application No. 60/221,703, filed on Jul. 31, 2000.

(51) Int. Cl.
*C12N 15/82* (2006.01)

(52) U.S. Cl. .................................... 435/468; 800/278

(58) Field of Classification Search ....................... None
See application file for complete search history.

(56) References Cited

U.S. PATENT DOCUMENTS

| | | | | |
|---|---|---|---|---|
| 4,846,872 | A | 7/1989 | Kamuro et al. | |
| 5,349,126 | A | 9/1994 | Chappell et al. | |
| 5,380,831 | A | 1/1995 | Adang et al. | |
| 5,436,391 | A | 7/1995 | Fujimoto et al. | |
| 5,545,816 | A | 8/1996 | Ausich et al. | |
| 5,877,402 | A * | 3/1999 | Maliga et al. | 800/298 |
| 6,395,959 | B1 * | 5/2002 | Dujon et al. | 800/18 |
| 7,129,392 | B2 * | 10/2006 | Hahn et al. | 800/282 |

FOREIGN PATENT DOCUMENTS

WO WO 02/099095 12/2002

OTHER PUBLICATIONS

Proudfoot et al 1982 (Part 2) Cell 31: 553-563.*

Topping et al 1995 Transgenic Research 4: 291-305.*

Boynton et al 1993, Methods in Enzymology vol. 217, pp. 510-536.*

Albrecht et al., "Novel Hydroxycarotenoids with Improved Antioxidative Properties Produced by Gene Combination in *Escherichia coli*.", 2000, *Nature Biotech*., pp. 843-846, vol. 18.

Allison et al., "MDMV Leader (Maize Dwarf Mosaic Virus)", 1986, *Virology*. pp. 9-20 vol. 154.

Altschul et al., "Basic Local Alignment Search Tool," 1990, *J. Mol. Biol*., pp. 403-410 vol. 215.

Ashby et al., "Elucidation of the Deficiency in Two Yeast Coenzyme Q Mutants: Characterization of the Structural Gene Encoding Hexaprenyl Pyrophosphate Synthetase." J. Biol. Chem. 265:13157-13164 (1990).

Ballas et al., "Efficient functioning of plant promoters and poly (A) sites in *Xenopus* oocytes," 1989, *Nucleic Acids Res*., pp. 7891-7903, vol. 17.

Beaucage et al., "Deoxynucleoside phosphoramidites—a new class of key intermediates for deoxypolynucleotide synthesis.", 1981, *Tetra. Letts*., pp. 1859-1862, vol. 22.

Bock, R. "Transgenic Plastids in Basic Research and Plant Biotechnology" 2001, *J. Mol. Biol*., pp. 425-438, vol. 312.

Bock et al., "Extranuclear Inheritance: Plastid Genetic: Manipulation of Plastid Genomes and Biotechnological Application." 2000, *Prog. Bot*. pp. 76-90, vol. 61.

Boyton et al., "Chloroplast Transformation in Chlamydomoas." 1993, *Methods Enzymol*., pp. 510-536, vol. 217.

Champenoy, S. et al., "Expression of the yeast mevalonate kinase gene in transgenic tobacco" *Molecular Breeding*, 1998, pp. 291-300, vol. 4.

Chappell et al. *Plant Physiology*, 1995, pp. 1337-1343, vol. 109.

Cho et al. "Expression Pattern of Bacterial Polycistronic Genes in Tobacco Cells," *J. Ferment. Bioengen*., 1995, pp. 111-117, vol. 80(2).

Clarke, "Protein Isoprenylation and Methylation at Carboxy-terminal Cysteine Residues," Annu. Rev. Biochem. 1992, pp. 355-386, vol. 61.

Cordier et al. "Heterologous Expression in *Saccharomyces cerevisiae* of an *Arabidopsis thaliana* cDNA Encoding Mevalonate Diphosphate Decarboxylase," *Plant Molecular Biology*, 1999, pp. 953-967, vol. 39.

(Continued)

*Primary Examiner*—David H Kruse
(74) *Attorney, Agent, or Firm*—Salwanchik, Lloyd & Saliwanchik

(57) ABSTRACT

Disclosed are the uses of inactive gene sites (the pseudogenes) to create a novel selection system and/or targeting sites for mediating the insertion of genetic material into plant and microalgae plastids, for expression of the inserted genetic material under control of the regulatory sequences of a pseudogene. The specific polynucleotides to be used, solely or in any combination thereof, are publicly available from GeneBank. Exemplified is insertion of constructs that contain open reading frames having sequences that upon expression will produce active proteins with the following enzyme activities: (a) acetoacetyl CoA thiolase (EC 2.3.1.9), (b) 3-hydroxy-3-methylglutaryl-coenzyme A (HMG-CoA) synthase (EC 4.1.3.5), (c) HMG-CoA reductase (EC 1.1.1.34), (d) mevalonate kinase (EC 2.7.1.36), (e) phosphomevalonate kinase (EC 2.7.4.2), (f) mevalonate diphosphate decarboxylase (EC 4.1.1.33), (g) isopentenyl diphosphate (IPP) isomerase (EC 5.3.3.2), and (h) phytoene synthase (EC 2.5.1.32).

19 Claims, 17 Drawing Sheets

OTHER PUBLICATIONS

Cunningham et al. "Genes and Enzymes of Carotenoid Biosynthesis in Plants," *Ann. Rev. Plant Mol. Biol.*, 1998, pp. 475-502, vol. 39.
Cunningham et al., "Evidence of a Role for LytB in the Nonmevalonate Pathway of Isoprenoid Biosynthesis," *J. Bacteriol.*, 2000, pp. 5841-5848, vol. 182.
Dale, P. J., "Spread of Engineered Genes to Wild Relatives," *Plant Physiol.*, 1987, pp. 965-968, vol. 84.
Daniell et al., "Containment of Herbicide Resistance Through Genetic Engineering of the Chloroplast Genome," *Nat. Biotechnol.*, 1998, pp. 345-348, vol. 16.
Del Campo et al., *Plant Physiol* 1997, p. 748 vol. 114.
Della-Cioppa et al., "Protein trafficking in plant cells," *Plant Physiol.*, 1987, pp. 965-968, vol. 84.
Deroles et al., "Expression and Inheritance of Kanamycin Resistance in a large Number of Transgenic Petunias Generated by Agrobacterium-Mediated Transformation." *Plant Molec. Biol.*, 1988, pp. 355-364, vol. 11.
Eisenreich et al., "The Deoxyxylulose Phosphate Pathway of Terpenoid Biosynthesis in Plants and Microorganisms." *Chemistry and Biology* 1998, pp. R221-R233, vol. 5.
Elroy-Stein et al., "Cap-independent translation of mRNA conferred by encephalomycarditis virus 5' sequence improves the performance of the vaccinia virus/bacteriophage T7hybrid expression system." *PNAS USA*, 1989, pp. 6126-6130, vol. 86.
Gallie et al., "Eukaryotic viral 5'-leader sequences act as translational enhancers in eukaryotes and prokaryotes," *Molecular Biology of RNA*. Ed. Cech., 1998, (Liss. New York), pp. 237-256.
Garret et al., "Accumulation of a Lipid A Precursor Lacking the 4'-Phosphate following Inactivation of the *Escherichia coli* IpxK Gene." *J. Biol. Chem.*, 1998, pp. 12457-12465, vol. 273.
Goldschmidt-Clermont M., "Transgenic Expression of Aminoglycoside Adenine Transferase in the Chloroplast: A Selectable Marker for Site-directed Transformation of Chlamydomonas," *Nucleic Acids Res.*, 1991, pp. 4083-4089, vol. 19.
Goodwin, "Biosynthesis of Carotenoids and Plant Triterpenes: the Fifth CIBA Medal Lecture," Biochem. J. 1971, pp. 293-329, vol. 123.
Guda et al., "Stable Expression for a Biodegradable Protein Based Polymer in Tobacco Chloroplasts," *Plant Cell Reports*, 2000, pp. 257-262, vol. 19.
Guerineau et al. "Effect of deletions in the cauliflower mosaic virus polyadenylation sequence on the choice of the polyadenylation sites in tobacco protoplasts." *Mol. Gen. Genet.*, 1991, pp. 141-144, vol. 226.
Guo, D. et al. "Developmental Regulation of Sterol Biosynthesis in *Zea mays", Lipids*, 1995, pp. 203-219, vol. 30(3).
Hahn et al., "1-Deoxy D-Xylulose 5-Phosphate Synthase, the Gene Product of Open Reading Frame (ORF) 2816 and ORF2895 in *Rhodobacter capsulatus." J. Bacteriol.*, 2001, pp. 1-11, vol. 183.
Hahn et al., "Isolation of *Schizosaccharomyces pombe* Isopentenyl Diphosphate Isomerase cDNA Clones by Complementation and Synthesis of the Enzyme in *Escherichia coli." J. Biol. Chem.*, 1995, pp. 11298-11303, vol. 270.
Hahn et al. "*Escherichia coli* Open Reading Frame 696 Is idi, a Nonessential Gene Encoding Isopentenyl Diphosphate Isomerase." *J. Bacteriol.*, 1999, pp. 4499-4504, vol. 181.
Hahn et al., "Open Reading Frame 176 in the Photosynthesis Gene Cluster of *Rhodobacter capsulatus* Encodes idi. A Gene for Isopentenyl Diphosphate Isomerase." *J. Bacteriol.*, 1996, pp. 619-624, vol. 178.
Hamilton et al., "New Method for Generating Deletions and Gene Replacements in *Escherichia coli." J. Bacteriol.*, 1989, pp. 4617-4622, vol. 171.
Harker et al., "Expression of Prokaryotic 1-Deocy-D-Xylulose 5-Phosphates in *Escherichia coli* Increases Carotenoid and Ubiquinone Biosynthesis," *Febs Letters*, 1999, pp. 115-119, 448.
Herbers, K. et al. "Manipulating Metabolic Partitioning in Transgenic Plants", *TIBTECH*, 1996, pp. 198-205, vol. 14.
Herz et al., "Biosynthesis of Terpenoids: YgbB Protein Converts 4-Diphosphocytidyl -2C-Methyl-D-Erythritol 2-Phosphate to 2C-Methyl-D-Erythritol 2.4-Cyclodiphosphate," *Proc. Natl. Acad. Sci. USA*, 2000, pp. 2486-2490, vol. 97.
Jobling et al., "Enhanced translation of chimaeric messenger RNAs containing a plant viral untranslated leader sequence.", 1987, *Nature*, pp. 622-625, vol. 325.
Joshi et al., "Putative polyadenylation signals in nuclear genes of higher plants: a compilation and analysis," *Nucleic Acid Res.*, 1987, pp. 9627-9639, vol. 15(23).
Kajiwara et al., "Expression of an Exogenous Isopentenyl Diphosphate Isomerase Gene Enhances Isoprenoid Biosynthesis in *Escherichia coli." Biochem. J.*, 1997, 421-426, vol. 324.
Kavanagh of al., Homeologous Plastid DNA Transformation in Tobacco is Mediated By Multiple Recombination Events. *Genetics*, 1999, pp. 1111-1122, vol. 152.
Keeler of al., "Movement of Crop Transgenes into Wild Plants," in *Herbicide Resistant Crops: Agricultural, Economic, Environmental, Regulatory and Technological Aspects*, 1996, (S.O. Duke, ed.) CRC Press, Boca Raton, FL, pp. 303-330.
Khan and Maliga, "Fluorescent Antibiotic Resistance Marker for Tracking Plastid Transformation in Higher Plants," *Nature Biotech.*, 1999, pp. 910-914, vol. 17.
Kota et al., "Overexpression of the *Bacilllus thuringiensis* (Bt) Cry2Aa2 Protein in Chloroplasts Confers Resistance to Plants Against Susceptible and Bt-resistant Insects," *Proc. Natl. Acad. Sci. USA*, 1999, pp. 1840-1845 vol. 96.
Kunkel, *Proc. Natl. Acad. Sci. USA*, 1985, pp. 488-492, vol. 82.
Kunkel et al., "Rapid and efficient site-specific mutagenesis without phenotypic selection," *Methods in Enzymol*, 1987, pp. 367-382, vol. 154.
Kuzuyama et al., "Direct Formation of 2-C Methyl D-Erythritol 4-Phosphate by 1-Deoxy-D-Xylulose 5-Phosphate Reductoisomerase, a New Enzyme in the Non-Mevalonate Pathway to Isopententyl Diphosphate," *Tetrahedron Lett.*, 1998, pp. 4509-4512, vol. 39.
Kuzuyama et al., "Fosmidomycin a Specific Inhibitor of 1-Deoxy-D-Xylulose 5-Phosphate Reductosisomerase in the Nonmevalonate Pathway for Terpenoid Biosynthesis," *Tetrahedron Lett*. 1998, pp. 7913-7916, vol. 39.
Kuzuyama et al., "An Unusual Isopentenyl Diphosphate Isomerase Found in the Mevalonate Pathway Gene Cluster from *Streptomyces* sp. strain CL190." *Proc. Natl. Acad. Sci. USA*, 2001, pp. 932-937, vol. 98.
Lange and Croteau, "Isopentenyl diphosphate biosynthesis via a mevalonate independent pathway: Isopentenyl monophosphate kinase catalyzes the terminal enzymatic step," *Proc. Natl. Acad. Sci. USA*, 1999, pp. 13714-13719, vol. 96.
Lichtenthaler et al., "Biosynthesis of Isoprenoids in Higher Plant Chloroplasts Proceeds via a Mevalonate-Independent Pathway," *FEBS Letters*, 1997, pp. 271-274, vol. 400.
Lluch et al. "Molecular Cloning and Expression Analysis of the Mevalonate Kinase Gene from *Arobidopsis thaliana," Plant Molecular Biology*., 2000, pp. 365-376, vol. 42.
Lois et al., "Cloning and Characterization of a Gene from *Escherichia coil* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," 1998, *Proc. Natl. Acad. Sci. USA*, pp. 2105-2110, vol. 95.
Lommel et al., "Identification of the maize chlorotic mottle virus capsid protein cistron and characterization of its subgenomic messenger RNA," *Virology*, 1991, pp. 382-385, vol. 181.
Lüttgen et al., "Biosynthesis of Terpenoids: YchB Protein of *Escherichia coli* Phosphorylates the 2-Hydroxy Group of 4-Diphosphocytidyl-2-C-Methyl-D-Erythritol," *Proc. Natl. Acad. Sci. USA*, 2000, pp. 1052-1067, vol. 97.
Macejak et al., "Internal initiation of translation mediated by the 5' leader of a cellular mRNA," *Nature*, 1991, pp. 90-94, vol. 353.
Mahmoud, S.S. et al., "Metabolic engineering of essential oil yield and composition in mint by altering expression of deomylulose phosphate reductoisomerase and menthofuran synthase" *PNAS*, 2001, vol. 8915-8920, vol. 98(15).
Maldonado-Mendoza, I. et al. , "Molecular Characterization of three differentially expressed members of the *Campotheca acuminate* 3-hydroxy-3-methylglutaryl CoA reductase (HMGR) gene family," *Plant Molecular Biology* 1997, pp. 781-790, vol. 34.

Mann et al., "Metabolic Engineering of Astaxanthin Production in Tobacco Flowers," *Nature Biotech.*, 2000, pp. 888-892, vol. 18.
Martin et al., "Gene Transfer to the Nucleus and the Evolution of Chloroplasts," *Nature*, 1998, pp. 162-165, vol. 393.
Martin et al., "Engineering a mevalonate pathway in *Escherichia coli* for production of terpenoids" *Nature Biotechnology*, 2003, pp. 796-802, vol. 21(7).
Matsuoka et al., "Variable Product Specificity of Microsomal Dehydrodolichyl Diphosphate Synthase from Rat Liver," *J. Biol. Chem.*, 1991, pp. 3464-3468, vol. 266.
Matteucci, M.D. et al., "Synthesis of deoxyoligonucleotides on a polymer support," *J. Am. Chem. Soc.*, 1981, pp. 3185-3191, vol. 103(11).
Matthews, P. D. et al., "Metabolic engineering of carotenoid accllmulation in *Escherichia coli* by modulation of the isoprenoid precursor pool with expression of deosysylulose phosphate smthase", 2000, *Appl. Microbial. Biotechnol.*, pp. 396-400. vol. 53.
Meinkoth, J. et al., "Hybridization of Nucleic Acids Immobilized on Solid Supports." *Anal. Biochem.*, 1984, pp. 267-284, vol. 138.
Meyer et al., "Homology-Dependent Gene Silencing in Plants," *Ann. Rev. Plat. Physiol. Mol. Biol.*, 1996, pp. 23-48, vol. 47.
Millen et al., "Many Parallel Losses of infA from Choloroplast DNA During Angiosperm Evolution with Multiple Independent Transfers to the Nucleus," *Plant Cell*, 2001, pp. 645-658, vol. 13.
Mogen et al., "Upstream Sequences Other Than AAUAAA Are Required For Efficient Messenger RNA 3'-end Formation in Plants." *Plant Cell*, 1990, pp. 1261-1272, vol. 2.
Munroe et al., "Tales Of Poly(A): A Review," *Gene*, 1990, pp. 151-158, vol. 91.
Murray et al., "Codon Usage In Plant Genes," *Nucleic Acids Res.*, 1989, pp. 477-498, vol. 17(2).
Needleman, S.B. and C.D. Wunsch "A General Method Applicable to the Search for Similarities in the Amino Acid Sequence of Two Proteins." *J. Mol. Biol.*, 1970, pp. 443-453, vol. 48.
Newman et al., "Genes Galore: A Summary of Methods for Accessing Results from Large-Scale Partial Sequencing of Anonymous *Arabidopsis* cDNA Clones." *Plant Physiology*, 1994, pp. 1241-1255, vol. 106.
Nielsen and Bloor, "Analysis and Developmental Profile of Carotenoid Pigments in Petals of Three Yellow Petunia Cultivars." *Scientia Hort*, 1997, pp. 257-266, vol. 71.
Pachuk et al., "Chain reaction cloning: a one-step method for directional ligation of multiple DNA fragments" *Gene*, 2000, pp. 19-25, vol. 243.
Pearson et al., "Improved tools for biological sequence comparison," *Proc. Natl. Acad. Sci.*, 1988, pp. 2444-2448, vol. 85.
Popjak, G., "Natural Substances Formed Biologically from Mevalonic Acid." Biochemical symposium No. 29 (T. W. Goodwin ed.), 1970, Academic Press. New York. pp. 17-33.
Proudfoot, Nick. "Poly(A) Signals," *Cell*, 1991, pp. 671-674, vol. 64.
Ramos-Valdivia et al., "Isopentenyl Diphosphate Isomerase: A Core Enzyme in Isoprenoid Biosynthesis: A Review of its Biochemistry and Function," *Nat. Prod. Rep.*, 1997, pp. 591-603, vol. 6.
Re et al. "Co-expression of Native and Introduced Genes Reveals Cryptic Regulation of HMG CoA Reductase Expression in *Arabidopsis," The Plant Journal*, 1995, pp. 771-784 vol. 7(5).
Rohdich et al., "Cytidine 5'-Triphosphate-Dependent Biosynthesis of Isoprenoids: YgbP Protein of *Escherichia coli* Catalyzes the Formation of 4-Diphosphocytidyl-2-C-methylerythritol." *Proc. Natl. Acad. Sci. USA*, 1999, pp. 11758-11763, vol. 96.
Romer, M., "Isoprenoid biosynthesis via the mevalonate-independent route, a novel target for antibacterial drugs?" *Progress in Drug Research*, 1998, pp. 137-154, vol. 50.
Sandmann, G. et al., "The biotechnological potential and design of novel carotenoids by gene combination in *Escherichia coli" Tib Tech*, 1999, pp. 233-237, vol. 17.
Sandmann, G. "Genetic manipulation of carotenoid biosynthesis: strategies, problems and achievements" *Trends in Plant Science*, 2001, pp. 14-17, vol. 547.
Sanfacon, H. et al., "A discussion of the cauliflower mosaic virus polyadenylation signal." *Genes & Dev.*, 1991, pp. 141-149, vol. 5.
Serino, G. et al. "A Negative Selection Scheme Based in the Expression of Cytosine Deaminase in Plastids," *Plant J*, 1997, pp. 697-701, vol. 12(3).
Shinozaki, K. et al. "The complete nucleotide sequence of the tobacco chloroplast genome: its gene organization and expression," *EmboJournal*, 1986, pp. 2043-2049, vol. 5(9).
Smith, T. et al., "Comparison of biosequences." *Adv. Appl. Math.*, 1981, pp. 482-489 vol. 2.
Sprenger et al., "Identification of a Thiamin-Dependent. Sythase in *Escherichia coli* Required for the Formation of the 1-Deoxyl-D-Xylulose 5-Phosphate Precursor to Isoprenoids, Thiamin and Pyridoxol." *Proc. Natl. Acad. Sci. USA*, 1997, pp. 12857-12862, vol. 94.
Stermer, B. A. et al., "Regulation of HMG-CoA Reductase Activity in Plants", *Journal of Lipid Research*, 1994, pp. 1133-1140, vol. 35.
Stevens and Purton. "Genetic Engineering of Eukaryotic Algae: Progress and prospects," *J. Phycol*, 1997, pp. 713-722, vol. 33.
Takagi at al., "A Gene Cluster for the Mevalonate Pathway from *Streptomyces* sp Strain CL190," J. Bacteriol. 182:4153-4157(2000).
Takahashi, S. et al., "Purification, Characterization and Cloning of a Eubacterial 3-Hydroxy-3-Methylglutaryl Coenzyme A Reductase, as Key Enzyme Involved in Biosynthesis of Terpenoids," *J. Bacteriol.*, 1999, pp. 1256-1263, vol. 181(4).
Thomas, F. et al., "Expression of the rp123 and rps19 genes in spinach chloroplasts," Nucleic Acids Research 16:2461-2472 (1988).
Toriyama and Hinata, "Cell Suspension and Protoplast Culture in Rice," *Plant Science*, 1985, pp. 179-183, vol. 41.
Tsudsuki, T., "Direct submission, bases 1-155939". Data Processing Center, Aichi-Gakuin University, Aixhi, Japan. 1998.
Ye et al., "Engineering the Provitamin A (β-Carotene) Biosynthetic Pathway into (Carotenoid-Free) Rice Endosperm," *Science*, 2000, pp. 303-305, vol. 287.

* cited by examiner

USE OF PSEUDOGENE INSERTION SITES TO CREATE NOVEL TRAITS IN TRANSGENIC ORGANISMS

CROSS-REFERENCE TO RELATED APPLICATION

This application is a division of U.S. application Ser. No. 10/835,516, filed Apr. 28, 2004 now U.S. Pat. No. 7,129,392, which is a continuation of U.S. application Ser. No. 09/918, 740, filed Jul. 31, 2001, now abandoned, and claims the benefit of U.S. Provisional Application No. 60/221,703, filed Jul. 31, 2000.

INCORPORATION BY REFERENCE

The Sequence Listing for this application is on duplicate compact discs labeled "Copy 1" and "Copy 2." Copy 1 and Copy 2 each contain only one file named "as.filed.doc" which was created on Jun. 3, 2005, and is 196 KB. The entire contents of each of the compact discs are incorporated herein by reference in their entireties.

FIELD OF THE INVENTION

This invention relates to the fields of biotechnology and genetic engineering, in particular to agricultural and aquacultural biotechnology. More specifically, the invention relates to transgenic plants and microalgae, in particular to transplastomic plants and microalgae and means for insertion of genetic material into plastids.

BACKGROUND OF THE INVENTION

The ubiquitous isoprenoid biosynthetic pathway is responsible for the formation of the most chemically diverse family of metabolites found in nature (Hahn et al., *J. Bacteriol.* 178:619-624, 1996) including sterols (Popjak, *Biochemical symposium no.* 29 (T. W. Goodwin, ed.), Academic Press, New York, pp 17-37, 1970), carotenoids (Goodwin, *Biochem. J.* 123:293-329, 1971), dolichols (Matsuoka et al., *J. Biol. Chem.* 266:3464-3468, 1991), ubiquinones (Ashby and Edwards, *J. Biol. Chem.* 265:13157-13164, 1990), and prenylated proteins (Clarke, *Annu. Rev. Biochem.* 61:355-386, 1992). Biosynthesis of isopentenyl diphosphate (IPP), the essential 5-carbon isoprenoid precursor, occurs by two distinct compartmentalized routes in plants (Lange and Croteau, *Proc. Natl. Acad. Sci. USA* 96:13714-13719, 1999). In the plant cytoplasm, IPP is assembled from three molecules of acetyl coenzyme A by the well-characterized mevalonate pathway (Lange and Croteau, *Proc. Natl. Acad. Sci. USA* 96:13714-13719, 1999). However, a recently discovered mevalonate-independent pathway is responsible for the synthesis of IPP in plant chloroplasts (Lichtenthaler et al. *FEBS Letters* 400:271-274, 1997).

Following the synthesis of IPP via the mevalonate route, the carbon-carbon double bond must be isomerized to create the potent electrophile dimethylally diphosphate (DMAPP). This essential activation step, carried out by IPP isomerase, insures the existence of the two 5-carbon isomers, EPP and DMAPP, which must join together in the first of a series of head to tail condensation reactions to create the essential allylic diphosphates of the isoprenoid pathway (Hahn and Poulter, *J. Biol. Chem.* 270:11298-11303,1995). Recently, it was reported that IPP isomerase activity was not essential in *E. coli*, one of many eubacteria containing only the non-mevalonate pathway for the synthesis of both 5-carbon isomers, suggesting the existence of two separate mevalonate-independent routes to IPP and DMAPP (Hahn et al., *J. Bacteriol.* 181:4499-4504, 1999). Thus, it is unclear whether an IPP isomerase is essential for the synthesis of isoprenoids in plant plastids as well. Regardless of whether IPP isomerase activity is present in plant plastids, the separation by compartmentalization of the two different biosynthetic routes, the mevalonate and deoxyxylulose phosphate pathways (or "non-mevalonate"), for IPP and DMAPP biosynthesis in plants is the fundamental tenet upon which the subject inventions are based.

The synthesis of IPP by the mevalonate pathway (Eisenreich et al., *Chemistry and Biology* 5:R221-R233, 1998) is cytoplasm based and occurs as follows: The condensation of two acetyl CoA molecules to yield acetoacetyl CoA is catalyzed by acetoacetyl CoA thiolase (EC 2.3.1.9). The addition of another molecule of acetyl CoA to acetoacetyl CoA is catalyzed by 3-hydroxy-3-methylglutaryl-coenzyme A (HMG-CoA) synthase (EC 4.1.3.5) to yield HMG-CoA, which is reduced in the subsequent step to mevalonate by HMG-CoA reductase (EC 1.1.1.34). Mevalonate is phosphorylated by mevalonate kinase (EC 2.7.1.36) to yield phosphomevalonate, which is phosphorylated, by phosphomevalonate kinase (EC 2.7.4.2) to form mevalonate diphosphate. The conversion of mevalonate diphosphate to IPP with the concomitant release of CO2 is catalyzed by mevalonate diphosphate decarboxylase (EC 4.1.1.33).

In organisms utilizing the deoxyxylulose phosphate pathway (aka "non-mevalonate pathway", "methylerythritol phosphate (MEP) pathway", and "Rohmer pathway"), the five carbon atoms in the basic isoprenoid unit are derived from pyruvate and D-glyceraldehyde phosphate (GAP) (Eisenreich et al., 1998). Thus, synthesis of IPP and/or DMAPP by the non-mevalonate route, which occurs in plastids, is as follows: Pyruvate and GAP are condensed to give 1-deoxy-D-xylulose 5-phosphate (DXP) by DXP synthase (Sprenger et al., *Proc. Natl. Acad. Sci. USA* 94:12857-12862, 1997). The rearrangement and reduction of DXP to form 2-C-methylerythritol 4-phosphate (MEP), the first committed intermediate in the non-mevalonate pathway for biosynthesis of isoprenoids is catalyzed by DXP reductoisomerase (Kuzuyama et al., *Tetrahedron Lett.* 39:4509-4512, 1998). MEP is then appended to CTP to form 4-(cytidine 5'-diphospho)-2-C-methyl-D-erythritol (Rohdich et al., *Proc. Natl. Acad. Sci. USA* 96:11758-11763, 1999), followed by phosphorylation of the C2 hydroxyl group (Lüttgen et al., *Proc. Natl. Acad. Sci. USA* 97:1062-1067, 2000) and elimination of CMP, to form a 2,4-cyclic diphosphate (Herz et al., *Proc. Natl. Acad. Sci. USA* 97:2486-2490, 2000). Interestingly, Herz et al. reported the possible existence of bifunctional proteins with both YgbP and YgbB activities. Once the remaining steps to the fundamental five-carbon isoprenoid building blocks, IPP and DMAPP, in the non-mevalonate pathway are discovered, they will serve as additional targets for inhibitors with antiobiotic and herbicidal activity.

Since the non-mevalonate pathway is ultimately responsible for the biosynthesis of compounds critical for photosynthesis such as the prenyl side-chain of chlorophylls, which serve as lipophillic anchors for the photoreceptors and the photoprotective carotenoid pigments, any enzyme, gene, or regulatory sequence involved in the biosynthesis of IPP and/or DMAPP can be a potential target for herbicides. For example, the antibiotic fosmidomycin, a specific inhibitor of the enzyme DXP reductoisomerase (Kuzuyama et al., *Tetrahedron Lett.* 39:7913-7916,1998) has been shown to have significant herbicidal activity, especially in combination with other herbicides (Kamuro et al. "Herbicide" U.S. Pat. No.

4,846,872; issued Jul. 11, 1989). The report of an *Arabidopsis thaliana* albino mutant being characterized as a disruption of the CLA1 gene, later revealed as encoding DXP synthase by Rohmer et al. (Lois et al., *Proc. Natl. Acad. Sci. USA* 95:2105-2110, 1998), also illustrates the potential of non-mevalonate pathway enzymes as targets for compounds with herbicidal activity. Accordingly, one of ordinary skill in the art can readily understand that as additional compounds are discovered exhibiting herbicidal activity based on their effects on the non-mevalonate pathway, those compounds could be used in accord with the teachings herein.

The synthesis of carotenoids from IPP and DMAPP takes place in plant plastids by a genetically- and enzymatically-defined pathway (Cunningham and Gantt, *Ann. Rev. Plant Mol. Biol.* 39:475-502, 1998). Enhanced production of carotenoids such as lycopene and B-carotene in plants is highly desirable due to the reported health benefits of their consumption (Kajiwara et al., Biochem. J. 324:421-426, 1997). Enhanced carotenoid production in plants can also have a dramatic effect on their coloration and be highly desirable to the growers of ornamentals, for example. The IPP isomerase reaction is considered to be a rate-limiting step for isoprenoid biosynthesis (Ramos-Valdivia et al., *Nat. Prod. Rep.* 6:591-603, 1997). Kajiwara et al. reported that the expression of heterologous IPP isomerase genes in a strain of *E. coli* specifically engineered to produce carotenoids resulted in over a 2-fold increase in β-carotene formation. Recently, it has been reported that expression of an additional gene for DXP synthase in an *E. coli* strain specifically engineered to produce carotenoids also increased the level of lycopene substantially (Harker and Bramley, *FEBS Letters* 448:115-119,1999). Increased isoprenoid production also has been shown in bacteria by combining carotenogenic genes from bacteria with an orf encoding IPP isomerase; and was even further enhanced when additionally combined with the dxs gene from the MEP pathway to supply the precursors IPP and DMAPP (Albrecht et al. *Nature Biotechnology* 18:843-846, 2000).

Accumulation of one specific isoprenoid, such as beta-carotene (yellow-orange) or astaxanthin (red-orange), can serve to enhance flower color or nutriceutical composition depending if the host is cultivated as an ornamental or as an output crop; and if the product accumulates in the tissue of interest (i.e. flower parts or harvestable tissue). In plants, tissue with intrinsic carotenoid enzymes can accumulate ketocarotenoids such as astaxanthin in chromoplasts of reproductive tissues of tobacco by addition of the biosynthetic enzyme beta-carotene ketolase (Mann et al., *Nature Biotechnology* 18:888-892, 2000). Astaxanthin is the main carotenoid pigment found in aquatic animals; in microalgae it accumulates in the *Chlorophyta* such as in species of *Haematococcus* and *Chlamydomonas*. Thus, an increase in the essential 5-carbon precursors, IPP and DMAPP, by expression of orfs encoding IPP isomerase and orfs upstream thereof, can feed into the production output of such valuable isoprenoids in organisms other than bacteria.

As a further example of utility, Petunia flower color is usually due to the presence of modified cyanidin and delphinidin anthocyanin pigments to produce shades in red to blue groupings. Recently produced yellow seed-propagated multiflora and grandiflora petunias obtain their coloration from the presence of beta-carotene, lutein and zeaxanthin carotenoid pigments in combination with colorless flavonols (Nielsen and Bloor, *Scienia Hort.* 71:257-266, 1997). Industry still lacks bright yellow and orange clonally propagated trailing petunias. Metabolic engineering of the carotenoid pathway is desired to introduce these colors in this popular potted and bedding plant.

Plant genetic engineering has evolved since the 1980s from arbitrarily located monocistronic insertions into a nuclear chromosome, often subject to multiple copies, rearrangements and methylation, to predetermined sites for defined multicistronic or multigenic operon insertions into a plastid chromosome (plastome), which thus far is thought impervious to typical nuclear gene inactivation. While breeding of crop plants by nuclear genome engineering is nevertheless a proven technology for major agronomic crops and for traits such as herbicide resistance, introgression of genes into the plastome is a highly promising breeding approach for several reasons as described by Bock and Hagemann (Bock and Hagemann, *Prog. Bot.* 61:76-90, 2000). Of note is the containment of transgenes in the transplastomic plant: Plastids are inherited through the maternal parent in most plant species and thus plastid-encoded transgenes are unable to spread in pollen to non-target species. Therefore plastid engineering can minimize negative impacts of genetically engineered plants. A report on potential transfer by pollen of herbicide resistance into weedy relatives of cultivated crops (Keeler et al., *Herbicide Resistant Crops: Agricultural, Economic, Environmental, Regulatory and Technological Aspects*, pp. 303-330, 1996) underscores the value of using plastid engineering rather than nuclear engineering for critical production traits such as herbicide resistance. Daniell et al. have recently demonstrated herbicide resistance through genetic engineering of the chloroplast genome (Daniell et al., *Nat. Biotechnol.,* 16:345-348, 1998).

Moreover, plastids are the site of essential biosynthetic activity. Although most associate photosynthesis as the primary function of the chloroplast, studies document that the chloroplast is the center of activity for functions involving carbon metabolism, nitrogen metabolism, sulfur metabolism, biochemical regulation, and various essential biosynthetic pathways including amino acid, vitamin, and phytohormone biosynthesis. Crop traits of interest such as nutritional enhancement require genetic manipulations that impact plastid biosynthetic pathways such as carotenoid production. While nuclear-encoded gene products can be exported from the engineered nucleus into the plastid for such manipulations, the biosynthetic genes themselves can be inserted into the plastid for expression and activity. As we begin to pyramid multiple genes often required for pathway manipulations (such as the aforementioned carotenoid biosynthesis) the repeated use of selection markers is expected to lead to unstable crops through homology-dependent gene silencing (Meyer and Saedler, *Ann. Rev. Plant. Physiol. Mol. Biol.* 47:23-48, 1996). In addition, the requirement for higher expression levels of transgenes for effective phenotypes such as vitamin levels and herbicide and pest resistance levels often falls short in nuclear transformations. These deficiencies are overcome through plastid transformation or combining plastid with nuclear transformations: The plastid recognizes strings of genes linked together in multicistronic operons and, due to the high copy number of genes within a plastid and within plastids in a cell, can produce a hundred- to thousand-fold the amount of transgene product. Accordingly, there is a continuing need for improved methods of producing plants having transformed plastids (transplastomic plants).

Golden rice is one example for which plastid engineering can complement nuclear engineering of pathways that reside in the plastid, yet have met with limited success. The metabolic pathway for beta-carotene (pro-vitamin A) was assembled in rice plastids by introduction into the nuclear genome of four separate genes, three encoding plastid-targeted proteins using three distinct promoters, plus a fourth selectable marker gene using a repeated promoter (Ye et al.,

*Science* 287:303-305, 2000). The wild-type rice endosperm is free of carotenoids but it does produce geranylgeranyl diphosphate; combining phytoene synthase, phytoene desaturase, and lycopene-beta cyclase resulted in accumulation of beta-carotene to make "golden rice". However, the quantity produced was lower than the minimum desired for addressing vitamin A deficiency. An increased supply of precursors for increasing intermediates, such as geranylgeranyl diphosphate, is predicted to significantly increase isoprenoid production. Insertion of an operon encoding the entire mevalonate pathway into the rice plastome of the "golden rice" genotype, using for example the methods as described in Khan and Maliga, *Nature Biotechnology* 17:910-914, 1999, can provide a means for making improvements in metabolic engineering of this important monocot crop.

Proplastid and chloroplast genetic engineering have been shown to varying degrees of homoplasmy for several major agronomic crops including potato, rice, maize, soybean, grape, sweet potato, and tobacco including starting from non-green tissues. Non-lethal selection on antibiotics is used to proliferate cells containing plastids with antibiotic resistance genes. Plastid transformation methods use two plastid-DNA flanking sequences that recombine with plastid sequences to insert chimeric DNA into the spacer regions between functional genes of the plastome, as is established in the field (see Bock and Hagemann, *Prog. Bot.* 61:76-90, 2000, and Guda et al, *Plant Cell Reports* 19:257-262, 2000, and references therein).

Antibiotics such as spectinomycin, streptomycin, and kanamycin can shut down gene expression in chloroplasts by ribosome inactivation. These antibiotics bleach leaves and form white callus when tissue is put onto regeneration medium in their presence. The bacterial genes aadA and neo encode the enzymes aminoglycoside-3'-adenyltransferase and neomycin phosphotransferase, which inactivate these antibiotics, and can be used for positive selection of plastids engineered to express these genes. Polynucleotides of interest can be linked to the selectable genes and thus can be enriched by selection during the sorting out of engineered and non-engineered plastids. Consequently, cells with plastids engineered to contain genes for these enzymes (and linkages thereto) can overcome the effects of inhibitors in the plant cell culture medium and can proliferate, while cells lacking engineered plastids cannot proliferate. Similarly, plastids engineered with polynucleotides encoding enzymes from the mevalonate pathway to produce IPP from acetyl CoA in the presence of inhibitors of the non-mevalonate pathway can overcome otherwise inhibitory culture conditions. By utilizing the polynucleotides disclosed herein in accord with this invention, an inhibitor targeting the non-mevalonate pathway and its components can be used for selection purposes of transplastomic plants produced through currently available methods, or any future methods which become known for production of transplastomic plants, to contain and express said polynucleotides and any linked coding sequences of interest.

This selection process of the subject invention is unique in that it is the first selectable trait that acts by pathway complementation to overcome inhibitors. This is distinguished from the state of the art of selection by other antibiotics to which resistance is conferred by inactivation of the antibiotic itself, e.g. compound inactivation as for the aminoglyoside 3'-adenyltransferase gene or neo gene. This method avoids the occurrence of resistant escapes due to random insertion of the resistance gene into the nuclear genome or by spontaneous mutation of the ribosomal target of the antibiotic, as is known to occur in the state of the art. Moreover, this method requires the presence of an entire functioning mevalonate pathway in plastids. For example, if one of the enzyme activities of the mevalonate pathway is not present in the plastid, resistance will not be conferred.

There is strong evidence indicating that the origin of plastids within the cell occurred via endosymbiosis and that plastids are derived from cyanobacteria. As such, the genetic organization of the plastid is prokaryotic in nature (as opposed to the eukaryotic nuclear genome of the plant cell). The plastid chromosome ranges from roughly 110 to 150 Kb in size (196 for the green alga *Chlamydomonas*), much smaller than that of most cyanobacteria. However, many of the bacterium genes have either been lost because their function was no longer necessary for survival, or were transferred to the chromosomes of the nuclear genome. Most, but not all, of the genes remaining on the plastid chromosome function in either carbon metabolism or plastid genetics. However, many genes involved in these functions, as well as the many other functions and pathways intrinsic to plastid function, are also nuclear encoded, and the translated products are transported from the cytoplasm to the plastid. Studies have documented nuclear encoded genes with known activity in the plastid that are genetically more similar to homologous genes in bacteria rather than genes of the same organism with the same function but activity in the cytoplasm as reviewed for example in Martin et al. (1998) *Nature* 393:162-165 and references therein.

The process whereby genes are transported from the plastid to the nucleus has been addressed. Evidence indicates that copies of many plastid genes are found among nuclear chromosomes. For some of these, promoter regions and transit peptides (small stretches of DNA encoding peptides that direct polypeptides to the plastid) become associated with the gene that allows it to be transcribed, and the translated polypeptide relocated back into the plastid. Once this genetic apparatus has become established, the genes present in the plastid chromosome may begin to degrade until they are no longer functional, i.e., any such gene becomes a pseudogene.

As is common in prokaryotic systems, many genes that have a common function are organized into an operon. An operon is a cluster of contiguous genes transcribed from one promoter to give rise to a polycistron mRNA. Proteins from each gene in the polycistron are then translated. There are 18 operons in the plastid chromosome of tobacco (*Nicotiana tabacum*). Although many of these involve as few as two genes, some are large and include many genes. Evolutionary studies indicate that gene loss—as pseudogenes or completely missing sequences—occurs as individuals rather than as blocks of genes or transcriptional units. Thus other genes surrounding a pseudogene in a polycistronic operon remain functional.

The rpl23 operon consists of genes whose products are involved in protein translation. Most of these genes are ribosomal proteins functioning in either the large or small ribosomal subunit. One particular gene of note, infA, encodes an initiation factor protein that is important in initiating protein translation. Although this gene is functional in many plants, it is a pseudogene in tobacco and all other members of that family (*Solanaceae*), including the horticulturally valuable tomato, petunia, and potato crops. A recent survey of plant groups has indicated that there have been numerous loses of functionality of infA (Millen et al., *Plant Cell* 13:645-658, 2001). This as well as other pseudogenes are identified in species whose chloroplast genomes have not yet been fully sequenced.

Pseudogenes such as infA become potential target sequences for insertion of intact orfs. Inserted orfs are controlled by regulatory upstream and downstream elements of the polycistron and are promoterless themselves. Pseudogenes are known for a multiplicity of crops and algae with chloroplast genomes that are already fully sequenced. Crops include grains such as rice and trees such as Pinus. Of note in the latter are the eleven ndh genes; all may serve as potential targets for transgene insertion.

Transplastomic solanaceous crops are highly desirable in order to eliminate the potential for gene transfer from engineered lines to wild species, as demonstrated in Lycopersicon (Dale, P. J. 1992. Spread of engineered genes to wild relatives. *Plant Physiol.* 100:13-15.). A method for plastid engineering that enables altered pigmentation, for improved nutrition in tomato or improved flower color in Petunia and ornamental tobacco as examples, is desirable for solanaceous crops. The infA gene is widely lost among rosids and some asterids; among the latter, infA is a pseudogene in all solanaceous species examined (representing 16 genera). The solanaceous infA DNA sequences show high similarity, with all nucleotide changes within infA being documented. Thus one set of flanking sequences of reasonable length as known in the art should serve for directed insertion of an individual or multiple orfs into the infA sites of the solanaceous species. It is documented in a solanaceous species that flanking sequences for genes to be inserted into the plastome are not required to be specific for the target species, as incompletely homologous plastid sequences are integrated at comparable frequencies (Kavanagh et al., *Genetics* 152:1111-1122, 1999).

The upstream 5' region, often referred to as the 5' UTR, is important on the expression level of a transcript as it is translated. Knowing the translation products of surrounding genes in a polycistron allows one to select a pseudogene site that is affiliated with a strong 5' UTR for optimizing plastid expression in a particular tissue. The plastid genome in many plant species can have multiple pseudogenes that are located in different polycistronic sites. So, if one has a choice, one can select a site based on whether it is actively transcribed in green vs non-green plastid; and then if the polycistron has high or low relative expression in that plastid type. Moreover, monocistronic mRNA of ndhD was detected in developed leaves but not in greening or expanding leaves of barley (Hordeum vulgare), despite this gene being part of a polycistronic unit as reported by del Campo et al. (1997) Plant Physiol 114:748. Thus, one can time transgene product production by treating an inactive gene, based on developmental expression, as a pseudogene for targetting and integration purposes using the invention disclosed herein.

Algal species are becoming increasingly exploited as sources of nutraceuticals, pharmaceuticals, and lend themselves to aquaculture. Mass production of the isoprenoid compound astaxanthin produced by the green microalga Haemotcoccus is one successful example of the above. Metabolic engineering that would increase product yields and composition in microalgae would significantly benefit the industry. The development of organellar transformation for the unicellular green alga *Chlamydomonas reinhardtii*, with its single large chloroplast, opens the door for conducting studies on genetic manipulation of the isoprenoid pathway. Filamentous or multicellular algae are also of interest as untapped biofactories, as are other nongreen algae whose pathways for producing unique fatty acids, amino acids, and pigments can be ameliorated for commercial benefit.

The biolistic DNA delivery method is a general means with which to transform the chloroplast of algae (Boynton and Gillham, *Methods Enzymol.* 217:510-536,1993). Sequencing of at least six plastomes from algae should facilitate transformation systems by confirming insertion sites, including pseudogene sites, and the regulatory elements directing heterologous gene expression. What is required is a dominant marker for selection of stable transformants to which natural resistance is absent (Stevens and Purton, *J. Phycol*33: 713-722, 1997). For *Chlamydomonas*, chloroplasts can be engineered using markers that confer spectinomycin resistance following their integration into the plastome via homologous recombination. By utilizing the polynucleotides disclosed herein in accord with this invention, an inhibitor targeting the non-mevalonate pathway and its components can be used for selection purposes of transplastomic algae produced through currently available methods, or any future methods which become known for production of transplastomic algae, to contain and express said polynucleotides and any linked coding sequences of interest. This is a novel selection vehicle for transplastomic algae. Moreover, elevating the supply of essential precursors for isoprenoid production in algae as described above is enabled by this invention.

BRIEF SUMMARY OF THE INVENTION

This invention relates to the presence of enzymatic activities necessary to form IPP from acetyl CoA, generally known as the mevalonate pathway, within plant and microalgae plastids. This invention may also require the presence of IPP isomerase activity within plastids resulting from the insertion into said plants and microalgae of a polynucleotide encoding a polypeptide with IPP isomerase activity. This invention may be achieved by the use of any polynucleotide, be it a DNA molecule or molecules, or any hybrid DNA/RNA molecule or molecules, containing at least one open reading frame that when expressed provides a polypeptide(s) exhibiting said activities within plastids. These open reading frames may be identical to their wild type progenitors, or alternatively may be altered in any manner (for example, with plastid-optimized codon usage), may be isolated from the host organism to be modified, may originate from another organism or organisms, or may be any combination of origin so long as the encoded proteins are able to provide the desired enzymatic activity within the target plastids. The described open reading frames may be inserted directly into plastids using established methodology or any methodology yet to be discovered. Alternatively, plastid localization of the desired activities may be achieved by modifying genes already residing in the cell nucleus, inserting foreign polynucleotides for nuclear residence, or inserting polynucleotides contained on exogenous, autonomous plasmids into the cell cytoplasm so that in all cases their encoded proteins are transported into the plastid. For example, a chloroplast transit (targeting) peptide can be fused to a protein of interest. Any combination of the above methods for realizing said activities in plant and microalgae plastids can be utilized. By causing the complete mevalonate pathway enzymatic activity to occur in plastids normally possessing only the non-mevalonate pathway, the presence of said activities within the chloroplasts of a specific plant or microalgae will endow it with resistance to a compound, molecule, etc. that targets a component of the non-mevalonate pathway, be it an enzyme, gene, regulatory sequence, etc., thereby also providing a useful selection system based on circumvention of the inhibition of the non-mevalonate pathway in transplastomic plants and microalgae.

In addition, this invention relates to the use of open reading frames encoding polypeptides with enzymatic activities able to convert acetyl CoA to IPP, generally known as the mevalonate pathway, and a polypeptide with IPP isomerase activity as a method for increasing the production of IPP, DMAPP, and isoprenoid pathway derived products whose level within plant and microalgae plastids is dependent on the level of IPP and/or DMAPP present within the plastids. The presence of exogenous genes encoding 1-deoxy-D-xylulose-5-phosphate synthase and IPP isomerase have been shown to increase the production of carotenoids in eubacteria, presumably due to an increased production of IPP and/or DMAPP. Thus, insertion of the entire mevalonate pathway, solely or coupled with an additional IPP isomerase, into plastids will increase the level of IPP and/or DMAPP, resulting in an increased level of carotenoids and other yet to be determined isoprenoid pathway derived products within plant and microalgae plastids. This invention can utilize an open reading frame encoding the enzymatic activity for IPP isomerase independently or in addition to said open reading frames comprising the entire mevalonate pathway to obtain the increased level of isoprenoid pathway derived products within plant and microalgae plastids. This invention may be achieved by the use of any DNA molecule or molecules, or any hybrid DNA/RNA molecule or molecules, containing open reading frames able to provide said activities within plant and microalgae plastids. These open reading frames may be identical to their wild type progenitors, may be altered in any manner, may be isolated from the plant to be modified, may originate from another organism or organisms, or may be any combination of origin so long as the encoded proteins are able to provide said activities within plastids. The described open reading frames may be inserted directly into plant and microalgae plastids using established methodology or any methodology yet to be discovered. Alternatively, plastid localization of the desired activities may be achieved by modifying genes already residing in the nucleus, inserting foreign genes for nuclear residence, or inserting genes contained on exogenous, autonomous plasmids into the cytoplasm so that in all cases their encoded proteins are transported into the plastid. Any combination of the above methods for realizing said activities in plastids can be utilized.

Further, this invention also relates to the direct insertion of any foreign gene into a plant or microalgae chloroplast by coupling it to the open reading frames encoding polypeptides with enzymatic activities able to convert acetyl CoA to IPP, thus comprising the entire mevalonate pathway. By utilizing a compound, molecule, etc. that targets a component of the non-mevalonate pathway be it an enzyme, gene, regulatory sequence, etc., a method of selection analogous to the use of kanamycin and spectinomycin resistance for the transformation event is achieved. As inhibition of the non-mevalonate pathway in a plant or microalgae results in the impairment of photosynthesis, the presence of the mevalonate pathway biosynthetic capability is apparent, thus enabling the facile screening of concomitant incorporation into plastids of a foreign gene coupled to the open reading frames comprising the entire mevalonate pathway. The use of a polynucleotide comprising an open reading frame encoding a polypeptide with IPP isomerase activity in addition to the open reading frames encoding the mevalonate pathway is a particularly preferred embodiment, which provides all enzymatic activities necessary to synthesize both IPP and DMAPP and overcome the effect(s) of inhibition of the non-mevalonate pathway.

Further, this invention is unique and novel in that the transforming DNA, that is integrated by two or more homologous/heterologous recombination events, is purposefully targeted into inactive gene sites selected based on prior knowledge of transcription in plastid type, developmental expression including post-transcriptional editing, and post-transcriptional stability. Additionally, this invention uses the regulatory elements of known inactive genes (pseudogenes) to drive production of a complete transforming gene unrelated to the inserted gene site. Thus, by utilizing the transgene insertion method disclosed herein in accord with this invention, any foreign gene can be targeted to an inactive gene site (the pseudogene) through currently available methods of gene transfer, or any future methods which become known for production of transgenic and transplastomic plants, to contain and express said foreign gene and any linked coding sequences of interest. This gene insertion process of the subject invention is unique in that it is the first method specifically acting by pseudogene insertion to overcome the need for promoters and other regulatory elements normally associated with a transforming DNA vector while permitting site-specific recombination in organellar genomes. The use of the infA pseudogene insertion site in the solanaceous crops in particular is a preferred embodiment for the transformation of plastids using the open reading frames for the mevalonate pathway as well as for providing the necessary precursors for modified output traits in plants.

BRIEF DESCRIPTION OF THE SEQUENCES

Figure 1:
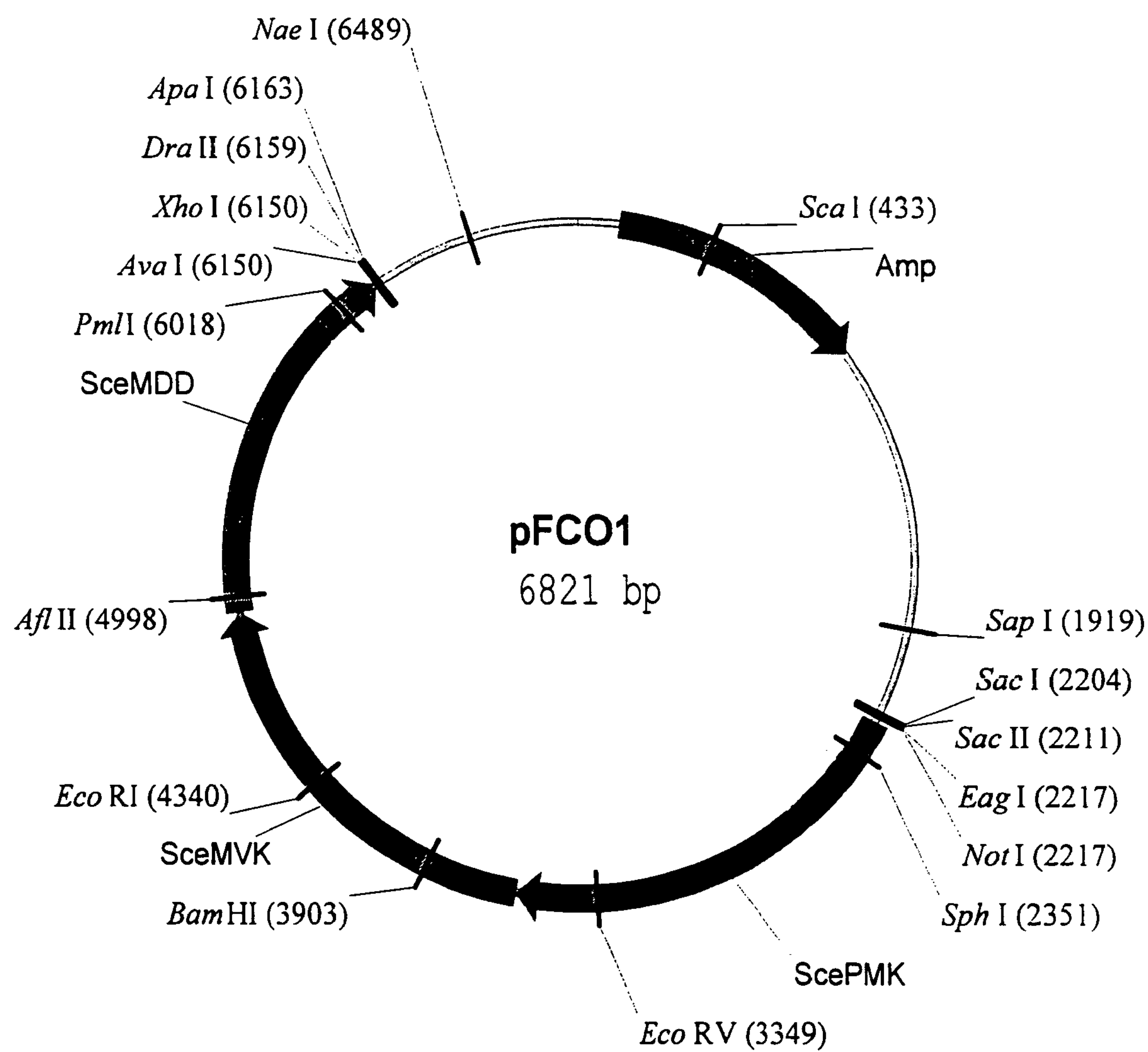
FIG. 1 is a map of cloning vector pFCO1 containing *S. cerevisiae* orfs encoding phosphomevalonate kinase (PMK), mevalonate kinase (MVK), and mevalonate diphosphate decarboxylase (MDD).

SEQ ID NO:1 is a PCR primer containing *Saccharomyces cerevisiae* DNA.

SEQ ID NO:2 is a PCR primer containing *S. cerevisiae* DNA.

SEQ ID NO:3 is a PCR primer containing *S. cerevisiae* DNA.

SEQ ID NO:4 is a PCR primer containing *S. cerevisiae* DNA.

SEQ ID NO:5 is a PCR primer containing *S. cerevisiae* DNA.

SEQ ID NO:6 is a PCR primer containing *S. cerevisiae* DNA.

SEQ ID NO:7 is a PCR primer containing *Arabidopsis thaliana* DNA.

SEQ ID NO:8 is a PCR primer containing *A. thaliana* DNA.

SEQ ID NO:9 is a PCR primer containing *A. thaliana* DNA.

SEQ ID NO:10 is a PCR primer containing *A. thaliana* DNA.

SEQ ID NO:11 is a PCR primer containing *S. cerevisiae* DNA.

SEQ ID NO:12 is a PCR primer containing *S. cerevisiae* DNA.

SEQ ID NO:13 is a Oligonucleotide containing *S. cerevisiae* DNA.

SEQ ID NO:14 is a Oligonucleotide containing *A. thaliana* and *S. cerevisiae* DNA.

SEQ ID NO:15 is an Oligonucleotide containing *S. cerevisiae* DNA.

SEQ ID NO:16 is an Oligonucleotide containing *S. cerevisiae* DNA.

SEQ ID NO:17 is Vector pBSNT27 containing *Nicotiana tabacum* DNA.

SEQ ID NO:18 is an Oligonucleotide containing *N. tabacum* and *S. cerevisiae* DNA.

SEQ ID NO:19 is an Oligonucleotide containing *N. tabacum* and *A. thaliana* DNA.

SEQ ID NO:20 is a PCR primer containing *Rhodobacter capsulatus* DNA.

SEQ ID NO:21 is a PCR is a primer containing *R. capsulatus* DNA.

SEQ ID NO:22 is a PCR primer containing *Schizosaccharomyces pombe* DNA.

SEQ ID NO:23 is a PCR primer containing *S. pombe* DNA.

SEQ ID NO:24 is a PCR primer containing *Streptomyces* sp CL190 DNA.

SEQ ID NO:25 PCR is a primer containing *Streptomyces* sp CL190 DNA.

SEQ ID NO:26 is an Oligonucleotide containing *S. cerevisiae* DNA.

SEQ ID NO:27 is an Oligonucleotide containing *S. cerevisiae* DNA.

SEQ ID NO:28 is an Oligonucleotide containing *Streptomyces* sp CL190 and *R. capsulatus* DNA.

SEQ ID NO:29 is an Oligonucleotide containing *R. capsulatus* DNA.

SEQ ID NO:30 is an Oligonucleotide containing *Streptomyces* sp CL190 and *S. cerevisiae* DNA.

SEQ ID NO:31 is an Oligonucleotide containing *Streptomyces* sp CL190 DNA.

SEQ ID NO:32 is an Oligonucleotide containing *N. tabacum* and *S. cerevisiae* DNA.

SEQ ID NO:33 is an Oligonucleotide containing *N. tabacum* and *R. capsulatus* DNA.

SEQ ID NO:34 is an Oligonucleotide containing *N. tabacum* and *S. cerevisiae* DNA.

SEQ ID NO:35 is an Oligonucleotide containing *N. tabacum* and *S. pombe* DNA.

SEQ ID NO:36 is an Oligonucleotide containing NotI restriction site.

SEQ ID NO:37 is an Oligonucleotide containing NotI restriction site.

SEQ ID NO:38 is an Oligonucleotide containing *S. cerevisiae* DNA.

SEQ ID NO:39 is an Oligonucleotide containing *A. thaliana* DNA.

SEQ ID NO:40 is an Oligonucleotide containing *S. cerevisiae* DNA.

SEQ ID NO:41 is an Oligonucleotide containing *R. capsulatus* DNA.

SEQ ID NO:42 is an Oligonucleotide containing *S. cerevisiae* DNA.

SEQ ID NO:43 is an Oligonucleotide containing *S. pombe* DNA.

SEQ ID NO:44 is an Oligonucleotide containing *R. capsulatus* DNA.

SEQ ID NO:45 is an Oligonucleotide containing *R. capsulatus* DNA.

SEQ ID NO:46 is an Oligonucleotide containing *S. pombe* DNA.

SEQ ID NO:47 is an Oligonucleotide containing *S. pombe* DNA.

SEQ ID NO:48 is *Saccharomyces cerevisiae* orf for phosphomevalonate kinase (ERG8).

SEQ ID NO:49 is *Saccharomyces cerevisiae* orf for mevalonate kinase (ERG12).

SEQ ID NO:50 is *Saccharomyces cerevisiae* orf for mevalonate diphosphate decarboxylase (ERG19).

SEQ ID NO:51 is *Saccharomyces cerevisiae* orf for acetoacetyl thiolase.

SEQ ID NO:52 is *Arabidopsis thaliana* orf for 3-hydroxy-3-methylglutaryl-coenzyme A (HMG-CoA) synthase.

SEQ ID NO:53 is *Arabidopsis thaliana* orf for HMG-CoA reductase.

SEQ ID NO:54 is *Schizosaccharomyces pombe* IDI1 (IPP isomerase).

SEQ ID NO:55 is *Rhodobacter capsulatus* idiB (IPP isomerase).

SEQ ID NO:56 is *Streptomyces* sp CL190 orf encoding HMG-CoA reductase.

SEQ ID NO:57 is *Streptomyces* sp CL190 gene cluster containing mevalonate pathway and IPP isomerase orfs.

SEQ ID NO:58 is Operon A containing *A. thaliana* and *S. cerevisiae* DNA

SEQ ID NO:59 is Operon B containing *A. thaliana* and *S. cerevisiae* DNA.

SEQ ID NO:60 is Operon C containing *A. thaliana, S. cerevisiae*, and *R. capsulatus* DNA.

SEQ ID NO:61 is Operon D containing *A. thaliana, S. cerevisiae*, and *Streptomycs* sp CL190 DNA.

SEQ ID NO:62 is Operon E containing *A. thaliana, S. cerevisiae, Streptomycs* sp CL190 DNA, and *R. capsulatus* DNA.

SEQ ID NO:63 is Operon F containing *S. cerevisiae* and *Streptomycs* sp CL190 DNA.

SEQ ID NO:64 is Operon G containing *A. thaliana, S. cerevisiae* and *S. pombe* DNA.

SEQ ID NO:65 is PCR primer containing *R. capsulatus* DNA.

SEQ ID NO:66 is PCR primer containing *R. capsulatus* DNA.

SEQ ID NO:67 is an Oligonucleotide containing *N. tabacum* and *R. capsulatus* DNA.

SEQ ID NO:68 is an Oligonucleotide containing *N. tabacum* and *R. capsulatus* DNA.

SEQ ID NO:69 is an Oligonucleotide containing *N. tabacum* and *S. cerevisiae* DNA.

SEQ ID NO:70 is an Oligonucleotide containing *N. tabacum* and *R. capsulatus* DNA.

SEQ ID NO:71 is *Rhodobacter capsulatus* orf encoding phytoene synthase (crtB).

SEQ ID NO:72 is plastid transformation vector pHKO4, containing Operon B, containing *A. thaliana* and *S. cerevisiae* DNA.

SEQ ID NO:73 is plastid transformation vector pHKO7, containing Operon C, containing *A. thaliana, S. cerevisiae*, and *R. capsulatus* DNA.

SEQ ID NO:74 is plastid transformation vector pHKO8, containing Operon G, containing *A. thaliana, S. cerevisiae*, and *S. pombe* DNA.

SEQ ID NO:75 is plastid transformation vector pFHO5 containing *R. capsulatus* DNA encoding phytoene synthase.

SEQ ID NO:76 is plastid transformation vector pFHO6, containing Operon E, containing *A. thaliana, S. cerevisiae, Streptomycs* sp CL190 DNA, and *R. capsulatus* DNA.

DETAILED DESCRIPTION

In the description that follows, a number of terms used in genetic engineering are utilized. In order to provide a clear and consistent understanding of the specification and claims, including the scope to be given such terms, the following definitions are provided.

A protein is considered an isolated protein if it is a protein isolated from a host cell in which it is naturally produced. It can be purified or it can simply be free of other proteins and biological materials with which it is associated in nature, for example, if it is recombinantly produced.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule, but is not flanked by both of the coding or noncoding sequences that flank that part of the molecule in the genome of the organism in which it naturally occurs; (b) a nucleic acid incorporated into a vector or into the genomic or plastomic DNA of a prokaryote or eukaryote in a manner such that the resulting molecule is not identical to any naturally occurring vector or genomic or plastomic DNA; (c) a separate molecule such as a cDNA, a genomic or plastomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to one another if the two are not derived from the same ultimate natural source, or are not naturally contiguous to each other. The sequences may be natural sequences, or at least one sequence can be derived from two different species or one sequence can be produced by chemical synthesis provided that the nucleotide sequence of the synthesized portion was not derived from the same organism as the other sequence.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, maybe operably linked even at a distance, i.e., even if not contiguous.

In a plastome, sequences are physically linked by virtue of the chromosome configuration, but they are not necessarily operably linked due to differential expression for example. Transgenes can be physically linked prior to transformation, or can become physically linked once they insert into a plastome. Transgenes can become operably linked if they share regulatory sequences upon insertion into a plastome.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

The polynucleotides may also be produced by chemical synthesis, e.g., by the phosphoramidite method described by Beaucage and Caruthers (1981) *Tetra. Letts.,* 22:1859-1862 or the triester method according to Matteuci et al. (1981) *J. Am. Chem. Soc.,* 103: 3185, and may be performed on commercial automated oligonucleotide synthesizers. A double-stranded fragment may be obtained from the single stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host will typically, but not always, comprise a replication system (i.e. vector) recognized by the host, including the intended polynucleotide fragment encoding the desired polypeptide, and will preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate, preferably from secreted polypeptides of the same or related species, which allow the protein to cross and/or lodge in cell membranes or be secreted from the cell.

Variants or sequences having substantial identity or homology with the polynucleotides encoding enzymes of the mevalonate pathway may be utilized in the practice of the invention. Such sequences can be referred to as variants or modified sequences. That is, a polynucleotide sequence may be modified yet still retain the ability to encode a polypeptide exhibiting the desired activity. Such variants or modified sequences are thus equivalents. Generally, the variant or modified sequence will comprise at least about 40%-60%, preferably about 60%-80%, more preferably about 80%-90%, and even more preferably about 90%-95% sequence identity with the native sequence.

Sequence relationships between two or more nucleic acids or polynucleotides are generally defined as sequence identity, percentage of sequence identity, and substantial identity. See, for example, "Pedestrian Guide to Analyzing Sequence Data Bases" at www.emblheidelberg.de/~schneide/paper/springer96/springer.html. In determining sequence identity, a "reference sequence" is used as a basis for sequence comparison. The reference may be a subset or the entirety of a specified sequence. That is, the reference sequence may be a full-length gene sequence or a segment of the gene sequence.

Methods for alignment of sequences for comparison are well known in the art. See, for example, Smith et al. (1981) *Adv. Appl. Math.* 2:482; Needleman et al. (1970) *J. Mol. Biol.* 48:443; Pearson et al. (1988) *Proc. Natl. Acad. Sci.* 85:2444; CLUSTAL in the PC/Gene Program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA. Preferred computer alignment methods also include the BLASTP, BLASTN, and BLASTX algorithms. See, Altschul et al. (1990) *J. Mol. Biol.* 215:403-410.

"Sequence identity" or "identity" in the context of nucleic acid or polypeptide sequences refers to the nucleic acid bases or residues in the two sequences that are the same when aligned for maximum correspondence over a specified comparison window. "Percentage of sequence identity" refers to the value determined by comparing two optimally aligned sequences over a comparison window, wherein the portion of the polynucleotide sequence in the comparison window may comprise additions or deletions as compared to the reference window for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Polynucleotide sequences having "substantial identity" are those sequences having at least about 50%-60% sequence identity, generally at least 70% sequence identity, preferably at least 80%, more preferably at least 90%, and most preferably at least 95%, compared to a reference sequence using one of the alignment programs described above. Preferably sequence identity is determined using the default parameters determined by the program. Substantial identity of amino acid sequence generally means sequence identity of at least 50%, more preferably at least 70%, 80%, 90%, and most preferably at least 95%.

Nucleotide sequences are generally substantially identical if the two molecules hybridize to each other under stringent conditions. Generally, stringent conditions are selected to be about 5° C. lower than the thermal melting point for the specific sequence at a defined ionic strength and pH. Nucleic acid molecules that do not hybridize to each other under stringent conditions may still be substantially identical if the polypeptides they encode are substantially identical. This may occur, for example, when a copy of a nucleic acid is created using the maximum codon degeneracy permitted by the genetic code.

As noted, hybridization of sequences may be carried out under stringent conditions. By "stringent conditions" is intended conditions under which a probe will hybridize to its target sequence to a detectably greater degree than to other sequences. Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary stringent conditions include hybridization with a buffer solution of 30to 35% formamide, 1.0 M NaCl, 1% SDS (sodium dodecyl sulphate) at 37° C., andawashin 1× to 2×SSC (20×SSC=3.0 M NaCl/0.3 M trisodium citrate) at 50 to 55° C. It is recognized that the temperature, salt, and wash conditions may be altered to increase or decrease stringency conditions. For the post-hybridization washes, the critical factors are the ionic strength and temperature of the final wash solution. See, Meinkoth and Wahl (1984) *Anal. Biochem.* 138:267-284.

As indicated, fragments and variants of the nucleotide sequences of the invention are encompassed herein. By "fragment" is intended a portion of the nucleotide sequence. Fragments of the polynucleotide sequence will generally encode polypeptides which retain the biological/enzymatic activity of the native protein. Those of skill in the art routinely generate fragments of polynucleotides of interest through use of commercially available restriction enzymes; synthetic construction of desired polynucleotides based on known sequences; or use of "erase-a-base" technologies such as Bal 31 exonuclease, by which the skilled artisan can generate hundreds of fragments of a known polynucleotide sequence from along the entire length of the molecule by time-controlled, limited digestion. Fragments that retain at least one biological or enzymatic activity of the native protein are equivalents of the native protein for that activity.

By "variants" is intended substantially similar sequences. For example, for nucleotide sequences, conservative variants include those sequences that, because of the degeneracy of the genetic code, encode the amino acid sequence of an enzyme of the mevalonate pathway. Variant nucleotide sequences include synthetically derived sequences, such as those generated for example, using site-directed mutagenesis. Generally, nucleotide sequence variants of the invention will have at least 40%, 50%, 60%, 70%, generally 80%, preferably 85%, 90%, up to 95% sequence identity to its respective native nucleotide sequence. Activity of polypeptides encoded by fragments or variants of polynucleotides can be confirmed by assays disclosed herein.

"Variant" in the context of proteins is intended to mean a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function. Such variants are equivalents of the native protein. Variant proteins that retain a desired biological activity are encompassed within the subject invention. Variant proteins of the invention may include those that are altered in various ways including amino acid substitutions, deletions, truncations, and insertions. Methods for such manipulation are generally known in the art. See, for example, Kunkel (1985) *Proc. Natl. Acad. Sci. USA* 82:488-492; Kunkel et al. (1987) *Methods and Enzymol;* 154:367-382; and the references cited therein.

An expression cassette may contain at least one polynucleotide of interest to be cotransformed into the organism. Such an expression cassette is preferably provided with a plurality of restriction sites for insertion of the sequences of the invention to be under the transcriptional regulation of the regulatory regions. The expression cassette may additionally contain selectable marker genes.

The cassette may include 5' and 3' regulatory sequences operably linked to a polynucleotide of interest. By "operably linked" is intended, for example, a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. When a polynucleotide comprises a plurality of coding regions that are operably linked such that they are under the control of a single promoter, the polynucleotide may be referred to as an "operon".

The expression cassette will optionally include in the 5'-3' direction of transcription, a transcriptional and translational initiation region, a polynucleotide sequence of interest and a transcriptional and translational termination region functional in plants or microalgae. The transcriptional initiation region, the promoter, is optional, but may be native or analogous, or foreign or heterologous, to the intended host. Additionally, the promoter may be the natural sequence or alternatively a synthetic sequence. By "foreign" is intended that the transcriptional initiation region is not found in the native organism into which the transcriptional initiation region is introduced. As used herein, a chimeric gene comprises a coding sequence operably linked to a transcriptional initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) Gene 91:151-158; Ballas et al. (1989) *Nucleic Acids Res.* 17:7891-7903; and Joshi et al. (1987) *Nucleic Acid Res.* 15:9627-9639.

Where appropriate, the polynucleotides of interest may be optimized for expression in the transformed organism. That is, the genes can be synthesized using plant or algae plastid-preferred codons corresponding to the plastids of the plant or algae of interest. Methods are available in the art for synthesizing such codon optimized polynucleotides. See, for example, U. S. Pat. Nos. 5,380,831 and 5,436,391, and Murray et al. (1989) *Nucleic Acids Res.* 17:477-498, herein incorporated by reference. Of course, the skilled artisan will appreciate that for the transplastomic purposes described herein, sequence optimization should be conducted with plastid codon usage frequency in mind, rather than the plant or algae genome codon usage exemplified in these references.

It is now well known in the art that when synthesizing a polynucleotide of interest for improved expression in a host cell it is desirable to design the gene such that its frequency of codon usage approaches the frequency of codon usage of the host cell. It is also well known that plastome codon usage may vary from that of the host plant or microalgae genome. For purposes of the subject invention, "frequency of preferred codon usage" refers to the preference exhibited by a specific host cell plastid in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a plastid can be calculated by averaging frequency of preferred codon usage in a number of genes expressed by the plastid. It usually is preferable that this analysis be limited to genes that are among those more highly expressed by the plastid. Alternatively, the polynucleotide of interest may be synthesized to have a greater number of the host plastid's most preferred codon for each amino acid, or to reduce the number of codons that are rarely used by the host.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region), Elroy-Stein et al. (1989) *PNAS USA* 86:6126-6130; potyvirus leaders, for example, TEV leader (Tobacco Etch Virus), Allison et al. (1986); MDMV Leader (Maize Dwarf Mosaic Virus) *Virology* 154:9-20; and human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625; tobacco mosaic virus leader (TMV), Gallie et al. (1989) in *Molecular Biology of RNA*, ed. Cech (Liss, N.Y.), pp. 237-256; and maize chlorotic mottle virus leader (MCMV), Lommel et al. (1991) *Virology* 81:382-385. See also, Della-Cioppa et al. (1987) *Plant Physiol.* 84:965-968. Other methods known to enhance translation can also be utilized, for example, introns, and the like.

In preparing an expression cassette, the various polynucleotide fragments may be manipulated, so as to provide for the polynucleotide sequences in the proper orientation and, as appropriate, in the proper reading frame. Toward this end, adapters or linkers may be employed to join the polynucleotide fragments or other manipulations maybe involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved.

In addition, expressed gene products may be localized to specific organelles in the target cell by ligating DNA or RNA coded for peptide leader sequences to the polynucleotide of interest. Such leader sequences can be obtained from several genes of either plant or other sources. These genes encode cytoplasmically-synthesized proteins directed to, for example, mitochondria (the F1-ATPase beta subunit from yeast or tobacco, cytochrome cl from yeast), chloroplasts (cytochrome oxidase subunit Va from yeast, small subunit of rubisco from pea), endoplasmic reticulum lumen (protein disulfide isomerase), vacuole (carboxypeptidase Y and proteinase A from yeast, phytohemagglutinin from French bean), peroxisomes (D-aminoacid oxidase, uricase) and lysosomes (hydrolases).

Following transformation, a plant may be regenerated, e.g., from single cells, callus tissue, or leaf discs, as is standard in the art. Almost any plant can be entirely regenerated from cells, tissues, and organs of the plant. Available techniques are reviewed in Vasil et al. (1984) in *Cell Culture and Somatic Cell Genetics of Plants, Vols. I, II, and III, Laboratory Procedures and Their Applications* (Academic press); and Weissbach et al. (1989) *Methods for Plant Mol. Biol.*

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved.

The particular choice of a transformation technology will be determined by its efficiency to transform certain target species, as well as the experience and preference of the person practicing the invention with a particular methodology of choice. It will be apparent to the skilled person that the particular choice of a transformation system to introduce nucleic acid into plant or microalgae plastids is not essential to or a limitation of the invention, nor is the choice of technique for plant regeneration.

Also according to the invention, there is provided a plant or microalgae cell having the constructs of the invention. A further aspect of the present invention provides a method of making such a plant cell involving introduction of a vector including the construct into a plant cell. For integration of the construct into the plastid genome (the "plastome"), such introduction will be followed by recombination between the vector and the plastome genome to introduce the operon sequence of nucleotides into the plastome. RNA encoded by the introduced nucleic acid construct (operon) may then be transcribed in the cell and descendants thereof, including cells in plants regenerated from transformed material. A gene stably incorporated into the plastome of a plant or microalgae is passed from generation to generation to descendants of the plant or microalgae, so such descendants should show the desired phenotype.

The present invention also provides a plant or microalgae culture comprising a plant cell as disclosed. Transformed seeds and plant parts are also encompassed. As used herein, the expressions "cell," "cell line," and "cell culture" are used interchangeably and all such designations include progeny, meaning descendants, not limited to the immediate generation of descendants but including all generations of descendants. Thus, the words "transformants" and "transformed cells" include the primary subject cell and cultures derived therefrom without regard for the number of transfers. It is also understood that all progeny may not be precisely identical in DNA content, due to naturally occurring, deliberate, or inadvertent caused mutations. Mutant progeny that have the same function or biological activity as screened for in the originally transformed cell are included. Where distinct designations are intended, it will be clear from the context.

In addition to a plant or microalgae, the present invention provides any clone of such a plant or microalgae, seed, selfed or hybrid or mated descendants, and any part of any of these, such as cuttings or seed for plants. The invention provides any plant propagule, that is any part which may be used in reproduction or propagation, sexual or asexual, including cuttings, seed, and so on. Also encompassed by the invention is a plant or microalgae which is a sexually or asexually propagated off-spring, clone, or descendant of such a plant or microalgae, or any part or propagule of said plant, off-spring, clone, or descendant. Plant or microalgae extracts and derivatives are also provided.

The present invention may be used for transformation of any plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* ssp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidental*), macadamia (*Macadamia integrifolia*), almond (*Prunus amygdalus*), sugar beets (*Beta vulgaris*), oats, barley, vegetables, ornamentals, and conifers.

Preferably, plants of the present invention are crop plants (for example, cereals and pulses, maize, wheat, potatoes, tapioca, rice, sorghum, millet, cassava, barley, pea, and other root, tuber, or seed crops. Important seed crops are oil-seed rape, sugar beet, maize, sunflower, soybean, and sorghum. Horticultural plants to which the present invention may be applied may include lettuce; endive; and vegetable brassicas including cabbage, broccoli, and cauliflower; and carnations and geraniums. The present invention may be applied to tobacco, cucurbits, carrot, strawberry, sunflower, tomato, pepper, chrysanthemum, petunia, rose, poplar, eucalyptus, and pine.

Grain plants that provide seeds of interest include oil-seed plants and leguminous plants. Seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Leguminous plants include beans and peas. Beans including guar, locust bean, fenugreek, soybean, garden beans, cowpea, mungbean, lima bean, fava bean, lentils, chickpea, etc.

Microalgae include but are not limited to the *Chlorophyta* and the *Rhodophyta* and may be such organisms as *Chlamydomonas, Haematococcus*, and *Ouneliella.*

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless indicated otherwise, the respective contents of the documents cited herein are hereby incorporated by reference to the extent they are not inconsistent with the teachings of this specification.

Percentages and ratios given herein are by weight, and temperatures are in degrees Celsius unless otherwise indicated. The references cited within this application are herein incorporated by reference to the extent applicable. Where necessary to better exemplify the invention, percentages and ratios may be cross-combined.

EXAMPLE 1

Isolation of ORFs Encoding Enzymes of the Mevalonate Pathway for the Construcion of Vectors pFCO1 and pFCO2

In an exemplified embodiment, vectors containing open reading frames (orfs) encoding enzymes of the mevalonate pathway are constructed. Polynucleotides derived from the yeast *Saccharomyces cerevisiae*, the plant *Arabidopsis thaliana*, and the eubacterium *Streptomyces* sp CL190 are used for the construction of vectors, including plastid delivery vehicles, containing orfs for biosynthesis of the mevalonate pathway enzymes. Construction of the vectors is not limited to the methods described. It is routine for one skilled in the art to choose alternative restriction sites, PCR primers, etc. to create analogous plasmids containing the same orfs or other orfs encoding the enzymes of the mevalonate pathway. Many of the steps in the construction of the plasmids of the subject invention can utilize the joining of blunt-end DNA fragments by ligation. As orientation with respect to the promoter upstream (5') of the described orfs can be critical for biosynthesis of the encoded polypeptides, restriction analysis is used to determine the orientation in all instances involving blunt-end ligations. A novel directional ligation methodology, chain reaction cloning (Pachuk et al, *Gene* 243:19-25, 2000), can also be used as an alternative to standard ligations in which the resultant orientation of the insert is not fixed. All PCR products are evaluated by sequence analysis as is well known in the art.

The construction of a synthetic operon comprising three yeast orfs encoding phosphomevalonate kinase, mevalonate kinase, and mevalonate diphosphate decarboxylase is described by Hahn et al. (Hahn et al., *J. Bacteriol.* 183:1-11, 2001). This same synthetic operon, contained within plasmid pFCO2, is able to synthesize, in vivo, polypeptides with enzymatic activities able to convert exogenously supplied mevalonate to IPP as demonstrated by the ability of the mevalonate pathway orfs to complement the temperature sensitive dxs::kanr lethal mutation in *E. coli* strain FH11 (Hahn et al., 2001).

Plasmids pFCO1 and pFCO2 containing a synthetic operon for the biosynthesis of IPP from mevalonate are constructed as follows: Three yeast orfs encoding mevalonate kinase, phosphomevalonate kinase, and mevalonate diphosphate decarboxylase are isolated from *S. cerevisiae* genomic DNA by PCR using the respective primer sets FH0129-2:
5'GGACTAGTCTGCAGGAGGAGTTTTAATGTCATTAC CGTTCTTAACTTCTGCACCGGG-3'(sense) (SEQ ID NO:1)
and FH0129-1:
5'TTCTCGAG*CTTAAGAGTAGCAATATTTACCGGAGC AGTTACACTAGCAGTATATACAGTC*ATTAAAACTCCT CCTGTGAAGTCCATGGTAAATTCG 3'(antisense); (SEQ ID NO:2)

FH0211-1:
5'TAGCGGCCGCAGGAGGAGTTCATATGTCAGAGTTG AGAGCCTTCAGTGCCCCAGGG 3'(sense) (SEQ ID NO:3)
and FH0211-2:
5'TTTCTGCAGTTTATCAAGATAAGTTTCCGGATCTT T 3'(antisense); (SEQ ID NO:4)

CT0419-1:
5'GGAATTCATGACCGTTTACACAGCATCCGTTACCG CACCCG 3'(sense); (SEQ ID NO:5)
and CT0419-2:
5'GGCTCGAGTTAAAACTCCTCTTCCTTTGGTAGACC AGTCTTTGCG 3'(antisense); (SEQ ID NO:6)

Figure 2:
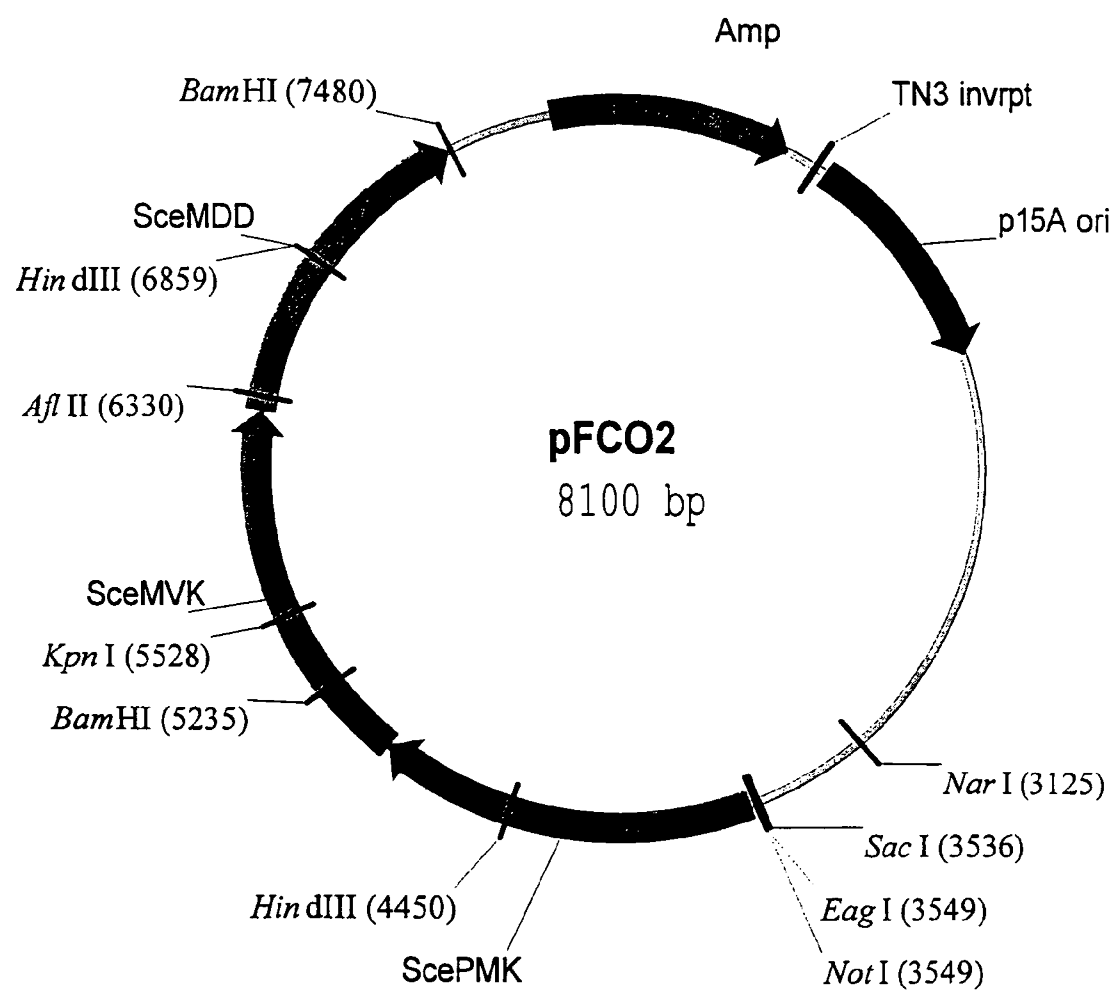
FIG. 2 is a map of expression vector pFCO2 containing *S. cerevisiae* orfs encoding phosphomevalonate kinase (PMK), mevalonate kinase (MVK), and mevalonate diphosphate decarboxylase (MDD).

Primer FH0129-2 includes a SpeI site (underlined). Primer FH0129-1 contains an XhoI site (underlined), an AflII site (double-underlined), and 54 nucleotides (bold italics) corresponding to the 5' end of the yeast orf for mevalonate diphosphate decarboxylase. Following PCR using primers FH0129-1 and FH0129-2, a product containing the orf encoding yeast mevalonate kinase is isolated by agarose gel electrophoresis and GeneClean purified. Following restriction with SpeI-XhoI, the PCR product is inserted into the SpeI-XhoI sites of pBluescript(SK+) (Stratagene, LaJolla, Calif.) by ligation to create pBRG12. Primers FH0211-1 and FH0211-2 contain a NotI site (underlined) and a PstI site (underlined), respectively. Following PCR using primers FH0211-1 and FH0211-2, a product containing the orf encoding yeast phosphomevalonate kinase is restricted with NotI-PstI, purified by GeneClean, and inserted into pGEM-T Easy (Promega Corp, Madison, Wis.) by ligation to create pERG8. An orf encoding yeast mevalonate diphosphate decarboxylase is isolated by PCR using primers CT0419-1 and CT0419-2 and inserted directly into pGEM-T Easy by ligation to create pERG19. Restriction of pERG8 with NotI-PstI yields a 1.4 Kb DNA fragment containing the orf for phosphomevalonate kinase. Restriction of pBRG12 with NotI-PstI is followed by the insertion of the 1.4 Kb NotI-PstI DNA fragment by ligation to create pBRG812 containing the orfs for both phosphomevalonate kinase and mevalonate kinase and the 5' end of the orf for yeast mevalonate diphosphate decarboxylase. Restriction of pERG19 with AflII-XhoI yields a 1.2 Kb DNA fragment containing the 3' end of the orf for yeast mevalonate diphosphate decarboxylase missing in pBRG812. Insertion of the 1.2 Kb AflII-XhoI DNA fragment into pBRG812/AflII-XhoI by ligation yields pFCO1 containing the three yeast mevalonate pathway orfs (FIG. 1). Restriction of pFCO1 with XhoI is followed by treatment with the Klenow fragment of T7 DNA polymerase and dNTPs to create blunt ends. Subsequent restriction of pFCO1/XhoI/Klenow with Sacd yields a 3.9 Kb DNA fragment containing the three yeast mevalonate pathway orfs. Following agarose gel electrophoresis and GeneClean purification of the 3.9 Kb DNA fragment, it is inserted into the SmaI-SacI sites of pNGH1-amp (Garrett et al., *J. Biol. Chem.* 273:12457-12465, 1998) by ligation to create pFCO2 (FIG. 2).

EXAMPLE 2

Construction of *E. coli* Strain FH11 (JM101/dxs::kan$^r$/pDX4)

A mutant *E. coli* strain containing a disruption of the chromosomal dxs gene is constructed as described by Hamilton et al. (Hamilton et al., *J. Bacteriol.* 171:4617-4622, 1989). The strains are grown at 30° C. or 44° C. in Luria-Bertani (LB) supplemented with the following antibiotics as necessary; ampicillin (Amp) (50 (g/ml), chloramphenicol (Cam) (30 (g/ml), and kanamycin (Kan) (25 (g/ml). Within phagemid DD92 (F. R. Blattner, University of Wisconsin, Madison, Wis.) is a 19.8 Kb EcoRI fragment of *E. coli* genomic DNA containing dxs, the gene for DXP synthase. Following the isolation of the phage from *E. coli* strain LE392, DD92 is restricted with SphI, and the resultant 6.3 Kb fragment is isolated by agarose gel electrophoresis. GeneClean purification of the SphI fragment and restriction with SmaI yields a 2.0 Kb SphI-SmaI fragment containing *E. coli* dxs. The 2.0 Kb fragment is purified by GeneClean and inserted by ligation into the SphI-HindII sites of pMAK705, a plasmid containing a temperature-sensitive origin of replication (Hamilton et al., *J. Bacteriol.* 171:4617-4622, 1989). The resulting plasmid containing wt dxs, pDX4, is restricted with SapI, a unique site located in the middle of the dxs gene, and the 5'-overhangs are filled in with Klenow and dNTPs. The blunt-ended DNA fragment is purified by GeneClean and treated with shrimp alkaline phosphatase (SAP, USB Corp., Cleveland, Ohio) according to the manufacturer's instructions. pUC4K (Amersham Pharmacia Biotech, Piscataway, N.J.) is restricted with EcoRI, Klenow-treated, and the resulting 1.3 Kb blunt-ended DNA fragment containing the gene for Kan resistance is inserted into the filled-in SapI site of pDX4 by blunt-end ligation to create pDX5 with a disruption in *E. coli* dxs. Competent *E. coli* JM101 cells are transformed with pDX5, a pMAK705 derivative containing dxs::kanr, and grown to an optical density (A600) of 0.6 at 30° C. Approximately 10,000 cells are plated out on LB/Cam medium prewarmed to 44° C. The plates were incubated at 44° C., and several of the resulting colonies are grown at 44° C. in 4 ml of LB/Cam medium. Four 50 ml LB/Cam cultures are started with 0.5 ml from four of the 4 ml cultures and grown overnight at 30° C. Four fresh 50 ml LB/Cam cultures are started with 100 μl of the previous cultures and grown overnight at 30° C. An aliquot of one of the 50 ml cultures is serially diluted 5×105 fold, and 5 μl is plated on LB/Cam medium. Following incubation at 30° C., the resulting colonies are used to individually inoculate 3 ml of LB medium containing Cam and Kan. Twelve LB/Cam/Kan cultures are grown overnight at 30° C. and used for plasmid DNA isolation. *E. coli* cells where the disrupted copy of dxs is incorporated into the genome are identified by restriction analysis of the isolated plasmid DNA and verified by sequence analysis of the DNA contained in the plasmids. The *E. coli* JM101 derivative containing the dxs::kanr mutation is designated FH11 (Hahn et al. 2001).

EXAMPLE 3

Assay Demonstrating Synthesis of IPP from Mevalonic Acid in *E. coli*

The episomal copy of dxs contained on pDX4 in *E. coli* strain FH11 is "turned off" at 44° C. due to a temperature sensitive origin of replication on the pMAK705 derivative (Hamilton et al., *J. Bacteriol.* 171:4617-4622, 1989). The inability of FH11 to grow at the restrictive temperature demonstrates that dxs is an essential single copy gene in *E. coli* (Hahn et al., 2001). A cassette containing three yeast mevalonate pathway orfs is removed from pFCO1 and inserted into pNGH1-Amp to form pFCO2 for testing the ability of the mevalonate pathway orfs to complement the dxs::kanr disruption when FH11 is grown at 44° C. on medium containing mevalonate. The utility of strain FH11 as a component of an assay for testing the ability of mevalonate pathway orfs to direct the synthesis of IPP is demonstrated as follows:

Colonies of *E. coli* strain FH11 transformed with pFCO2 or pNGH1-Amp, the expression vector without an insert, are isolated by incubation at 30° C. on LB plates containing Kan and Amp. Four ml LB/Kan/Amp cultures containing either FH11/pFCO2 or FH11/pNGH1-Amp are grown overnight at 30° C. Following a 10,000-fold dilution, 10 μl portions from the cultures are spread on LB/Kan/Amp plates that are prewarmed to 44° C. or are at rt. Approximately 1.3 mg of mevalonic acid is spread on each plate used for FH11/pFCO2. The prewarmed plates are incubated at 44° C., and the rt plates are incubated at 30° C. overnight.

FH11/pNGH1-amp cells will not grow at the restrictive temperature of 44° C. and FH11/pFCO2 cells are unable to grow at of 44° C. unless mevalonic acid (50 mg/L) is added to the growth medium thus establishing the ability of the polypeptides encoded by the mevalonate pathway orfs contained in the synthetic operon within pFCO2 to form IPP from mevalonate in vivo (Hahn et al., 2001).

EXAMPLE 4

Isolation of Mevalonate Pathway ORFs

In a specific, exemplified embodiment, the isolation of orfs, each encoding a polypeptide with either HMG-CoA synthase enzyme activity, HMG-CoA reductase enzyme activity, or acetoacetyl-CoA thiolase enzyme activity, and construction of vectors containing these orfs is as follows: Synthesis of *A. thaliana* first strand cDNAs is performed utilizing POWERSCRIPT™ reverse transcriptase (Clontech Laboratories, Inc., Palo Alto, Calif.) according to the manufacturer's instructions. Specifically, a microfuge tube containing 5 μl of *A. thaliana* RNA (Arabidopsis Biological Resource Center, Ohio State University, Columbus, Ohio), 1.8 μl poly(dT)15 primer (0.28 μg/μl, Integrated DNA Technologies, Inc. Coralville, Iowa), and 6.2 μl DEPC-treated $H_2O$ is heated at 70° C. for 10 min and then immediately cooled on ice. The mixture is spun down by centrifugation and 4 µl of 5× First-Strand Buffer (Clontech), 2 µl Advantage UltraPure PCR dNTP mix (10 mM each, Clontech) and 2 µl 100 mM DTT are added and the entire contents mixed by pipetting. Following the addition of 1 µl reverse transcriptase (Clontech) and mixing by pipetting, the contents are incubated at 42° C. for 90 min and then heated at 70° C. for 15 min to terminate the reaction.

The resulting *A. thaliana* first strand cDNAs are used as templates for the synthesis of an orf encoding HMG-CoA synthase and a truncated HMG-CoA reductase by PCR in a Perkin-Elmer GeneAmp PCR System 2400 thermal cycler utilizing the ADVANTAGE™ HF 2 PCR Kit (Clontech) according to the manufacturer's instructions. An *A. thaliana* HMG-CoA synthase orf is isolated using the following PCR primers:

```
1)
5' GCTCTAGATGCGCAGGAGGCACATATGGCGAAGA  (SEQ ID NO:7)
ACGTTGGGATTTTGGCTATGGATATCTATTTCCC 3'
(sense);
and

2)
5''CG CTCGAGTCGACGGATCCTCAGTGTCCATTGGC  (SEQ ID NO:8)
TACAGATCCATCTTCACCTTTCTTGCC 3'
(antisense);
```

containing the restriction site XbaI shown underlined, the restriction site XhoI shown in bold italic and the restriction site SalI shown double underlined. Specifically, 2 (l cDNA, 5 µ(l 10×HF 2 PCR Buffer (Clontech), 5 µl 10×HF 2 dNTP Mix (Clontech), 1 µl each of the primers described above, 1 µl 50× Advantage-HF 2 Polymerase Mix (Clontech), and 35 µl PCR-Grade H2O (Clontech) are combined in a 0.5 ml PCR tube. The mixture is heated at 94° C. for 15 sec then subjected to 40 PCR cycles consisting of 15 sec at 94° C. and 4 min at 68° C. After a final incubation at 68° C. for 3 min, the reaction is cooled to 4° C. Agarose gel electrophoresis is performed on a 10 µl aliquot to confirm the presence of a DNA fragment of the predicted size of 1.4 Kb. The PCR is repeated in triplicate to generate enough product for its isolation by gel excision and purification by GeneClean (Qbiogene, Inc., Carlsbad Calif.). Following restriction with XbaI-XhoI and purification by GeneClean, the 1.4 Kb PCR product is inserted into the XbaI-XhoI sites of pBluescript(SK+) by ligation to form putative pBSHMGS constructs. Sequence analysis of several of the candidate constructs is performed to identify inserts with DNA identical to the published *A. thaliana* orf for HMG-CoA synthase and are used for the construction of pBSHMGSR as described below.

An *A. thaliana* orf encoding a polypeptide with HMG-CoA reductase enzyme activity is synthesized by PCR essentially as described above using the following primers:

```
3) 5' CCGCTCGAGCACGTGGAGGCACATATGCAATGCTGTGAGATGCC
TGTTGGATACATTCAGATTCCTGTTGGG 3'
(sense) (SEQ ID NO:9);
and
4) 5' GGGGTACCTGCGGCCGGATCCCGGGTCATGTTGTTGTTGTTGTC
GTTGTCGTTGCTCCAGAGATGTCTCGG 3'
(antisense) (SEQ ID NO:10);
```

containing the restriction site XhoI shown underlined, the restriction site KpnI shown in italic, the restriction site EagI shown in bold, and the restriction site SmaI shown double underlined. The 1.1 Kb PCR product is isolated by agarose gel electrophoresis, purified by GeneClean and inserted into the pT7Blue-3 vector (Novagen, Inc., Madison, Wis.) using the PERFECTLY BLUNT™ Cloning Kit (Novagen) according to the manufacturer's instructions. Sequence analysis is performed to identify constructs containing *A. thaliana* DNA encoding the desired C-terminal portion of the published HMG-CoA reductase amino acid sequence and are designated pHMGR.

PCR is performed on *S. cerevisiae* genomic DNA (Invitrogen, Corp., Carlsbad, Calif.) by using the ADVANTAGE™-HF 2 PCR Kit (Clontech) according to the manufacturer's instructions and the following primers:

```
5)
5' ACAACACCGCGGCGGCCGCGTCGACTACGTAGG (SEQ ID NO:11)
AGGCACATATGTCTCAGAACGTTTACATTGTATCGA
CTGCC 3'(sense);
and

6)
5' GCTCTAGAGGATCCTCATATCTTTTCAATGACA (SEQ ID NO:12)
ATAGAGGAAGCACCACCACC 3'(antisense);
```

containing the restriction site NotI shown underlined, the restriction site SacII shown in italic, the restriction site SalI shown in bold, the restriction site SnaBI shown double underlined, and the restriction site XbaI in bold italic. The 1.2 Kb PCR product is isolated by agarose gel electrophoresis, purified by GeneClean and inserted into the vector pT7Blue-3 (Novagen,) using the PERFECTLY BLUNT™ Cloning Kit (Novagen) according to the manufacturer's instructions. Sequence analysis is performed to identify constructs containing *S. cerevisiae* DNA identical to the published orf encoding acetoacetyl-CoA thiolase and they are designated pAACT.

EXAMPLE 5

Construction of pHKO1

Figure 3:
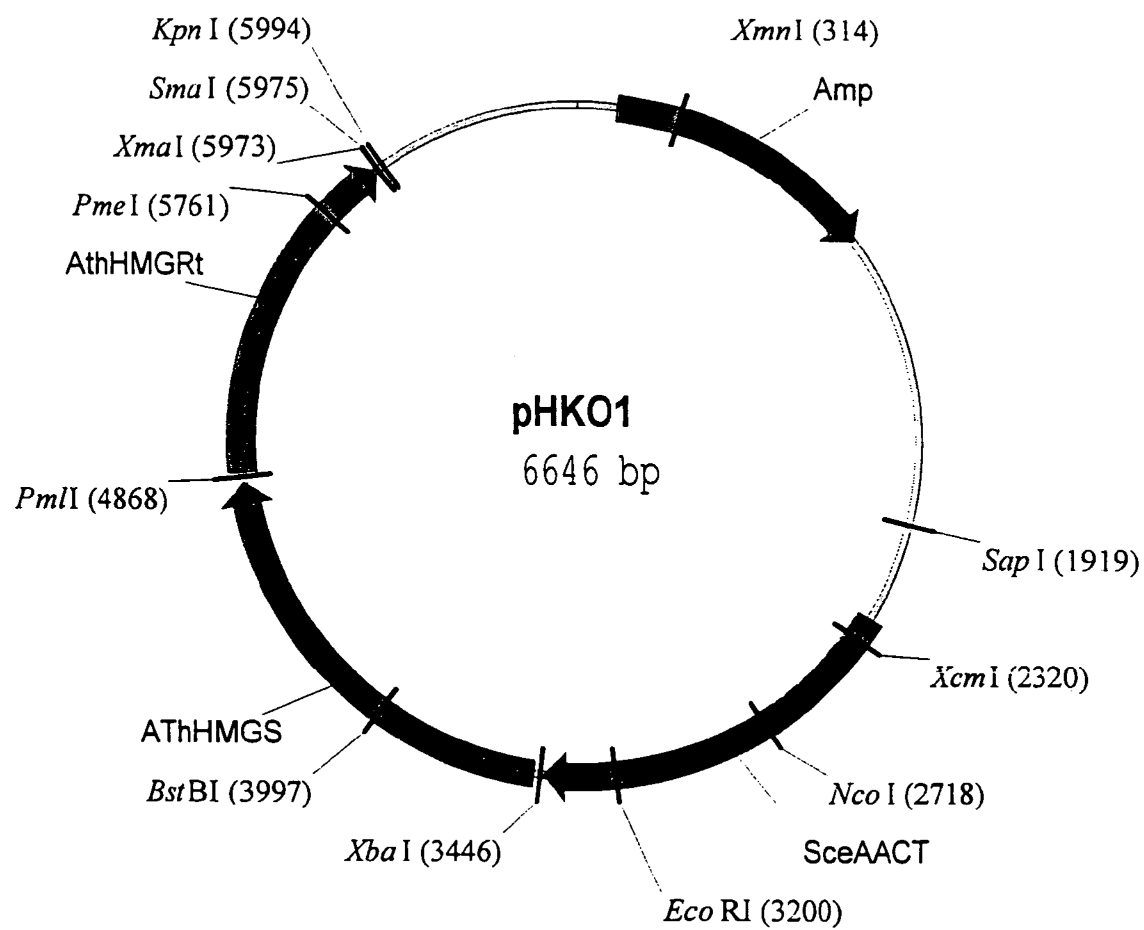
FIG. 3 is a map of cloning vector pHKO1 containing *S. cerevisiae* orf encoding acetoacetyl thiolase (AACT); *A. thaliana* orfs encoding HMG-CoA synthase (HMGS), HMG-CoA reductase (HMGRt).

In an exemplified embodiment, a pBluescript(SK+) derivative containing an operon with orfs encoding polypeptides with enzymatic activities for HMG-CoA synthase, HMG-CoA reductase, and acetoacetyl-CoA thiolase is constructed as follows: Following restriction of pHMGR with XhoI-KpnI, isolation of the 1.1 Kb DNA fragment by agarose gel electrophoresis, and purification by GeneClean, the 1.1 Kb XhoI-KpnI DNA fragment containing the orf encoding the C-terminal portion of *A. thaliana* HMG-CoA reductase is inserted into the SalI-KpnI sites of pBSHMGS by ligation to create pBSHMGSR. Following restriction of pAACT with SacII-XbaI, isolation of the 1.2 Kb DNA fragment containing the orf encoding yeast acetoacetyl-CoA thiolase by agarose gel electrophoresis, and purification by GeneClean, the 1.2 Kb SacII-XbaI DNA fragment is inserted into the SacII-XbaI sites of pBSHMGSR by ligation to create pHKO1 (FIG. 3).

EXAMPLE 6

Construction of pHKO2

Figure 4:
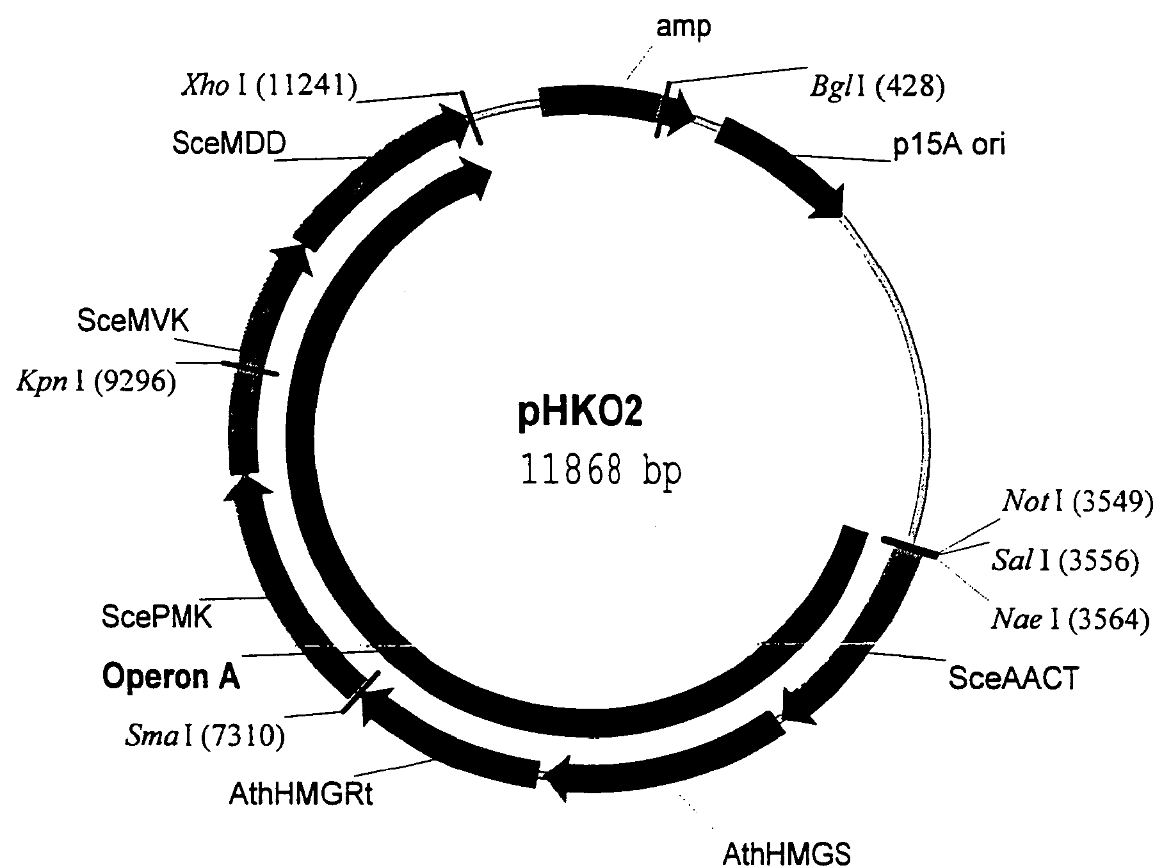
FIG. 4 is a map of expression vector pHKO2 containing *S. cerevisiae* orfs encoding phosphomevalonate kinase (PMK), mevalonate kinase (MVK), mevalonate diphosphate decarboxylase (MDD), and acetoacetyl thiolase (AACT); *A. thaliana* orfs encoding HMG-CoA synthase (HMGS), HMG-CoA reductase (HMGRt) which in their summation are designated Operon A, encoding the entire mevalonate pathway.

In a specific, exemplified embodiment, a vector containing a synthetic operon consisting of six orfs encoding polypeptides with acetoacetyl-CoA thiolase, HMG-CoA synthase, HMG-CoA reductase, mevalonate kinase, phosphomevalonate kinase, and mevalonate diphosphate decarboxylase enzymatic activities, thus comprising the entire mevalonate pathway, is constructed as follows: Restriction of pHKO1 with EagI yields a 3.7 Kb DNA fragment containing orfs encoding yeast acetoacetyl-CoA thiolase, *A. thaliana* HMG-CoA synthase, and a truncated *A. thaliana* HMG-CoA reductase. Following isolation of the 3.7 Kb EagI DNA fragment by agarose gel electrophoresis and purification by GeneClean, it is directionally inserted into the NotI site of pFCO2 (Hahn et al., 2001) utilizing the methodology of chain reaction cloning (Pachuk et al., 2000), thermostable AMPLIGASE™ (Epicentre Technologies, Madison, Wis.), and the following bridge oligonucleotide primers:

```
1)
5' TGGAATTCGAGCTCCACCGCGGTGGCGGCCGCG (SEQ ID NO:13)
TCGACGCCGGCGGAGGCACATATGTCT 3';
and

2)
5' AACAACAACAACATGACCCGGGATCCGGCCGCA (SEQ ID NO:14)
GGAGGAGTTCATATGTCAGAGTTGAGA 3';
```

as follows: Agarose gel electrophoresis is performed on the 8.1 Kb pFCO2/NotI DNA fragment and the 3.7 Kb EagI DNA fragment isolated from pHKO1 to visually estimate their relative concentrations. Approximately equivalent amounts of each fragment totaling 4.5 μl, 1 μl of each bridge oligo at a concentration of 200 nM, 5 μl AMPLIGASE™ 10× Reaction Buffer (Epicentre), 3 μl AMPLIGASE™ (5 U/(l) (Epicentre), and 35.5 μl PCR grade H2O are added to a 0.5 ml PCR tube. The mixture is heated at 94° C. for 2 min then subjected to 50 PCR cycles consisting of 30 sec at 94° C., 30 sec at 60° C., and 1 min at 66° C. After a final incubation at 66° C. for 5 min, the reaction is cooled to 4° C. Colonies resulting from the transformation of *E. coli* strain NovaBlue (Novagen) with 1 μl of the directional ligation reaction are grown in LB medium supplemented with ampicillin at a final concentration of 50 μg/ml. Restriction analysis with NaeI-KpnI of mini-prep plasmid DNA from the liquid cultures is performed to identify candidate pHKO2 constructs by the presence of both a 5.7 and a 6.2 Kb DNA fragment. Further analysis by restriction with SmaI-XhoI to generate both a 3.9 and 7.9 Kb DNA fragment confirms the successful construction of pHKO2 (FIG. 4).

EXAMPLE 7

Assay Demonstrating the Synthesis of IPP from Acetyl-CoA in *E. coli*

Figure 5:
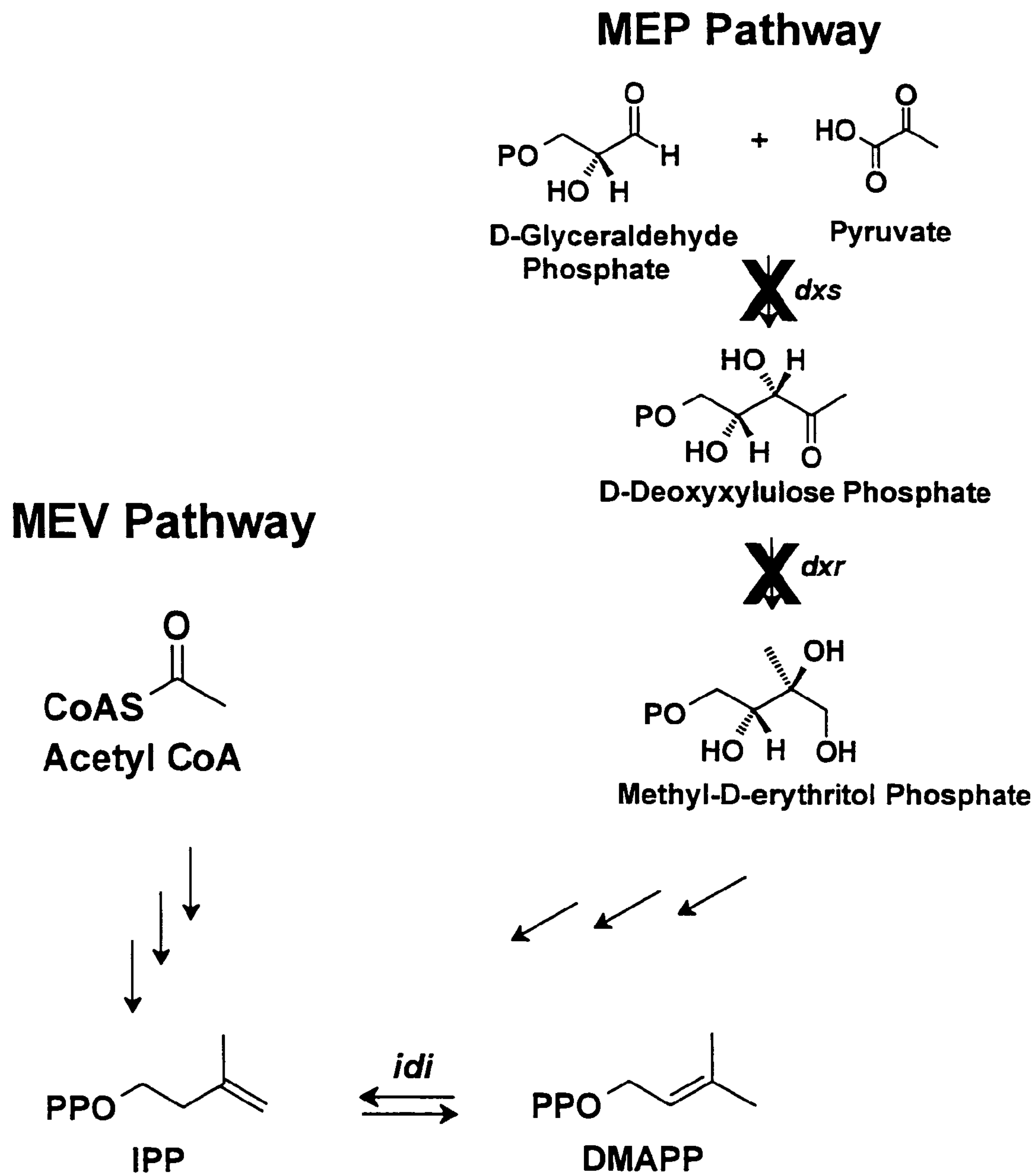
FIG. 5 is a map of cloning vector pHKO3 containing *S. cerevisiae* orfs encoding phosphomevalonate kinase (PMK), mevalonate kinase (MVK), mevalonate diphosphate decarboxylase (MDD), and acetoacetyl thiolase (AACT); *A. thaliana* orfs encoding HMG-CoA synthase (HMGS), HMG-CoA reductase (HMGRt) which in their summation are designated Operon B, encoding the entire mevalonate pathway.

In a specific, exemplified embodiment, a derivative of pNGH1-amp (Hahn et al., 2001), containing the entire mevalonate pathway, is assayed (FIG. 5) for its ability to synthesize IPP from endogenous acetyl-CoA in *E. coli* strain FH11, containing the temperature sensitive dxs::kanr$^r$ knockout (Hahn et al., 2001), as follows: Colonies resulting from the transformation of FH11, by pHKO2, containing orfs encoding polypeptides with enzymatic activities for acetoacetyl-CoA thiolase, HMG-CoA synthase, HMG-CoAreductase, mevalonate kinase, phosphomevalonate kinase, and mevalonate diphosphate decarboxylase, are isolated by incubation at 30° C. on LB plates containing Kan and Amp. Several 4 ml LB/Kan/amp samples are individually inoculated with single colonies from the FH11/pHKO2 transformation. Following growth at 30° C. overnight, the FH11/pHKO2 cultures are diluted 100,000-fold, and 5 μl aliquots are spread on LB/Kan/amp plates at room temperature (rt) or that are prewarmed to 44° C. The prewarmed plates are incubated at 44° C., and the rt plates are incubated at 30° C. overnight. FH11 and FH11/pNGH1 amp cells will not grow at the restrictive temperature of 44° C. (Hahn et al., 2001). FH11/pHKO2 cells are able to grow at 44° C., thus establishing the ability, of a synthetic operon comprising the entire mevalonate pathway, to form IPP from acetyl-CoA and thereby overcome the dxs::kan$^r$ block to MEP pathway biosynthesis of IPP in *E. coli* strain FH11.

EXAMPLE 8

Construction of pHKO3

Figure 6:
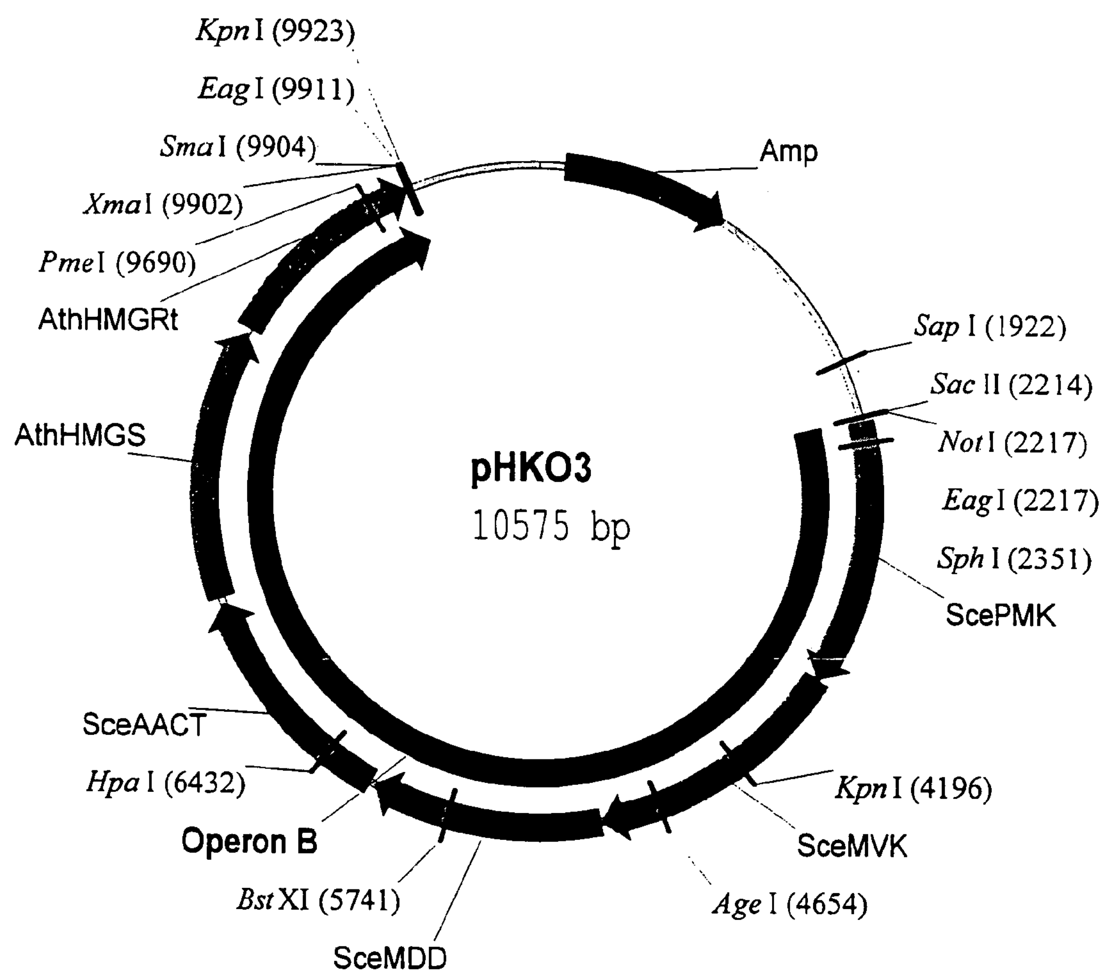
FIG. 6 is an illustration of how the mevalonate (MEV) pathway, by providing an alternative biosynthetic route to IPP, circumvents blocks in the MEP pathway due to a mutation in the gene for deoxyxylulose phosphate synthase (dxs) and due to inhibtion by fosmidomycin of deoxyxylulose phosphate reductoisomerase (dxr).

In another exemplified embodiment, a derivative of pBluescript(SK+) containing an operon comprising orfs, which in their summation is the entire mevalonate pathway, is constructed as follows: pHKO1, containing orfs encoding acetoacetyl-CoA thiolase, HMG-CoA synthase, and an N-terminal truncated HMG-CoA reductase, is restricted with SalI-NotI and purified by GeneClean. The pBluescript(SK+) derivative pFCO1, containing the orfs encoding mevalonate kinase, phosphomevalonate kinase, and mevalonate diphosphate decarboxylase, has been described above in Example 1. Following restriction of pFCO1 with XhoI-NotI, isolation by agarose gel electrophoresis, and purification by GeneClean, the 3.9 Kb DNA fragment containing the mevalonate pathway orfs is inserted into pHKO1/SalI-NotI by directional ligation (Pachuk et al., 2000) utilizing thermostable AMPLIGASE™ (Epicentre Technologies, Madison, Wis.), and the following bridging oligonucleotides:

```
1)
5' CTCAACTCTGACATATGAACTCCTCCTGCGGCC (SEQ ID NO:15)
GCCGCGGTGGAGCTCCAGCTTTTGTTCCC 3';
and

2)
5' GGTCTACCAAAGGAAGAGGAGTTTTAACTCGAC (SEQ ID NO:16)
GCCGGCGGAGGCACATATGTCTCAGAACG 3';
```

essentially as described for the construction of pHKO2. Restriction analysis is performed with KpnI to confirm the successful construction of pHKO3 (FIG. 6).

Figure 7:
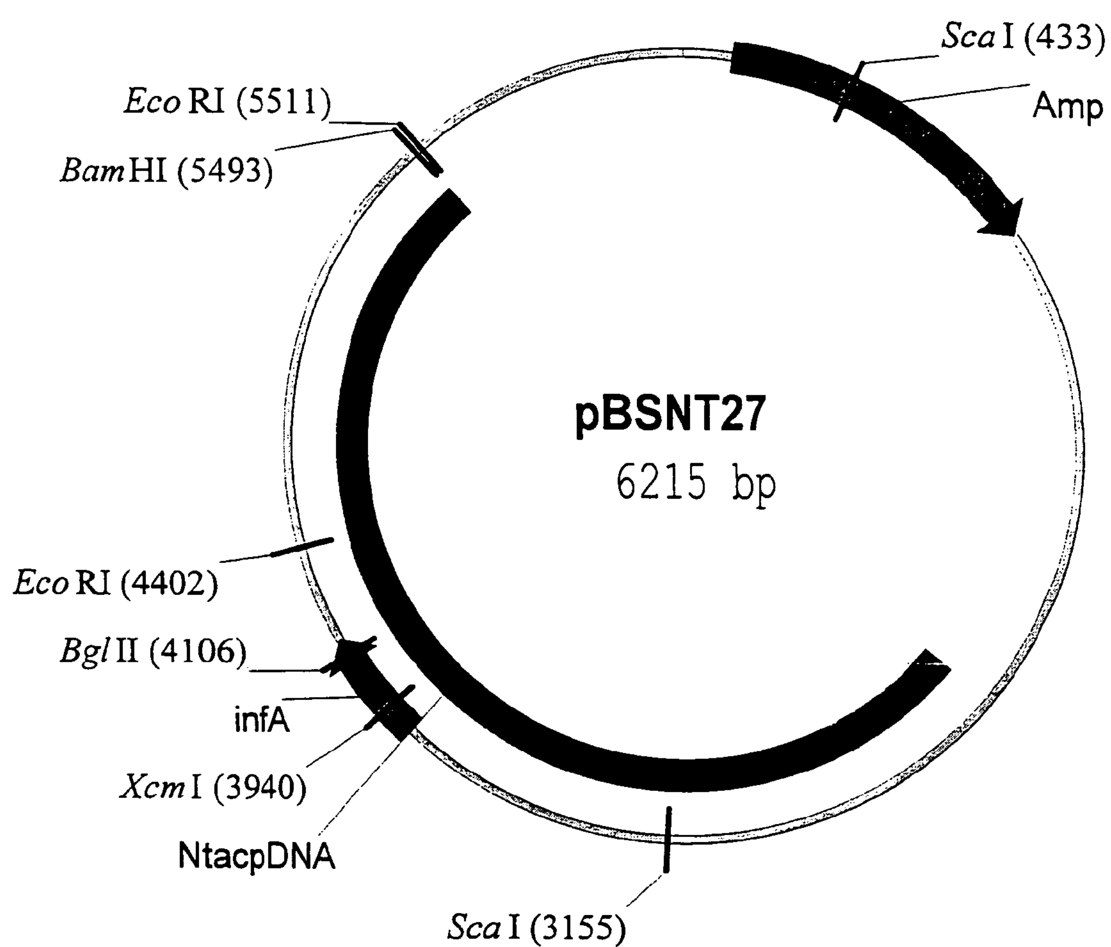
FIG. 7 is a map of vector pBSNT27 containing *N. tabcum* chloroplast DNA (cpDNA) and the *N. tabcum* infA pseudogene and pBSNT27 sequence (SEQ ID NO:17).
Figure 8:
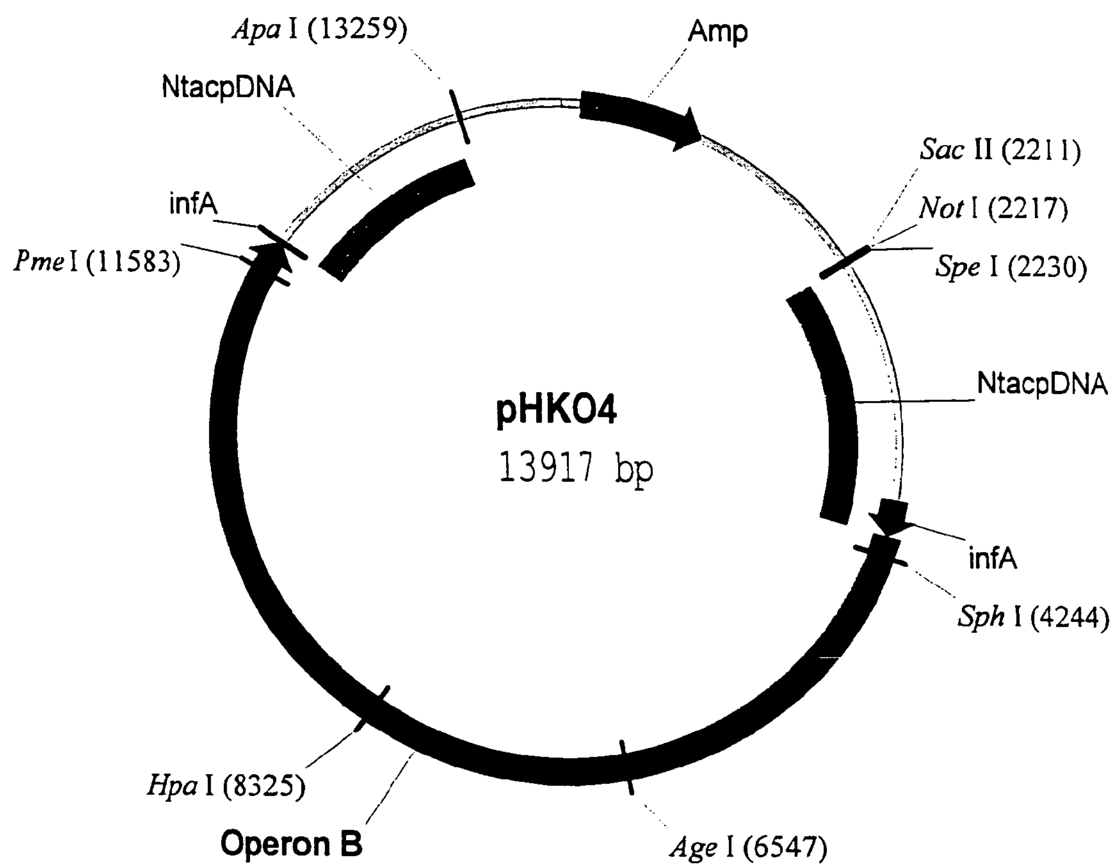
FIG. 8 is a map of plastid transformation vector pHKO4 containing *N. tabcum* chloroplast DNA (cpDNA) flanking the insertion of Operon B into the infA pseudogene.

In an exemplified embodiment, a vector containing a *Nicotiana tabacum* plastid pseudogene is utilized to create a plastid transformation vector as follows: The pBluescript (SK+) derivative designated as pBSNT27 (FIG. 7, SEQ ID NO:17) contains a 3.3 Kb BglII-BamHI DNA fragment of the *N. tabacum* chloroplast genome corresponding approximately to base-pairs 80553-83810 of the published nucleotide sequence (Sugiura, M., 1986, and Tsudsuki, T., 1998.). Aunique restriction site contained within the tobacco infA pseudogene located on pBSNT27 is cleaved with BglII and the resulting 5' overhangs are filled in with Klenow and dNTPs. The resulting 6.2 Kb blunt-ended DNA fragment is GeneClean purified. Following restriction of pHKO3 with EagI, filling in of the resulting 5' overhangs with Klenow and dNTPs, isolation by agarose gel electrophoresis, and purification by GeneClean, the resulting 7.7 Kb blunt-ended DNA fragment, containing orfs encoding the entire mevalonate pathway, is directionally inserted into the blunt-ended BglII site of pBSNT27 utilizing chain reaction cloning (Pachuk et al., 2000.), thermostable AMPLIGASE™ (Epicentre Technologies, Madison, Wis.), and the following bridging oligonucleotides:

```
1)
5' GATCTTTCCTGAAACATAATTTATAAT-      (SEQ ID NO:18)
CAGATCG
GCCGCAGGAGGAGTTCATATGTCAGAGTTGAG 3';
and

2)
GACAACAACAACAACATGACCCGGGATCCGGCCGAT (SEQ ID NO:19)
CTAAACAAACCCGGAACAGACCGTTGGGAA 3';
```

to form the tobacco plastid-specific transformation vector pHKO4 (FIG. 8).

Alternatively, other derivatives of pBSNT27 can be constructed, using skills as known in the art, that are not reliant upon an available restriction site(s) in the pseudogene. For example, although the infA pseudogene comprises basepairs 3861-4150 in pBSNT27, there are unique restriction sites in close proximity, upsteam and downstream, that can be utilized to excise the entire pseudogene followed by its replacement with an orf or gene cluster comprising multiple orfs, e.g. the complete mevalonate pathway described above. Specifically, there is a unique BsrGI site at 3708 base pairs and a unique SexAI restriction site at 4433 base pairs within pBSNT27. Thus, as will be readily apparent to those skilled in the art, one can replace the infA pseudogene entirely by inserting a BsrGI-SexAI DNA fragment containing DNA, comprising orfs encoding the entire mevalonate pathway, that is flanked by the excised DNA originally flanking the infA pseudogene, i.e. DNA corresponding to 3708-3860 and 4151-4433 base pairs in pBSNT27. The resultant construct will be missing the pseudogene, but will contain the excised flanking DNA restored to its original position and now surrounding the mevalonate pathway orfs. Also, a similar strategy, that will also be apparent to those skilled in the art in view of this disclosure, can be employed that restores the intact pseudogene to a location between the DNA originally flanking it, yet linked to an orf or orfs located upstream and/or downstream of the pseudogene and adjacent to the original flanking DNA.

EXAMPLE 10

Construction of Vectors Containing ORFs Encoding IPP Isomerase (pHKO5 and pHKO6)

Figure 9:
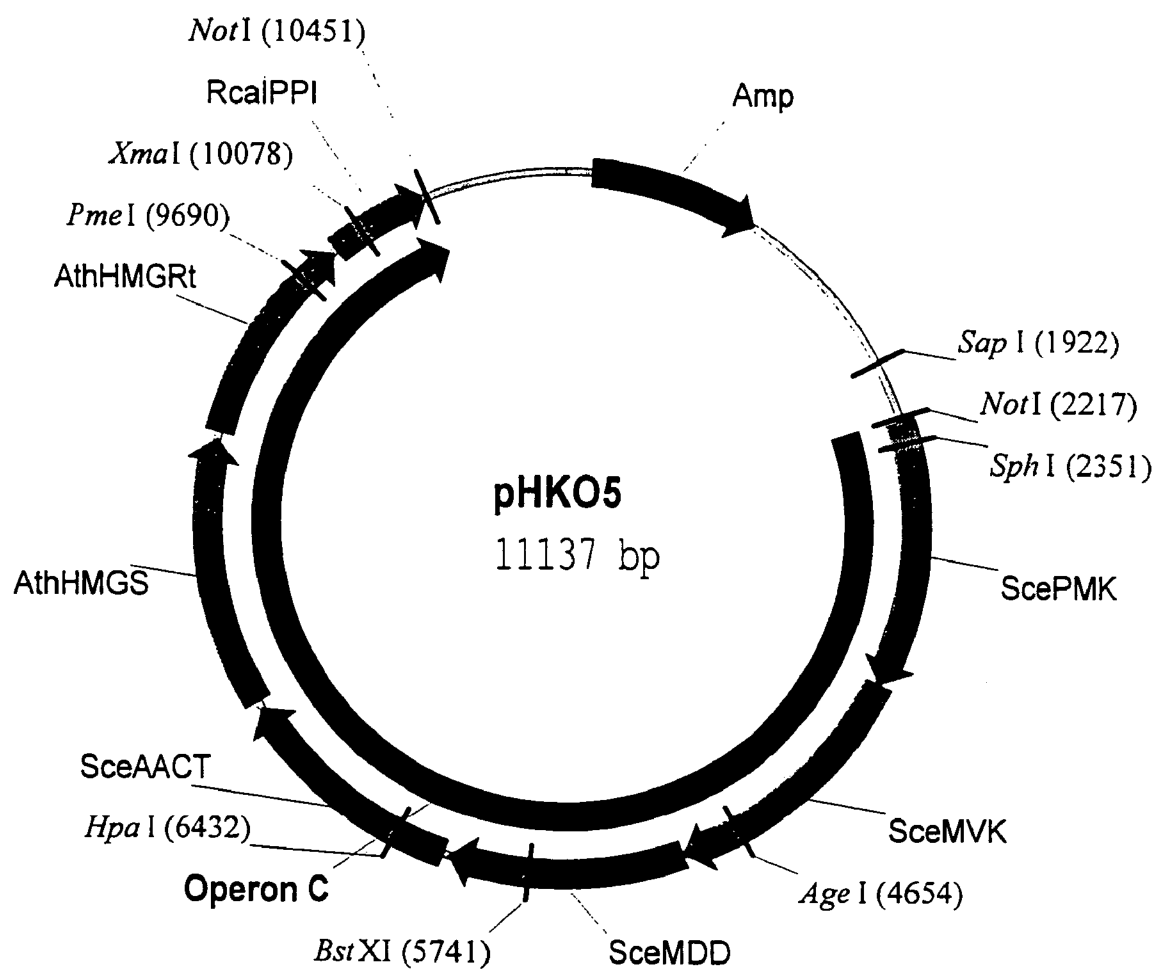
FIG. 9 is a map of cloning vector pHKO5 containing *S. cerevisiae* orfs encoding phosphomevalonate kinase (PMK), mevalonate kinase (MVK), and mevalonate diphosphate decarboxylase (MDD), and acetoacetyl thiolase (AACT); *A. thaliana* orfs encoding HMG-CoA synthase (HMGS), HMG-CoA reductase (HMGRt); *R. capsulatus* orf encoding IPP isomerase (IPPI) which in their summation are designated Operon C, encoding the entire mevalonate pathway and IPP isomerase.

In a specific, exemplified embodiment, orfs encoding IPP isomerase are isolated and vectors containing an operon comprising orfs for the entire mevalonate pathway and an additional orf for IPP isomerase are constructed as follows: A *Rhodobacter capsulatus* orf encoding a polypeptide with IPP isomerase activity is isolated by PCR from genomic DNA (J. E. Hearst, Lawrence Berkeley Laboratories, Berkeley, Calif.) using the following primers:

```
1)
5' CGCTCGAGTACGTAAGGAGGCACATATGAGTGA (SEQ ID NO:20)
GCTTATACCCGCCTGGGTTGG 3'(sense);
and

2)
5' GCTCTAGAGATATCGGATCCGCGGCCGCTCAGC (SEQ ID NO:21)
CGCGCAGGATCGATCCGAAAATCC 3'
(antisense);
```

containing the restriction sites XhoI shown underlined, BsaAI shown in bold, XbaI shown in italic, EcoRV shown double underlined, and NotI shown in bold italic. The PCR product is restricted with XhoI-XbaI, isolated by agarose gel electrophoresis, purified by GeneClean, and inserted into the XhoI-XbaI sites of pBluescript(SK+) by ligation to form pBSIDI. Sequence analysis is performed to identify the plasmids containing *R. capsulatus* DNA identical to the complementary sequence of base pairs 34678-34148, located on contig rc04 (*Rhodobacter* Capsulapedia, University of Chicago, Chicago, Ill.). Following restriction of pBSIDI with BsaAI-EcoRV, agarose gel electrophoresis and GeneClean purification, the 0.5 Kb BsaAI-EcoRV DNA fragment containing the *R. capsulatus* orfis inserted into the dephosphorylated SmaI site of pHKO3 by blunt-end ligation to create pHKO5 (FIG. 9). This establishes the isolation of a previously unknown and unique orf encoding *R. capsulatus* IPP isomerase.

A *Schizosaccharomyces pombe* orf encoding a polyp eptide with IPP isomerase activity is isolated from plasmid pBSF19 (Hahn and Poulter, J. Biol. Chem. 270:11298-11303, 1995) by PCR using the following primers

```
3)
5' GCTCTAGATACGTAGGAGGCACATATGAGTTCC (SEQ ID NO:22)
CAACAAGAGAAAAAGGATTATGATGAAGAACAATTA
AGG 3'(sense);
and

4)
5' CGCTCGAGCCCGGGGGATCCTTAGCAAC      (SEQ ID NO:23)
GATGAATTAAGGTATCTTGGAATTTTGACGC 3'
(antisense);
```

containing the restriction site BsaAI shown in bold and the restriction site SmaI shown double underlined. The 0.7 Kb PCR product is isolated by agarose gel electrophoresis, purified by GeneClean and inserted into the pT7Blue-3 vector (Novagen, Inc., Madison, Wis.) using the PERFECTLY BLUNT™ Cloning Kit (Novagen) according to the manufacturer's instructions. Sequence analysis is performed to identify constructs containing *S. pombe* DNA identical to the published DNA sequence (Hahn and Poulter, 1995) and are designated pIDI. Following restriction of pIDI with BsaAI-SmaI, isolation by agarose gel electrophoresis, and purification by GeneClean, the 0.7 Kb BsaAI-SmaI DNA fragment containing the orf encoding *S. pombe* IPP isomerase is inserted into the dephosphorylated SmaI site of pHKO3 by blunt-end ligation to create pHKO6.

EXAMPLE 11

Construction of Vectors Containing Alternative ORFs for Mevalonate Pathway Enzymes and IPP Isomerase In another exemplified embodiment, vectors containing open reading frames (orfs) encoding enzymes of the mevalonate pathway and IPP isomerase other than those described above are constructed. Polynucleotides derived from the yeast *Saccharomyces cerevisiae*, the plant *Arabidopsis thaliana*, and the bacteria *Rhodobacter capsulatus* and *Streptomyces* sp strain CL190 are used for the construction of vectors, including plastid delivery vehicles, containing orfs for biosynthesis of the encoded enzymes. Construction of the vectors is not limited to the methods described. One skilled in the art may choose alternative restriction sites, PCR primers, etc. to create analogous plasmids containing the same orfs or other orfs encoding the enzymes of the mevalonate pathway and IPP isomerase.

Specifically, by way of example, genomic DNA is isolated from *Streptomyces* sp strain CL190 (American Type Culture Collection, Manassas, Va.) using the DNeasy Tissue Kit (Qiagen) according to the manufacturer's instructions. An orf encoding a polypeptide with HMG-CoA reductase activity (Takahashi et al., J. Bacteriol. 181:1256-1263, 1999) is isolated from the *Streptomyces* DNA by PCR using the following primers:

```
1)
5' CCGCTCGAGCACGTGAGGAGGCACATATGACGG (SEQ ID NO:24)
AAACGCACGCCATAGCCGGGGTCCCGATGAGG 3'
(sense);
and

2)
5' GGGGTACCGCGGCCGCACGCGTCTATGCACCAA (SEQ ID NO:25)
CCTTTGCGGTCTTGTTGTCGCGTTCCAGCTGG 3'
(antisense);
```

containing the restriction site XhoI shown underlined, the restriction site KpnI shown in italics, the restriction site NotI shown in bold, and the restriction site MluI shown double underlined. The 1.1 Kb PCR product is isolated by agarose gel electrophoresis, purified by GeneClean and inserted into the pT7Blue-3 vector (Novagen, Inc., Madison, Wis.) using the PERFECTLY BLUNT™ Cloning Kit (Novagen) according to the manufacturer's instructions. Sequence analysis is performed to identify constructs containing *Streptomyces* sp CL190 DNA identical to the published sequence and are designated pHMGR2.

Alternatively, using skills as known in the art, an orf encoding a truncated *S. cerevisiae* HMG-CoA reductase (Chappel et al., U.S. Pat. No. 5,349,126 1994) can be isolated by PCR and inserted into pT7Blue-3 (Novagen, Inc., Madison, Wis.) to construct a vector for use in building a gene cluster comprising the entire mevalonate pathway, in an analgous fashion to the use of the *Streptomyces* sp CL190 orf encoding HMG-CoA reductase, as described herein.

Figure 10:
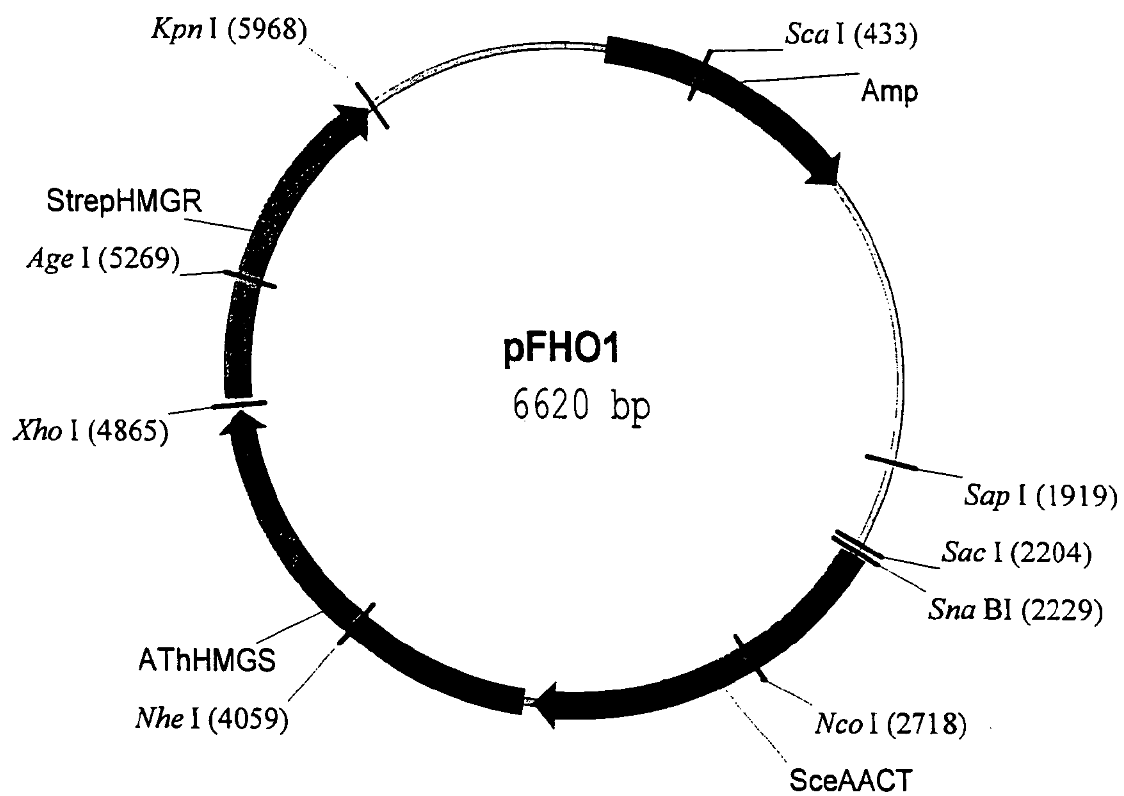
FIG. 10 is a map of cloning vector pFHO1 containing *S. cerevisiae* orf encoding acetoacetyl thiolase (AACT); *A. thaliana* orf encoding HMG-CoA synthase (HMGS); *Streptomyces* sp CL190 orf encoding HMG-CoA reductase (HMGR).

Following restriction of pAACT (see Example 4) with SacII-XbaI, isolation of the 1.2 Kb DNA fragment containing the orf encoding yeast acetoacetyl-CoA thiolase by agarose gel electrophoresis, and purification by GeneClean, the 1.2 Kb SacII-XbaI DNA fragment is inserted into the SacII-XbaI sites of pBSHMGS (see Example 4) by ligation to create pBSCTGS. Following restriction of pHMGR2 with XhoI-KpnI, isolation of the 1.1 Kb DNA fragment by agarose gel electrophoresis, and purification by GeneClean, the 1.1 Kb XhoI-KpnI DNA fragment containing the orf encoding *Streptomyces* sp CL190 HMG-CoA reductase is inserted into the XhoI-KpnI sites of pBSCTGS by ligation to create the pBluescript(SK+) derivative, pFHO1 (FIG. 10).

Figure 11:
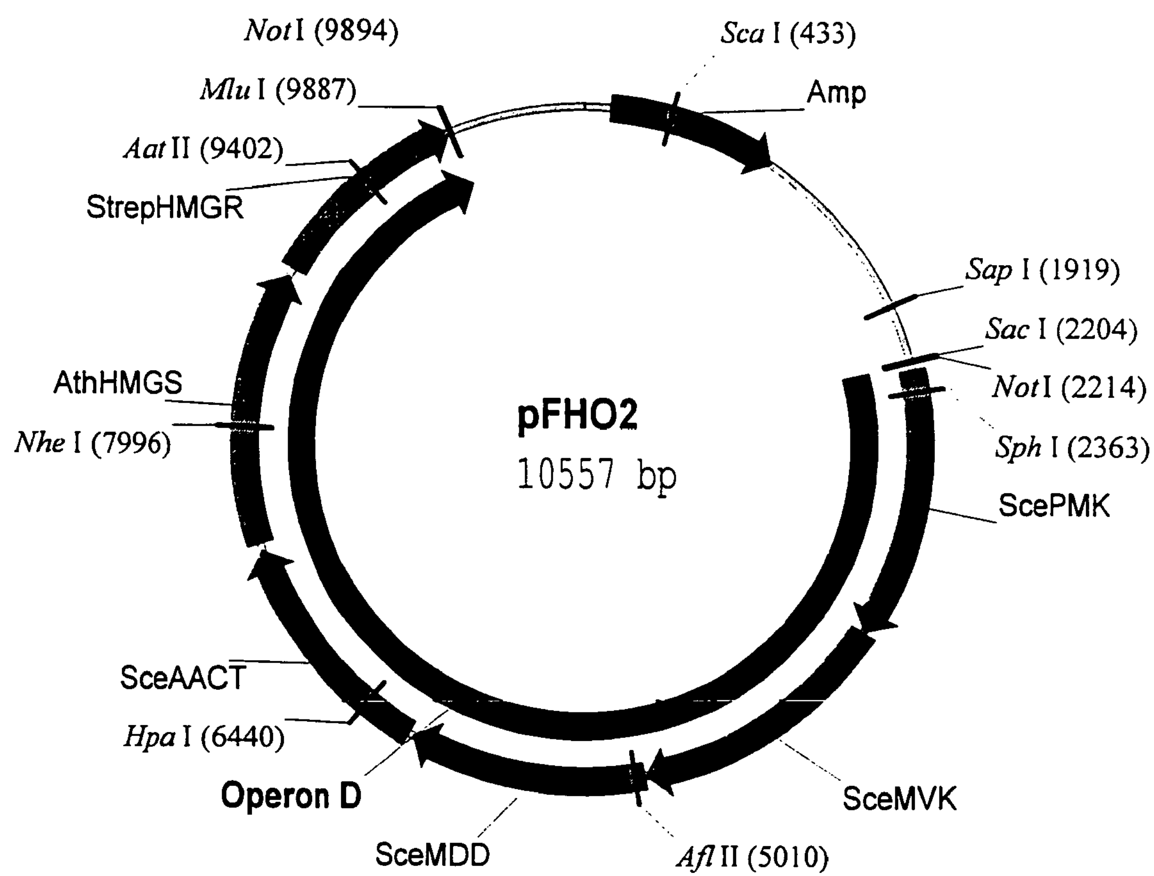
FIG. 11 is a map of cloning vector pFHO2 containing *S. cerevisiae* orfs encoding phosphomevalonate kinase (PMK), mevalonate kinase (MVK), and mevalonate diphosphate decarboxylase (MDD), and acetoacetyl thiolase (AACT); *A. thaliana* orf encoding HMG-CoA synthase (HMGS); *Streptomyces* sp CL190 orf encoding HMG-CoA reductase (HMGR) which in their summation are designated Operon D, encoding the entire mevalonate pathway.

A derivative of pFHO1 containing an operon with orfs, which in their summation comprise the entire mevalonate pathway, is constructed as follows: pFHO1 is restricted with SnaBI and the resulting 6.6 Kb blunt-ended DNA fragment is purified by GeneClean. Following the restriction of pFCO1. (see Example 1) with NotI-XhoI, the resulting 3.9 Kb DNA fragment is isolated by agarose gel electrophoresis and purified by GeneClean. The 5' overhangs of the 3.9 Kb DNA fragment are filled in with Klenow and dNTPs. Following purification by GeneClean, the blunt-ended DNA fragment containing three mevalonate pathway orfs (Hahn et al., 2001) is inserted into the SnaBI site of pFHO1 utilizing directional ligation methodology (Pachuk et al., 2000), thermostable AMPLIGASE™ (Epicentre Technologies, Madison, Wis.), and the bridging oligonucleotides:

```
3)
5' GAGCTCCACCGCGGCGGCCCGCGTCGACTACGGC (SEQ ID NO:26)
CGCAGGAGGAGTTCATATGTCAGAGTT 3';
and

4)
5' TCTACCAAAGGAAGAGGAGTTTTAACTCGAGTA (SEQ ID NO:27)
GGAGGCACATATGTCTCAGAACGTTTA 3';
```

to form pFHO2 (FIG. 11).

Figure 12:
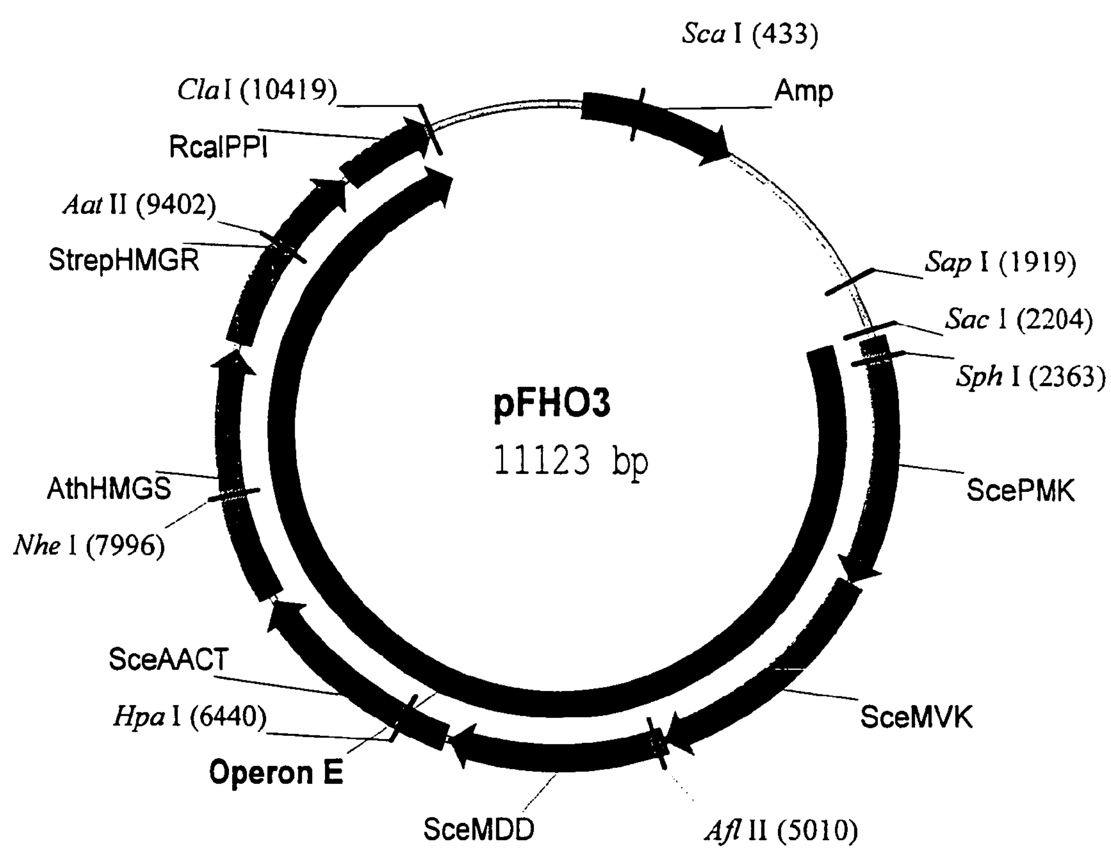
FIG. 12 is a map of cloning vector pFHO3 containing *S. cerevisiae* orfs encoding phosphomevalonate kinase (PMK), mevalonate kinase (MVK), and mevalonate diphosphate decarboxylase (MDD), and acetoacetyl thiolase (AACT); *A. thaliana* orf encoding HMG-CoA synthase (HMGS); *Streptomyces* sp CL190 orf encoding HMG-CoA reductase (HMGR); *R. capsulatus* orf encoding IPP isomerase (IPPI) which in their summation are designated Operon E, encoding the entire mevalonate pathway and IPP isomerase.

A derivative of pFHO2 containing an operon with orfs, which in their summation comprise the entire mevalonate pathway and an orf encoding IPP isomerase is constructed as follows: pFHO2 is restricted with MluI and the resulting 5' overhangs are filled in with Klenow and dNTPs. The 10.6 Kb blunt-ended DNA fragment is purified by GeneClean. Following restriction of pBSIDI with BsaAI-EcoRV, agarose gel electrophoresis and GeneClean purification, the resulting blunt-ended 0.5 Kb DNA fragment containing the *R. capsulatus* IPP isomerase orf is inserted into the filled in MluI site of pFHO2 utilizing directional ligation methodology (Pachuk et al., 2000), thermostable AMPLIGASE™ (Epicentre Technologies, Madison, Wis.), and the following bridging oligonucleotides:

```
5)
5' CAAGACCGCAAAGGTTGGTGCATAGACGCGGTA (SEQ ID NO:28)
AGGAGGCACATATGAGTGAGCTTATAC 3';
and

6)
5' CCTGCGCGGCTGAGCGGCCGCGGATCCGATCGC (SEQ ID NO:29)
GTGCGGCCGCGGTACCCAATTCGCCCT 3';
```

to form pFHO3 (FIG. 12).

Figure 13:
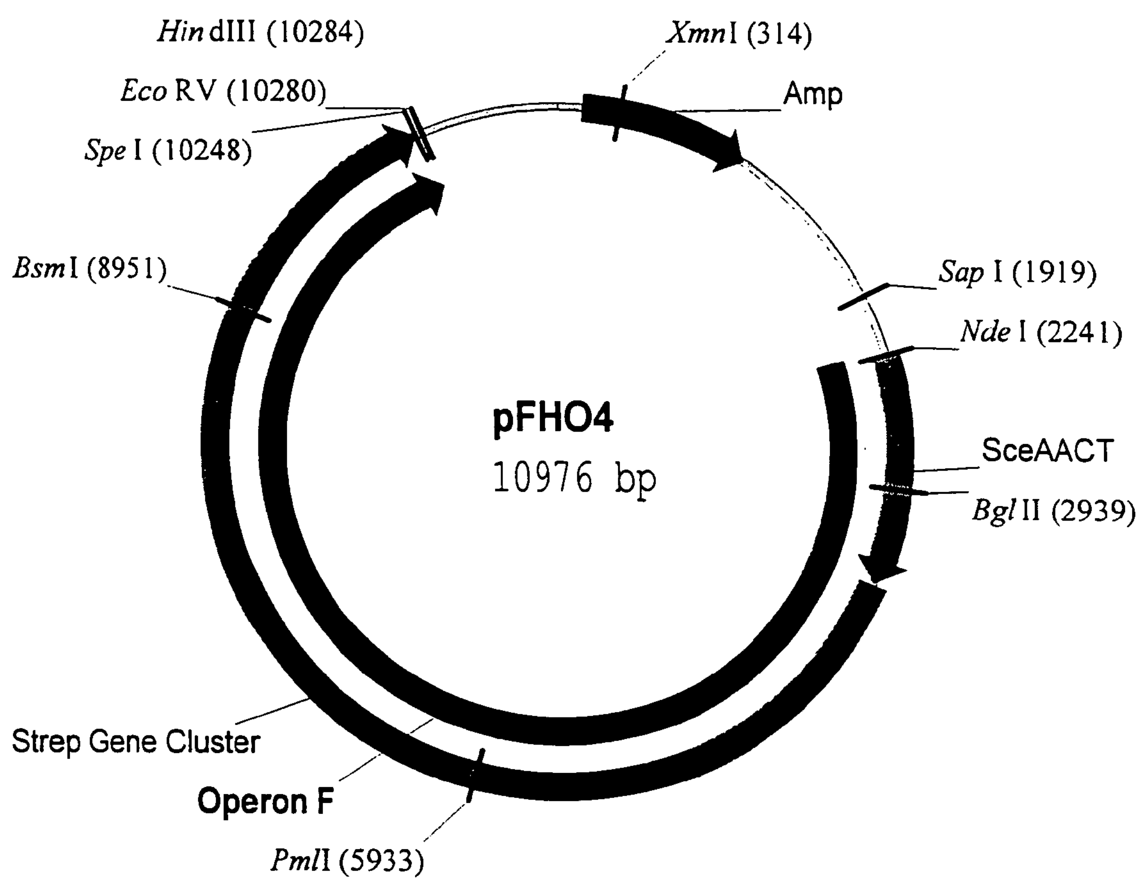
FIG. 13 is a map of cloning vector pFHO4 containing a *S. cerevisiae* orf encoding acetoacetyl thiolase (AACT) coupled to the *Streptomyces* sp CL190 gene cluster which in their summation are designated Operon F, encoding the entire mevalonate pathway and IPP isomerase.

Following the restriction of pBluescript(SK+) with SacII-XbaI and purification by GeneClean, a 1.3 Kb SacII-XbaI DNA fragment containing the orf encoding *S. cerevisiae* acetoacetyl-CoA thiolase, isolated from pAACT (see Example 4) by restriction and agarose gel electrophoresis, is inserted into pBluescript(SK+)/SacII-XbaI by ligation. The resulting plasmid, pBSAACT, is restricted with XbaI, treated with Klenow and dNTPs, and purified by GeneClean. Following restriction of *Streptomyces* sp CL190 genomic DNA with SnaBI, a blunt-ended 6.8 Kb DNA fragment, containing five (5) orfs encoding polypeptides with HMG-CoA synthase, HMG-CoA reductase, mevalonate kinase, phosphomevalonate kinase, mevalonate diphosphate decarboxylase and IPP isomerase enzymatic activities (Takagi et al., J. Bacteriol. 182:4153-4157, 2000 and Kuzuyama et al., Proc. Natl. Acad. Sci. USA 98:932-7, 2001), is isolated by agarose gel electrophoresis, purified by GeneClean and inserted into the filled in XbaI site of pBSAACT utilizing directional ligation methodology (Pachuk et al., 2000), thermostable AMPLIGASE™ (Epicentre Technologies, Madison, Wis.), and the bridging oligonucleotides:

```
7)
5' TGTCATTGAAAAGATATGAGGATCCTCTAGGTA (SEQ ID NO:30)
CTTCCCTGGCGTGTGCAGCGGTTGACG 3';
and

8)
5' CGATTCCGCATTATCGGTACGGGTGCCTACCTA (SEQ ID NO:31)
GAACTAGTGGATCCCCCGGGCTGCAGG 3';
```

to form pFHO4 (FIG. 13). Transformation experiments to isolate pFHO4 constructs are performed with *E. coli* competent cells utilizing media containing ampicillin. Alternatively, media containing only fosmidomycin (20 μg/ml) as the selection agent is used for the direct isolation of pFHO4 constructs containing the *Streptomyces* sp CL190 gene cluster.

The construction of vectors pHKO2, pHKO3, pHKO5, pHKO6, pFHO2, pFHO3, and pFHO4, illustrates the many ways of combining orfs isolated from a variety of organisms to encode polypeptides such that in their summation they comprise the entire mevalonate pathway or comprise the entire mevalonate pathway and IPP isomerase.

EXAMPLE 12

Construction of Tobacco Plastid Transformation Vectors pHKO7 and pHKO8

Figure 14:
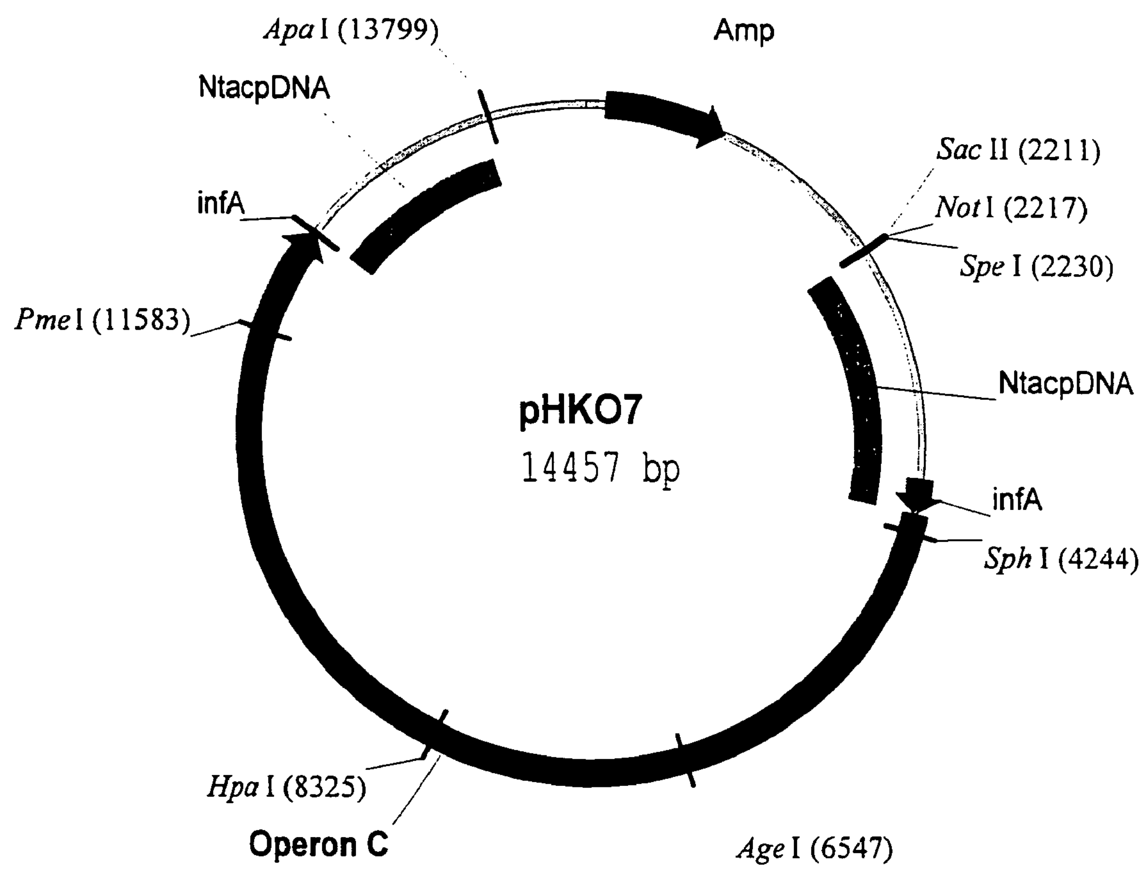
FIG. 14 is a plastid transformation vector pHKO7 containing *N. tabacum* chloroplast DNA (cpDNA) flanking the insertion of Operon C into the infA pseudogene.

In a specific, exemplified embodiment, tobacco plastid-specific transformation vectors containing orfs, which in their summation comprise the mevalonate pathway, and an additional orf encoding IPP isomerase are constructed as follows: Restriction of pHKO5 with NotI generates a DNA fragment containing six orfs comprising the entire mevalonate pathway and an additional orf encoding *R. capsulatus* IPP isomerase. Restriction of pHKO6 with EagI generates a DNA fragment containing the six orfs comprising the complete mevalonate pathway and an additional orf encoding *S. pombe* IPP isomerase. Following isolation by agarose gel electrophoresis and purification by GeneClean, the 8.2 Kb NotI DNA fragment from pHKO5 is blunt-ended with Klenow and dNTPs and inserted into the blunt-ended BglII site of pBSNT27 utilizing chain reaction cloning (Pachuk et al., 2000), thermostable AMPLIGASE™ (Epicentre Technologies, Madison, Wis.), and the following bridging oligonucleotides:

```
1)
5' CTTTCCTGAAACATAATTTATAATCAGATCGGC (SEQ ID NO:32)
CGCAGGAGGAGTTCATATGTCAGAGTT 3';
and

2)
5'TTCGGATCGATCCTGCGCGGCTGAGCG-       (SEQ ID NO:33)
GCCGATCTA
AACAAACCCGGAACAGACCGTTGG 3';
```

to create the plastid delivery vehicle pHKO7 (FIG. 14) containing orfs encoding the entire mevalonate pathway and an orf encoding *R. capsulatus* IPP isomerase. Following isolation by agarose gel electrophoresis and purification by GeneClean, the 8.4 Kb EagI DNA fragment from pHKO6 is blunt-ended with Klenow and dNTPs and inserted into the blunt-ended BglII site of pBSNT27 utilizing chain reaction cloning (Pachuk et al., 2000), thermostable AMPLIGASE™ (Epicentre Technologies, Madison, Wis.), and the following bridging oligonucleotides:

```
3)
5' CTTTCCTGAAACATAATTTATAATCAGATCGGC (SEQ ID NO:34)
CGCAGGAGGAGTTCATATGTCAGAGT 3';
and

4)
5' TCGTTGCTAAGGATCCCCCGGGATCCGGCCGAT (SEQ ID NO:35)
CTAAACAAACCCGGAACAGACCGTTGG 3';
```

to create the plastid delivery vehicle pHKO8 containing orfs encoding the entire mevalonate pathway plus the *S. pombe* IPP isomerase orf.

Alternatively, either of the IPP isomerase orfs described above can be solely inserted, without orfs for the mevalonate pathway, directly into pBSNT27 (or into any suitable plant transformation vector, known in the art), using skills known in the art.

EXAMPLE 13

Construction of Vectors Used for Increasing Carotenoid Production (pHKO9, pHK10, pHK11, pHK12, and pHK13)

Figure 15:
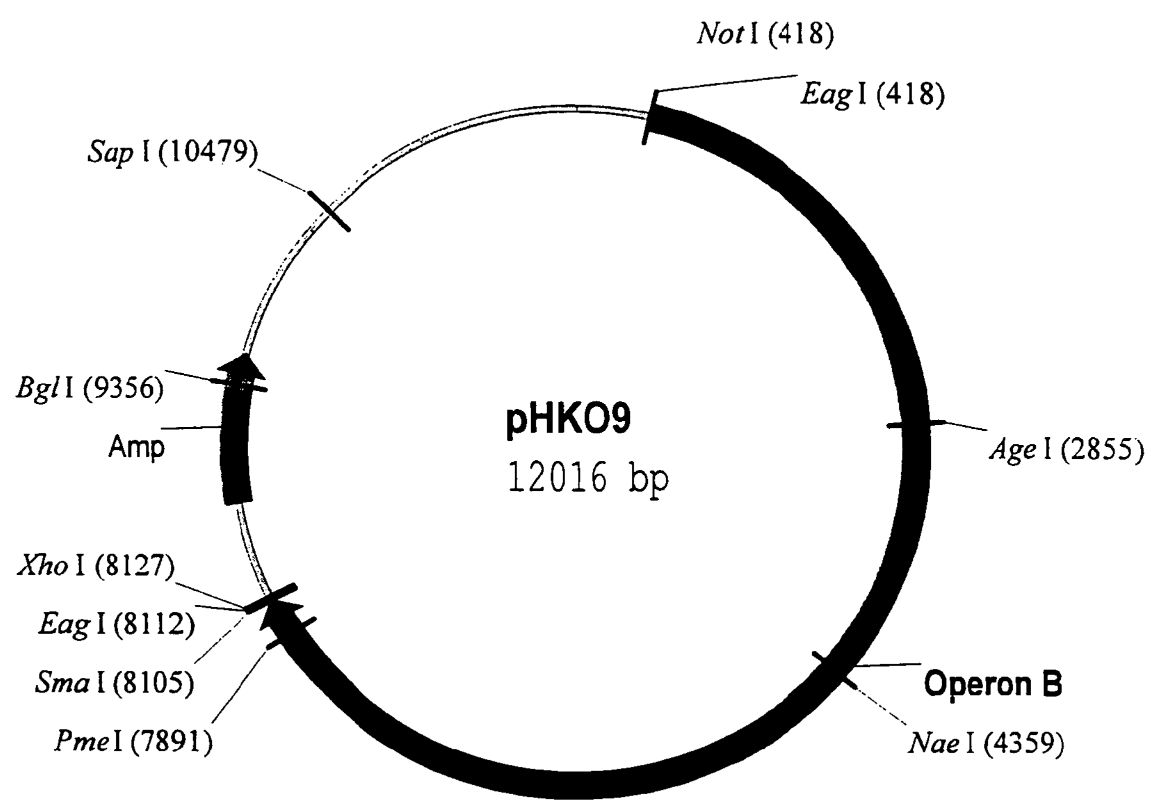
FIG. 15 is a map of expression vector pHKO9 containing Operon B.

In yet another exemplified embodiment, a derivative of pTrcHisB (Invitrogen) containing a synthetic operon comprising orfs, which in their summation is the entire mevalonate pathway, is constructed as follows: A unique NotI site was inserted into pTrcHisB utilizing the following oligonucleotides:

```
1)     5' CATGGCGGCCGCG 3';    (SEQ ID NO:36)
       and

2)     5' GATCCGCGGCCGC 3';    (SEQ ID NO:37)
```

that upon annealing, form a double-stranded DNA linker containing NotI with 5' overhangs compatible with StyI and BamHI. Following restriction of pTrcHisB with StyI-BamHI, isolation of the resulting 4.3 Kb DNA fragment by agarose gel electrophoresis, and its purification by GeneClean, the NotI linker was inserted into pTrcHisB/StyI-BamHI by ligation. Restriction analysis with BsaAI-NotI confirms the successful construction of pTrcHisB-NotI (pTHBN1) by the presence of both 2.5 and 1.8 Kb DNA fragments. Following restriction of pHKO3 with EagI, the 7.7 Kb DNA fragment, containing the six mevalonate pathway orfs, is isolated by agarose gel electrophoresis, purified by GeneClean, and inserted into the NotI site of pTHBN1 utilizing directional ligation methodology (Pachuk et al., 2000), thermostable AMPLIGASE™ (Epicentre Technologies, Madison, Wis.), and the bridging oligonucleotides:

```
3)
5' TTAAATAAGGAGGAATAAACCATGGCGGCCGCA (SEQ ID NO:38)
GGAGGAGTTCATATGTCAGAGTTGAGA 3';
and

4)
5' AACAACAACAACATGACCCGGGATCCGGCGCGA (SEQ ID NO:39)
TCCGAGCTCGAGATCTGCAGCTGGTA 3';
```

to form pHKO9 (FIG. 15).

Figure 16:
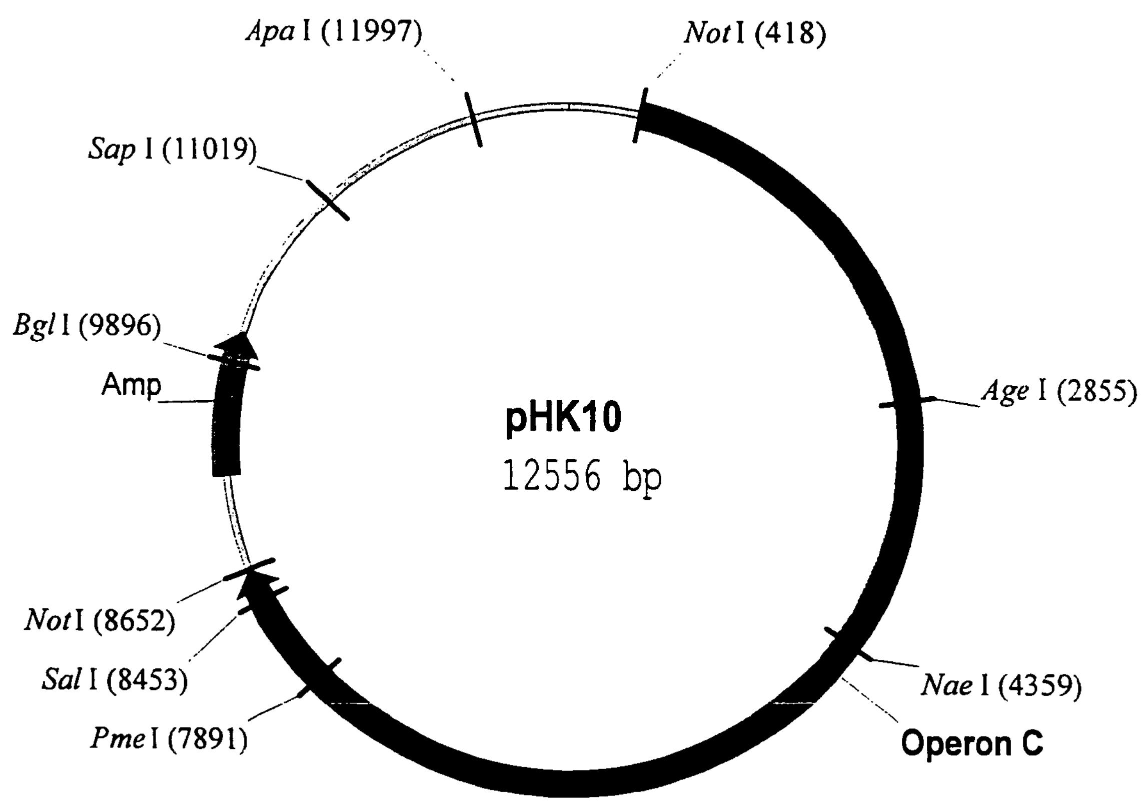
FIG. 16 is a map of expression vector pHK10 containing Operon C.

Derivatives of pTHBN1 containing the entire mevalonate pathway plus an additional orf encoding IPP isomerase are constructed as follows: Following restriction of pHKO5 with NotI, the 8.2 Kb DNA fragment, containing the six mevalonate pathway orfs plus an orf encoding *R. capsulatus* IPP isomerase, is isolated by agarose gel electrophoresis, purified by GeneClean, and inserted into the NotI site of pTHBN1 utilizing directional ligation methodology (Pachuk et al., 2000), thermostable AMPLIGASE™ (Epicentre Technologies, Madison, Wis.), and the bridging oligonucleotides:

5)
5' TCGATTAAATAAGGAGGAATAAACCATGGCGGC (SEQ ID NO:40)
CGCAGGAGGAGTTCATATGTCAGAGTT 3';
and 6)
5' GATTTTCGGATCGATCCTGCGCGGCTGAGCGGC (SEQ ID NO:41)
CGCGATCCGAGCTCGAGATCTGCAGCT 3';

to form pHK10 (FIG. 16). Following restriction of pHKO6 with EagI, the 8.4 Kb DNA fragment, containing the six mevalonate pathway orfs plus an orf encoding *S. pombe* IPP isomerase, is isolated by agarose gel electrophoresis, purified by GeneClean, and inserted into the NotI site of pTHBN1 utilizing directional ligation methodology (Pachuk et al., 2000), thermostable AMPLIGASE™ (Epicentre Technologies, Madison, Wis.), and the following bridging oligonucleotides:

7)
50 TCGATTAAATAAGGAGGAATAAACCATGGCGGC (SEQ ID NO:42)
CGCAGGAGGAGTTCATATGTCAGAGTT 3';
and 8)
5' TTCATCGTTGCTAAGGATCCCCCGGGAT (SEQ ID NO:43)
CCGGCCGCGATCCGAGCTCGAGATCTGCAGCT 3';

to form pHK11.

Derivatives of pTHBN1 containing only an orf encoding IPP isomerase are constructed as follows: pTHBN1 is restricted with NotI and the resulting 5' overhangs are filled in with Klenow and dNTPs. The 4.3 Kb pTHBN1/NotI blunt-ended DNA fragment is GeneClean purified. Following restriction of pBSIDI with BsaAI-EcoRV, agarose gel electrophoresis and GeneClean purification, the resulting blunt-ended 0.5 Kb DNA fragment containing the *R. capsulatus* IPP isomerase orf is inserted into the filled in NotI site of pTHBN1 utilizing chain reaction cloning (Pachuk et al., 2000), thermostable AMPLIGASE™ (Epicentre Technologies, Madison, Wis.), and the following bridging oligonucleotides:

9)
5' TTAAATAAGGAGGAATAAACCATGGCGGCCGTA (SEQ ID NO:44)
AGGAGGCACATATGAGTGAGCTTATAC T 3';
and 10)
5' GCCTGCGCGGCTGAGCGGCCGCGGATCCGATGG (SEQ ID NO:45)
CCGCGATCCGAGCTCGAGATCTGCAGCT 3';

to form pHK12. Following restriction of pIDI with BsaAI-SmaI, agarose gel electrophoresis and GeneClean purification, the resulting blunt-ended 0.7 Kb DNA fragment containing the *S. pombe* IPP isomerase orf is inserted into the filled in NotI site of pTHBN1 utilizing chain reaction cloning (Pachuk et al., 2000), thermostable AMPLIGASE™ (Epicentre Technologies, Madison, Wis.), and the bridging oligonucleotides:

11)
5' TTAAATAAGGAGGAATAAACCATGGCGGCCGTA (SEQ ID NO:46)
GGAGGCACATATGAGTTCCCAACAAGA 3';
and
12)
5' ACCTTAATTCATCGTTGCTAAGGATCCCCCGGC (SEQ ID NO:47)
CGCGATCCGAGCTCGAGATCTGCAGCT 3';

to form pHK13.

EXAMPLE 14

Increased Isoprenoid Production in Cells Containing the MEP Pathway

In another exemplified embodiment, a carotenoid producing *E. coli* strain is utilized to demonstrate the effect of the insertion of orfs encoding the entire mevalonate pathway, or orfs encoding the entire mevalonate pathway and IPP isomerase, or an orf encoding just IPP isomerase, on production of lycopene as follows: Following the transformation of *E. coli* TOP10 F' (Invitrogen) with pAC-LYC (Cunningham et al., *J. Bacteriol.* 182:5841-5848, 2000), transformed cells are isolated on LB/Cam (30 μg/ml) plates grown at 30° C. TOP10 F'/pAC-LYC competent cells are prepared by the $CaCl_2$ method (Sambrook et al., 1989) following growth in LB/Cam in darkness at 28° C. and 225 rpm to an optical density ($A_{600}$) of 0.6. Competent TOP10 F'/pAC-LYC cells are transformed with one of the following plasmids: pTrcHisB; pHKO9, a pTrcHisB derivative containing the entire mevalonate pathway; pHK10, a pTrcHisB derivative containing the entire mevalonate pathway plus the orf encoding *R. capsulatus* IPP isomerase; pHK11, a pTrcHisB derivative containing the entire mevalonate pathway plus the orf encoding *S. pombe* IPP isomerase; pHK12, a pTrcHisB derivative containing the orf encoding *R. capsulatus* IPP isomerase; and pHK13, a pTrcHisB derivative containing the orf encoding *S. pombe* IPP isomerase. The bacterial strains described above, comprising pTHBN1 derivatives containing the mevalonate pathway orfs and/or an orf encoding IPP isomerase, are designated HK1, HK2, HK3, HK4, and HK5 respectively. The resulting transformants are isolated as colonies from LB/Cam/amp plates grown at 30° C. Single colonies of TOP10 F'/pAC-LYC/pTrcHisB and HK1 (TOP10 F'/pAC-LYC/pHKO9) are used to individually inoculate 4 ml LB/Cam/amp cultures and grown overnight in the dark at 28° C. and 225 rpm. The cultures are serially diluted 10,000 to 100,000-fold, plated on LB/Cam/amp medium containing IPTG, and grown in the dark at rt for 2 to 10 days. The plates are visually examined for an increase in lycopene production as evident by a "darkening" of the light pink colored colonies that are present on the control plates corresponding to TOP10 F'/pAC-LYC/pTrcHisB. The same experiments are performed with strains HK2, HK3, HK4, and HK5 to determine, visually, the effect of the orfs contained within pHK10, pHK11, pHK12, and pHK13 on lycopene production in TOP10 F'/pAC-LYC cells. The quantification of the carotenoid lycopene in cells, identified as potential overproducers due to their darker color when compared to the color of TOP10 F'/pAC-LYC/pTHBN1 cells, is performed utilizing a spectrophotometric assay as described by Cunningham et al. (Cunningham et al., 2000). Increased production of lycopene in *E. coli* cells containing the entire mevalonate pathway or the entire mevalonate pathway plus an additional orf for IPP isomerase establishes that the presence in cells of an additional biosynthetic pathway for the formation of IPP or IPP and DMAPP enhances the production of isoprenoid compounds, such as carotenoids, that are derived from IPP and DMAPP.

EXAMPLE 15

Demonstration of Antibiotic Resistance Due to the Mevalonate Pathway in MEP Pathway Dependent Cells In still another exemplified embodiment, *E. coli* cells are transformed with DNA containing orfs, which in their summation comprise the entire mevalonate pathway, and the resulting cells are tested for resistance to the antibiotic fosmidomycin as follows: Following the separate transformation of *E. coli* TOP10 F' (Invitrogen) with pHKO2, pHKO3 and pHKO9, transformed cells are isolated on LB/Amp (50 μg/ml) plates grown at 30° C. Single colonies of TOP10 F'/pHKO2 (designated strain HK6), TOP10 F'/pHKO3 (designated strain HK7), and TOP10 F'/pHKO9 (designated strain HK8), are used to individually inoculate 4 ml LB/amp cultures and grown overnight at 30° C., 225 rpm. The HK6 and HK7 cultures are serially diluted 10,000 to 100,000-fold and plated on LB containing fosmidomycin (20 μg/ml). The HK8 cultures are serially diluted 10,000 to 100,000-fold and plated on LB/IPTG containing fosmidomycin (20 μg/ml) Controls are performed with cells comprising TOP10 F' transformed with the parent vectors of pHKO2, pHKO3 and pHKO9, by plating on the appropriate medium containing fosmidomycin establishing that *E. coli* control cells are unable to grow on medium containing fosmidomycin. The ability of transformed *E. coli* cells to grow in the presence of the antibiotic fosmidomycin establishes that the inserted DNA, comprising the entire mevalonate pathway and thus an alternative biosynthetic route to IPP, is functional and can circumvent the inhibition of an enzyme in the trunk line of the MEP pathway.

EXAMPLE 16

Construction of Plastid Transformation Vectors

In a specific, exemplified embodiment, a plant plastid transformation vector containing a synthetic operon comprising orfs, which in their summation is the entire mevalonate pathway, is constructed as follows: Plasmid pHKO3, a pBluescript derivative containing all six mevalonate pathway orfs, is assembled by restriction of pFCO1 to yield a 3.9 Kb NotI-XhoI DNA fragments containing three mevalonate orfs and its subsequent insertion into the SalI-NotI sites of pHKO1 by directional ligation as described above in Example 8. The plastid transformation vehicle, pHK14 containing the entire mevalonate pathway is constructed as follows: Plastid vector pGS104 (Serino and Maliga, *Plant J.* 12:687-701, 1997) is restricted with NcoI-XbaI and the two resulting DNA fragment are separated by agarose gel electrophoresis. Following isolation of the larger DNA fragment by gel excision and its purification by GeneClean, the NcoI-XbaI 5' overhangs are dephosphorylated using SAP and filled in with Klenow and dNTPs. The resulting blunt-ended, dephosphorylated DNA fragment derived from pGS104 is GeneClean purified. Following restriction of pHKO3 with EagI, isolation by agarose gel electrophoresis, and purification by GeneClean, the 7.7 Kb DNA fragment is treated with Klenow and dNTPs to fill in the 5' overhangs. The resulting blunt-ended DNA fragment containing the mevalonate pathway is purified by GeneClean and inserted into the dephosphorylated, Klenow-treated NcoI-XbaI sites of pGS 104 by blunt-end ligation to yield pHK14.

Derivatives of pGS104 containing the entire mevalonate pathway plus an additional orf encoding IPP isomerase are constructed as follows: Following restriction of pHKO5 with NotI and treatment with Klenow and dNTPs, the resulting 8.2 Kb blunt-ended DNA fragment, containing the six mevalonate pathway orfs plus an orf encoding *R. capsulatus* IPP isomerase, is isolated by agarose gel electrophoresis, purified by GeneClean, and inserted into the dephosphorylated, filled in NcoI-XbaI sites of pGS104 by blunt-end ligation to yield pHK15. Following restriction of pHKO6 with EagI and treatment with Klenow and dNTPs, the resulting 8.4 Kb blunt-ended DNA fragment, containing the six mevalonate pathway orfs plus an orf encoding *S. pombe* IPP isomerase, is isolated by agarose gel electrophoresis, purified by GeneClean, and inserted into the dephosphorylated, filled in NcoI-XbaI sites of pGS104 by blunt-end ligation to yield pHK16.

Derivatives of pGS104 containing only an orf encoding IPP isomerase are constructed as follows: Following restriction of pBSIDI with BsaAI-EcoRV, agarose gel electrophoresis and GeneClean purification, the resulting blunt-ended 0.5 Kb DNA fragment containing the *R. capsulatus* IPP isomerase orf is inserted into the dephosphorylated, filled in NcoI-XbaI sites of pGS104 by blunt-end ligation to yield pHK17. Following restriction of pIDI with BsaAI-SmaI, agarose gel electrophoresis and GeneClean purification, the resulting blunt-ended 0.7 Kb DNA fragment containing the *S. pombe* IPP isomerase orf is inserted into the dephosphorylated, filled in NcoI-XbaI sites of pGS104 by blunt-end ligation to yield pHK18.

EXAMPLE 17

Construction of Transplastomic Plants Containing ORFs Encoding the Mevalonate Pathway or ORFs Encoding the Mevalonate Pathway Coupled with IPP Isomerase In another exemplified embodiment, tobacco is engineered at the plastid level by using any of the plastid transformation vectors described above, or their equivalents, such as variants of those plastid transformation vectors as can be routinely constructed by means known in the art and containing the orfs as taught and described above. Specifically, *Nicotiana tabacum* var. 'Xanthi NC' leaf sections (1×0.5 cm strips from in vitro plants with 3 to 5 cm long leaves) are centered in the dish, top side up and bombarded with 1 μm gold micro particles (Kota et al., 1999) coated with DNA containing orfs, which in their summation comprise the entire mevalonate pathway, using a PDS 1000 He device, at 1100 psi. Toxicity is evident in tobacco after three weeks of growth on medium containing the antibiotic fosmidomycin at a concentration of at least 500 micromolar. Transplastomic plants are recovered from leaf sections cultured under lights on standard RMOP shoot regeneration medium or on a Murashige-Skoog salts shoot regeneration medium with 3% sucrose, Gamborg's B5 vitamins, 2 mg/L 6-benzylamino-purine and Phytagel (2.7 g/L), containing 500 μM fosmidomycin for the direct selection of insertion of the entire mevalonate pathway into plastids. Alternatively, the regeneration medium contains an antibiotic, e.g. spectinomycin, for selection based on antibiotic resistance due to any co-transformed gene on the transforming DNA vector, as would be readily apparent to the skilled artisan. De novo green leaf tissue is visible after three weeks. Tissue is removed to undergo a second round of selection on shoot regeneration medium with 500 μM fosmidomycin to encourage homoplasmy and plants are rooted. Genomic DNA is isolated from T0 tissue or T1 leaf tissue derived from in vitro germinated transplastomic seeds utilizing the DNeasy Plant Mini Kit (Qiagen Inc, Valencia, Calif.) according to the manufacturer's instructions and is subjected to analysis as is known in the art to confirm homoplasmy. The ability to select directly for a transformation event corresponding to the successful insertion of the mevalonate pathway orfs into plastids establishes the use of orfs, which in their summation comprise the entire mevalonate pathway, as a selectable marker for plastid transformation. The construction of fosmidomycin resistant plants establishes the ability of the mevalonate pathway, when functioning in plant plastids, to provide an alternate biosynthetic route to IPP, thus overcoming the effect of an inhibitor targeting an enzyme in the trunk line of the MEP pathway.

EXAMPLE 18

Metabolic Engineering in Transplastomic *Solanaceae* Plants

In another exemplified embodiment, *Solanaceae* species are engineered at the plastid level using infA pseudogene insertion of a selectable marker and orfs for expression. Specifically, leaf sections of a genetically defined white petunia (or other petunia), are engineered, as for the *Solanaceous* species tobacco (see Example 16), using vectors pHK04 or pHKO7, or their equivalents, for insertion of orfs encoding the entire mevalonate pathway or orfs encoding the entire mevalonate pathway and IPP isomerase. Transplastomic Solanaceae plants containing orfs encoding the entire mevalonate pathway and IPP isomerase, and containing an additional orf encoding phytoene synthase, are created by insertion of a pBSNT27 (see Example 9) derived vector, constructed as follows:

A *Rhodobacter capsulatus* orf encoding a polypeptide with phytoene synthase activity is isolated by PCR from genomic DNA using the primers

```
1) 5' GCGATATCGGATCCAGGAGGACCATATGA (SEQ ID NO:65)
   TCGCCGAAGCGGATATGGAGGTCTGC 3'
   (sense)

2) 5' GCGATATCAAGCTTGGATCCTCAATCCAT (SEQ ID NO:66)
   CGCCAGGCCGCGGTCGCGCGC 3'
   (antisense)
```

containing the restriction site BamHI shown underlined. The 1.1 Kb PCR product is isolated by agarose gel electrophoresis, purified by GeneClean and inserted into the pT7Blue-3 vector (Novagen) using the Perfectly Blunt(Cloning Kit (Novagen) according to the manufacturer's instructions. Sequence analysis is performed to identify constructs containing *R. capsulatus* DNA identical to the published DNA sequence (SEQ ID NO:71) and are designated pPHS. Following restriction of pPHS with BamHI, isolation by agarose gel electrophoresis, and purification by GeneClean, the 1.1 Kb BamHI DNA fragment containing the orf encoding *R. capsulatus* phytoene synthase is inserted into the BglII site of pBSNT27 utilizing chain reaction cloning (Pachuk et al., 2000), thermostable Ampligase((Epicentre Technologies, Madison, Wis.), and the bridging oligonucleotides

```
3) 5' CTTTCCTGAAACATAATTTATAATCAGAT (SEQ ID NO:67)
   CCAGGAGGACCATATGATCGCCGAAG
   CGGAT 3';
and

4) 5' CGACCGCGGCCTGGCGATGGATTGAGGAT (SEQ ID NO:68)
   CTAAACAAACCCGGAACAGACCGT
   TGGGAAG 3';
```

to create plastid transformation vector pFHO5. Following restriction of pFHO5 with XcmI, a unique site in the infA pseudogene, and purification by GeneClean, the resulting 3' overhangs are removed by treatment with Mung Bean nuclease and the resulting blunt-ended DNA fragment is purified by GeneClean. Vector pFHO3 is restricted with NotI and the resulting 8.3 Kb DNA fragment, containing Operon E, is isolated by agarose gel electrophoresis and purified by GeneClean. The 5' overhangs of the isolated DNA fragment are filled in with Klenow and dNTPs and the resulting blunt end DNA fragment, containing Operon E, is inserted into the Mung Bean nuclease treated XcmI site of pFHO5 utilizing chain reaction cloning (Pachuk et al., 2000), thermostable Ampligase((Epicentre Technologies, Madison, Wis.), and the bridging oligonucleotides

Figure 17:
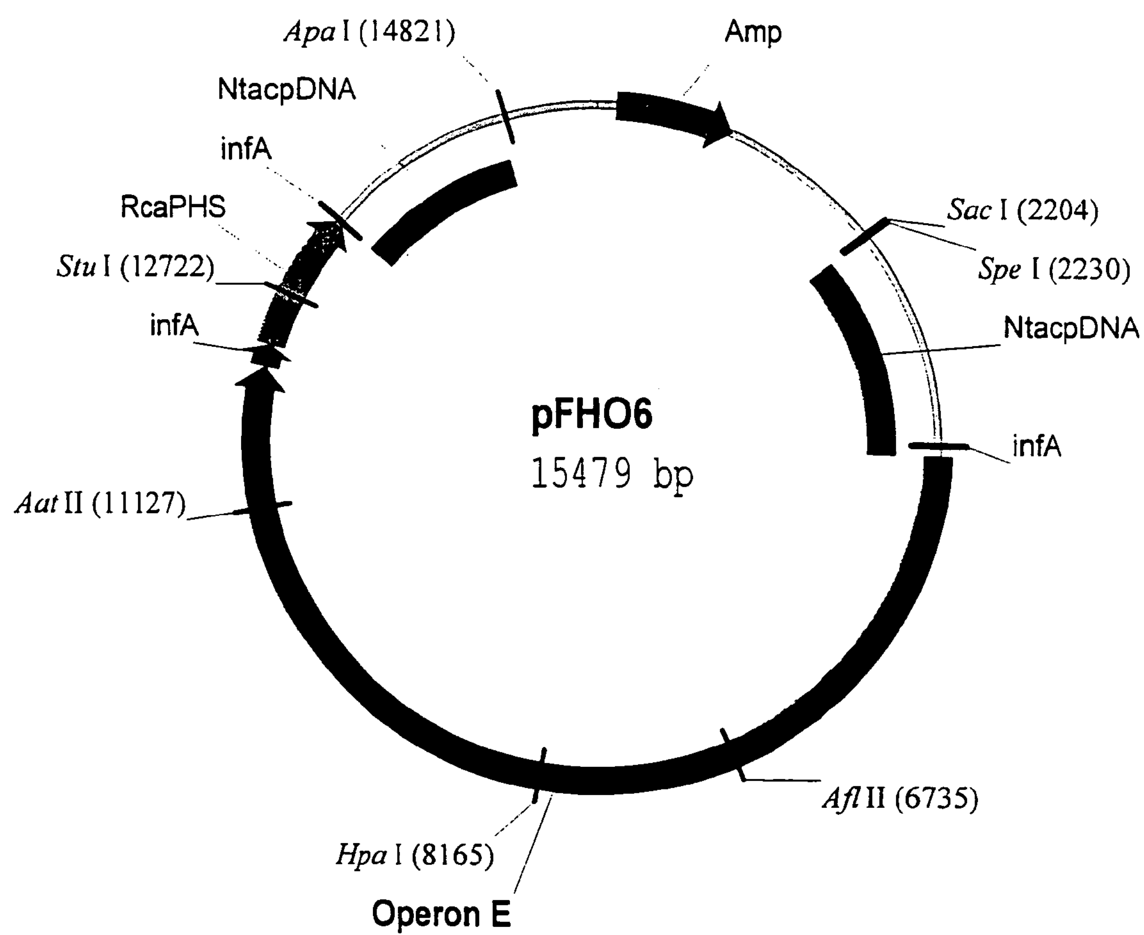
FIG. 17 is a map of plastid transformation vector pFHO6 containing *N. tabacum* chloroplast DNA (cpDNA) flanking the insertion of both Operon E and the *R. capsulatus* orf encoding phytoene synthase (PHS) into the infA pseudogene.

```
5) 5' ATTTTTCATCTCGAATTGTATTCCCACGA (SEQ ID NO:69)
   AGGCCGCGTCGACTACGGCCGCAGG
   AGGAGT 3';
and

6) 5' TTCGGATCGATCCTGCGCGGCTGAGCGGC (SEQ ID NO:70)
   CGGAATGGTGAAGTTGAAAAACGA
   ATCCTTC 3';
```

to create the plastid transformation vector pFHO6 (FIG. 17).

Alternatively, an orf encoding IPP isomerase can be inserted into the XcmI site of pFHO5, utilizing skills as known in the art, to create a plastid transformation vector containing both an orf encoding phytoene synthase and an orf encoding IPP isomerase. Another alternative uses the infA pseudogene as an insertion site for orfs, encoding phytoene synthase, and/or IPP isomerase, and/or the entire mevalonate pathway, linked with the aadA gene as is known in the art for selection of transplastomic plastids on 500 microgram per liter spectinomycin.

The BioRad PDS 1000 He gene gun is used to deliver BioRad tungsten M10 (0.7 micron approx.) microspheres into petunia (Petunia hybrida 'Mitchell') leaves positioned top-side up. Intact leaves, or equivalent tissues of about 6-8 $cm^2$ per sample are plated onto shoot regeneration medium consisting of Murashige and Skoog basal medium, B5 vitamins, 3% sucrose, 0.7% (w/v) agar and 3 mg/l BA (6-benzylamino-purine), 0.1 mg/l IAA (Deroles and Gardner, Plant Molec. Biol. 11: 355-364, 1988) in 100×10 mm plastic Petri dishes. Leaves are centered in the target zone of the gene gun for bombardment at 1100 psi, third shelf from bottom, ~5.6 cm gap, 28 mgHg vacuum. M10 microspheres are coated with DNA using standard procedures of $CaCl_2$ and spermidine precipitation, 1.5 to 2 ug DNA/bombardment. After bombardment, tissues are cultured in light in the presence of antibiotic (500 micromolar fosmidomycin). Each leaf sample is then cut into about 6 pieces and cultured on petunia shooting medium containing 500 micromolar fosmidomycin for 3 to 8 weeks, with subculture onto fresh medium every three weeks. Any green shoots are removed and leaves plated onto the same medium containing 500 micromolar fosmidomycin. Plantlets with at least four leaves and of solid green color (no bleaching on petioles or whorls) are transferred for rooting onto solidified hormone-free Murashige and Skoog salts with B5 vitamins and 2% sucrose and are grown to flowering. The dependency of increased carotenoid production in Solanacae on the combination of the orfs inserted, be it an orf encoding phytoene synthase alone; or orfs encoding the entire mevalonate pathway and phytoene synthase; or orfs encoding phytoene synthase, the entire mevalonate pathway and IPP isomerase; or orfs for phytoene synthase and IPP isomerase, establishes that the addition of the mevalonate pathway and/or IPP isomerase to plant plastids enhances the production of isoprenoid compounds that are derived from IPP and DMAPP; and the suitability of a pseudogene insertion site for creating transplastomic Petunia.

EXAMPLE 19

Transformation of Microalgae

In a specific exemplified embodiment, chloroplast transformants are obtained by microprojectile bombardment of *Chlamydomonas* reinhardtii cells and subsequent selection on fosmidomycin. Specifically, a genecluster containing the complete mevalonate pathway is substituted, as a selectable marker, for the coding sequence of the aadA gene in the pUC18 derived vector containing 5-atpA:aadA:rbcL-3 (Goldschmidt-Clermont M., Nucleic Acids Res. 19:4083-4089, 1991) as follows: Plasmid pUC-atpX-AAD is restricted with NcoI, purified by GeneCleanand treated with Mung Bean nuclease to remove the resulting 5' overhangs. Following GeneClean purification, the blunt ended DNA fragment is restricted with Hindifi to remove the aadA orf and the remaining DNA fragment, containing approximately 653 base pairs of the *C. reinhardtii* atpA gene and approximately 437 base pairs of the *C. reinhardtii* rbcL gene (Goldschmidt-Clermont M., 1991), is isolated by agarose gel electrophoresis and purified by GeneClean. Plasmid pFHO4 is restricted with NdeI, purified by GeneClean, and the resulting 5 overhangs are filled in with Klenow and dNTPs. Following GeneClean purification, the blunt ended DNA fragment is restricted with HindIII and the resulting DNA fragment, containing Operon F (see FIG. 13), is isolated by agarose gel electrophoresis and purified by GeneClean. The blunt end-HindIII fragment is inserted into the blunt end HindIII sites of the DNA fragment isolated from pUC-atpX-AAD by ligation resulting in the orf encoding *S. cerevisiae* acetoacetylCoA thiolase, located at the beginning of Operon F, to be in frame with the ATG start codon of the 5atpA DNA in pUC-atpX-AAD (Goldschmidt-Clermont M., 1991). The resulting modified yeast orf only encodes 2 extra amino acids, Met and Ser, appended to the N-terminal Met of the acetoacetylCoA thiolase polypeptide encoded by Operon F. The resulting *Chlamydomonas* plastid transformation vector is designated pHK19. About 10,000 cells are spread on TAP plates containing 200 micromolar fosmidomycin, plates are dried, and then cells are immediately bombarded with M10 or 1 micron gold particles coated with about 2 micrograms of plasmid DNA using the PDS-1000 He gene gun, 1100 psi, fourth shelf from bottom, ~2 cm gap, ~28 mgHg vacuum (alternatively cells are spread over a Nytran nylon 0.45 micron membrane placed on top of TAP agar and bombarded without a drying phase). Plates are incubated in low light for two to three weeks before colonies are counted. Fosmidomycin-resistant colonies are green (vs yellowish for susceptible cells) and transformants are characterized using skills as known in the art. This demonstrates use of orfs encoding the entire mevalonate pathway as a selectable marker for green algae and by virtue of its functioning demonstrates its utility for overproduction of isoprenoid metabolites in microalgae.

EXAMPLE 20

Metabolic Engineering in Transplastomic Grain Crops (Rice)

In another exemplified embodiment, an operon comprising orfs encoding the entire mevalonate pathway are inserted into the plastids of rice as follows: A DNA fragment isolated from pHKO3, containing the complete mevalonate pathway, or from pFHO2, containing orfs encoding the entire mevalonate pathway and IPP isomerase, is inserted into the NcoI-XbaI sites of plasmid pMSK49 to replace the gfp coding region adjacent to the coding region for streptomycin resistance, aadA; or inserted into the BstXI-NcoI digested DNA of plasmid pMSK48 using skills as is known in the art for direct selection on fosmidomycin. The resulting plasmids contain rice-specific insertion sequences of pMSK35 as described in Khan and Maliga, Nature Biotechnology 17: 910-914, 1999. Embryonic suspensions, induced as previously described (Khan and Maliga 1999), of japonica rice 5*Oryza sativa* 'Taipei 309' engineered with the beta-carotene pathway (Ye et al. *Science* 287:303-305) are plated into filter paper and bombarded with the PDS1000 He device as described in Example 17. After two days on non-selective medium and then one to two weeks in selective AA medium (Toriyama and Hinata, Plant Science 41: 179-183, 1985) tissue is transferred to agar solidified medium of MS salts, and vitamins, 100 mg/L myo-inositol, 4 mg/L 6-benzylaminopurine, 0.5 mg/L indoleacetic acid, 0.5 mg/L1-napthaleneacetic acide, 3% sucrose, 4% maltose and 100 mg/L streptomycin sulfate or 500 μM fosmidomycin. Transplastomic shoots appear following cultivation in the light after three weeks and leaf samples are analyzed for the operon by PCR.

REFERENCES CITED

U.S. Patent Documents

Adang et al., "Synthetic Insecticidal Crystal Protein Gene," U.S. Pat. No. 5,380,831 (1995)

Chappel et al., "Process for Composition for Increasing Squalene and Sterol Accumulation in Higher Plants," U.S. Pat. No. 5,349,126 (1994)

Fujimoto et al., "Synthetic Insecticidal Gene, Plants of the Genus Oryza Transformed with the Gene, and Production Thereof," U.S. Pat. No. 5,436,391 (1995)

Kamuro et al. "Herbicide" U.S. Pat. No. 4,846,872 (1989)

OTHER REFERENCES

Albrecht et al., "Novel Hydroxycarotenoids with Improved Antioxidative Properties Produced by Gene Combination in *Escherichia coli,*" Nature Biotech. 18:843-846 (2000)

Allison et al., MDMV Leader (Maize Dwarf Mosaic Virus) Virology 154:9-20 (1986)

Altschul et al., J. Mol. Biol. 215:403-410 (1990)

Ashby and Edwards, "Elucidation of the Deficiency in Two Yeast Coenzyme Q Mutants: Characterization of the Structural Gene Encoding Hexaprenyl Pyrophosphate Synthetase," J. Biol. Chem. 265:13157-13164 (1990)

Ballas et al., Nucleic Acids Res. 17:7891-7903 (1989)

Beaucage and Caruthers, Tetra. Letts., 22:1859-1862 (1981)

Bock and Hagemann, "Extranuclear Inheritance: Plastid Genetic: Manipulation of Plastid Genomes and Biotechnological Application," Prog. Bot. 61:76-90 (2000)

Boyton and Gillham, "Chloroplast Transformation in *Chlamydomoas,*" Methods Enzymol. 217:510-536 (1993)

Clarke, "Protein Isoprenylation and Methylation at Carboxy-terminal Cysteine Residues," Annu. Rev. Biochem. 61:355-386 (1992)

Cunningham and Gantt, "Genes and Enzymes of Carotenoid Biosynthesis in Plants," Ann. Rev. Plant Mol. Biol. 39:475-502 (1998)

Cunningham et al., "Evidence of a Role for LytB in the Nonmevalonate Pathway of Isoprenoid Biosyhthesis," J. Bacteriol. 182:5841-5848 (2000)

Dale, P. J., "Spread of Engineered Genes to Wild Relatives," Plant Physiol. 100:13-15 (1992)

Daniell et al., "Containment of Herbicide Resistance Through Genetic Engineering of the Chloroplast Genome," Nat. Biotechnol. 16:345-348 (1998)

del Campo et al, Plant Physiol 114:748 (1997)

Della-Cioppa et al., Plant Physiol. 84:965-968 (1987)

Deroles and Gardner, "Expression and Inheritance of Kanamycin Resistance in a large Number of Transgenic Petunias Generated by *Agrobacterium*-Mediated Transformation," Plant Molec. Biol. 11:355-364 (1988)

Eisenreich et al., "The Deoxyxylulose Phosphate Pathway of Terpenoid Biosynthesis in Plants and Microorganisms," Chemistry and Biology 5:R221-R233 (1998)

Elroy-Stein et al., PNAS USA 86:6126-6130 (1989)

Gallie et al., in Molecular Biology of RNA, ed. Cech, (Liss, N.Y.) 237-256 (1989)

Garrett et al., "Accumulation of a Lipid A Precursor Lacking the 4'-Phosphate following Inactivation of the *Escherichia coli* 1pxK Gene," J. Biol. Chem. 273:12457-12465 (1998)

Goldschmidt-Clermont M., "Transgenic Expression of Aminoglycoside Adenine Transferase in the Chloroplast: A Selectable Marker for Site-directed Transformation of *Chlamydomonas,*" Nucleic Acids Res.19:4083-4089 (1991)

Goodwin, "Biosynthesis of Carotenoids and Plant Triterpenes: the Fifth CIBA Medal Lecture," Biochem. J. 123:293-329 (1971)

Guda et al., "Stable Expression for a Biodegradable Protein Based Polymer in Tobacco Chloroplasts," Plant Cell Reports 19:257-262 (2000)

Guerineau et al., Mol. Gen. Genet. 262:141-144 (1991)

Hahn et al., "1-Deoxy-D-Xylulose 5-Phosphate Synthase, the Gene Product of Open Reading Frame (ORF) 2816 and ORF2895 in *Rhodobacter capsulatus,*" J. Bacteriol. 183: 1-11 (2001)

Hahn and Poulter, "Isolation of *Schizosaccharomyces pombe* Isopentenyl Diphosphate Isomerase cDNA Clones by Complementation and Synthesis of the Enzyme in *Escherichia coli,*" J. Biol. Chem. 270:11298-11303 (1995)

Hahn et al., "*Escherichia coli* Open Reading Frame 696 Is idi, a Nonessential Gene Encoding Isopentenyl Diphosphate Isomerase," J. Bacteriol. 181:4499-4504 (1999)

Hahn et al., "Open Reading Frame 176 in the Photosynthesis Gene Cluster of *Rhodobacter capsulatus* Encodes idi, a Gene for Isopentenyl Diphosphate Isomerase," J. Bacteriol. 178:619-624 (1996)

Hamilton et al., "New Method for Generating Deletions and Gene Replacements in *Escherichia coli,*" J. Bacteriol. 171: 4617-4622 (1989)

Harker and Bramley, "Expression of Prokaryotic 1-Deoxy-D-Xylulose 5-Phosphates in *Escherichia coli* Increases Carotenoid and Ubiquinone Biosynthesis," FEBS Letters 448:115-119 (1999)

Herz et al., "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," Proc. Natl. Acad. Sci. USA 97:2486-2490 (2000)

Jobling et al., Nature 325:622-625 (1987)

Joshi et al., Nucleic Acid Res. 15:9627-9639 (1987)

Kajiwara et al., "Expression of an Exogenous Isopentenyl Diphosphate Isomerase Gene Enhances Isoprenoid Biosynthesis in *Escherichia coli,*" Biochem. J. 324:421-426 (1997)

Kavanagh et al., "Homeologous Plastid DNA Transformation in Tobacco is Mediated by Multiple Recombination Events," Genetics 152:1111-1122 (1999)

Keeler et al., "Movement of Crop Transgenes into Wild Plants," in Herbicide Resistant Crops: Agricultural, Economic, Environmental, Regulatory and Technological Aspects, (S. O. Duke, ed.) CRC Press, Boca Rotan, Fla., pp 303-330 (1996)

Khan and Maliga, "Fluorescent Antibiotic Resistance Marker for Tracking Plastid Transformation in Higher Plants," Nature Biotech. 17:910-914 (1999)

Kota et al., "Overexpression of the *Bacilllus thuringiensis* (Bt) Cry2Aa2 Protein in Chloroplasts Confers Resistance to Plants Against Susceptible and Bt-resistant Insects," Proc. Natl. Acad. Sci. USA 96:1840-1845 (1999)

Kunkel, Proc. Natl. Acad. Sci. USA 82:488-492 (1985)

Kunkel et al., Methods and Enzymol; 154:367-382 (1987)

Kuzuyama et al., "Direct Formation of 2-C-Methyl-D-Erythritol 4-Phosphate by 1-Deoxy-D-Xylulose 5-Phosphate Reductoisomerase, a New Enzyme in the Non-Mevalonate Pathway to Isopentenyl Diphosphate," Tetrahedron Lett. 39:4509-4512 (1998)

Kuzuyama et al., "Fosmidomycin, a Specific Inhibitor of 1-Deoxy-D-Xylulose 5-Phosphate Reductoisomerase in the Nonmevalonate Pathway for Terpenoid Biosynthesis," Tetrahedron Lett. 39:7913-7916 (1998)

Kuzuyama et al., "An Unusual Isopentenyl Diphosphate Isomerase Found in the Mevalonate Pathway Gene Cluster from *Streptomyces* sp. strain CL190," Proc. Natl. Acad. Sc.i USA 98:932-7 (2001)

Lange and Croteau, "Isopentenyl diphosphate biosynthesis via a mevalonate independent pathway: Isopentenyl monophosphate kinase catalyzes the terminal enzymatic step," Proc. Natl. Acad. Sci. USA 96:13714-13719 (1999)

Lichtenthaler et al., "Biosynthesis of Isoprenoids in Higher Plant Chloroplasts Proceeds via a Mevalonate-Independent Pathway," FEBS Letters 400:271-274 (1997)

Lois et al, "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," Proc. Natl. Acad. Sci. USA 95:2105-2110 (1998)

Lommel et al., Virology 81:382-385 (1991)

Lüttgen et al., "Biosynthesis of Terpenoids: YchB Protein of *Escherichia coli* Phosphorylates the 2-Hydroxy Group of 4-Diphosphocytidyl-2-C-Methyl-D-Erythritol," Proc. Natl. Acad. Sci. USA 97:1062-1067 (2000)

Macejak et al., Nature 353:90-94 (1991)

Mann et al., "Metabolic Engineering of Astaxanthin Production in Tobacco Flowers," Nature Biotech. 18:888-892 (2000)

Martin et al., "Gene Transfer to the Nucleus and the Evolution of Chloroplasts," Nature 393:162-165 (1998)

Matsuoka et al., "Variable Product Specificity of Microsomal Dehydrodolichyl Diphosphate Synthase from Rat Liver," J. Biol. Chem. 266:3464-3468 (1991)

Matteuci et al., J. Am. Chem. Soc., 103: 3185 (1981)

Meinkoth and Wahl, Anal. Biochem. 138:267-284 (1984)

Meyer and Saedler, "Homology-Dependent Gene Silencing in Plants," Ann. Rev. Plant. Physiol. Mol. Biol. 47:23-48 (1996)

Millen et al., "Many Parallel Losses of infA from Chloroplast DNA During Angiosperm Evolution with Multiple Independent Transfers to the Nucleus," Plant Cell 13: 645-658 (2001)

Mogen et al., Plant Cell 2:1261-1272 (1990)

Munroe et al., Gene 91:151-158 (1990)

Murray et al., Nucleic Acids Res. 17:477-498 (1989)

Needleman et al., J. Mol. Biol. 48:443 (1970)

Newman et al., "Genes Galore: A Summary of Methods for Accessing Results from Large-Scale Partial Sequencing of Anonymous Arabidopsis cDNA Clones," Plant Physiology 106:1241-1255 (1994)

Nielsen and Bloor, "Analysis and Developmental Profile of Carotenoid Pigments in Petals of Three Yellow Petunia Cultivars," Scientia Hort. 71:257-266 (1997)

Pachuk et al., Gene 243:19-25 (2000)

Pearson et al., Proc. Natl. Acad. Sci. 85:2444 (1988)

Popjak, "Natural Substances Formed Biologically from Mevalonic Acid," Biochemical symposium no. 29 (T. W. Goodwin, ed.) Academic Press, New York, pp 17-37 (1970)

Proudfoot, Cell 64:671-674 (1991)

Ramos-Valdivia et al., "Isopentenyl Diphosphate Isomerase: A Core Enzyme in Isoprenoid Biosynthesis: A Review of its Biochemistry and Function," Nat. Prod. Rep. 6:591-603 (1997)

Rohdich et al., "Cytidine 5'-Triphosphate-Dependent Biosynthesis of Isoprenoids: YgbP Protein of *Escherichia coli* Catalyzes the Formation of 4-Diphosphocytidyl-2-C-methylerythritol," Proc. Natl. Acad. Sci. USA 96:11758-11763 (1999)

Sambrook et al., "Molecular Cloning: A Laboratory Manual," 2nd ed., Cold Spring Harbor Laboratory Press, Cold Spring Harbor, N.Y. (1989)

Sanfacon et al., Genes Dev. 5:141-149 (1991)

Serino and Maliga, "A Negative Selection Scheme Based on the Expression of Cytosine Deaminase in Plastids," Plant J. 12:687-701 (1997)

Smith et al., Adv. Appl. Math. 2:482 (1981)

Sprenger et al., "Identification of a Thiamin-Dependent. Synthase in *Escherichia coli* Required for the Formation of the 1-Deoxy-D-Xylulose 5-Phosphate Precursor to Isoprenoids, Thiamin, and Pyridoxol," Proc. Natl. Acad. Sci. USA 94:12857-12862 (1997)

Stevens and Burton, "Genetic Engineering of Eukaryotic Algae: Progress and prospects," J. Phycol 33:713-722 (1997)

Sugiura, M., "Direct submission to the EMBL/GenBank/DDBJ databases, bases 1-155939," (1986)

Takagi et al., "A Gene Cluster for the Mevalonate Pathway from *Streptomyces* sp Strain CL190," J. Bacteriol. 182: 4153-4157 (2000)

Takahashi, et al., "Purification, Characterization, and Cloning of a Eubacterial 3-Hydroxy-3-Methylglutaryl Coenzyme A Reductase, a Key Enzyme Involved in Biosynthesis of Terpenoids," J. Bacteriol. 181:1256-1263 (1999)

Toriyama and Hinata, "Cell Suspension and Protoplast Culture in Rice," Plant Science 41:179-183 (1985)

Tsudsuki, T., "Direct submission, bases 1-155939. Data Processing Center, Aichi-Gakuin University, Aichi, Japan," (1998)

Vasil et al., in Cell Culture and Somatic Cell Genetics of Plants, Vols. I, II, and III, Laboratory Procedures and Their Applications (Academic press) (1984)

Weissbach et al., Methods for Plant Mol. Biol. (1989)

Ye et al., Science 287:303-30 (2000)

I claim:

1. A method of providing a cell with an inserted polynucleotide sequence encoding one or more products of interest, said method comprising:

providing a plurality of target cells having an identified endogenous plastidic pseudogene site located within an operon;

providing an isolated polynucleotide lacking transcriptional regulatory sequences and comprising polynucleotide sequences of said pseudogene site flanking at least one heterologous coding sequence of interest;

introducing said isolated polynucleotide into a plurality of said target cells;

selecting at least one target cell which contains the heterologous coding sequence of interest inserted into said pseudogene site, wherein the coding sequence of interest is operably linked to the regulatory sequences of the operon containing the pseudogene and is transcribed.

2. The method according to claim 1, wherein said pseudogene is a defunct gene located in an active operon from which polycistronic RNA is produced.

3. The method according to claim 2, wherein said operon is the rpl23 operon.

4. The method according to claim 2, wherein said pseudogene is infA.

5. The method according to claim 3, wherein the inserted coding sequence of interest is operably linked to the regulatory sequences of the rpl23 operon.

6. The method according to claim 1, wherein the isolated polynucleotide further comprises additional flanking sequences that themselves flank the pseudogene sequences, and wherein said additional flanking sequences, in their native state, flank the pseudogene in its native state.

7. The method according to claim 6, wherein the inserted polynucleotide replaces the pseudogene in its entirety.

8. The method according to claim 6, wherein said additional flanking sequences are native plastid sequences.

9. The method according to claim 1, wherein said target cell is a plant cell.

10. The method according to claim 1, wherein said target cell is a microalgae cell.

11. The method according to claim 9, wherein said isolated polynucleotide is introduced into a plastid of said target cell.

12. The method according to claim 10, wherein said isolated polynucleotide is introduced into a plastid of said target cell.

13. The method according to claim 9, wherein said plant cell is selected from the group consisting of the rosids, asterids, and liliales.

14. The method according to claim 9, wherein said plant cell is from a solanaceous species.

15. The method according to claim 14, wherein said plant cell is selected from the group consisting of petunia, tomato, potato, and tobacco cells.

16. The method according to claim 1, wherein said coding sequence of interest comprises a polynucleotide sequence encoding phytoene synthase.

17. The method according to claim 1, wherein said isolated polynucleotide is promoterless.

18. The method according to claim 17, wherein said isolated polynucleotide further comprises a translation initiation region.

19. The method according to claim 1, wherein the transcribed coding sequence is translated into a protein to produce a functional desired product.

* * * * *

UNITED STATES PATENT AND TRADEMARK OFFICE
CERTIFICATE OF CORRECTION

PATENT NO. : 7,618,819 B2
APPLICATION NO. : 11/053541
DATED : November 17, 2009
INVENTOR(S) : Adelheid R. Kuehnle It is certified that error appears in the above-identified patent and that said Letters Patent is hereby corrected as shown below:

Column 1,
Line 60, "5-carbon isomers, EPP" should read --5-carbon isomers, IPP--.

Column 2,
Line 46, "(Lüittgen et al.," should read --(Lüttgen et al.,--.

Column 16,
Line 67, "30to 35% formamide." should read --30 to 35% formamide,--.

Column 17,
Line 2, "andawashin 1x to 2xSCC" should read --and a wash in 1X to 2X SCC--.

Column 19,
Line 41, "cytochrome cl" should read --cytochrome c1--.

Column 22,
Lines 27-29,
"5'TTCTCGAG*CTTAAGAGTAGCAATATTTACCGGAGC AGTTACACTAGCAGTATATACAGTC*ATTAAAACTCCT CCTGTGAAGTCCATGGTAAATTCG 3'"
should read
--5'TTCTCGAG*CTTAAGAGTAGCAATATTTACCGGAGC AGTTACACTAGC AGTATATACAGTC*ATTAAAACTCCT CCTGTGAAGTCCATGGTAAATTCG 3'--.

Column 23,
Line 15, "Sacd yields" should read --SacI yields--.

Column 25,
Lines 60-61,
"4) 5' GGG*GTACC*TGCGGCCGGATCCCGGGTCATGTTGTTGTTGTTGTC GTTGTCGTTGCTCCAGAGATGTCTCGG 3'"
should read
--4) 5' GG*GGTACC*TGCGGCCGGATCCCGGGTCATGTTGTTGTTGTTGTC GTTGTCGTTGCTCCAGAGATGTCTCGG 3'--.

Column 27,
Line 29, "H2O" should read --$H_2O$--.

Column 28,
Lines 45-46,
"successful construction of pHKO3 (FIG. 6).
In an exemplified embodiment, a vector"
should read
--successful construction of pHKO3 (FIG. 6).
EXAMPLE 9: Construction of Tobacco Plastid Transformation Vector pHKO4
In an exemplified embodiment, a vector--.

Line 54, "Aunique restriction" should read --A unique restriction--.

Column 29,
Lines 59-61,
"2) 5' GCTCTAGAGATATCGGATCCGCGGCCGCTCAGC
CGCGCAGGATCGATCCGAAAATCC 3'"
should read
--2) 5' GC*TCTAGA*GATATCGGATCCGCGGCCGCTCAGC
CGCGCAGGATCGATCCGAAAATCC 3'--.

Column 30,
Lines 15-16, "encoding a polyp
eptide with" should read --encoding a polypeptide with--.

Lines 26-28,
"4) 5' CGCTCGAGCCCGGGGATCCTTAGCAAC
GATGAATTAAGGTATCTTGGAATTTTGACGC 3'"
should read
--4) 5' CGCTCGAGCCCGGGGATCCTTAGCAAC
GATGAATTAAGGTATCTTGGAATTTTGACGC 3'--.

Column 31,
Lines 14-16,
"2) 5' GGGGTACCGCGGCCGCACGCGTCTATGCACCAA
CCTTTGCGGTCTTGTTGTCGCGTTCCAGCTGG 3'"
should read
--2) 5' GG*GGTACC*GCGGCCGCACGCGTCTATGCACCAA
CCTTTGCGGTCTTGTTGTCGCGTTCCAGCTGG 3'--.

Column 34,
Lines 52-54,
"4) 5' AACAACAACAACATGACCCGGGATCCGGCGCGA
TCCGAGCTCGAGATCTGCAGCTGGTA 3'"
should read
--4) 5' AACAACAACAACATGACCCGGGATCCGGCCGCGA
TCCGAGCTCGAGATCTGCAGCTGGTA 3'--.

Column 39,
Line 3, "from T0 tissue or T1 leaf tissue" should read
--from T0 leaf tissue or T1 leaf tissue--.

Lines 56-57, "Perfectly Blunt(Cloning Kit (Novagen)" should read
--PERFECTLY BLUNT™ Cloning Kit (Novagen)--.

Lines 66-67, "Ampligase((Epicentre Technologies, Madison, Wis.)," should read
--AMPLIGASE™ (Epicentre Technologies, Madison, Wis.),--.

Column 41,
Line 33, "restricted with Hindifi" should read --restricted with HindIII--.

Line 53, "*Chlamydomonas* plastid" should read --chlamydomonas plastid--.

Column 42,
Line 24, "5*Oryza sativa*" should read --*Oryza sativa*--.

Line 33, "acide, 3%" should read --acid, 3%--.

Signed and Sealed this

Second Day of March, 2010

David J. Kappos
*Director of the United States Patent and Trademark Office*

SEQUENCE LISTING

```
<160> NUMBER OF SEQ ID NOS: 76

<210> SEQ ID NO 1
<211> LENGTH: 57
<212> TYPE: DNA
<213> ORGANISM: Artificial Sequence
<220> FEATURE:
<223> OTHER INFORMATION: PCR primer containing Saccharomyces cerevisiae
      DNA

<400> SEQUENCE: 1

ggactagtct gcaggaggag ttttaatgtc attaccgttc ttaacttctg caccggg        57


<210> SEQ ID NO 2
<211> LENGTH: 96
<212> TYPE: DNA
<213> ORGANISM: Artificial Sequence
<220> FEATURE:
<223> OTHER INFORMATION: PCR primer containing S. cerevisiae DNA

<400> SEQUENCE: 2

ttctcgagct taagagtagc aatatttacc ggagcagtta cactagcagt atatacagtc     60

attaaaactc ctcctgtgaa gtccatggta aattcg                                96
```

<210> SEQ ID NO 3
<211> LENGTH: 56
<212> TYPE: DNA
<213> ORGANISM: Artificial Sequence
<220> FEATURE:
<223> OTHER INFORMATION: PCR primer containing S. cerevisiae DNA

<400> SEQUENCE: 3
tagcggccgc aggaggagtt catatgtcag agttgagagc cttcagtgcc ccaggg 56

<210> SEQ ID NO 4
<211> LENGTH: 36
<212> TYPE: DNA
<213> ORGANISM: Artificial Sequence
<220> FEATURE:
<223> OTHER INFORMATION: PCR primer containing S. cerevisiae DNA

<400> SEQUENCE: 4
tttctgcagt ttatcaagat aagtttccgg atcttt 36

<210> SEQ ID NO 5
<211> LENGTH: 41
<212> TYPE: DNA
<213> ORGANISM: Artificial Sequence
<220> FEATURE:
<223> OTHER INFORMATION: PCR primer containing S. cerevisiae DNA

<400> SEQUENCE: 5
ggaattcatg accgtttaca cagcatccgt taccgcaccc g 41

<210> SEQ ID NO 6
<211> LENGTH: 45
<212> TYPE: DNA
<213> ORGANISM: Artificial Sequence
<220> FEATURE:
<223> OTHER INFORMATION: PCR primer containing S. cerevisiae DNA

<400> SEQUENCE: 6
ggctcgagtt aaaactcctc ttcctttggt agaccagtct ttgcg 45

<210> SEQ ID NO 7
<211> LENGTH: 68
<212> TYPE: DNA
<213> ORGANISM: Artificial Sequence
<220> FEATURE:
<223> OTHER INFORMATION: PCR primer containing Arabidopsis thaliana DNA

<400> SEQUENCE: 7
gctctagatg cgcaggaggc acatatggcg aagaacgttg ggattttggc tatggatatc 60
tatttccc 68

<210> SEQ ID NO 8
<211> LENGTH: 61
<212> TYPE: DNA
<213> ORGANISM: Artificial Sequence
<220> FEATURE:
<223> OTHER INFORMATION: PCR primer containing A. thaliana DNA

<400> SEQUENCE: 8
cgctcgagtc gacggatcct cagtgtccat tggctacaga tccatcttca cctttcttgc 60
c 61

<210> SEQ ID NO 9

-continued

```
<211> LENGTH: 72
<212> TYPE: DNA
<213> ORGANISM: Artificial Sequence
<220> FEATURE:
<223> OTHER INFORMATION: PCR primer containing A. thaliana DNA

<400> SEQUENCE: 9

ccgctcgagc acgtggaggc acatatgcaa tgctgtgaga tgcctgttgg atacattcag     60

attcctgttg gg                                                         72


<210> SEQ ID NO 10
<211> LENGTH: 71
<212> TYPE: DNA
<213> ORGANISM: Artificial Sequence
<220> FEATURE:
<223> OTHER INFORMATION: PCR primer containing A. thaliana DNA

<400> SEQUENCE: 10

ggggtacctg cggccggatc ccgggtcatg ttgttgttgt tgtcgttgtc gttgctccag     60

agatgtctcg g                                                          71


<210> SEQ ID NO 11
<211> LENGTH: 74
<212> TYPE: DNA
<213> ORGANISM: Artificial Sequence
<220> FEATURE:
<223> OTHER INFORMATION: PCR primer containing S. cerevisiae DNA

<400> SEQUENCE: 11

acaacaccgc ggcggccgcg tcgacgccgg cggaggcaca tatgtctcag aacgtttaca     60

ttgtatcgac tgcc                                                       74


<210> SEQ ID NO 12
<211> LENGTH: 53
<212> TYPE: DNA
<213> ORGANISM: Artificial Sequence
<220> FEATURE:
<223> OTHER INFORMATION: PCR primer containing S. cerevisiae DNA

<400> SEQUENCE: 12

gctctagagg atcctcatat cttttcaatg acaatagagg aagcaccacc acc            53


<210> SEQ ID NO 13
<211> LENGTH: 65
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 13

gctctagata cgtaggaggc acatatgagt gagcttatac ccgcctgggt tggtgacaga     60

ctggc                                                                 65


<210> SEQ ID NO 14
<211> LENGTH: 61
<212> TYPE: DNA
<213> ORGANISM: Artificial Sequence
<220> FEATURE:
<223> OTHER INFORMATION: Oligonucleotide containing A. thaliana and S.
      cerevisiae DNA

<400> SEQUENCE: 14

cgctcgagcc cgggggatcc tcagccgcgc aggatcgatc cgaaaatccg gtcaagatgg     60
```

-continued

```
c                                                                    61


<210> SEQ ID NO 15
<211> LENGTH: 72
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 15

gctctagata cgtaggaggc acatatgagt tcccaacaag agaaaaagga ttatgatgaa     60

gaacaattaa gg                                                        72


<210> SEQ ID NO 16
<211> LENGTH: 59
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 16

cgctcgagcc cgggggatcc ttagcaacga tgaattaagg tatcttggaa ttttgacgc      59


<210> SEQ ID NO 17
<211> LENGTH: 6215
<212> TYPE: DNA
<213> ORGANISM: Artificial Sequence
<220> FEATURE:
<221> NAME/KEY: misc_feature
<222> LOCATION: ()..()
<223> OTHER INFORMATION: Vector pBSNT27 containing Nicotiana tabacum DNA

<400> SEQUENCE: 17

gcacttttcg gggaaatgtg cgcggaaccc ctatttgttt atttttctaa atacattcaa     60

atatgtatcc gctcatgaga caataaccct gataaatgct tcaataatat tgaaaaagga    120

agagtatgag tattcaacat ttccgtgtcg cccttattcc cttttttgcg gcattttgcc    180

ttcctgtttt tgctcaccca gaaacgctgg tgaaagtaaa agatgctgaa gatcagttgg    240

gtgcacgagt gggttacatc gaactggatc tcaacagcgg taagatcctt gagagttttc    300

gccccgaaga acgttttcca atgatgagca cttttaaagt tctgctatgt ggcgcggtat    360

tatcccgtat tgacgccggg caagagcaac tcggtcgccg catacactat tctcagaatg    420

acttggttga gtactcacca gtcacagaaa agcatcttac ggatggcatg acagtaagag    480

aattatgcag tgctgccata accatgagtg ataacactgc ggccaactta cttctgacaa    540

cgatcggagg accgaaggag ctaaccgctt ttttgcacaa catgggggat catgtaactc    600

gccttgatcg ttgggaaccg gagctgaatg aagccatacc aaacgacgag cgtgacacca    660

cgatgcctgt agcaatggca acaacgttgc gcaaactatt aactggcgaa ctacttactc    720

tagcttcccg gcaacaatta atagactgga tggaggcgga taaagttgca ggaccacttc    780

tgcgctcggc ccttccggct ggctggttta ttgctgataa atctggagcc ggtgagcgtg    840

ggtctcgcgg tatcattgca gcactggggc cagatggtaa gccctcccgt atcgtagtta    900

tctacacgac ggggagtcag gcaactatgg atgaacgaaa tagacagatc gctgagatag    960

gtgcctcact gattaagcat tggtaactgt cagaccaagt ttactcatat atactttaga   1020

ttgatttaaa acttcatttt taatttaaaa ggatctaggt gaagatcctt tttgataatc   1080

tcatgaccaa aatcccttaa cgtgagtttt cgttccactg agcgtcagac cccgtagaaa   1140

agatcaaagg atcttcttga gatccttttt ttctgcgcgt aatctgctgc ttgcaaacaa   1200
```

-continued

```
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
agttaggcca ccacttcaag aactctgtag caccgcctac atacctcgct ctgctaatcc   1380
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccagggggaa acgcctggta tctttatagt cctgtcgggt   1680
ttcgccacct ctgacttgag cgtcgatttt tgtgatgctc gtcagggggg cggagcctat   1740
ggaaaaacgc cagcaacgcg gcctttttac ggttcctggc cttttgctgg ccttttgctc   1800
acatgttctt tcctgcgtta tcccctgatt ctgtggataa ccgtattacc gcctttgagt   1860
gagctgatac cgctcgccgc agccgaacga ccgagcgcag cgagtcagtg agcgaggaag   1920
cggaagagcg cccaatacgc aaaccgcctc tccccgcgcg ttggccgatt cattaatgca   1980
gctggcacga caggtttccc gactggaaag cgggcagtga gcgcaacgca attaatgtga   2040
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctccaccgc ggtggcggcc   2220
gctctagaac tagtggatct tcttggctgt tattcaaaag gtccaacaat gtatatatat   2280
tggacatttt gaggcaatta tagatcctgg aaggcaattc tgattggtca ataaaaatcg   2340
atttcaatgc tatttttttt ttgtttttta tgagtttagc caatttatca tgaaaggtaa   2400
aaggggataa aggaaccgtg tgttgattgt cctgtaaata taagttgtct tcctccatat   2460
gtaaaaaggg aataaataaa tcaattaaat ttcgggatgc ttcatgaagt gcttctttcg   2520
gagttaaact tccgtttgtc catatttcga gaaaaagtat ctcttgtttt tcattcccat   2580
tcccataaga atgaatacta tgattcgcgt ttcgaacagg catgaataca gcatctatag   2640
gataacttcc atcttgaaag ttatgtggcg tttttataag atatccacga tttctctcta   2700
tttgtaatcc aatacaaaaa tcaattggtt ccgttaaact ggctatatgt tgtgtattat   2760
caacgatttc tacataaggc ggcaagatga tatcttgggc agttacagat ccaggaccct   2820
tgacacaaat agatgcgtca gaagttccat atagattact tcttaatata atttctttca   2880
aattcattaa aatttcatgt accgattctt gaatgcccgt tatggtagaa tattcatgtg   2940
ggactttctc agattttaca cgtgtgatac atgttccttc tatttctcca agtaaagctc   3000
ttcgcatcgc aatgcctatt gtgtcggctt ggcctttcat aagtggagac agaataaagc   3060
gtccataata aaggcgttta ctgtctgttc ttgattcaac acacttccac tgtagtgtcc   3120
gagtagatac tgttactttc tctcgaacca tagtactatt atttgattag atcatcgaat   3180
cttttatttc tcttgagatt tcttcaatgt tcagttctac acacgtcttt ttttcggagg   3240
tctacagcca ttatgtggca taggagttac atcccgtacg aaagttaata gtataccact   3300
tcgacgaata gctcgtaatg ctgcatctct tccgagaccg ggacctttta tcatgacttc   3360
tgctcgttgc ataccttgat ccactactgt acggatagcg tttgctgctg cggtttgagc   3420
agcaaacggt gttcctcttc tcgtaccttt gaatccagaa gtaccggcgg aggaccaaga   3480
aactactcga ccccgtacat ctgtaacagt gacaatggta ttattgaaac ttgcttgaac   3540
```

-continued

```
atgaataact ccctttggta ttctacgtgc acccttacgt gaaccaatac gtccattcct   3600
acgcgaacta attttcggta tagcttttgc catattttat catctcgtaa atatgagtca   3660
gagatatatg gatatatcca tttcatgtca aaacagattc tttatttgta catcggctct   3720
tctggcaagt ctgattatcc ctgtctttgt ttatgtctcg ggttggaaca aattactata   3780
attcgtcccc gcctacggat tagtcgacat ttttcacaaa ttttacgaac ggaagctctt   3840
attttcatat ttctcattcc ttaccttaat tctgaatcta tttcttggaa gaaaataagt   3900
ttcttgaaat ttttcatctc gaattgtatt cccacgaaag gaatggtgaa gttgaaaaac   3960
gaatccttca aatctttgtt gtggagtcga taaattatac gccctttggt tgaatcataa   4020
ggacttactt caattttgac tctatctcct ggcagtatcc gtataaaact atgccggatc   4080
tttcctgaaa cataatttat aatcagatct aaacaaaccc ggaacagacc gttgggaagc   4140
gattcagtaa ttaaagcttc atgactcctt tttggttctt aaagtccctt tgaggtatca   4200
actaataaga aagatattag acaacccccc ttttttcttt ttcacaaata ggaagtttcg   4260
aatccaattt ggatattaaa aggattacca gatataacac aaaatctctc cacctattcc   4320
ttctagtcga gcctctcggt ctgtcattat acctcgagaa gtagaaagaa ttacaatccc   4380
cattccacct aaaattcgcg gaattcgttg ataattagaa tagattcgta gaccaggtcg   4440
actgattcgt tttaaattta aaatatttct atagggtctt ttcctattcc ttctatgtcg   4500
cagggttaaa accaaaaaat atttgttttt ttctcgatgt tttctcacgt tttcgataaa   4560
accttctcgt aaaagtattt gaacaatatt ttcggtaata ttagtagatg ctattcgaac   4620
caccctttttt cgatccatat cagcatttcg tatagaagtt attatctcag caatagtgtc   4680
cctacccatg atgaactaaa attattgggg cctccaaatt tgatataatc aacgtgtttt   4740
ttacttattt ttttttgaa tatgatatga attattaaag atatatgcgt gagacacaat   4800
ctactaatta atctatttct ttcaaatacc ccactagaaa cagatcacaa tttcatttta   4860
taatacctcg ggagctaatg aaactatttt agtaaaattt aattctctca attcccgggc   4920
gattgcacca aaaattcgag ttccttttga tttccttcct tcttgatcaa taacaactgc   4980
agcattgtca tcatatcgta ttatcatccc gttgtcacgt ttgagttctt tacaggtccg   5040
cacaattaca gctctgacta cttctgatct ttctaggggc atatttggta cggcttcttt   5100
gatcacagca acaataacgt caccaatatg agcatatcga cgattgctag ctcctatgat   5160
tcgaatacac atcaattctc gagccccgct gttatccgct acatttaaat gggtctgagg   5220
ttgaatcatt tttttaatcc gttctttgaa tgcaaagggc gaagaaaaaa aagaaatatt   5280
tttgtccaaa aaaaaagaaa catgcggttt cgtttcatat ctaagagccc tttccgcatt   5340
tttttctatt acattacgaa ataatgaatt gagttcgtat aggcatttta gatgctgcta   5400
gtgaaatagc ccttctggct atattttctg ttactccacc catttcataa agtattcgac   5460
ccggtttaac aacagctacc caatattcag gggatccccc gggctgcagg aattcgatat   5520
caagcttatc gataccgtcg acctcgaggg ggggcccggt acccaattcg ccctatagtg   5580
agtcgtatta caattcactg gccgtcgttt tacaacgtcg tgactgggaa aaccctggcg   5640
ttacccaact taatcgcctt gcagcacatc ccccttttcgc cagctggcgt aatagcgaag   5700
aggcccgcac cgatcgccct tcccaacagt tgcgcagcct gaatggcgaa tgggacgcgc   5760
cctgtagcgg cgcattaagc gcggcgggtg tggtggttac gcgcagcgtg accgctacac   5820
ttgccagcgc cctagcgccc gctcctttcg ctttcttccc ttcctttctc gccacgttcg   5880
ccggctttcc ccgtcaagct ctaaatcggg ggctcccttt agggttccga tttagtgctt   5940
```

```
tacggcacct cgaccccaaa aaacttgatt agggtgatgg ttcacgtagt gggccatcgc   6000

cctgatagac ggtttttcgc cctttgacgt tggagtccac gttctttaat agtggactct   6060

tgttccaaac tggaacaaca ctcaacccta tctcggtcta ttcttttgat ttataaggga   6120

ttttgccgat ttcggcctat tggttaaaaa atgagctgat ttaacaaaaa tttaacgcga   6180

attttaacaa aatattaacg cttacaattt aggtg                               6215
```

```
<210> SEQ ID NO 18
<211> LENGTH: 1332
<212> TYPE: DNA
<213> ORGANISM: Artificial Sequence
<220> FEATURE:
<223> OTHER INFORMATION: Oligonucleotide containing N. tabacum and S.
      cerevisiae DNA

<400> SEQUENCE: 18

atgtcattac cgttcttaac ttctgcaccg ggaaaggtta ttatttttgg tgaacactct     60

gctgtgtaca acaagcctgc cgtcgctgct agtgtgtctg cgttgagaac ctacctgcta    120

ataagcgagt catctgcacc agatactatt gaattggact tcccggacat tagctttaat    180

cataagtggt ccatcaatga tttcaatgcc atcaccgagg atcaagtaaa ctcccaaaaa    240

ttggccaagg ctcaacaagc caccgatggc ttgtctcagg aactcgttag tcttttggat    300

ccgttgttag ctcaactatc cgaatccttc cactaccatg cagcgttttg tttcctgtat    360

atgtttgttt gcctatgccc ccatgccaag aatattaagt tttctttaaa gtctacttta    420

cccatcggtg ctgggttggg ctcaagcgcc tctatttctg tatcactggc cttagctatg    480

gcctacttgg gggggttaat aggatctaat gacttggaaa agctgtcaga aaacgataag    540

catatagtga atcaatgggc cttcataggt gaaaagtgta ttcacggtac cccttcagga    600

atagataacg ctgtggccac ttatggtaat gccctgctat ttgaaaaaga ctcacataat    660

ggaacaataa acacaaacaa ttttaagttc ttagatgatt tcccagccat tccaatgatc    720

ctaacctata ctagaattcc aaggtctaca aaagatcttg ttgctcgcgt tcgtgtgttg    780

gtcaccgaga aatttcctga agttatgaag ccaattctag atgccatggg tgaatgtgcc    840

ctacaaggct tagagatcat gactaagtta agtaaatgta aaggcaccga tgacgaggct    900

gtagaaacta ataatgaact gtatgaacaa ctattggaat tgataagaat aaatcatgga    960

ctgcttgtct caatcggtgt ttctcatcct ggattagaac ttattaaaaa tctgagcgat   1020

gatttgagaa ttggctccac aaaacttacc ggtgctggtg gcggcggttg ctctttgact   1080

ttgttacgaa gagacattac tcaagagcaa attgacagct tcaaaaagaa attgcaagat   1140

gattttagtt acgagacatt tgaaacagac ttgggtggga ctggctgctg tttgttaagc   1200

gcaaaaaatt tgaataaaga tcttaaaatc aaatccctag tattccaatt atttgaaaat   1260

aaaactacca caaagcaaca aattgacgat ctattattgc caggaaacac gaatttacca   1320

tggacttcat aa                                                        1332
```

```
<210> SEQ ID NO 19
<211> LENGTH: 1191
<212> TYPE: DNA
<213> ORGANISM: Artificial Sequence
<220> FEATURE:
<223> OTHER INFORMATION: Oligonucleotide containing N. tabacum and A.
      thaliana DNA

<400> SEQUENCE: 19
```

-continued

```
atgaccgttt acacagcatc cgttaccgca cccgtcaaca tcgcaaccct taagtattgg      60

gggaaaaggg acacgaagtt gaatctgccc accaattcgt ccatatcagt gactttatcg     120

caagatgacc tcagaacgtt gacctctgcg gctactgcac ctgagtttga acgcgacact     180

ttgtggttaa atggagaacc acacagcatc gacaatgaaa gaactcaaaa ttgtctgcgc     240

gacctacgcc aattaagaaa ggaaatggaa tcgaaggacg cctcattgcc cacattatct     300

caatggaaac tccacattgt ctccgaaaat aactttccta cagcagctgg tttagcttcc     360

tccgctgctg gctttgctgc attggtctct gcaattgcta agttatacca attaccacag     420

tcaacttcag aaatatctag aatagcaaga aaggggtctg gttcagcttg tagatcgttg     480

tttggcggat acgtggcctg ggaaatggga aaagctgaag atggtcatga ttccatggca     540

gtacaaatcg cagacagctc tgactggcct cagatgaaag cttgtgtcct agttgtcagc     600

gatattaaaa aggatgtgag ttccactcag ggtatgcaat tgaccgtggc aacctccgaa     660

ctatttaaag aaagaattga acatgtcgta ccaaagagat ttgaagtcat gcgtaaagcc     720

attgttgaaa aagatttcgc cacctttgca aaggaaacaa tgatggattc caactctttc     780

catgccacat gtttggactc tttccctcca atattctaca tgaatgacac ttccaagcgt     840

atcatcagtt ggtgccacac cattaatcag ttttacggag aaacaatcgt tgcatacacg     900

tttgatgcag gtccaaatgc tgtgttgtac tacttagctg aaaatgagtc gaaactcttt     960

gcatttatct ataaattgtt tggctctgtt cctggatggg acaagaaatt tactactgag    1020

cagcttgagg ctttcaacca tcaatttgaa tcatctaact ttactgcacg tgaattggat    1080

cttgagttgc aaaaggatgt tgccagagtg attttaactc aagtcggttc aggcccacaa    1140

gaaacaaacg aatctttgat tgacgcaaag actggtctac caaaggaata a             1191
```

<210> SEQ ID NO 20
<211> LENGTH: 1197
<212> TYPE: DNA
<213> ORGANISM: Artificial Sequence
<220> FEATURE:
<223> OTHER INFORMATION: PCR primer containing Rhodobacter capsulatus DNA

<400> SEQUENCE: 20

```
atgtctcaga acgtttacat tgtatcgact gccagaaccc caattggttc attccagggt      60

tctctatcct ccaagacagc agtggaattg ggtgctgttg ctttaaaagg cgccttggct     120

aaggttccag aattggatgc atccaaggat tttgacgaaa ttatttttgg taacgttctt     180

tctgccaatt tgggccaagc tccggccaga caagttgctt tggctgccgg tttgagtaat     240

catatcgttg caagcacagt taacaaggtc tgtgcatccg ctatgaaggc aatcattttg     300

ggtgctcaat ccatcaaatg tggtaatgct gatgttgtcg tagctggtgg ttgtgaatct     360

atgactaacg caccatacta catgccagca gcccgtgcgg gtgccaaatt tggccaaact     420

gttcttgttg atggtgtcga aagagatggg ttgaacgatg cgtacgatgg tctagccatg     480

ggtgtacacg cagaaaagtg tgcccgtgat tgggatatta ctagagaaca acaagacaat     540

tttgccatcg aatcctacca aaaatctcaa aaatctcaaa aggaaggtaa attcgacaat     600

gaaattgtac ctgttaccat taagggattt agaggtaagc ctgatactca agtcacgaag     660

gacgaggaac ctgctagatt acacgttgaa aaattgagat ctgcaaggac tgttttccaa     720

aaagaaaacg gtactgttac tgccgctaac gcttctccaa tcaacgatgg tgctgcagcc     780

gtcatcttgg tttccgaaaa agttttgaag gaaaagaatt tgaagccttt ggctattatc     840
```

-continued

```
aaaggttggg gtgaggccgc tcatcaacca gctgatttta catgggctcc atctcttgca    900

gttccaaagg ctttgaaaca tgctggcatc gaagacatca attctgttga ttactttgaa    960

ttcaatgaag ccttttcggt tgtcggtttg gtgaacacta agattttgaa gctagaccca   1020

tctaaggtta atgtatatgg tggtgctgtt gctctaggtc acccattggg ttgttctggt   1080

gctagagtgg ttgttacact gctatccatc ttacagcaag aaggaggtaa gatcggtgtt   1140

gccgccattt gtaatggtgg tggtggtgct tcctctattg tcattgaaaa gatatga      1197
```

<210> SEQ ID NO 21
<211> LENGTH: 1386
<212> TYPE: DNA
<213> ORGANISM: Artificial Sequence
<220> FEATURE:
<223> OTHER INFORMATION: PCR primer containing R. capsulatus DNA

<400> SEQUENCE: 21

```
atggcgaaga acgttgggat tttggctatg gatatctatt tccctcccac ctgtgttcaa     60

caggaagctt tggaagcaca tgatggagca agtaaaggga aatacactat tggacttggc    120

caagattgtt tagctttttg cactgagctt gaagatgtta tctctatgag tttcaatgcg    180

gtgacatcac tttttgagaa gtataagatt gaccctaacc aaatcgggcg tcttgaagta    240

ggaagtgaga ctgttattga caaaagcaag tccatcaaga ccttcttgat gcagctcttt    300

gagaaatgtg gaaacactga tgtcgaaggt gttgactcga ccaatgcttg ctatggtgga    360

actgcagctt tgttaaactg tgtcaattgg gttgagagta actcttggga tggacgttat    420

ggcctcgtca tttgtactga cagcgcggtt tatgcagaag gacccgcaag gcccactgga    480

ggagctgcag cgattgctat gttgatagga cctgatgctc ctatcgtttt cgaaagcaaa    540

ttgagagcaa gccacatggc tcatgtctat gacttttaca agcccaatct tgctagcgag    600

tacccggttg ttgatggtaa gctttcacag acttgctacc tcatggctct tgactcctgc    660

tataaacatt tatgcaacaa gttcgagaag atcgagggca aagagttctc cataaatgat    720

gctgattaca ttgttttcca ttctccatac aataaacttg tacagaaaag ctttgctcgt    780

ctcttgtaca acgacttctt gagaaacgca agctccattg acgaggctgc caaagaaaag    840

ttcacccctt attcatcttt gacccttgac gagagttacc aaagccgtga tcttgaaaag    900

gtgtcacaac aaatttcgaa accgttttat gatgctaaag tgcaaccaac gactttaata    960

ccaaaggaag tcggtaacat gtacactgct tctctctacg ctgcatttgc ttccctcatc   1020

cacaataaac acaatgattt ggcgggaaag cgggtggtta tgttctctta tggaagtggc   1080

tccaccgcaa caatgttctc attacgcctc aacgacaata agcctccttt cagcatttca   1140

aacattgcat ctgtaatgga tgttggcggt aaattgaaag ctagacatga gtatgcacct   1200

gagaagtttg tggagacaat gaagctaatg gaacataggt atggagcaaa ggactttgtg   1260

acaaccaagg agggtattat agatcttttg gcaccgggaa cttattatct gaaagaggtt   1320

gattccttgt accggagatt ctatggcaag aaaggtgaag atggatctgt agccaatgga   1380

cactga                                                              1386
```

<210> SEQ ID NO 22
<211> LENGTH: 1779
<212> TYPE: DNA
<213> ORGANISM: Artificial Sequence
<220> FEATURE:
<223> OTHER INFORMATION: PCR primer containing Schizosaccharomyces pombe DNA -continued

<400> SEQUENCE: 22

```
atggatctcc gtcggaggcc tcctaaacca ccggttacca acaacaacaa ctccaacgga     60
tctttccgtt cttatcagcc tcgcacttcc gatgacgatc atcgtcgccg ggctacaaca    120
attgctcctc caccgaaagc atccgacgcg cttcctcttc cgttatatct cacaaacgcc    180
gtttcttca cgctcttctt ctccgtcgcg tattacctcc tccaccggtg gcgtgacaag    240
atccgttaca atacgcctct tcacgtcgtc actatcacag aactcggcgc cattattgct    300
ctcatcgctt cgtttatcta tctcctaggg ttttttggta ttgactttgt tcagtcattt    360
atctcacgtg cctctggtga tgcttgggat ctcgccgata cgatcgatga tgatgaccac    420
cgccttgtca cgtgctctcc accgactccg atcgtttccg ttgctaaatt acctaatccg    480
gaacctattg ttaccgaatc gcttcctgag gaagacgagg agattgtgaa atcggttatc    540
gacggagtta ttccatcgta ctcgcttgaa tctcgtctcg gtgattgcaa aagagcggcg    600
tcgattcgtc gtgaggcgtt gcagagagtc accgggagat cgattgaagg gttaccgttg    660
gatggatttg attatgaatc gattttgggg caatgctgtg agatgcctgt tggatacatt    720
cagattcctg ttgggattgc tggtccattg ttgcttgatg gttatgagta ctctgttcct    780
atggctacaa ccgaaggttg tttggttgct agcactaaca gaggctgcaa ggctatgttt    840
atctctggtg gcgccaccag taccgttctt aaggacggta tgacccgagc acctgttgtt    900
cggttcgctt cggcgagacg agcttcggag cttaagtttt tcttggagaa tccagagaac    960
tttgatactt tggcagtagt cttcaacagg tcgagtagat ttgcaagact gcaaagtgtt   1020
aaatgcacaa tcgcggggaa gaatgcttat gtaaggttct gttgtagtac tggtgatgct   1080
atggggatga atatggtttc taaaggtgtg cagaatgttc ttgagtatct taccgatgat   1140
ttccctgaca tggatgtgat tggaatctct ggtaacttct gttcggacaa gaaacctgct   1200
gctgtgaact ggattgaggg acgtggtaaa tcagttgttt gcgaggctgt aatcagagga   1260
gagatcgtga acaaggtctt gaaaacgagc gtggctgctt tagtcgagct caacatgctc   1320
aagaacctag ctggctctgc tgttgcaggc tctctaggtg gattcaacgc tcatgccagt   1380
aacatagtgt ctgctgtatt catagctact ggccaagatc cagctcaaaa cgtggagagt   1440
tctcaatgca tcaccatgat ggaagctatt aatgacggca aagatatcca tatctcagtc   1500
actatgccat ctatcgaggt ggggacagtg ggaggaggaa cacagcttgc atctcaatca   1560
gcgtgtttaa acctgctcgg agttaaagga gcaagcacag agtcgccggg aatgaacgca   1620
aggaggctag cgacgatcgt agccggagca gttttagctg gagagttatc tttaatgtca   1680
gcaattgcag ctggacagct tgtgagaagt cacatgaaat acaatagatc cagccgagac   1740
atctctggag caacgacaac gacaacaaca acaacatga                          1779
```

<210> SEQ ID NO 23
<211> LENGTH: 684
<212> TYPE: DNA
<213> ORGANISM: Artificial Sequence
<220> FEATURE:
<223> OTHER INFORMATION: PCR primer containing *S. pombe* DNA

<400> SEQUENCE: 23

```
atgagttccc aacaagagaa aaaggattat gatgaagaac aattaaggtt gatggaagaa     60
gtttgtatcg ttgtagatga aaatgatgtc cctttaagat atggaacgaa aaaggagtgt    120
catttgatgg aaaatataaa taaaggtctt ttgcatagag cattctctat gttcatcttt    180
gatgagcaaa atcgcctttt acttcagcag cgtgcagaag agaaaattac atttccatcc    240
```

```
ttatggacga atacatgttg ctcccaccca ttggatgttg ctggtgaacg tggtaatact    300

ttacctgaag ctgttgaagg tgttaagaat gcagctcaac gcaagctgtt ccatgaattg    360

ggtattcaag ccaagtatat tcccaaagac aaatttcagt ttcttacacg aatccattac    420

cttgctccta gtactggtgc ttggggagag catgaaattg actacattct tttcttcaaa    480

ggtaaagttg agctggatat caatcccaat gaagttcaag cctataagta tgttactatg    540

gaagagttaa aagagatgtt ttccgatcct caatatggat tcacaccatg gttcaaactt    600

atttgtgagc attttatgtt taaatggtgg caggatgtag atcatgcgtc aaaattccaa    660

gataccttaa ttcatcgttg ctaa                                           684
```

<210> SEQ ID NO 24
<211> LENGTH: 531
<212> TYPE: DNA
<213> ORGANISM: Artificial Sequence
<220> FEATURE:
<223> OTHER INFORMATION: PCR primer containing Streptomyces sp CL190 DNA

<400> SEQUENCE: 24

```
atgagtgagc ttatacccgc ctgggttggt gacagactgg ctccggtgga caagttggag     60

gtgcatttga aagggctccg ccacaaggcg gtgtctgttt tcgtcatgga tggcgaaaac    120

gtgctgatcc agcgccgctc ggaggagaaa tatcactctc ccgggctttg ggcgaacacc    180

tgctgcaccc atccgggctg gaccgaacgc cccgaggaat gcgcggtgcg gcggctgcgc    240

gaggagctgg ggatcaccgg gctttatccc gcccatgccg accggctgga atatcgcgcc    300

gatgtcggcg gcggcatgat cgagcatgag gtggtcgaca tctatctggc ctatgccaaa    360

ccgcatatgc ggatcacccc cgatccgcgc gaagtggccg aggtgcgctg gatcggcctt    420

tacgatctgg cggccgaggc cggtcggcat cccgagcggt tctcgaaatg gctcaacatc    480

tatctgtcga gccatcttga ccggattttc ggatcgatcc tgcgcggctg a             531
```

<210> SEQ ID NO 25
<211> LENGTH: 65
<212> TYPE: DNA
<213> ORGANISM: Artificial Sequence
<220> FEATURE:
<223> OTHER INFORMATION: PCR primer containing Streptomyces sp CL190 DNA

<400> SEQUENCE: 25

```
ggggtaccgc ggccgcacgc gtctatgcac caacctttgc ggtcttgttg tcgcgttcca     60

gctgg                                                                 65
```

<210> SEQ ID NO 26
<211> LENGTH: 60
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 26

```
gagctccacc gcggcggccg cgtcgactac ggccgcagga ggagttcata tgtcagagtt     60
```

<210> SEQ ID NO 27
<211> LENGTH: 60
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 27
tctaccaaag gaagaggagt tttaactcga gtaggaggca catatgtctc agaacgttta 60

<210> SEQ ID NO 28
<211> LENGTH: 60
<212> TYPE: DNA
<213> ORGANISM: Artificial Sequence
<220> FEATURE:
<223> OTHER INFORMATION: Oligonucleotide containing Streptomyces sp CL190 and R. capsulatus DNA

<400> SEQUENCE: 28
caagaccgca aaggttggtg catagacgcg gtaaggaggc acatatgagt gagcttatac 60

<210> SEQ ID NO 29
<211> LENGTH: 60
<212> TYPE: DNA
<213> ORGANISM: Artificial Sequence
<220> FEATURE:
<223> OTHER INFORMATION: Oligonucleotide containing R. capsulatus DNA

<400> SEQUENCE: 29
cctgcgcggc tgagcggccg cggatccgat cgcgtgcggc cgcggtaccc aattcgccct 60

<210> SEQ ID NO 30
<211> LENGTH: 60
<212> TYPE: DNA
<213> ORGANISM: Artificial Sequence
<220> FEATURE:
<223> OTHER INFORMATION: Oligonucleotide containing Streptomyces sp CL190 and S. cerevisiae DNA

<400> SEQUENCE: 30
tgtcattgaa aagatatgag gatcctctag gtacttccct ggcgtgtgca gcggttgacg 60

<210> SEQ ID NO 31
<211> LENGTH: 60
<212> TYPE: DNA
<213> ORGANISM: Artificial Sequence
<220> FEATURE:
<223> OTHER INFORMATION: Oligonucleotide containing Streptomyces sp CL190 DNA

<400> SEQUENCE: 31
cgattccgca ttatcggtac gggtgcctac ctagaactag tggatccccc gggctgcagg 60

<210> SEQ ID NO 32
<211> LENGTH: 60
<212> TYPE: DNA
<213> ORGANISM: Artificial Sequence
<220> FEATURE:
<223> OTHER INFORMATION: Oligonucleotide containing N. tabacum and S. cerevisiae DNA

<400> SEQUENCE: 32
ctttcctgaa acataattta taatcagatc ggccgcagga ggagttcata tgtcagagtt 60

<210> SEQ ID NO 33
<211> LENGTH: 60
<212> TYPE: DNA
<213> ORGANISM: Artificial Sequence
<220> FEATURE:
<223> OTHER INFORMATION: Oligonucleotide containing N. tabacum and R. capsulatus DNA

<400> SEQUENCE: 33

-continued ttcggatcga tcctgcgcgg ctgagcggcc gatctaaaca aacccggaac agaccgttgg 60

<210> SEQ ID NO 34
<211> LENGTH: 59
<212> TYPE: DNA
<213> ORGANISM: Artificial Sequence
<220> FEATURE:
<223> OTHER INFORMATION: Oligonucleotide containing N. tabacum and S. cerevisiae DNA

<400> SEQUENCE: 34
ctttcctgaa acataattta taatcagatc ggccgcagga ggagttcata tgtcagagt 59

<210> SEQ ID NO 35
<211> LENGTH: 60
<212> TYPE: DNA
<213> ORGANISM: Artificial Sequence
<220> FEATURE:
<223> OTHER INFORMATION: Oligonucleotide containing N. tabacum and S. pombe DNA

<400> SEQUENCE: 35
tcgttgctaa ggatccccg ggatccggcc gatctaaaca aacccggaac agaccgttgg 60

<210> SEQ ID NO 36
<211> LENGTH: 13
<212> TYPE: DNA
<213> ORGANISM: Artificial Sequence
<220> FEATURE:
<223> OTHER INFORMATION: Oligonucleotide containing NotI restriction site

<400> SEQUENCE: 36
catggcggcc gcg 13

<210> SEQ ID NO 37
<211> LENGTH: 13
<212> TYPE: DNA
<213> ORGANISM: Artificial Sequence
<220> FEATURE:
<223> OTHER INFORMATION: Oligonucleotide containing NotI restriction site

<400> SEQUENCE: 37
gatccgcggc cgc 13

<210> SEQ ID NO 38
<211> LENGTH: 60
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 38
ttaaataagg aggaataaac catggcggcc gcaggaggag ttcatatgtc agagttgaga 60

<210> SEQ ID NO 39
<211> LENGTH: 60
<212> TYPE: DNA
<213> ORGANISM: Artificial Sequence
<220> FEATURE:
<223> OTHER INFORMATION: Oligonucleotide containing A. thaliana DNA

<400> SEQUENCE: 39
aacaacaaca acatgacccg ggatccggcc gcgatccgag ctcgagatct gcagctggta 60

<210> SEQ ID NO 40
<211> LENGTH: 60
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 40
tcgattaaat aaggaggaat aaaccatggc ggccgcagga ggagttcata tgtcagagtt 60

<210> SEQ ID NO 41
<211> LENGTH: 60
<212> TYPE: DNA
<213> ORGANISM: Artificial Sequence
<220> FEATURE:
<223> OTHER INFORMATION: Oligonucleotide containing R. capsulatus DNA

<400> SEQUENCE: 41
gattttcgga tcgatcctgc gcggctgagc ggccgcgatc cgagctcgag atctgcagct 60

<210> SEQ ID NO 42
<211> LENGTH: 60
<212> TYPE: DNA
<213> ORGANISM: Artificial Sequence
<220> FEATURE:
<223> OTHER INFORMATION: Oligonucleotide containing S. cerevisiae DNA

<400> SEQUENCE: 42
tcgattaaat aaggaggaat aaaccatggc ggccgcagga ggagttcata tgtcagagtt 60

<210> SEQ ID NO 43
<211> LENGTH: 60
<212> TYPE: DNA
<213> ORGANISM: Artificial Sequence
<220> FEATURE:
<223> OTHER INFORMATION: Oligonucleotide containing S. pombe DNA

<400> SEQUENCE: 43
ttcatcgttg ctaaggatcc cccgggatcc ggccgcgatc cgagctcgag atctgcagct 60

<210> SEQ ID NO 44
<211> LENGTH: 61
<212> TYPE: DNA
<213> ORGANISM: Artificial Sequence
<220> FEATURE:
<223> OTHER INFORMATION: Oligonucleotide containing R. capsulatus DNA

<400> SEQUENCE: 44
ttaaataagg aggaataaac catggcggcc gtaaggaggc acatatgagt gagcttatac 60
t 61

<210> SEQ ID NO 45
<211> LENGTH: 61
<212> TYPE: DNA
<213> ORGANISM: Artificial Sequence
<220> FEATURE:
<223> OTHER INFORMATION: Oligonucleotide containing R. capsulatus DNA

<400> SEQUENCE: 45
gcctgcgcgg ctgagcggcc gcggatccga tggccgcgat ccgagctcga gatctgcagc 60
t 61

<210> SEQ ID NO 46
<211> LENGTH: 60
<212> TYPE: DNA

<213> ORGANISM: Artificial Sequence
<220> FEATURE:
<223> OTHER INFORMATION: Oligonucleotide containing S. pombe DNA

<400> SEQUENCE: 46
ttaaataagg aggaataaac catggcggcc gtaggaggca catatgagtt cccaacaaga 60

<210> SEQ ID NO 47
<211> LENGTH: 60
<212> TYPE: DNA
<213> ORGANISM: Artificial Sequence
<220> FEATURE:
<223> OTHER INFORMATION: Oligonucleotide containing S. pombe DNA

<400> SEQUENCE: 47
accttaattc atcgttgcta aggatccccc ggccgcgatc cgagctcgag atctgcagct 60

<210> SEQ ID NO 48
<211> LENGTH: 1356
<212> TYPE: DNA
<213> ORGANISM: Saccharomyces cerevisiae

<400> SEQUENCE: 48
atgtcagagt tgagagcctt cagtgcccca gggaaagcgt tactagctgg tggatattta 60
gttttagata caaaatatga agcatttgta gtcggattat cggcaagaat gcatgctgta 120
gcccatcctt acggttcatt gcaagggtct gataagtttg aagtgcgtgt gaaaagtaaa 180
caatttaaag atggggagtg gctgtaccat ataagtccta aaagtggctt cattcctgtt 240
tcgataggcg gatctaagaa ccctttcatt gaaaaagtta tcgctaacgt atttagctac 300
tttaaaccta acatggacga ctactgcaat agaaacttgt tcgttattga tattttctct 360
gatgatgcct accattctca ggaggatagc gttaccgaac atcgtggcaa cagaagattg 420
agttttcatt cgcacagaat tgaagaagtt cccaaaacag ggctgggctc ctcggcaggt 480
ttagtcacag ttttaactac agctttggcc tcctttttg tatcggacct ggaaaataat 540
gtagacaaat atagagaagt tattcataat ttagcacaag ttgctcattg tcaagctcag 600
ggtaaaattg gaagcgggtt tgatgtagcg gcggcagcat atggatctat cagatataga 660
agattcccac ccgcattaat ctctaatttg ccagatattg gaagtgctac ttacggcagt 720
aaactggcgc atttggttga tgaagaagac tggaatatta cgattaaaag taaccattta 780
ccttcgggat taactttatg gatgggcgat attaagaatg gttcagaaac agtaaaactg 840
gtccagaagg taaaaaattg gtatgattcg catatgccag aaagcttgaa aatatataca 900
gaactcgatc atgcaaattc tagatttatg gatggactat ctaaactaga tcgcttacac 960
gagactcatg acgattacag cgatcagata tttgagtctc ttgagaggaa tgactgtacc 1020
tgtcaaaagt atcctgaaat cacagaagtt agagatgcag ttgccacaat tagacgttcc 1080
tttagaaaaa taactaaaga atctggtgcc gatatcgaac ctcccgtaca aactagctta 1140
ttggatgatt gccagacctt aaaaggagtt cttacttgct taatacctgg tgctggtggt 1200
tatgacgcca ttgcagtgat tactaagcaa gatgttgatc ttagggctca aaccgctaat 1260
gacaaaagat tttctaaggt tcaatggctg gatgtaactc aggctgactg gggtgttagg 1320
aaagaaaaag atccggaaac ttatcttgat aaataa 1356

<210> SEQ ID NO 49
<211> LENGTH: 1332
<212> TYPE: DNA
<213> ORGANISM: Saccharomyces cerevisiae -continued

<400> SEQUENCE: 49

```
atgtcattac cgttcttaac ttctgcaccg ggaaaggtta ttatttttgg tgaacactct     60
gctgtgtaca acaagcctgc cgtcgctgct agtgtgtctg cgttgagaac ctacctgcta    120
ataagcgagt catctgcacc agatactatt gaattggact tcccggacat tagctttaat    180
cataagtggt ccatcaatga tttcaatgcc atcaccgagg atcaagtaaa ctcccaaaaa    240
ttggccaagg ctcaacaagc caccgatggc ttgtctcagg aactcgttag tcttttggat    300
ccgttgttag ctcaactatc cgaatccttc cactaccatg cagcgttttg tttcctgtat    360
atgtttgttt gcctatgccc ccatgccaag aatattaagt tttctttaaa gtctacttta    420
cccatcggtg ctgggttggg ctcaagcgcc tctatttctg tatcactggc cttagctatg    480
gcctacttgg gggggttaat aggatctaat gacttggaaa agctgtcaga aaacgataag    540
catatagtga atcaatgggc cttcataggt gaaaagtgta ttcacggtac cccttcagga    600
atagataacg ctgtggccac ttatggtaat gccctgctat ttgaaaaaga ctcacataat    660
ggaacaataa acacaaacaa ttttaagttc ttagatgatt tcccagccat tccaatgatc    720
ctaacctata ctagaattcc aaggtctaca aaagatcttg ttgctcgcgt tcgtgtgttg    780
gtcaccgaga aatttcctga agttatgaag ccaattctag atgccatggg tgaatgtgcc    840
ctacaaggct tagagatcat gactaagtta agtaaatgta aaggcaccga tgacgaggct    900
gtagaaacta ataatgaact gtatgaacaa ctattggaat tgataagaat aaatcatgga    960
ctgcttgtct caatcggtgt ttctcatcct ggattagaac ttattaaaaa tctgagcgat   1020
gatttgagaa ttggctccac aaaacttacc ggtgctggtg gcggcggttg ctctttgact   1080
ttgttacgaa gagacattac tcaagagcaa attgacagct tcaaaaagaa attgcaagat   1140
gattttagtt acgagacatt tgaaacagac ttgggtggga ctggctgctg tttgttaagc   1200
gcaaaaaatt tgaataaaga tcttaaaatc aaatccctag tattccaatt atttgaaaat   1260
aaaactacca caaagcaaca aattgacgat ctattattgc caggaaacac gaatttacca   1320
tggacttcat aa                                                        1332
```

<210> SEQ ID NO 50
<211> LENGTH: 1191
<212> TYPE: DNA
<213> ORGANISM: Saccharomyces cerevisiae

<400> SEQUENCE: 50

```
atgaccgttt acacagcatc cgttaccgca cccgtcaaca tcgcaaccct taagtattgg     60
gggaaaaggg acacgaagtt gaatctgccc accaattcgt ccatatcagt gactttatcg    120
caagatgacc tcagaacgtt gacctctgcg gctactgcac ctgagtttga acgcgacact    180
ttgtggttaa atggagaacc acacagcatc gacaatgaaa gaactcaaaa ttgtctgcgc    240
gacctacgcc aattaagaaa ggaaatggaa tcgaaggacg cctcattgcc cacattatct    300
caatggaaac tccacattgt ctccgaaaat aactttccta cagcagctgg tttagcttcc    360
tccgctgctg gctttgctgc attggtctct gcaattgcta agttatacca attaccacag    420
tcaacttcag aaatatctag aatagcaaga aaggggtctg gttcagcttg tagatcgttg    480
tttggcggat acgtggcctg ggaaatggga aaagctgaag atggtcatga ttccatggca    540
gtacaaatcg cagacagctc tgactggcct cagatgaaag cttgtgtcct agttgtcagc    600
gatattaaaa aggatgtgag ttccactcag ggtatgcaat tgaccgtggc aacctccgaa    660
```

-continued

```
ctatttaaag aaagaattga acatgtcgta ccaaagagat ttgaagtcat gcgtaaagcc    720
attgttgaaa aagatttcgc cacctttgca aaggaaacaa tgatggattc caactctttc    780
catgccacat gtttggactc tttccctcca atattctaca tgaatgacac ttccaagcgt    840
atcatcagtt ggtgccacac cattaatcag ttttacggag aaacaatcgt tgcatacacg    900
tttgatgcag gtccaaatgc tgtgttgtac tacttagctg aaaatgagtc gaaactcttt    960
gcatttatct ataaattgtt tggctctgtt cctggatggg acaagaaatt tactactgag   1020
cagcttgagg ctttcaacca tcaatttgaa tcatctaact ttactgcacg tgaattggat   1080
cttgagttgc aaaaggatgt tgccagagtg attttaactc aagtcggttc aggcccacaa   1140
gaaacaaacg aatctttgat tgacgcaaag actggtctac caaaggaata a            1191
```

<210> SEQ ID NO 51
<211> LENGTH: 1197
<212> TYPE: DNA
<213> ORGANISM: Saccharomyces cerevisiae

<400> SEQUENCE: 51

```
atgtctcaga acgtttacat tgtatcgact gccagaaccc caattggttc attccagggt     60
tctctatcct ccaagacagc agtggaattg ggtgctgttg ctttaaaagg cgccttggct    120
aaggttccag aattggatgc atccaaggat tttgacgaaa ttatttttgg taacgttctt    180
tctgccaatt tgggccaagc tccggccaga caagttgctt tggctgccgg tttgagtaat    240
catatcgttg caagcacagt taacaaggtc tgtgcatccg ctatgaaggc aatcattttg    300
ggtgctcaat ccatcaaatg tggtaatgct gatgttgtcg tagctggtgg ttgtgaatct    360
atgactaacg caccatacta catgccagca gcccgtgcgg gtgccaaatt tggccaaact    420
gttcttgttg atggtgtcga aagagatggg ttgaacgatg cgtacgatgg tctagccatg    480
ggtgtacacg cagaaaagtg tgcccgtgat tgggatatta ctagagaaca acaagacaat    540
tttgccatcg aatcctacca aaaatctcaa aaatctcaaa aggaaggtaa attcgacaat    600
gaaattgtac ctgttaccat taagggattt agaggtaagc ctgatactca agtcacgaag    660
gacgaggaac ctgctagatt acacgttgaa aaattgagat ctgcaaggac tgttttccaa    720
aaagaaaacg gtactgttac tgccgctaac gcttctccaa tcaacgatgg tgctgcagcc    780
gtcatcttgg tttccgaaaa agttttgaag gaaaagaatt tgaagccttt ggctattatc    840
aaaggttggg gtgaggccgc tcatcaacca gctgatttta catgggctcc atctcttgca    900
gttccaaagg ctttgaaaca tgctggcatc gaagacatca attctgttga ttactttgaa    960
ttcaatgaag ccttttcggt tgtcggtttg gtgaacacta agattttgaa gctagaccca   1020
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct tcctctattg tcattgaaaa gatatga      1197
```

<210> SEQ ID NO 52
<211> LENGTH: 1386
<212> TYPE: DNA
<213> ORGANISM: Arabidopsis thaliana

<400> SEQUENCE: 52

```
atggcgaaga acgttgggat tttggctatg gatatctatt tccctcccac ctgtgttcaa     60
caggaagctt tggaagcaca tgatggagca agtaaaggga aatacactat tggacttggc    120
caagattgtt tagctttttg cactgagctt gaagatgtta tctctatgag tttcaatgcg    180
```

-continued

```
gtgacatcac tttttgagaa gtataagatt gaccctaacc aaatcgggcg tcttgaagta    240
ggaagtgaga ctgttattga caaaagcaag tccatcaaga ccttcttgat gcagctcttt    300
gagaaatgtg gaaacactga tgtcgaaggt gttgactcga ccaatgcttg ctatggtgga    360
actgcagctt tgttaaactg tgtcaattgg gttgagagta actcttggga tggacgttat    420
ggcctcgtca tttgtactga cagcgcggtt tatgcagaag gacccgcaag gcccactgga    480
ggagctgcag cgattgctat gttgatagga cctgatgctc ctatcgtttt cgaaagcaaa    540
ttgagagcaa gccacatggc tcatgtctat gacttttaca agcccaatct tgctagcgag    600
tacccggttg ttgatggtaa gctttcacag acttgctacc tcatggctct tgactcctgc    660
tataaacatt tatgcaacaa gttcgagaag atcgagggca aagagttctc cataaatgat    720
gctgattaca ttgttttcca ttctccatac aataaacttg tacagaaaag ctttgctcgt    780
ctcttgtaca acgacttctt gagaaacgca agctccattg acgaggctgc caaagaaaag    840
ttcacccctt attcatcttt gacccttgac gagagttacc aaagccgtga tcttgaaaag    900
gtgtcacaac aaatttcgaa accgttttat gatgctaaag tgcaaccaac gactttaata    960
ccaaaggaag tcggtaacat gtacactgct tctctctacg ctgcatttgc ttccctcatc   1020
cacaataaac acaatgattt ggcgggaaag cgggtggtta tgttctctta tggaagtggc   1080
tccaccgcaa caatgttctc attacgcctc aacgacaata agcctccttt cagcatttca   1140
aacattgcat ctgtaatgga tgttggcggt aaattgaaag ctagacatga gtatgcacct   1200
gagaagtttg tggagacaat gaagctaatg gaacataggt atggagcaaa ggactttgtg   1260
acaaccaagg agggtattat agatcttttg gcaccgggaa cttattatct gaaagaggtt   1320
gattccttgt accggagatt ctatggcaag aaaggtgaag atggatctgt agccaatgga   1380
cactga                                                              1386
```

<210> SEQ ID NO 53
<211> LENGTH: 1779
<212> TYPE: DNA
<213> ORGANISM: Arabidopsis thaliana

<400> SEQUENCE: 53

```
atggatctcc gtcggaggcc tcctaaacca ccggttacca acaacaacaa ctccaacgga     60
tctttccgtt cttatcagcc tcgcacttcc gatgacgatc atcgtcgccg ggctacaaca    120
attgctcctc caccgaaagc atccgacgcg cttcctcttc cgttatatct cacaaacgcc    180
gttttcttca cgctcttctt ctccgtcgcg tattacctcc tccaccggtg gcgtgacaag    240
atccgttaca atacgcctct tcacgtcgtc actatcacag aactcggcgc cattattgct    300
ctcatcgctt cgtttatcta tctcctaggg tttttttggta ttgactttgt tcagtcattt    360
atctcacgtg cctctggtga tgcttgggat ctcgccgata cgatcgatga tgatgaccac    420
cgccttgtca cgtgctctcc accgactccg atcgtttccg ttgctaaatt acctaatccg    480
gaacctattg ttaccgaatc gcttcctgag gaagacgagg agattgtgaa atcggttatc    540
gacggagtta ttccatcgta ctcgcttgaa tctcgtctcg gtgattgcaa aagagcggcg    600
tcgattcgtc gtgaggcgtt gcagagagtc accgggagat cgattgaagg gttaccgttg    660
gatggatttg attatgaatc gattttgggg caatgctgtg agatgcctgt tggatacatt    720
cagattcctg ttgggattgc tggtccattg ttgcttgatg gttatgagta ctctgttcct    780
atggctacaa ccgaaggttg tttggttgct agcactaaca gaggctgcaa ggctatgttt    840
```

-continued

```
atctctggtg gcgccaccag taccgttctt aaggacggta tgacccgagc acctgttgtt    900

cggttcgctt cggcgagacg agcttcggag cttaagtttt tcttggagaa tccagagaac    960

tttgatactt tggcagtagt cttcaacagg tcgagtagat ttgcaagact gcaaagtgtt   1020

aaatgcacaa tcgcggggaa gaatgcttat gtaaggttct gttgtagtac tggtgatgct   1080

atggggatga atatggtttc taaaggtgtg cagaatgttc ttgagtatct taccgatgat   1140

ttccctgaca tggatgtgat tggaatctct ggtaacttct gttcggacaa gaaacctgct   1200

gctgtgaact ggattgaggg acgtggtaaa tcagttgttt gcgaggctgt aatcagagga   1260

gagatcgtga acaaggtctt gaaaacgagc gtggctgctt tagtcgagct caacatgctc   1320

aagaacctag ctggctctgc tgttgcaggc tctctaggtg gattcaacgc tcatgccagt   1380

aacatagtgt ctgctgtatt catagctact ggccaagatc cagctcaaaa cgtggagagt   1440

tctcaatgca tcaccatgat ggaagctatt aatgacggca aagatatcca tatctcagtc   1500

actatgccat ctatcgaggt ggggacagtg ggaggaggaa cacagcttgc atctcaatca   1560

gcgtgtttaa acctgctcgg agttaaagga gcaagcacag agtcgccggg aatgaacgca   1620

aggaggctag cgacgatcgt agccggagca gttttagctg gagagttatc tttaatgtca   1680

gcaattgcag ctggacagct tgtgagaagt cacatgaaat acaatagatc cagccgagac   1740

atctctggag caacgacaac gacaacaaca acaacatga                          1779
```

```
<210> SEQ ID NO 54
<211> LENGTH: 684
<212> TYPE: DNA
<213> ORGANISM: Artificial Sequence
<220> FEATURE:
<223> OTHER INFORMATION: Schizosaccharomyces pombe IDI1 (IPP isomerase)

<400> SEQUENCE: 54

atgagttccc aacaagagaa aaaggattat gatgaagaac aattaaggtt gatggaagaa     60

gtttgtatcg ttgtagatga aaatgatgtc cctttaagat atggaacgaa aaaggagtgt    120

catttgatgg aaaatataaa taaaggtctt ttgcatagag cattctctat gttcatcttt    180

gatgagcaaa atcgcctttt acttcagcag cgtgcagaag agaaaattac atttccatcc    240

ttatggacga atacatgttg ctcccaccca ttggatgttg ctggtgaacg tggtaatact    300

ttacctgaag ctgttgaagg tgttaagaat gcagctcaac gcaagctgtt ccatgaattg    360

ggtattcaag ccaagtatat tcccaaagac aaatttcagt ttcttacacg aatccattac    420

cttgctccta gtactggtgc ttggggagag catgaaattg actacattct tttcttcaaa    480

ggtaaagttg agctggatat caatcccaat gaagttcaag cctataagta tgttactatg    540

gaagagttaa aagagatgtt ttccgatcct caatatggat tcacaccatg gttcaaactt    600

atttgtgagc attttatgtt taaatggtgg caggatgtag atcatgcgtc aaaattccaa    660

gataccttaa ttcatcgttg ctaa                                           684
```

```
<210> SEQ ID NO 55
<211> LENGTH: 531
<212> TYPE: DNA
<213> ORGANISM: Artificial Sequence
<220> FEATURE:
<223> OTHER INFORMATION: Rhodobacter capsulatus idiB (IPP isomerase)

<400> SEQUENCE: 55

atgagtgagc ttatacccgc ctgggttggt gacagactgg ctccggtgga caagttggag     60

gtgcatttga aagggctccg ccacaaggcg gtgtctgttt tcgtcatgga tggcgaaaac    120
```

-continued

```
gtgctgatcc agcgccgctc ggaggagaaa tatcactctc ccgggctttg ggcgaacacc    180

tgctgcaccc atccgggctg gaccgaacgc cccgaggaat gcgcggtgcg gcggctgcgc    240

gaggagctgg ggatcaccgg gctttatccc gcccatgccg accggctgga atatcgcgcc    300

gatgtcggcg gcggcatgat cgagcatgag gtggtcgaca tctatctggc ctatgccaaa    360

ccgcatatgc ggatcacccc cgatccgcgc gaagtggccg aggtgcgctg gatcggcctt    420

tacgatctgg cggccgaggc cggtcggcat cccgagcggt tctcgaaatg gctcaacatc    480

tatctgtcga gccatcttga ccggattttc ggatcgatcc tgcgcggctg a             531

<210> SEQ ID NO 56
<211> LENGTH: 1059
<212> TYPE: DNA
<213> ORGANISM: Streptomyces sp.

<400> SEQUENCE: 56

atgacggaaa cgcacgccat agccggggtc ccgatgaggt gggtgggacc ccttcgtatt     60

tccgggaacg tcgccgagac cgagacccag gtcccgctcg ccacgtacga gtcgccgctg    120

tggccgtcgg tgggccgcgg ggcgaaggtc tcccggctga cggagaaggg catcgtcgcc    180

accctcgtcg acgagcggat gacccgctcg gtgatcgtcg aggcgacgga cgcgcagacc    240

gcgtacatgg ccgcgcagac catccacgcc cgcatcgacg agctgcgcga ggtggtgcgc    300

ggctgcagcc ggttcgccca gctgatcaac atcaagcacg agatcaacgc gaacctgctg    360

ttcatccggt tcgagttcac caccggtgac gcctccggcc acaacatggc cacgctcgcc    420

tccgatgtgc tcctggggca cctgctggag acgatccctg gcatctccta cggctcgatc    480

tccggcaact actgcacgga caagaaggcc accgcgatca acggcatcct cggccgcggc    540

aagaacgtga tcaccgagct gctggtgccg cgggacgtcg tcgagaacaa cctgcacacc    600

acggctgcca agatcgtcga gctgaacatc cgcaagaacc tgctcggcac cctgctcgcc    660

ggcggcatcc gctcggccaa cgcccacttc gcgaacatgc tgctcggctt ctacctggcc    720

accggccagg acgccgccaa catcgtcgag ggctcgcagg gcgtcgtcat ggccgaggac    780

cgcgacggcg acctctactt cgcctgcacc ctgccgaacc tgatcgtcgg cacggtcggc    840

aacggcaagg gtctcggctt cgtggagacg aacctcgccc ggctcggctg ccgagccgac    900

cgcgaacccg gggagaacgc ccgccgcctc gccgtcatcg cggcagcgac cgtgctgtgc    960

ggtgaactct cgctgctcgc ggcacagacg aacccgggcg aactcatgcg cgcgcacgtc   1020

cagctggaac gcgacaacaa gaccgcaaag gttggtgca                          1059

<210> SEQ ID NO 57
<211> LENGTH: 6798
<212> TYPE: DNA
<213> ORGANISM: Artificial Sequence
<220> FEATURE:
<223> OTHER INFORMATION: Streptomyces sp CL190 gene cluster containing
      mevalonate pathway and IPP isomerase orfs

<400> SEQUENCE: 57

tacgtacttc cctggcgtgt gcagcggttg acgcgccgtg ccctcgctgc gagcggcgcg     60

cacatctgac gtcctgcttt attgctttct cagaactcgg gacgaagcga tcccatgatc    120

acgcgatctc catgcagaaa agacaaaggg agctgagtgc gttgacacta ccgacctcgg    180

ctgagggggt atcagaaagc caccgggccc gctcggtcgg catcggtcgc gcccacgcca    240

aggccatcct gctgggagag catgcggtcg tctacggagc gccggcactc gctctgccga    300
```

-continued

```
ttccgcagct cacggtcacg gccagcgtcg gctggtcgtc cgaggcctcc gacagtgcgg    360
gtggcctgtc ctacacgatg accggtacgc cgtcgcgggc actggtgacg caggcctccg    420
acggcctgca ccggctcacc gcggaattca tggcgcggat gggcgtgacg aacgcgccgc    480
acctcgacgt gatcctggac ggcgcgatcc cgcacggccg gggtctcggc tccagcgcgg    540
ccggctcacg cgcgatcgcc ttggccctcg ccgacctctt cggccacgaa ctggccgagc    600
acacggcgta cgaactggtg cagacggccg agaacatggc gcacggccgg gccagcggcg    660
tggacgcgat gacggtcggc gcgtcccggc cgctgctgtt ccagcagggc cgcaccgagc    720
gactggccat cggctgcgac agcctgttca tcgtcgccga cagcggcgtc ccgggcagca    780
ccaaggaagc ggtcgagatg ctgcgggagg gattcacccg cagcgccgga acacaggagc    840
ggttcgtcgg ccgggcgacg gaactgaccg aggccgcccg gcaggccctc gccgacggcc    900
ggcccgagga gctgggctcg cagctgacgt actaccacga gctgctccat gaggcccgcc    960
tgagcaccga cggcatcgat gcgctggtcg aggccgcgct gaaggcaggc agcctcggag   1020
ccaagatcac cggcggtggt ctgggcggct gcatgatcgc acaggcccgg cccgaacagg   1080
cccgggaggt cacccggcag ctccacgagg ccggtgccgt acagacctgg gtcgtaccgc   1140
tgaaagggct cgacaaccat gcgcagtgaa cacccgacca cgaccgtgct ccagtcgcgg   1200
gagcagggca gcgcggccgg cgccaccgcg gtcgcgcacc caaacatcgc gctgatcaag   1260
tactggggca agcgcgacga gcggctgatc ctgccctgca ccaccagcct gtcgatgacg   1320
ctggacgtct tccccacgac caccgaggtc cggctcgacc ccgccgccga gcacgacacg   1380
gccgccctca acggcgaggt ggccacgggc gagacgctgc gccgcatcag cgccttcctc   1440
tccctggtgc gggaggtggc gggcagcgac cagcgggccg tggtggacac ccgcaacacc   1500
gtgcccaccg gggcgggcct ggcgtcctcc gccagcgggt tcgccgccct cgccgtcgcg   1560
gccgcggccg cctacgggct cgaactcgac gaccgcgggc tgtcccggct ggcccgacgt   1620
ggatccggct ccgcctcgcg gtcgatcttc ggcggcttcg ccgtctggca cgccggcccc   1680
gacggcacgg ccacggaagc ggacctcggc tcctacgccg agccggtgcc cgcggccgac   1740
ctcgacccgg cgctggtcat cgccgtggtc aacgccggcc ccaagcccgt ctccagccgc   1800
gaggccatgc gccgcaccgt cgacacctcg ccgctgtacc ggccgtgggc cgactccagt   1860
aaggacgacc tggacgagat gcgctcggcg ctgctgcgcg gcgacctcga ggccgtgggc   1920
gagatcgcgg agcgcaacgc gctcggcatg cacgccacca tgctggccgc ccgccccgcg   1980
gtgcggtacc tgtcgccggc cacggtcacc gtgctcgaca gcgtgctcca gctccgcaag   2040
gacggtgtcc tggcctacgc gaccatggac gccggtccca acgtgaaggt gctgtgccgg   2100
cgggcggacg ccgagcgggt ggccgacgtc gtacgcgccg ccgcgtccgg cggtcaggtc   2160
ctcgtcgccg ggccgggaga cggtgcccgc ctgctgagcg agggcgcatg acgacaggtc   2220
agcgcacgat cgtccggcac gcgccgggca agctgttcgt cgcgggcgag tacgcggtcg   2280
tggatccggg caacccggcg atcctggtag cggtcgaccg gcacatcagc gtcaccgtgt   2340
ccgacgccga cgcggacacc ggggccgccg acgtcgtgat ctcctccgac ctcggtccgc   2400
aggcggtcgg ctggcgctgg cacgacggcc ggctcgtcgt ccgcgacccg gacgacgggc   2460
agcaggcgcg cagcgccctg gcccacgtgg tgtcggcgat cgagaccgtg ggccggctgc   2520
tgggcgaacg cggacagaag gtccccgctc tcaccctctc cgtcagcagc cgcctgcacg   2580
aggacggccg gaagttcggc ctgggctcca gcggcgcggt gaccgtggcg accgtagccg   2640
```

-continued

```
ccgtcgccgc gttctgcgga ctcgaactgt ccaccgacga acggttccgg ctggccatgc   2700
tcgccaccgc ggaactcgac cccaagggct ccggcgggga cctcgccgcc agcacctggg   2760
gcggctggat cgcctaccag gcgcccgacc gggcctttgt gctcgacctg gcccggcgcg   2820
tgggagtcga ccggacactg aaggcgccct ggccggggca ctcggtgcgc cgactgccgg   2880
cgcccaaggg cctcaccctg gaggtcggct ggaccggaga gcccgcctcc accgcgtccc   2940
tggtgtccga tctgcaccgc cgcacctggc ggggcagcgc ctcccaccag aggttcgtcg   3000
agaccacgac cgactgtgtc cgctccgcgg tcaccgccct ggagtccggc gacgacacga   3060
gcctgctgca cgagatccgc cgggcccgcc aggagctggc ccgcctggac gacgaggtcg   3120
gcctcggcat cttcacaccc aagctgacgg cgctgtgcga cgccgccgaa gccgtcggcg   3180
gcgcggccaa gccctccggg gcaggcggcg gcgactgcgg catcgccctg ctggacgccg   3240
aggcgtcgcg ggacatcaca catgtacggc aacggtggga gacagccggg gtgctgcccc   3300
tgcccctgac tcctgccctg gaagggatct aagaatgacc agcgcccaac gcaaggacga   3360
ccacgtacgg ctcgccatcg agcagcacaa cgcccacagc ggacgcaacc agttcgacga   3420
cgtgtcgttc gtccaccacg ccctggccgg catcgaccgg ccggacgtgt ccctggccac   3480
gtccttcgcc gggatctcct ggcaggtgcc gatctacatc aacgcgatga ccggcggcag   3540
cgagaagacc ggcctcatca accgggacct ggccaccgcc gcccgcgaga ccggcgtccc   3600
catcgcgtcc gggtccatga acgcgtacat caaggacccc tcctgcgccg acacgttccg   3660
tgtgctgcgc gacgagaacc ccaacgggtt cgtcatcgcg aacatcaacg ccaccacgac   3720
ggtcgacaac gcgcagcgcg cgatcgacct gatcgaggcg aacgccctgc agatccacat   3780
caacacggcg caggagacgc cgatgccgga gggcgaccgg tcgttcgcgt cctgggtccc   3840
gcagatcgag aagatcgcgg cggccgtcga catccccgtg atcgtcaagg aggtcggcaa   3900
cggcctgagc cggcagacca tcctgctgct cgccgacctc ggcgtgcagg cggcggacgt   3960
cagcggccgc ggcggcacgg acttcgcccg catcgagaac ggccgccggg agctcggcga   4020
ctacgcgttc ctgcacggct gggggcagtc caccgccgcc tgcctgctgg acgcccagga   4080
catctccctg cccgtcctcg cctccggcgg tgtgcgtcac ccgctcgacg tggtccgcgc   4140
cctcgcgctc ggcgcccgcg ccgtcggctc ctccgccggc ttcctgcgca ccctgatgga   4200
cgacggcgtc gacgcgctga tcacgaagct cacgacctgg ctggaccagc tggcggcgct   4260
gcagaccatg ctcggcgcgc gcaccccggc cgacctcacc cgctgcgacg tgctgctcca   4320
cggcgagctg cgtgacttct gcgccgaccg gggcatcgac acgcgccgcc tcgcccagcg   4380
ctccagctcc atcgaggccc tccagacgac gggaagcaca cgatgacgga aacgcacgcc   4440
atagccgggg tcccgatgag gtgggtggga ccccttcgta tttccgggaa cgtcgccgag   4500
accgagaccc aggtcccgct cgccacgtac gagtcgccgc tgtggccgtc ggtgggccgc   4560
ggggcgaagg tctcccggct gacggagaag ggcatcgtcg ccaccctcgt cgacgagcgg   4620
atgacccgct cggtgatcgt cgaggcgacg gacgcgcaga ccgcgtacat ggccgcgcag   4680
accatccacg cccgcatcga cgagctgcgc gaggtggtgc gcggctgcag ccggttcgcc   4740
cagctgatca acatcaagca cgagatcaac gcgaacctgc tgttcatccg gttcgagttc   4800
accaccggtg acgcctccgg ccacaacatg gccacgctcg cctccgatgt gctcctgggg   4860
cacctgctgg agacgatccc tggcatctcc tacggctcga tctccggcaa ctactgcacg   4920
gacaagaagg ccaccgcgat caacggcatc ctcggccgcg gcaagaacgt gatcaccgag   4980
ctgctggtgc cgcgggacgt cgtcgagaac aacctgcaca ccacggctgc caagatcgtc   5040
```

```
gagctgaaca tccgcaagaa cctgctcggc accctgctcg ccggcggcat ccgctcggcc   5100

aacgcccact tcgcgaacat gctgctcggc ttctacctgg ccaccggcca ggacgccgcc   5160

aacatcgtcg agggctcgca gggcgtcgtc atggccgagg accgcgacgg cgacctctac   5220

ttcgcctgca ccctgccgaa cctgatcgtc ggcacggtcg gcaacggcaa gggtctcggc   5280

ttcgtggaga cgaacctcgc ccggctcggc tgccgagccg accgcgaacc cggggagaac   5340

gcccgccgcc tcgccgtcat cgcggcagcg accgtgctgt gcggtgaact ctcgctgctc   5400

gcggcacaga cgaacccggg cgaactcatg cgcgcgcacg tccagctgga acgcgacaac   5460

aagaccgcaa aggttggtgc atagggcatg tccatctcca taggcattca cgacctgtcg   5520

ttcgccacaa ccgagttcgt cctgccgcac acggcgctcg ccgagtacaa cggcaccgag   5580

atcggcaagt accacgtcgg catcggccag cagtcgatga gcgtgccggc cgccgacgag   5640

gacatcgtga ccatggccgc gaccgcggcg cggcccatca tcgagcgcaa cggcaagagc   5700

cggatccgca cggtcgtgtt cgccacggag tcgtcgatcg accaggcgaa ggcgggcggc   5760

gtgtacgtgc actccctgct ggggctggag tcggcctgcc gggtcgtcga gctgaagcag   5820

gcctgctacg gggccaccgc cgcccttcag ttcgccatcg gcctggtgcg gcgcgacccc   5880

gcccagcagg tcctggtcat cgccagtgac gtctccaagt acgagctgga cagccccggc   5940

gaggcgaccc agggcgcggc cgcggtggcc atgctggtcg gcgccgaccc ggccctgctg   6000

cgtatcgagg agccgtcggg cctgttcacc gccgacgtca tggacttctg gcggcccaac   6060

tacctcacca ccgctctggt cgacggccag gagtccatca acgcctacct gcaggccgtc   6120

gagggcgcct ggaaggacta cgcggagcag gacggccggt cgctggagga gttcgcggcg   6180

ttcgtctacc accagccgtt cacgaagatg gcctacaagg cgcaccgcca cctgctgaac   6240

ttcaacggct acgacaccga caaggacgcc atcgagggcg ccctcggcca gacgacggcg   6300

tacaacaacg tcatcggcaa cagctacacc gcgtcggtgt acctgggcct ggccgccctg   6360

ctcgaccagg cggacgacct gacgggccgt tccatcggct tcctgagcta cggctcgggc   6420

agcgtcgccg agttcttctc gggcaccgtc gtcgccgggt accgcgagcg tctgcgcacc   6480

gaggcgaacc aggaggcgat cgcccggcgc aagagcgtcg actacgccac ctaccgcgag   6540

ctgcacgagt acacgctccc gtccgacggc ggcgaccacg ccaccccggt gcagaccacc   6600

ggccccttcc ggctggccgg gatcaacgac cacaagcgca tctacgaggc gcgctagcga   6660

cacccctcgg caacggggtg cgccactgtt cggcgcaccc cgtgccgggc tttcgcacag   6720

ctattcacga ccatttgagg ggcgggcagc cgcatgaccg acgtccgatt ccgcattatc   6780

ggtacgggtg cctacgta                                                 6798
```

<210> SEQ ID NO 58
<211> LENGTH: 7693
<212> TYPE: DNA
<213> ORGANISM: Artificial Sequence
<220> FEATURE:
<223> OTHER INFORMATION: Operon containing A. thaliana and S. cerevisiae DNA

<400> SEQUENCE: 58

```
ggccgcgtcg acgccggcgg aggcacatat gtctcagaac gtttacattg tatcgactgc     60

cagaacccca attggttcat tccagggttc tctatcctcc aagacagcag tggaattggg    120

tgctgttgct ttaaaaggcg ccttggctaa ggttccagaa ttggatgcat ccaaggattt    180

tgacgaaatt atttttggta acgttctttc tgccaatttg ggccaagctc cggccagaca    240
```

-continued

```
agttgctttg gctgccggtt tgagtaatca tatcgttgca agcacagtta acaaggtctg    300
tgcatccgct atgaaggcaa tcattttggg tgctcaatcc atcaaatgtg gtaatgctga    360
tgttgtcgta gctggtggtt gtgaatctat gactaacgca ccatactaca tgccagcagc    420
ccgtgcgggt gccaaatttg gccaaactgt tcttgttgat ggtgtcgaaa gagatgggtt    480
gaacgatgcg tacgatggtc tagccatggg tgtacacgca gaaaagtgtg cccgtgattg    540
ggatattact agagaacaac aagacaattt tgccatcgaa tcctaccaaa aatctcaaaa    600
atctcaaaag gaaggtaaat tcgacaatga aattgtacct gttaccatta agggatttag    660
aggtaagcct gatactcaag tcacgaagga cgaggaacct gctagattac acgttgaaaa    720
attgagatct gcaaggactg ttttccaaaa agaaaacggt actgttactg ccgctaacgc    780
ttctccaatc aacgatggtg ctgcagccgt catcttggtt tccgaaaaag ttttgaagga    840
aaagaatttg aagcctttgg ctattatcaa aggttggggt gaggccgctc atcaaccagc    900
tgattttaca tgggctccat ctcttgcagt tccaaaggct ttgaaacatg ctggcatcga    960
agacatcaat tctgttgatt actttgaatt caatgaagcc ttttcggttg tcggtttggt   1020
gaacactaag attttgaagc tagacccatc taaggttaat gtatatggtg gtgctgttgc   1080
tctaggtcac ccattgggtt gttctggtgc tagagtggtt gttacactgc tatccatctt   1140
acagcaagaa ggaggtaaga tcggtgttgc cgccatttgt aatggtggtg gtggtgcttc   1200
ctctattgtc attgaaaaga tatgaggatc ctctagatgc gcaggaggca catatggcga   1260
agaacgttgg gattttggct atggatatct atttccctcc cacctgtgtt caacaggaag   1320
ctttggaagc acatgatgga gcaagtaaag ggaaatacac tattggactt ggccaagatt   1380
gtttagcttt ttgcactgag cttgaagatg ttatctctat gagtttcaat gcggtgacat   1440
cactttttga gaagtataag attgacccta accaaatcgg gcgtcttgaa gtaggaagtg   1500
agactgttat tgacaaaagc aagtccatca agaccttctt gatgcagctc tttgagaaat   1560
gtggaaacac tgatgtcgaa ggtgttgact cgaccaatgc ttgctatggt ggaactgcag   1620
ctttgttaaa ctgtgtcaat tgggttgaga gtaactcttg ggatggacgt tatggcctcg   1680
tcatttgtac tgacagcgcg gtttatgcag aaggacccgc aaggcccact ggaggagctg   1740
cagcgattgc tatgttgata ggtcctgatg ctcctatcgt tttcgaaagc aaattgagag   1800
caagccacat ggctcatgtc tatgactttt acaagcccaa tcttgctagc gagtacccgg   1860
ttgttgatgg taagctttca cagacttgct acctcatggc tcttgactcc tgctataaac   1920
atttatgcaa caagttcgag aagatcgagg gcaaagagtt ctccataaat gatgctgatt   1980
acattgtttt ccattctcca tacaataaac ttgtacagaa aagctttgct cgtctcttgt   2040
acaacgactt cttgagaaac gcaagctcca ttgacgaggc tgccaaagaa aagttcaccc   2100
cttattcatc tttgaccctt gacgagagtt accaaagccg tgatcttgaa aaggtgtcac   2160
aacaaattgc gaaaccgttt tatgatgcta aagtgcaacc aacgacttta ataccaaagg   2220
aagtcggtaa catgtacact gcttctctct acgctgcatt tgcttccctc atccacaaga   2280
aacacaatga tttggcggga aagcgggtgg ttatgttctc ttatggaagt ggctcaaccg   2340
caacaatgtt ctcattacgc ctcaacgaca ataagcctcc tttcagcatt tcaaacattg   2400
catctgtaat ggatgttggc ggtaaattga aagctagaca tgagtatgca cctgagaagt   2460
ttgtggagac aatgaagcta atggaacata ggtatggagc aaaggacttt gtgacaacca   2520
aggagggtat tatagatctt ttggcaccgg gaacttatta tctgaaagag gttgattcct   2580
```

-continued

```
tgtaccggag attctatggc aagaaaggtg aagatggatc tgtagccaat ggacactgag   2640
gatccgtcga gcacgtggag gcacatatgc aatgctgtga gatgcctgtt ggatacattc   2700
agattcctgt tgggattgct ggtccattgt tgcttgatgg ttatgagtac tctgttccta   2760
tggctacaac cgaaggttgt ttggttgcta gcactaacag aggctgcaag gctatgttta   2820
tctctggtgg cgccaccagt accgttctta aggacggtat gacccgagca cctgttgttc   2880
ggttcgcttc ggcgagacga gcttcggagc ttaagttttt cttggagaat ccagagaact   2940
ttgatacttt ggcagtagtc ttcaacaggt cgagtagatt tgcaagactg caaagtgtta   3000
aatgcacaat cgcggggaag aatgcttatg taaggttctg ttgtagtact ggtgatgcta   3060
tggggatgaa tatggtttct aaaggtgtgc agaatgttct tgagtatctt accgatgatt   3120
tccctgacat ggatgtgatt ggaatctctg gtaacttctg ttcggacaag aaacctgctg   3180
ctgtgaactg gattgaggga cgtggtaaat cagttgtttg cgaggctgta atcagaggag   3240
agatcgtgaa caaggtcttg aaaacgagcg tggctgcttt agtcgagctc aacatgctca   3300
agaacctagc tggctctgct gttgcaggct ctctaggtgg attcaacgct catgccagta   3360
acatagtgtc tgctgtattc atagctactg gccaagatcc agctcaaaac gtggagagtt   3420
ctcaatgcat caccatgatg gaagctatta atgacggcaa agatatccat atctcagtca   3480
ctatgccatc tatcgaggtg gggacagtgg gaggaggaac acagcttgca tctcaatcag   3540
cgtgtttaaa cctgctcgga gttaaaggag caagcacaga gtcgccggga atgaacgcaa   3600
ggaggctagc gacgatcgta gccggagcag ttttagctgg agagttatct ttaatgtcag   3660
caattgcagc tggacagctt gtgagaagtc acatgaaata caatagatcc agccgagaca   3720
tctctggagc aacgacaacg acaacaacaa caacatgacc cgggatccgg ccgcaggagg   3780
agttcatatg tcagagttga gagccttcag tgccccaggg aaagcgttac tagctggtgg   3840
atatttagtt ttagatacaa aatatgaagc atttgtagtc ggattatcgg caagaatgca   3900
tgctgtagcc catccttacg gttcattgca agggtctgat aagtttgaag tgcgtgtgaa   3960
aagtaaacaa tttaaagatg gggagtggct gtaccatata agtcctaaaa gtggcttcat   4020
tcctgtttcg ataggcggat ctaagaaccc tttcattgaa aaagttatcg ctaacgtatt   4080
tagctacttt aaacctaaca tggacgacta ctgcaataga aacttgttcg ttattgatat   4140
tttctctgat gatgcctacc attctcagga ggatagcgtt accgaacatc gtggcaacag   4200
aagattgagt tttcattcgc acagaattga agaagttccc aaaacagggc tgggctcctc   4260
ggcaggttta gtcacagttt taactacagc tttggcctcc ttttttgtat cggacctgga   4320
aaataatgta gacaaatata gagaagttat tcataattta gcacaagttg ctcattgtca   4380
agctcagggt aaaattggaa gcgggtttga tgtagcggcg gcagcatatg gatctatcag   4440
atatagaaga ttcccacccg cattaatctc taatttgcca gatattggaa gtgctactta   4500
cggcagtaaa ctggcgcatt tggttgatga agaagactgg aatattacga ttaaaagtaa   4560
ccatttacct tcgggattaa ctttatggat gggcgatatt aagaatggtt cagaaacagt   4620
aaaactggtc cagaaggtaa aaaattggta tgattcgcat atgccagaaa gcttgaaaat   4680
atatacagaa ctcgatcatg caaattctag atttatggat ggactatcta aactagatcg   4740
cttacacgag actcatgacg attacagcga tcagatattt gagtctcttg agaggaatga   4800
ctgtacctgt caaaagtatc ctgaaatcac agaagttaga gatgcagttg ccacaattag   4860
acgttccttt agaaaaataa ctaaagaatc tggtgccgat atcgaacctc ccgtacaaac   4920
tagcttattg gatgattgcc agaccttaaa aggagttctt acttgcttaa tacctggtgc   4980
```

-continued

```
tggtggttat gacgccattg cagtgattac taagcaagat gttgatctta gggctcaaac   5040
cgctaatgac aaaagatttt ctaaggttca atggctggat gtaactcagg ctgactgggg   5100
tgttaggaaa gaaaaagatc cggaaactta tcttgataaa ctgcaggagg agttttaatg   5160
tcattaccgt tcttaacttc tgcaccggga aaggttatta tttttggtga acactctgct   5220
gtgtacaaca agcctgccgt cgctgctagt gtgtctgcgt tgagaaccta cctgctaata   5280
agcgagtcat ctgcaccaga tactattgaa ttggacttcc cggacattag ctttaatcat   5340
aagtggtcca tcaatgattt caatgccatc accgaggatc aagtaaactc ccaaaaattg   5400
gccaaggctc aacaagccac cgatggcttg tctcaggaac tcgttagtct tttggatccg   5460
ttgttagctc aactatccga atccttccac taccatgcag cgttttgttt cctgtatatg   5520
tttgtttgcc tatgccccca tgccaagaat attaagtttt ctttaaagtc tactttaccc   5580
atcggtgctg ggttgggctc aagcgcctct atttctgtat cactggcctt agctatggcc   5640
tacttggggg ggttaatagg atctaatgac ttggaaaagc tgtcagaaaa cgataagcat   5700
atagtgaatc aatgggcctt cataggtgaa aagtgtattc acggtacccc ttcaggaata   5760
gataacgctg tggccactta tggtaatgcc ctgctatttg aaaaagactc acataatgga   5820
acaataaaca caaacaattt taagttctta gatgatttcc cagccattcc aatgatccta   5880
acctatacta gaattccaag gtctacaaaa gatcttgttg ctcgcgttcg tgtgttggtc   5940
accgagaaat ttcctgaagt tatgaagcca attctagatg ccatgggtga atgtgcccta   6000
caaggcttag agatcatgac taagttaagt aaatgtaaag gcaccgatga cgaggctgta   6060
gaaactaata atgaactgta tgaacaacta ttggaattga taagaataaa tcatggactg   6120
cttgtctcaa tcggtgtttc tcatcctgga ttagaactta ttaaaaatct gagcgatgat   6180
ttgagaattg gctccacaaa acttaccggt gctggtggcg gcggttgctc tttgactttg   6240
ttacgaagag acattactca agagcaaatt gacagcttca aaaagaaatt gcaagatgat   6300
tttagttacg agacatttga aacagacttg ggtgggactg gctgctgttt gttaagcgca   6360
aaaaatttga ataaagatct taaaatcaaa tccctagtat tccaattatt tgaaaataaa   6420
actaccacaa agcaacaaat tgacgatcta ttattgccag gaaacacgaa tttaccatgg   6480
acttcacagg aggagtttta atgactgtat atactgctag tgtaactgct ccggtaaata   6540
ttgctactct taagtattgg gggaaaaggg acacgaagtt gaatctgccc accaattcgt   6600
ccatatcagt gactttatcg caagatgacc tcagaacgtt gacctctgcg gctactgcac   6660
ctgagtttga acgcgacact ttgtggttaa atggagaacc acacagcatc gacaatgaaa   6720
gaactcaaaa ttgtctgcgc gacctacgcc aattaagaaa ggaaatggaa tcgaaggacg   6780
cctcattgcc cacattatct caatggaaac tccacattgt ctccgaaaat aactttccta   6840
cagcagctgg tttagcttcc tccgctgctg gctttgctgc attggtctct gcaattgcta   6900
agttatacca attaccacag tcaacttcag aaatatctag aatagcaaga aaggggtctg   6960
gttcagcttg tagatcgttg tttggcggat acgtggcctg ggaaatggga aaagctgaag   7020
atggtcatga ttccatggca gtacaaatcg cagacagctc tgactggcct cagatgaaag   7080
cttgtgtcct agttgtcagc gatattaaaa aggatgtgag ttccactcag ggtatgcaat   7140
tgaccgtggc aacctccgaa ctatttaaag aaagaattga acatgtcgta ccaaagagat   7200
ttgaagtcat gcgtaaagcc attgttgaaa aagatttcgc cacctttgca aaggaaacaa   7260
tgatggattc caactctttc catgccacat gtttggactc tttccctcca atattctaca   7320
```

-continued

```
tgaatgacac ttccaagcgt atcatcagtt ggtgccacac cattaatcag ttttacggag   7380

aaacaatcgt tgcatacacg tttgatgcag gtccaaatgc tgtgttgtac tacttagctg   7440

aaaatgagtc gaaactcttt gcatttatct ataaattgtt tggctctgtt cctggatggg   7500

acaagaaatt tactactgag cagcttgagg ctttcaacca tcaatttgaa tcatctaact   7560

ttactgcacg tgaattggat cttgagttgc aaaaggatgt tgccagagtg attttaactc   7620

aagtcggttc aggcccacaa gaaacaaacg aatctttgat tgacgcaaag actggtctac   7680

caaaggaata act                                                      7693
```

<210> SEQ ID NO 59
<211> LENGTH: 7695
<212> TYPE: DNA
<213> ORGANISM: Artificial Sequence
<220> FEATURE:
<223> OTHER INFORMATION: Operon B containing A. thaliana and S. cerevisiae DNA

<400> SEQUENCE: 59

```
ggccgcagga ggagttcata tgtcagagtt gagagccttc agtgccccag ggaaagcgtt     60

actagctggt ggatatttag ttttagatac aaaatatgaa gcatttgtag tcggattatc    120

ggcaagaatg catgctgtag cccatcctta cggttcattg caagggtctg ataagtttga    180

agtgcgtgtg aaaagtaaac aatttaaaga tggggagtgg ctgtaccata taagtcctaa    240

aagtggcttc attcctgttt cgataggcgg atctaagaac cctttcattg aaaaagttat    300

cgctaacgta tttagctact ttaaacctaa catggacgac tactgcaata gaaacttgtt    360

cgttattgat attttctctg atgatgccta ccattctcag gaggatagcg ttaccgaaca    420

tcgtggcaac agaagattga gttttcattc gcacagaatt gaagaagttc ccaaaacagg    480

gctgggctcc tcggcaggtt tagtcacagt tttaactaca gctttggcct cctttttttgt    540

atcggacctg gaaaataatg tagacaaata tagagaagtt attcataatt tagcacaagt    600

tgctcattgt caagctcagg gtaaaattgg aagcgggttt gatgtagcgg cggcagcata    660

tggatctatc agatatagaa gattcccacc cgcattaatc tctaatttgc cagatattgg    720

aagtgctact tacggcagta aactggcgca tttggttgat gaagaagact ggaatattac    780

gattaaaagt aaccatttac cttcgggatt aactttatgg atgggcgata ttaagaatgg    840

ttcagaaaca gtaaaactgg tccagaaggt aaaaaattgg tatgattcgc atatgccaga    900

aagcttgaaa atatatacag aactcgatca tgcaaattct agatttatgg atggactatc    960

taaactagat cgcttacacg agactcatga cgattacagc gatcagatat ttgagtctct   1020

tgagaggaat gactgtacct gtcaaaagta tcctgaaatc acagaagtta gagatgcagt   1080

tgccacaatt agacgttcct ttagaaaaat aactaaagaa tctggtgccg atatcgaacc   1140

tcccgtacaa actagcttat tggatgattg ccagacctta aaaggagttc ttacttgctt   1200

aatacctggt gctggtggtt atgacgccat tgcagtgatt actaagcaag atgttgatct   1260

tagggctcaa accgctaatg acaaaagatt ttctaaggtt caatggctgg atgtaactca   1320

ggctgactgg ggtgttagga aagaaaaaga tccggaaact tatcttgata aactgcagga   1380

ggagttttaa tgtcattacc gttcttaact tctgcaccgg gaaaggttat tatttttggt   1440

gaacactctg ctgtgtacaa caagcctgcc gtcgctgcta gtgtgtctgc gttgagaacc   1500

tacctgctaa taagcgagtc atctgcacca gatactattg aattggactt cccggacatt   1560

agctttaatc ataagtggtc catcaatgat ttcaatgcca tcaccgagga tcaagtaaac   1620
```

-continued

```
tcccaaaaat tggccaaggc tcaacaagcc accgatggct tgtctcagga actcgttagt   1680
cttttggatc cgttgttagc tcaactatcc gaatccttcc actaccatgc agcgttttgt   1740
ttcctgtata tgtttgtttg cctatgcccc catgccaaga atattaagtt ttctttaaag   1800
tctactttac ccatcggtgc tgggttgggc tcaagcgcct ctatttctgt atcactggcc   1860
ttagctatgg cctacttggg ggggttaata ggatctaatg acttggaaaa gctgtcagaa   1920
aacgataagc atatagtgaa tcaatgggcc ttcataggtg aaaagtgtat tcacggtacc   1980
ccttcaggaa tagataacgc tgtggccact tatggtaatg ccctgctatt tgaaaaagac   2040
tcacataatg gaacaataaa cacaaacaat tttaagttct tagatgattt cccagccatt   2100
ccaatgatcc taacctatac tagaattcca aggtctacaa aagatcttgt tgctcgcgtt   2160
cgtgtgttgg tcaccgagaa atttcctgaa gttatgaagc caattctaga tgccatgggt   2220
gaatgtgccc tacaaggctt agagatcatg actaagttaa gtaaatgtaa aggcaccgat   2280
gacgaggctg tagaaactaa taatgaactg tatgaacaac tattggaatt gataagaata   2340
aatcatggac tgcttgtctc aatcggtgtt tctcatcctg gattagaact tattaaaaat   2400
ctgagcgatg atttgagaat tggctccaca aaacttaccg gtgctggtgg cggcggttgc   2460
tctttgactt tgttacgaag agacattact caagagcaaa ttgacagctt caaaaagaaa   2520
ttgcaagatg attttagtta cgagacattt gaaacagact tgggtgggac tggctgctgt   2580
ttgttaagcg caaaaaattt gaataaagat cttaaaatca aatccctagt attccaatta   2640
tttgaaaata aaactaccac aaagcaacaa attgacgatc tattattgcc aggaaacacg   2700
aatttaccat ggacttcaga cgaggagttt taatgactgt atatactgct agtgtaactg   2760
ctccggtaaa tattgctact cttaagtatt gggggaaaag ggacacgaag ttgaatctgc   2820
ccaccaattc gtccatatca gtgactttat cgcaagatga cctcagaacg ttgacctctg   2880
cggctactgc acctgagttt gaacgcgaca ctttgtggtt aaatggagaa ccacacagca   2940
tcgacaatga aagaactcaa aattgtctgc gcgacctacg ccaattaaga aaggaaatgg   3000
aatcgaagga cgcctcattg cccacattat ctcaatggaa actccacatt gtctccgaaa   3060
ataactttcc tacagcagct ggtttagctt cctccgctgc tggctttgct gcattggtct   3120
ctgcaattgc taagttatac caattaccac agtcaacttc agaaatatct agaatagcaa   3180
gaaaggggtc tggttcagct tgtagatcgt tgtttggcgg atacgtggcc tgggaaatgg   3240
gaaaagctga agatggtcat gattccatgg cagtacaaat cgcagacagc tctgactggc   3300
ctcagatgaa agcttgtgtc ctagttgtca gcgatattaa aaaggatgtg agttccactc   3360
agggtatgca attgaccgtg gcaacctccg aactatttaa agaaagaatt gaacatgtcg   3420
taccaaagag atttgaagtc atgcgtaaag ccattgttga aaaagatttc gccacctttg   3480
caaaggaaac aatgatggat tccaactctt tccatgccac atgtttggac tctttccctc   3540
caatattcta catgaatgac acttccaagc gtatcatcag ttggtgccac accattaatc   3600
agttttacgg agaaacaatc gttgcataca cgtttgatgc aggtccaaat gctgtgttgt   3660
actacttagc tgaaaatgag tcgaaactct ttgcatttat ctataaattg tttggctctg   3720
ttcctggatg ggacaagaaa tttactactg agcagcttga ggctttcaac catcaatttg   3780
aatcatctaa ctttactgca cgtgaattgg atcttgagtt gcaaaaggat gttgccagag   3840
tgattttaac tcaagtcggt tcaggcccac aagaaacaaa cgaatctttg attgacgcaa   3900
agactggtct accaaaggaa gaggagtttt aactcgacgc cggcggaggc acatatgtct   3960
cagaacgttt acattgtatc gactgccaga accccaattg gttcattcca gggttctcta   4020
```

-continued

```
tcctccaaga cagcagtgga attgggtgct gttgctttaa aaggcgcctt ggctaaggtt   4080
ccagaattgg atgcatccaa ggattttgac gaaattattt ttggtaacgt tctttctgcc   4140
aatttgggcc aagctccggc cagacaagtt gctttggctg ccggtttgag taatcatatc   4200
gttgcaagca cagttaacaa ggtctgtgca tccgctatga aggcaatcat tttgggtgct   4260
caatccatca aatgtggtaa tgctgatgtt gtcgtagctg gtggttgtga atctatgact   4320
aacgcaccat actacatgcc agcagcccgt gcgggtgcca aatttggcca aactgttctt   4380
gttgatggtg tcgaaagaga tgggttgaac gatgcgtacg atggtctagc catgggtgta   4440
cacgcagaaa agtgtgcccg tgattgggat attactagag aacaacaaga caattttgcc   4500
atcgaatcct accaaaaatc tcaaaaatct caaaaggaag gtaaattcga caatgaaatt   4560
gtacctgtta ccattaaggg atttagaggt aagcctgata ctcaagtcac gaaggacgag   4620
gaacctgcta gattacacgt tgaaaaattg agatctgcaa ggactgtttt ccaaaaagaa   4680
aacggtactg ttactgccgc taacgcttct ccaatcaacg atggtgctgc agccgtcatc   4740
ttggtttccg aaaaagtttt gaaggaaaag aatttgaagc ctttggctat tatcaaaggt   4800
tggggtgagg ccgctcatca accagctgat tttacatggg ctccatctct tgcagttcca   4860
aaggctttga aacatgctgg catcgaagac atcaattctg ttgattactt tgaattcaat   4920
gaagcctttt cggttgtcgg tttggtgaac actaagattt tgaagctaga cccatctaag   4980
gttaatgtat atggtggtgc tgttgctcta ggtcacccat tgggttgttc tggtgctaga   5040
gtggttgtta cactgctatc catcttacag caagaaggag gtaagatcgg tgttgccgcc   5100
atttgtaatg gtggtggtgg tgcttcctct attgtcattg aaaagatatg aggatcctct   5160
agatgcgcag gaggcacata tggcgaagaa cgttgggatt ttggctatgg atatctattt   5220
ccctcccacc tgtgttcaac aggaagcttt ggaagcacat gatggagcaa gtaaagggaa   5280
atacactatt ggacttggcc aagattgttt agctttttgc actgagcttg aagatgttat   5340
ctctatgagt ttcaatgcgg tgacatcact tttgagaaag tataagattg accctaacca   5400
aatcgggcgt cttgaagtag gaagtgagac tgttattgac aaaagcaagt ccatcaagac   5460
cttcttgatg cagctctttg agaaatgtgg aaacactgat gtcgaaggtg ttgactcgac   5520
caatgcttgc tatggtggaa ctgcagcttt gttaaactgt gtcaattggg ttgagagtaa   5580
ctcttgggat ggacgttatg gcctcgtcat ttgtactgac agcgcggttt atgcagaagg   5640
acccgcaagg cccactggag gagctgcagc gattgctatg ttgataggac ctgatgctcc   5700
tatcgttttc gaaagcaaat tgagagcaag ccacatggct catgtctatg acttttacaa   5760
gcccaatctt gctagcgagt acccggttgt tgatggtaag ctttcacaga cttgctacct   5820
catggctctt gactcctgct ataaacattt atgcaacaag ttcgagaaga tcgagggcaa   5880
agagttctcc ataaatgatg ctgattacat tgttttccat tctccataca ataaacttgt   5940
acagaaaagc tttgctcgtc tcttgtacaa cgacttcttg agaaacgcaa gctccattga   6000
cgaggctgcc aaagaaaagt tcacccctta ttcatctttg acccttgacg agagttacca   6060
aagccgtgat cttgaaaagg tgtcacaaca aatttcgaaa ccgttttatg atgctaaagt   6120
gcaaccaacg actttaatac caaaggaagt cggtaacatg tacactgctt ctctctacgc   6180
tgcatttgct tccctcatcc acaataaaca caatgatttg gcgggaaagc gggtggttat   6240
gttctcttat ggaagtggct ccaccgcaac aatgttctca ttacgcctca acgacaataa   6300
gcctcctttc agcatttcaa acattgcatc tgtaatggat gttggcggta aattgaaagc   6360
```

-continued

```
tagacatgag tatgcacctg agaagtttgt ggagacaatg aagctaatgg aacataggta   6420

tggagcaaag gactttgtga caaccaagga gggtattata gatcttttgg caccgggaac   6480

ttattatctg aaagaggttg attccttgta ccggagattc tatggcaaga aaggtgaaga   6540

tggatctgta gccaatggac actgaggatc cgtcgagcac gtggaggcac atatgcaatg   6600

ctgtgagatg cctgttggat acattcagat tcctgttggg attgctggtc cattgttgct   6660

tgatggttat gagtactctg ttcctatggc tacaaccgaa ggttgtttgg ttgctagcac   6720

taacagaggc tgcaaggcta tgtttatctc tggtggcgcc accagtaccg ttcttaagga   6780

cggtatgacc cgagcacctg ttgttcggtt cgcttcggcg agacgagctt cggagcttaa   6840

gtttttcttg gagaatccag agaactttga tactttggca gtagtcttca acaggtcgag   6900

tagatttgca agactgcaaa gtgttaaatg cacaatcgcg ggaagaaatg cttatgtaag   6960

gttctgttgt agtactggtg atgctatggg gatgaatatg gtttctaaag gtgtgcagaa   7020

tgttcttgag tatcttaccg atgatttccc tgacatggat gtgattggaa tctctggtaa   7080

cttctgttcg gacaagaaac ctgctgctgt gaactggatt gagggacgtg gtaaatcagt   7140

tgtttgcgag gctgtaatca gaggagagat cgtgaacaag gtcttgaaaa cgagcgtggc   7200

tgctttagtc gagctcaaca tgctcaagaa cctagctggc tctgctgttg caggctctct   7260

aggtggattc aacgctcatg ccagtaacat agtgtctgct gtattcatag ctactggcca   7320

agatccagct caaaacgtgg agagttctca atgcatcacc atgatggaag ctattaatga   7380

cggcaaagat atccatatct cagtcactat gccatctatc gaggtgggga cagtgggagg   7440

aggaacacag cttgcatctc aatcagcgtg tttaaacctg ctcggagtta aaggagcaag   7500

cacagagtcg ccgggaatga acgcaaggag gctagcgacg atcgtagccg gagcagtttt   7560

agctggagag ttatctttaa tgtcagcaat tgcagctgga cagcttgtga gaagtcacat   7620

gaaatacaat agatccagcc gagacatctc tggagcaacg acaacgacaa caacaacaac   7680

atgacccggg atccg                                                    7695
```

```
<210> SEQ ID NO 60
<211> LENGTH: 8235
<212> TYPE: DNA
<213> ORGANISM: Artificial Sequence
<220> FEATURE:
<223> OTHER INFORMATION: Operon C containing A. thaliana, S. cerevisiae,
      and R. capsulatus DNA

<400> SEQUENCE: 60

ggccgcagga ggagttcata tgtcagagtt gagagccttc agtgccccag ggaaagcgtt     60

actagctggt ggatatttag ttttagatac aaaatatgaa gcatttgtag tcggattatc    120

ggcaagaatg catgctgtag cccatcctta cggttcattg caagggtctg ataagtttga    180

agtgcgtgtg aaaagtaaac aatttaaaga tggggagtgg ctgtaccata taagtcctaa    240

aagtggcttc attcctgttt cgataggcgg atctaagaac cctttcattg aaaaagttat    300

cgctaacgta tttagctact ttaaacctaa catggacgac tactgcaata gaaacttgtt    360

cgttattgat attttctctg atgatgccta ccattctcag gaggatagcg ttaccgaaca    420

tcgtggcaac agaagattga gttttcattc gcacagaatt gaagaagttc ccaaaacagg    480

gctgggctcc tcggcaggtt tagtcacagt tttaactaca gctttggcct cctttttgt     540

atcggacctg gaaaataatg tagacaaata tagagaagtt attcataatt tagcacaagt    600

tgctcattgt caagctcagg gtaaaattgg aagcgggttt gatgtagcgg cggcagcata    660
```

-continued

```
tggatctatc agatatagaa gattcccacc cgcattaatc tctaatttgc cagatattgg     720
aagtgctact tacggcagta aactggcgca tttggttgat gaagaagact ggaatattac     780
gattaaaagt aaccatttac cttcgggatt aactttatgg atgggcgata ttaagaatgg     840
ttcagaaaca gtaaaactgg tccagaaggt aaaaaattgg tatgattcgc atatgccaga     900
aagcttgaaa atatatacag aactcgatca tgcaaattct agatttatgg atggactatc     960
taaactagat cgcttacacg agactcatga cgattacagc gatcagatat ttgagtctct    1020
tgagaggaat gactgtacct gtcaaaagta tcctgaaatc acagaagtta gagatgcagt    1080
tgccacaatt agacgttcct ttagaaaaat aactaaagaa tctggtgccg atatcgaacc    1140
tcccgtacaa actagcttat tggatgattg ccagacctta aaggagttc ttacttgctt     1200
aatacctggt gctggtggtt atgacgccat tgcagtgatt actaagcaag atgttgatct    1260
tagggctcaa accgctaatg acaaaagatt ttctaaggtt caatggctgg atgtaactca    1320
ggctgactgg ggtgttagga aagaaaaaga tccggaaact tatcttgata aactgcagga    1380
ggagttttaa tgtcattacc gttcttaact tctgcaccgg gaaaggttat tatttttggt    1440
gaacactctg ctgtgtacaa caagcctgcc gtcgctgcta gtgtgtctgc gttgagaacc    1500
tacctgctaa taagcgagtc atctgcacca gatactattg aattggactt cccggacatt    1560
agctttaatc ataagtggtc catcaatgat ttcaatgcca tcaccgagga tcaagtaaac    1620
tcccaaaaat tggccaaggc tcaacaagcc accgatggct tgtctcagga actcgttagt    1680
cttttggatc cgttgttagc tcaactatcc gaatccttcc actaccatgc agcgttttgt    1740
ttcctgtata tgtttgtttg cctatgcccc catgccaaga atattaagtt ttctttaaag    1800
tctactttac ccatcggtgc tgggttgggc tcaagcgcct ctatttctgt atcactggcc    1860
ttagctatgg cctacttggg ggggttaata ggatctaatg acttggaaaa gctgtcagaa    1920
aacgataagc atatagtgaa tcaatgggcc ttcataggtg aaaagtgtat tcacggtacc    1980
ccttcaggaa tagataacgc tgtggccact tatggtaatg ccctgctatt tgaaaaagac    2040
tcacataatg gaacaataaa cacaaacaat tttaagttct tagatgattt cccagccatt    2100
ccaatgatcc taacctatac tagaattcca aggtctacaa aagatcttgt tgctcgcgtt    2160
cgtgtgttgg tcaccgagaa atttcctgaa gttatgaagc caattctaga tgccatgggt    2220
gaatgtgccc tacaaggctt agagatcatg actaagttaa gtaaatgtaa aggcaccgat    2280
gacgaggctg tagaaactaa taatgaactg tatgaacaac tattggaatt gataagaata    2340
aatcatggac tgcttgtctc aatcggtgtt tctcatcctg gattagaact tattaaaaat    2400
ctgagcgatg atttgagaat tggctccaca aaacttaccg gtgctggtgg cggcggttgc    2460
tctttgactt tgttacgaag agacattact caagagcaaa ttgacagctt caaaaagaaa    2520
ttgcaagatg attttagtta cgagacattt gaaacagact tgggtgggac tggctgctgt    2580
ttgttaagcg caaaaaattt gaataaagat cttaaaatca aatccctagt attccaatta    2640
tttgaaaata aaactaccac aaagcaacaa attgacgatc tattattgcc aggaaacacg    2700
aatttaccat ggacttcaga cgaggagttt taatgactgt atatactgct agtgtaactg    2760
ctccggtaaa tattgctact cttaagtatt gggggaaaag ggacacgaag ttgaatctgc    2820
ccaccaattc gtccatatca gtgactttat cgcaagatga cctcagaacg ttgacctctg    2880
cggctactgc acctgagttt gaacgcgaca ctttgtggtt aaatggagaa ccacacagca    2940
tcgacaatga aagaactcaa aattgtctgc gcgacctacg ccaattaaga aaggaaatgg    3000
aatcgaagga cgcctcattg cccacattat ctcaatggaa actccacatt gtctccgaaa    3060
```

-continued

```
ataactttcc tacagcagct ggtttagctt cctccgctgc tggctttgct gcattggtct   3120
ctgcaattgc taagttatac caattaccac agtcaacttc agaaatatct agaatagcaa   3180
gaaaggggtc tggttcagct tgtagatcgt tgtttggcgg atacgtggcc tgggaaatgg   3240
gaaaagctga agatggtcat gattccatgg cagtacaaat cgcagacagc tctgactggc   3300
ctcagatgaa agcttgtgtc ctagttgtca gcgatattaa aaaggatgtg agttccactc   3360
agggtatgca attgaccgtg gcaacctccg aactatttaa agaaagaatt gaacatgtcg   3420
taccaaagag atttgaagtc atgcgtaaag ccattgttga aaaagatttc gccacctttg   3480
caaaggaaac aatgatggat tccaactctt tccatgccac atgtttggac tctttccctc   3540
caatattcta catgaatgac acttccaagc gtatcatcag ttggtgccac accattaatc   3600
agttttacgg agaaacaatc gttgcataca cgtttgatgc aggtccaaat gctgtgttgt   3660
actacttagc tgaaaatgag tcgaaactct ttgcatttat ctataaattg tttggctctg   3720
ttcctggatg ggacaagaaa tttactactg agcagcttga ggctttcaac catcaatttg   3780
aatcatctaa ctttactgca cgtgaattgg atcttgagtt gcaaaaggat gttgccagag   3840
tgattttaac tcaagtcggt tcaggcccac aagaaacaaa cgaatctttg attgacgcaa   3900
agactggtct accaaaggaa gaggagtttt aactcgacgc cggcggaggc acatatgtct   3960
cagaacgttt acattgtatc gactgccaga accccaattg gttcattcca gggttctcta   4020
tcctccaaga cagcagtgga attgggtgct gttgctttaa aaggcgcctt ggctaaggtt   4080
ccagaattgg atgcatccaa ggattttgac gaaattattt ttggtaacgt tctttctgcc   4140
aatttgggcc aagctccggc cagacaagtt gctttggctg ccggtttgag taatcatatc   4200
gttgcaagca cagttaacaa ggtctgtgca tccgctatga aggcaatcat tttgggtgct   4260
caatccatca aatgtggtaa tgctgatgtt gtcgtagctg gtggttgtga atctatgact   4320
aacgcaccat actacatgcc agcagcccgt gcgggtgcca aatttggcca aactgttctt   4380
gttgatggtg tcgaaagaga tgggttgaac gatgcgtacg atggtctagc catgggtgta   4440
cacgcagaaa agtgtgcccg tgattgggat attactagag aacaacaaga caattttgcc   4500
atcgaatcct accaaaaatc tcaaaaatct caaaaggaag gtaaattcga caatgaaatt   4560
gtacctgtta ccattaaggg atttagaggt aagcctgata ctcaagtcac gaaggacgag   4620
gaacctgcta gattacacgt tgaaaaattg agatctgcaa ggactgtttt ccaaaaagaa   4680
aacggtactg ttactgccgc taacgcttct ccaatcaacg atggtgctgc agccgtcatc   4740
ttggtttccg aaaaagtttt gaaggaaaag aatttgaagc ctttggctat tatcaaaggt   4800
tggggtgagg ccgctcatca accagctgat tttacatggg ctccatctct tgcagttcca   4860
aaggctttga aacatgctgg catcgaagac atcaattctg ttgattactt tgaattcaat   4920
gaagcctttt cggttgtcgg tttggtgaac actaagattt tgaagctaga cccatctaag   4980
gttaatgtat atggtggtgc tgttgctcta ggtcacccat tgggttgttc tggtgctaga   5040
gtggttgtta cactgctatc catcttacag caagaaggag gtaagatcgg tgttgccgcc   5100
atttgtaatg gtggtggtgg tgcttcctct attgtcattg aaaagatatg aggatcctct   5160
agatgcgcag gaggcacata tggcgaagaa cgttgggatt ttggctatgg atatctattt   5220
ccctcccacc tgtgttcaac aggaagcttt ggaagcacat gatggagcaa gtaaagggaa   5280
atacactatt ggacttggcc aagattgttt agctttttgc actgagcttg aagatgttat   5340
ctctatgagt ttcaatgcgg tgacatcact tttgagaag tataagattg accctaacca   5400
```

-continued

```
aatcgggcgt cttgaagtag gaagtgagac tgttattgac aaaagcaagt ccatcaagac   5460
cttcttgatg cagctctttg agaaatgtgg aaacactgat gtcgaaggtg ttgactcgac   5520
caatgcttgc tatggtggaa ctgcagcttt gttaaactgt gtcaattggg ttgagagtaa   5580
ctcttgggat ggacgttatg gcctcgtcat ttgtactgac agcgcggttt atgcagaagg   5640
acccgcaagg cccactggag gagctgcagc gattgctatg ttgataggac ctgatgctcc   5700
tatcgttttc gaaagcaaat tgagagcaag ccacatggct catgtctatg acttttacaa   5760
gcccaatctt gctagcgagt acccggttgt tgatggtaag ctttcacaga cttgctacct   5820
catggctctt gactcctgct ataaacattt atgcaacaag ttcgagaaga tcgagggcaa   5880
agagttctcc ataaatgatg ctgattacat tgttttccat tctccataca ataaacttgt   5940
acagaaaagc tttgctcgtc tcttgtacaa cgacttcttg agaaacgcaa gctccattga   6000
cgaggctgcc aaagaaaagt tcacccctta ttcatctttg acccttgacg agagttacca   6060
aagccgtgat cttgaaaagg tgtcacaaca aatttcgaaa ccgttttatg atgctaaagt   6120
gcaaccaacg actttaatac caaaggaagt cggtaacatg tacactgctt ctctctacgc   6180
tgcatttgct tccctcatcc acaataaaca caatgatttg gcgggaaagc gggtggttat   6240
gttctcttat ggaagtggct ccaccgcaac aatgttctca ttacgcctca acgacaataa   6300
gcctcctttc agcatttcaa acattgcatc tgtaatggat gttggcggta aattgaaagc   6360
tagacatgag tatgcacctg agaagtttgt ggagacaatg aagctaatgg aacataggta   6420
tggagcaaag gactttgtga caaccaagga gggtattata gatcttttgg caccgggaac   6480
ttattatctg aaagaggttg attccttgta ccggagattc tatggcaaga aaggtgaaga   6540
tggatctgta gccaatggac actgaggatc cgtcgagcac gtggaggcac atatgcaatg   6600
ctgtgagatg cctgttggat acattcagat tcctgttggg attgctggtc cattgttgct   6660
tgatggttat gagtactctg ttcctatggc tacaaccgaa ggttgtttgg ttgctagcac   6720
taacagaggc tgcaaggcta tgtttatctc tggtggcgcc accagtaccg ttcttaagga   6780
cggtatgacc cgagcacctg ttgttcggtt cgcttcggcg agacgagctt cggagcttaa   6840
gtttttcttg gagaatccag agaactttga tactttggca gtagtcttca acaggtcgag   6900
tagatttgca agactgcaaa gtgttaaatg cacaatcgcg ggaagaaatg cttatgtaag   6960
gttctgttgt agtactggtg atgctatggg gatgaatatg gtttctaaag gtgtgcagaa   7020
tgttcttgag tatcttaccg atgatttccc tgacatggat gtgattggaa tctctggtaa   7080
cttctgttcg gacaagaaac ctgctgctgt gaactggatt gagggacgtg gtaaatcagt   7140
tgtttgcgag gctgtaatca gaggagagat cgtgaacaag gtcttgaaaa cgagcgtggc   7200
tgctttagtc gagctcaaca tgctcaagaa cctagctggc tctgctgttg caggctctct   7260
aggtggattc aacgctcatg ccagtaacat agtgtctgct gtattcatag ctactggcca   7320
agatccagct caaaacgtgg agagttctca atgcatcacc atgatggaag ctattaatga   7380
cggcaaagat atccatatct cagtcactat gccatctatc gaggtgggga cagtgggagg   7440
aggaacacag cttgcatctc aatcagcgtg tttaaacctg ctcggagtta aaggagcaag   7500
cacagagtcg ccgggaatga acgcaaggag gctagcgacg atcgtagccg gagcagtttt   7560
agctggagag ttatctttaa tgtcagcaat tgcagctgga cagcttgtga gaagtcacat   7620
gaaatacaat agatccagcc gagacatctc tggagcaacg acaacgacaa caacaacaac   7680
atgacccgta aggaggcaca tatgagtgag cttatacccg cctgggttgg tgacagactg   7740
gctccggtgg acaagttgga ggtgcatttg aaagggctcc gccacaaggc ggtgtctgtt   7800
```

-continued

```
ttcgtcatgg atggcgaaaa cgtgctgatc cagcgccgct cggaggagaa atatcactct   7860

cccgggcttt gggcgaacac ctgctgcacc catccgggct ggaccgaacg ccccgaggaa   7920

tgcgcggtgc ggcggctgcg cgaggagctg gggatcaccg ggctttatcc cgcccatgcc   7980

gaccggctgg aatatcgcgc cgatgtcggc ggcggcatga tcgagcatga ggtggtcgac   8040

atctatctgg cctatgccaa accgcatatg cggatcaccc ccgatccgcg cgaagtggcc   8100

gaggtgcgct ggatcggcct ttacgatctg gcggccgagg ccggtcggca tcccgagcgg   8160

ttctcgaaat ggctcaacat ctatctgtcg agccatcttg accggatttt cggatcgatc   8220

ctgcgcggct gagcg                                                    8235
```

<210> SEQ ID NO 61
<211> LENGTH: 7681
<212> TYPE: DNA
<213> ORGANISM: Artificial Sequence
<220> FEATURE:
<223> OTHER INFORMATION: Operon C containing A. thaliana, S. cerevisiae, and Streptomyces sp CL190 DNA, and R. capsulatus DNA

<400> SEQUENCE: 61

```
ggccgcgtcg actacggccg caggaggagt tcatatgtca gagttgagag ccttcagtgc     60

cccagggaaa gcgttactag ctggtggata tttagtttta gatacaaaat atgaagcatt    120

tgtagtcgga ttatcggcaa gaatgcatgc tgtagcccat ccttacggtt cattgcaagg    180

gtctgataag tttgaagtgc gtgtgaaaag taaacaattt aaagatgggg agtggctgta    240

ccatataagt cctaaaagtg gcttcattcc tgtttcgata ggcggatcta agaacccttt    300

cattgaaaaa gttatcgcta acgtatttag ctactttaaa cctaacatgg acgactactg    360

caatagaaac ttgttcgtta ttgatatttt ctctgatgat gcctaccatt ctcaggagga    420

tagcgttacc gaacatcgtg gcaacagaag attgagtttt cattcgcaca gaattgaaga    480

agttcccaaa acagggctgg gctcctcggc aggtttagtc acagttttaa ctacagcttt    540

ggcctccttt tttgtatcgg acctggaaaa taatgtagac aaatatagag aagttattca    600

taatttagca caagttgctc attgtcaagc tcagggtaaa attggaagcg ggtttgatgt    660

agcggcggca gcatatggat ctatcagata tagaagattc ccacccgcat taatctctaa    720

tttgccagat attggaagtg ctacttacgg cagtaaactg gcgcatttgg ttgatgaaga    780

agactggaat attacgatta aaagtaacca tttaccttcg ggattaactt tatggatggg    840

cgatattaag aatggttcag aaacagtaaa actggtccag aaggtaaaaa attggtatga    900

ttcgcatatg ccagaaagct tgaaaatata tacagaactc gatcatgcaa attctagatt    960

tatggatgga ctatctaaac tagatcgctt acacgagact catgacgatt acagcgatca   1020

gatatttgag tctcttgaga ggaatgactg tacctgtcaa aagtatcctg aaatcacaga   1080

agttagagat gcagttgcca caattagacg ttcctttaga aaaataacta aagaatctgg   1140

tgccgatatc gaacctcccg tacaaactag cttattggat gattgccaga ccttaaaagg   1200

agttcttact tgcttaatac ctggtgctgg tggttatgac gccattgcag tgattactaa   1260

gcaagatgtt gatcttaggg ctcaaaccgc taatgacaaa agattttcta aggttcaatg   1320

gctggatgta actcaggctg actggggtgt taggaaagaa aaagatccgg aaacttatct   1380

tgataaactg caggaggagt tttaatgtca ttaccgttct taacttctgc accgggaaag   1440

gttattattt ttggtgaaca ctctgctgtg tacaacaagc ctgccgtcgc tgctagtgtg   1500

tctgcgttga gaacctacct gctaataagc gagtcatctg caccagatac tattgaattg   1560
```

-continued

```
gacttcccgg acattagctt taatcataag tggtccatca atgatttcaa tgccatcacc   1620
gaggatcaag taaactccca aaaattggcc aaggctcaac aagccaccga tggcttgtct   1680
caggaactcg ttagtctttt ggatccgttg ttagctcaac tatccgaatc cttccactac   1740
catgcagcgt tttgtttcct gtatatgttt gtttgcctat gcccccatgc caagaatatt   1800
aagttttctt taaagtctac tttacccatc ggtgctgggt tgggctcaag cgcctctatt   1860
tctgtatcac tggccttagc tatggcctac ttgggggggt taataggatc taatgacttg   1920
gaaaagctgt cagaaaacga taagcatata gtgaatcaat gggccttcat aggtgaaaag   1980
tgtattcacg gtaccccttc aggaatagat aacgctgtgg ccacttatgg taatgccctg   2040
ctatttgaaa aagactcaca taatggaaca ataaacacaa acaattttaa gttcttagat   2100
gatttcccag ccattccaat gatcctaacc tatactagaa ttccaaggtc tacaaaagat   2160
cttgttgctc gcgttcgtgt gttggtcacc gagaaatttc ctgaagttat gaagccaatt   2220
ctagatgcca tgggtgaatg tgccctacaa ggcttagaga tcatgactaa gttaagtaaa   2280
tgtaaaggca ccgatgacga ggctgtagaa actaataatg aactgtatga acaactattg   2340
gaattgataa gaataaatca tggactgctt gtctcaatcg gtgtttctca tcctggatta   2400
gaacttatta aaaatctgag cgatgatttg agaattggct ccacaaaact taccggtgct   2460
ggtggcggcg gttgctcttt gactttgtta cgaagagaca ttactcaaga gcaaattgac   2520
agcttcaaaa agaaattgca agatgatttt agttacgaga catttgaaac agacttgggt   2580
gggactggct gctgtttgtt aagcgcaaaa aatttgaata aagatcttaa aatcaaatcc   2640
ctagtattcc aattatttga aaataaaact accacaaagc aacaaattga cgatctatta   2700
ttgccaggaa acacgaattt accatggact tcagacgagg agttttaatg actgtatata   2760
ctgctagtgt aactgctccg gtaaatattg ctactcttaa gtattggggg aaaagggaca   2820
cgaagttgaa tctgcccacc aattcgtcca tatcagtgac tttatcgcaa gatgacctca   2880
gaacgttgac ctctgcggct actgcacctg agtttgaacg cgacactttg tggttaaatg   2940
gagaaccaca cagcatcgac aatgaaagaa ctcaaaattg tctgcgcgac ctacgccaat   3000
taagaaagga aatggaatcg aaggacgcct cattgcccac attatctcaa tggaaactcc   3060
acattgtctc cgaaaataac tttcctacag cagctggttt agcttcctcc gctgctggct   3120
ttgctgcatt ggtctctgca attgctaagt tataccaatt accacagtca acttcagaaa   3180
tatctagaat agcaagaaag gggtctggtt cagcttgtag atcgttgttt ggcggatacg   3240
tggcctggga aatgggaaaa gctgaagatg gtcatgattc catggcagta caaatcgcag   3300
acagctctga ctggcctcag atgaaagctt gtgtcctagt tgtcagcgat attaaaaagg   3360
atgtgagttc cactcagggt atgcaattga ccgtggcaac ctccgaacta tttaaagaaa   3420
gaattgaaca tgtcgtacca aagagatttg aagtcatgcg taaagccatt gttgaaaaag   3480
atttcgccac ctttgcaaag gaaacaatga tggattccaa ctctttccat gccacatgtt   3540
tggactcttt ccctccaata ttctacatga atgacacttc caagcgtatc atcagttggt   3600
gccacaccat taatcagttt tacggagaaa caatcgttgc atacacgttt gatgcaggtc   3660
caaatgctgt gttgtactac ttagctgaaa atgagtcgaa actctttgca tttatctata   3720
aattgtttgg ctctgttcct ggatgggaca agaaatttac tactgagcag cttgaggctt   3780
tcaaccatca atttgaatca tctaacttta ctgcacgtga attggatctt gagttgcaaa   3840
aggatgttgc cagagtgatt ttaactcaag tcggttcagg cccacaagaa acaaacgaat   3900
```

-continued

```
ctttgattga cgcaaagact ggtctaccaa aggaagagga gttttaactc gagtaggagg   3960
cacatatgtc tcagaacgtt tacattgtat cgactgccag aaccccaatt ggttcattcc   4020
agggttctct atcctccaag acagcagtgg aattgggtgc tgttgcttta aaaggcgcct   4080
tggctaaggt tccagaattg gatgcatcca aggattttga cgaaattatt tttggtaacg   4140
ttctttctgc caatttgggc caagctccgg ccagacaagt tgctttggct gccggtttga   4200
gtaatcatat cgttgcaagc acagttaaca aggtctgtgc atccgctatg aaggcaatca   4260
ttttgggtgc tcaatccatc aaatgtggta atgctgatgt tgtcgtagct ggtggttgtg   4320
aatctatgac taacgcacca tactacatgc cagcagcccg tgcgggtgcc aaatttggcc   4380
aaactgttct tgttgatggt gtcgaaagag atgggttgaa cgatgcgtac gatggtctag   4440
ccatgggtgt acacgcagaa aagtgtgccc gtgattggga tattactaga gaacaacaag   4500
acaattttgc catcgaatcc taccaaaaat ctcaaaaatc tcaaaaggaa ggtaaattcg   4560
acaatgaaat tgtacctgtt accattaagg gatttagagg taagcctgat actcaagtca   4620
cgaaggacga ggaacctgct agattacacg ttgaaaaatt gagatctgca aggactgttt   4680
tccaaaaaga aaacggtact gttactgccg ctaacgcttc tccaatcaac gatggtgctg   4740
cagccgtcat cttggtttcc gaaaaagttt tgaaggaaaa gaatttgaag cctttggcta   4800
ttatcaaagg ttggggtgag gccgctcatc aaccagctga ttttacatgg gctccatctc   4860
ttgcagttcc aaaggctttg aaacatgctg gcatcgaaga catcaattct gttgattact   4920
ttgaattcaa tgaagccttt tcggttgtcg gtttggtgaa cactaagatt ttgaagctag   4980
acccatctaa ggttaatgta tatggtggtg ctgttgctct aggtcaccca ttgggttgtt   5040
ctggtgctag agtggttgtt acactgctat ccatcttaca gcaagaagga ggtaagatcg   5100
gtgttgccgc catttgtaat ggtggtggtg gtgcttcctc tattgtcatt gaaaagatat   5160
gaggatcctc tagatgcgca ggaggcacat atggcgaaga acgttgggat tttggctatg   5220
gatatctatt tccctcccac ctgtgttcaa caggaagctt tggaagcaca tgatggagca   5280
agtaaaggga aatacactat tggacttggc caagattgtt tagctttttg cactgagctt   5340
gaagatgtta tctctatgag tttcaatgcg gtgacatcac tttttgagaa gtataagatt   5400
gaccctaacc aaatcgggcg tcttgaagta ggaagtgaga ctgttattga caaaagcaag   5460
tccatcaaga ccttcttgat gcagctcttt gagaaatgtg gaaacactga tgtcgaaggt   5520
gttgactcga ccaatgcttg ctatggtgga actgcagctt tgttaaactg tgtcaattgg   5580
gttgagagta actcttggga tggacgttat ggcctcgtca tttgtactga cagcgcggtt   5640
tatgcagaag gacccgcaag gcccactgga ggagctgcag cgattgctat gttgatagga   5700
cctgatgctc ctatcgtttt cgaaagcaaa ttgagagcaa gccacatggc tcatgtctat   5760
gacttttaca agcccaatct tgctagcgag tacccggttg ttgatggtaa gctttcacag   5820
acttgctacc tcatggctct tgactcctgc tataaacatt tatgcaacaa gttcgagaag   5880
atcgagggca aagagttctc cataaatgat gctgattaca ttgttttcca ttctccatac   5940
aataaacttg tacagaaaag ctttgctcgt ctcttgtaca acgacttctt gagaaacgca   6000
agctccattg acgaggctgc caaagaaaag ttcacccctt attcatcttt gacccttgac   6060
gagagttacc aaagccgtga tcttgaaaag gtgtcacaac aaatttcgaa accgttttat   6120
gatgctaaag tgcaaccaac gactttaata ccaaaggaag tcggtaacat gtacactgct   6180
tctctctacg ctgcatttgc ttccctcatc cacaataaac acaatgattt ggcgggaaag   6240
cgggtggtta tgttctctta tggaagtggc tccaccgcaa caatgttctc attacgcctc   6300
```

aacgacaata agcctccttt cagcatttca aacattgcat ctgtaatgga tgttggcggt 6360
aaattgaaag ctagacatga gtatgcacct gagaagtttg tggagacaat gaagctaatg 6420
gaacataggt atggagcaaa ggactttgtg acaaccaagg agggtattat agatcttttg 6480
gcaccgggaa cttattatct gaaagaggtt gattccttgt accggagatt ctatggcaag 6540
aaaggtgaag atggatctgt agccaatgga cactgaggat ccgtcgactc gagcacgtga 6600
ggaggcacat atgacggaaa cgcacgccat agccggggtc ccgatgaggt gggtgggacc 6660
ccttcgtatt tccgggaacg tcgccgagac cgagacccag gtcccgctcg ccacgtacga 6720
gtcgccgctg tggccgtcgg tgggccgcgg ggcgaaggtc tcccggctga cggagaaggg 6780
catcgtcgcc accctcgtcg acgagcggat gacccgctcg gtgatcgtcg aggcgacgga 6840
cgcgcagacc gcgtacatgg ccgcgcagac catccacgcc cgcatcgacg agctgcgcga 6900
ggtggtgcgc ggctgcagcc ggttcgccca gctgatcaac atcaagcacg agatcaacgc 6960
gaacctgctg ttcatccggt tcgagttcac caccggtgac gcctccggcc acaacatggc 7020
cacgctcgcc tccgatgtgc tcctggggca cctgctggag acgatccctg gcatctccta 7080
cggctcgatc tccggcaact actgcacgga caagaaggcc accgcgatca acggcatcct 7140
cggccgcggc aagaacgtga tcaccgagct gctggtgccg cgggacgtcg tcgagaacaa 7200
cctgcacacc acggctgcca agatcgtcga gctgaacatc cgcaagaacc tgctcggcac 7260
cctgctcgcc ggcggcatcc gctcggccaa cgcccacttc gcgaacatgc tgctcggctt 7320
ctacctggcc accggccagg acgccgccaa catcgtcgag ggctcgcagg gcgtcgtcat 7380
ggccgaggac cgcgacggcg acctctactt cgcctgcacc ctgccgaacc tgatcgtcgg 7440
cacggtcggc aacggcaagg gtctcggctt cgtggagacg aacctcgccc ggctcggctg 7500
ccgagccgac cgcgaacccg gggagaacgc ccgccgcctc gccgtcatcg cggcagcgac 7560
cgtgctgtgc ggtgaactct cgctgctcgc ggcacagacg aacccgggcg aactcatgcg 7620
cgcgcacgtc cagctggaac gcgacaacaa gaccgcaaag gttggtgcat agacgcgtgc 7680
g 7681

<210> SEQ ID NO 62
<211> LENGTH: 8224
<212> TYPE: DNA
<213> ORGANISM: Artificial Sequence
<220> FEATURE:
<223> OTHER INFORMATION: Operon E containing A. thaliana, S. cerevesiae, Steptomyces sp CL190 DNA, and R. capsulatus

<400> SEQUENCE: 62
ggccgcgtcg actacggccg caggaggagt tcatatgtca gagttgagag ccttcagtgc 60
cccagggaaa gcgttactag ctggtggata tttagtttta gatacaaaat atgaagcatt 120
tgtagtcgga ttatcggcaa gaatgcatgc tgtagcccat ccttacggtt cattgcaagg 180
gtctgataag tttgaagtgc gtgtgaaaag taaacaattt aaagatgggg agtggctgta 240
ccatataagt cctaaaagtg gcttcattcc tgtttcgata ggcggatcta agaacccttt 300
cattgaaaaa gttatcgcta acgtatttag ctactttaaa cctaacatgg acgactactg 360
caatagaaac ttgttcgtta ttgatatttt ctctgatgat gcctaccatt ctcaggagga 420
tagcgttacc gaacatcgtg gcaacagaag attgagtttt cattcgcaca gaattgaaga 480
agttcccaaa acagggctgg gctcctcggc aggtttagtc acagttttaa ctacagcttt 540
ggcctccttt tttgtatcgg acctggaaaa taatgtagac aaatatagag aagttattca 600

```
taatttagca caagttgctc attgtcaagc tcagggtaaa attggaagcg ggtttgatgt    660
agcggcggca gcatatggat ctatcagata tagaagattc ccacccgcat taatctctaa    720
tttgccagat attggaagtg ctacttacgg cagtaaactg gcgcatttgg ttgatgaaga    780
agactggaat attacgatta aaagtaacca tttaccttcg ggattaactt tatggatggg    840
cgatattaag aatggttcag aaacagtaaa actggtccag aaggtaaaaa attggtatga    900
ttcgcatatg ccagaaagct tgaaaatata tacagaactc gatcatgcaa attctagatt    960
tatggatgga ctatctaaac tagatcgctt acacgagact catgacgatt acagcgatca   1020
gatatttgag tctcttgaga ggaatgactg tacctgtcaa aagtatcctg aaatcacaga   1080
agttagagat gcagttgcca caattagacg ttcctttaga aaaataacta aagaatctgg   1140
tgccgatatc gaacctcccg tacaaactag cttattggat gattgccaga ccttaaaagg   1200
agttcttact tgcttaatac ctggtgctgg tggttatgac gccattgcag tgattactaa   1260
gcaagatgtt gatcttaggg ctcaaaccgc taatgacaaa agattttcta aggttcaatg   1320
gctggatgta actcaggctg actggggtgt taggaaagaa aaagatccgg aaacttatct   1380
tgataaactg caggaggagt tttaatgtca ttaccgttct taacttctgc accgggaaag   1440
gttattattt ttggtgaaca ctctgctgtg tacaacaagc ctgccgtcgc tgctagtgtg   1500
tctgcgttga gaacctacct gctaataagc gagtcatctg caccagatac tattgaattg   1560
gacttcccgg acattagctt taatcataag tggtccatca atgatttcaa tgccatcacc   1620
gaggatcaag taaactccca aaaattggcc aaggctcaac aagccaccga tggcttgtct   1680
caggaactcg ttagtctttt ggatccgttg ttagctcaac tatccgaatc cttccactac   1740
catgcagcgt tttgtttcct gtatatgttt gtttgcctat gcccccatgc caagaatatt   1800
aagttttctt taaagtctac tttacccatc ggtgctgggt tgggctcaag cgcctctatt   1860
tctgtatcac tggccttagc tatggcctac ttgggggggt taataggatc taatgacttg   1920
gaaaagctgt cagaaaacga taagcatata gtgaatcaat gggccttcat aggtgaaaag   1980
tgtattcacg gtaccccttc aggaatagat aacgctgtgg ccacttatgg taatgccctg   2040
ctatttgaaa aagactcaca taatggaaca ataaacacaa acaattttaa gttcttagat   2100
gatttcccag ccattccaat gatcctaacc tatactagaa ttccaaggtc tacaaaagat   2160
cttgttgctc gcgttcgtgt gttggtcacc gagaaatttc ctgaagttat gaagccaatt   2220
ctagatgcca tgggtgaatg tgccctacaa ggcttagaga tcatgactaa gttaagtaaa   2280
tgtaaaggca ccgatgacga ggctgtagaa actaataatg aactgtatga acaactattg   2340
gaattgataa gaataaatca tggactgctt gtctcaatcg gtgtttctca tcctggatta   2400
gaacttatta aaaatctgag cgatgatttg agaattggct ccacaaaact taccggtgct   2460
ggtggcggcg gttgctcttt gactttgtta cgaagagaca ttactcaaga gcaaattgac   2520
agcttcaaaa agaaattgca agatgatttt agttacgaga catttgaaac agacttgggt   2580
gggactggct gctgtttgtt aagcgcaaaa aatttgaata aagatcttaa aatcaaatcc   2640
ctagtattcc aattatttga aaataaaact accacaaagc aacaaattga cgatctatta   2700
ttgccaggaa acacgaattt accatggact tcagacgagg agttttaatg actgtatata   2760
ctgctagtgt aactgctccg gtaaatattg ctactcttaa gtattggggg aaaagggaca   2820
cgaagttgaa tctgcccacc aattcgtcca tatcagtgac tttatcgcaa gatgacctca   2880
gaacgttgac ctctgcggct actgcacctg agtttgaacg cgacactttg tggttaaatg   2940
```

-continued

```
gagaaccaca cagcatcgac aatgaaagaa ctcaaaattg tctgcgcgac ctacgccaat   3000
taagaaagga aatggaatcg aaggacgcct cattgcccac attatctcaa tggaaactcc   3060
acattgtctc cgaaaataac tttcctacag cagctggttt agcttcctcc gctgctggct   3120
ttgctgcatt ggtctctgca attgctaagt tataccaatt accacagtca acttcagaaa   3180
tatctagaat agcaagaaag gggtctggtt cagcttgtag atcgttgttt ggcggatacg   3240
tggcctggga aatgggaaaa gctgaagatg gtcatgattc catggcagta caaatcgcag   3300
acagctctga ctggcctcag atgaaagctt gtgtcctagt tgtcagcgat attaaaaagg   3360
atgtgagttc cactcagggt atgcaattga ccgtggcaac ctccgaacta tttaaagaaa   3420
gaattgaaca tgtcgtacca aagagatttg aagtcatgcg taaagccatt gttgaaaaag   3480
atttcgccac ctttgcaaag gaaacaatga tggattccaa ctctttccat gccacatgtt   3540
tggactcttt ccctccaata ttctacatga atgacacttc caagcgtatc atcagttggt   3600
gccacaccat taatcagttt tacggagaaa caatcgttgc atacacgttt gatgcaggtc   3660
caaatgctgt gttgtactac ttagctgaaa atgagtcgaa actctttgca tttatctata   3720
aattgtttgg ctctgttcct ggatgggaca agaaatttac tactgagcag cttgaggctt   3780
tcaaccatca atttgaatca tctaacttta ctgcacgtga attggatctt gagttgcaaa   3840
aggatgttgc cagagtgatt ttaactcaag tcggttcagg cccacaagaa acaaacgaat   3900
ctttgattga cgcaaagact ggtctaccaa aggaagagga gttttaactc gagtaggagg   3960
cacatatgtc tcagaacgtt tacattgtat cgactgccag aaccccaatt ggttcattcc   4020
agggttctct atcctccaag acagcagtgg aattgggtgc tgttgcttta aaaggcgcct   4080
tggctaaggt tccagaattg gatgcatcca aggattttga cgaaattatt tttggtaacg   4140
ttctttctgc caatttgggc caagctccgg ccagacaagt tgctttggct gccggtttga   4200
gtaatcatat cgttgcaagc acagttaaca aggtctgtgc atccgctatg aaggcaatca   4260
ttttgggtgc tcaatccatc aaatgtggta atgctgatgt tgtcgtagct ggtggttgtg   4320
aatctatgac taacgcacca tactacatgc cagcagcccg tgcgggtgcc aaatttggcc   4380
aaactgttct tgttgatggt gtcgaaagag atgggttgaa cgatgcgtac gatggtctag   4440
ccatgggtgt acacgcagaa aagtgtgccc gtgattggga tattactaga gaacaacaag   4500
acaattttgc catcgaatcc taccaaaaat ctcaaaaatc tcaaaaggaa ggtaaattcg   4560
acaatgaaat tgtacctgtt accattaagg gatttagagg taagcctgat actcaagtca   4620
cgaaggacga ggaacctgct agattacacg ttgaaaaatt gagatctgca aggactgttt   4680
tccaaaaaga aaacggtact gttactgccg ctaacgcttc tccaatcaac gatggtgctg   4740
cagccgtcat cttggtttcc gaaaaagttt tgaaggaaaa gaatttgaag cctttggcta   4800
ttatcaaagg ttggggtgag gccgctcatc aaccagctga ttttacatgg gctccatctc   4860
ttgcagttcc aaaggctttg aaacatgctg gcatcgaaga catcaattct gttgattact   4920
ttgaattcaa tgaagccttt tcggttgtcg gtttggtgaa cactaagatt ttgaagctag   4980
acccatctaa ggttaatgta tatggtggtg ctgttgctct aggtcaccca ttgggttgtt   5040
ctggtgctag agtggttgtt acactgctat ccatcttaca gcaagaagga ggtaagatcg   5100
gtgttgccgc catttgtaat ggtggtggtg gtgcttcctc tattgtcatt gaaaagatat   5160
gaggatcctc tagatgcgca ggaggcacat atggcgaaga acgttgggat tttggctatg   5220
gatatctatt tccctcccac ctgtgttcaa caggaagctt tggaagcaca tgatggagca   5280
agtaaaggga aatacactat tggacttggc caagattgtt tagctttttg cactgagctt   5340
```

```
gaagatgtta tctctatgag tttcaatgcg gtgacatcac tttttgagaa gtataagatt   5400

gaccctaacc aaatcgggcg tcttgaagta ggaagtgaga ctgttattga caaaagcaag   5460

tccatcaaga ccttcttgat gcagctcttt gagaaatgtg gaaacactga tgtcgaaggt   5520

gttgactcga ccaatgcttg ctatggtgga actgcagctt tgttaaactg tgtcaattgg   5580

gttgagagta actcttggga tggacgttat ggcctcgtca tttgtactga cagcgcggtt   5640

tatgcagaag gacccgcaag gcccactgga ggagctgcag cgattgctat gttgatagga   5700

cctgatgctc ctatcgtttt cgaaagcaaa ttgagagcaa gccacatggc tcatgtctat   5760

gacttttaca agcccaatct tgctagcgag tacccggttg ttgatggtaa gctttcacag   5820

acttgctacc tcatggctct tgactcctgc tataaacatt tatgcaacaa gttcgagaag   5880

atcgagggca aagagttctc cataaatgat gctgattaca ttgttttcca ttctccatac   5940

aataaacttg tacagaaaag ctttgctcgt ctcttgtaca acgacttctt gagaaacgca   6000

agctccattg acgaggctgc caaagaaaag ttcacccctt attcatcttt gacccttgac   6060

gagagttacc aaagccgtga tcttgaaaag gtgtcacaac aaatttcgaa accgttttat   6120

gatgctaaag tgcaaccaac gactttaata ccaaaggaag tcggtaacat gtacactgct   6180

tctctctacg ctgcatttgc ttccctcatc cacaataaac acaatgattt ggcgggaaag   6240

cgggtggtta tgttctctta tggaagtggc tccaccgcaa caatgttctc attacgcctc   6300

aacgacaata agcctccttt cagcatttca aacattgcat ctgtaatgga tgttggcggt   6360

aaattgaaag ctagacatga gtatgcacct gagaagtttg tggagacaat gaagctaatg   6420

gaacataggt atggagcaaa ggactttgtg acaaccaagg agggtattat agatcttttg   6480

gcaccgggaa cttattatct gaaagaggtt gattccttgt accggagatt ctatggcaag   6540

aaaggtgaag atggatctgt agccaatgga cactgaggat ccgtcgactc gagcacgtga   6600

ggaggcacat atgacggaaa cgcacgccat agccggggtc ccgatgaggt gggtgggacc   6660

ccttcgtatt tccgggaacg tcgccgagac cgagacccag gtcccgctcg ccacgtacga   6720

gtcgccgctg tggccgtcgg tgggccgcgg ggcgaaggtc tcccggctga cggagaaggg   6780

catcgtcgcc accctcgtcg acgagcggat gacccgctcg gtgatcgtcg aggcgacgga   6840

cgcgcagacc gcgtacatgg ccgcgcagac catccacgcc cgcatcgacg agctgcgcga   6900

ggtggtgcgc ggctgcagcc ggttcgccca gctgatcaac atcaagcacg agatcaacgc   6960

gaacctgctg ttcatccggt tcgagttcac caccggtgac gcctccggcc acaacatggc   7020

cacgctcgcc tccgatgtgc tcctggggca cctgctggag acgatccctg gcatctccta   7080

cggctcgatc tccggcaact actgcacgga caagaaggcc accgcgatca acggcatcct   7140

cggccgcggc aagaacgtga tcaccgagct gctggtgccg cgggacgtcg tcgagaacaa   7200

cctgcacacc acggctgcca agatcgtcga gctgaacatc cgcaagaacc tgctcggcac   7260

cctgctcgcc ggcggcatcc gctcggccaa cgcccacttc gcgaacatgc tgctcggctt   7320

ctacctggcc accggccagg acgccgccaa catcgtcgag ggctcgcagg gcgtcgtcat   7380

ggccgaggac cgcgacggcg acctctactt cgcctgcacc ctgccgaacc tgatcgtcgg   7440

cacggtcggc aacggcaagg gtctcggctt cgtggagacg aacctcgccc ggctcggctg   7500

ccgagccgac cgcgaacccg gggagaacgc ccgccgcctc gccgtcatcg cggcagcgac   7560

cgtgctgtgc ggtgaactct cgctgctcgc ggcacagacg aacccgggcg aactcatgcg   7620

cgcgcacgtc cagctggaac gcgacaacaa gaccgcaaag gttggtgcat agacgcggta   7680
```

```
aggaggcaca tatgagtgag cttatacccg cctgggttgg tgacagactg gctccggtgg   7740

acaagttgga ggtgcatttg aaagggctcc gccacaaggc ggtgtctgtt ttcgtcatgg   7800

atggcgaaaa cgtgctgatc cagcgccgct cggaggagaa atatcactct cccgggcttt   7860

gggcgaacac ctgctgcacc catccgggct ggaccgaacg ccccgaggaa tgcgcggtgc   7920

ggcggctgcg cgaggagctg gggatcaccg ggctttatcc cgcccatgcc gaccggctgg   7980

aatatcgcgc cgatgtcggc ggcggcatga tcgagcatga ggtggtcgac atctatctgg   8040

cctatgccaa accgcatatg cggatcaccc ccgatccgcg cgaagtggcc gaggtgcgct   8100

ggatcggcct ttacgatctg gcggccgagg ccggtcggca tcccgagcgg ttctcgaaat   8160

ggctcaacat ctatctgtcg agccatcttg accggatttt cggatcgatc ctgcgcggct   8220

gagc                                                                8224
```

<210> SEQ ID NO 63
<211> LENGTH: 8077
<212> TYPE: DNA
<213> ORGANISM: Artificial Sequence
<220> FEATURE:
<223> OTHER INFORMATION: Operon F containing A. thaliana, S. cerevisiae, and Streptomyces sp CL190 DNA

<400> SEQUENCE: 63

```
ccaccgcggc ggccgcgtcg acgccggcgg aggcacatat gtctcagaac gtttacattg     60

tatcgactgc cagaacccca attggttcat tccagggttc tctatcctcc aagacagcag    120

tggaattggg tgctgttgct ttaaaaggcg ccttggctaa ggttccagaa ttggatgcat    180

ccaaggattt tgacgaaatt atttttggta acgttctttc tgccaatttg ggccaagctc    240

cggccagaca agttgctttg gctgccggtt tgagtaatca tatcgttgca agcacagtta    300

acaaggtctg tgcatccgct atgaaggcaa tcattttggg tgctcaatcc atcaaatgtg    360

gtaatgctga tgttgtcgta gctggtggtt gtgaatctat gactaacgca ccatactaca    420

tgccagcagc ccgtgcgggt gccaaatttg gccaaactgt tcttgttgat ggtgtcgaaa    480

gagatgggtt gaacgatgcg tacgatggtc tagccatggg tgtacacgca gaaaagtgtg    540

cccgtgattg ggatattact agagaacaac aagacaattt tgccatcgaa tcctaccaaa    600

aatctcaaaa atctcaaaag gaaggtaaat tcgacaatga aattgtacct gttaccatta    660

agggatttag aggtaagcct gatactcaag tcacgaagga cgaggaacct gctagattac    720

acgttgaaaa attgagatct gcaaggactg ttttccaaaa agaaaacggt actgttactg    780

ccgctaacgc ttctccaatc aacgatggtg ctgcagccgt catcttggtt tccgaaaaag    840

ttttgaagga aaagaatttg aagcctttgg ctattatcaa aggttggggt gaggccgctc    900

atcaaccagc tgattttaca tgggctccat ctcttgcagt tccaaaggct ttgaaacatg    960

ctggcatcga agacatcaat tctgttgatt actttgaatt caatgaagcc ttttcggttg   1020

tcggtttggt gaacactaag attttgaagc tagacccatc taaggttaat gtatatggtg   1080

gtgctgttgc tctaggtcac ccattgggtt gttctggtgc tagagtggtt gttacactgc   1140

tatccatctt acagcaagaa ggaggtaaga tcggtgttgc cgccatttgt aatggtggtg   1200

gtggtgcttc ctctattgtc attgaaaaga tatgaggatc ctctaggtac ttccctggcg   1260

tgtgcagcgg ttgacgcgcc gtgccctcgc tgcgagcggc gcgcacatct gacgtcctgc   1320

tttattgctt tctcagaact cgggacgaag cgatcccatg atcacgcgat ctccatgcag   1380

aaaagacaaa gggagctgag tgcgttgaca ctaccgacct cggctgaggg ggtatcagaa   1440
```

-continued

```
agccaccggg cccgctcggt cggcatcggt cgcgcccacg ccaaggccat cctgctggga   1500
gagcatgcgg tcgtctacgg agcgccggca ctcgctctgc cgattccgca gctcacggtc   1560
acggccagcg tcggctggtc gtccgaggcc tccgacagtg cgggtggcct gtcctacacg   1620
atgaccggta cgccgtcgcg ggcactggtg acgcaggcct ccgacggcct gcaccggctc   1680
accgcggaat tcatggcgcg gatgggcgtg acgaacgcgc cgcacctcga cgtgatcctg   1740
gacggcgcga tcccgcacgg ccggggtctc ggctccagcg cggccggctc acgcgcgatc   1800
gccttggccc tcgccgacct cttcggccac gaactggccg agcacacggc gtacgaactg   1860
gtgcagacgg ccgagaacat ggcgcacggc cgggccagcg gcgtggacgc gatgacggtc   1920
ggcgcgtccc ggccgctgct gttccagcag ggccgcaccg agcgactggc catcggctgc   1980
gacagcctgt tcatcgtcgc cgacagcggc gtcccgggca gcaccaagga agcggtcgag   2040
atgctgcggg agggattcac ccgcagcgcc ggaacacagg agcggttcgt cggccgggcg   2100
acggaactga ccgaggccgc ccggcaggcc ctcgccgacg gccggcccga ggagctgggc   2160
tcgcagctga cgtactacca cgagctgctc catgaggccc gcctgagcac cgacggcatc   2220
gatgcgctgg tcgaggccgc gctgaaggca ggcagcctcg gagccaagat caccggcggt   2280
ggtctgggcg gctgcatgat cgcacaggcc cggcccgaac aggcccggga ggtcacccgg   2340
cagctccacg aggccggtgc cgtacagacc tgggtcgtac cgctgaaagg gctcgacaac   2400
catgcgcagt gaacacccga ccacgaccgt gctccagtcg cgggagcagg gcagcgcggc   2460
cggcgccacc gcggtcgcgc acccaaacat cgcgctgatc aagtactggg gcaagcgcga   2520
cgagcggctg atcctgccct gcaccaccag cctgtcgatg acgctggacg tcttccccac   2580
gaccaccgag gtccggctcg accccgccgc cgagcacgac acggccgccc tcaacggcga   2640
ggtggccacg ggcgagacgc tgcgccgcat cagcgccttc ctctccctgg tgcgggaggt   2700
ggcgggcagc gaccagcggg ccgtggtgga cacccgcaac accgtgccca ccggggcggg   2760
cctggcgtcc tccgccagcg ggttcgccgc cctcgccgtc gcggccgcgg ccgcctacgg   2820
gctcgaactc gacgaccgcg ggctgtcccg gctggcccga cgtggatccg gctccgcctc   2880
gcggtcgatc ttcggcggct tcgccgtctg gcacgccggc cccgacggca cggccacgga   2940
agcggacctc ggctcctacg ccgagccggt gcccgcggcc gacctcgacc cggcgctggt   3000
catcgccgtg gtcaacgccg gccccaagcc cgtctccagc cgcgaggcca tgcgccgcac   3060
cgtcgacacc tcgccgctgt accggccgtg ggccgactcc agtaaggacg acctggacga   3120
gatgcgctcg gcgctgctgc gcggcgacct cgaggccgtg ggcgagatcg cggagcgcaa   3180
cgcgctcggc atgcacgcca ccatgctggc cgcccgcccc gcggtgcggt acctgtcgcc   3240
ggccacggtc accgtgctcg acagcgtgct ccagctccgc aaggacggtg tcctggccta   3300
cgcgaccatg gacgccggtc ccaacgtgaa ggtgctgtgc cggcgggcgg acgccgagcg   3360
ggtggccgac gtcgtacgcg ccgccgcgtc cggcggtcag gtcctcgtcg ccgggccggg   3420
agacggtgcc cgcctgctga gcgagggcgc atgacgacag gtcagcgcac gatcgtccgg   3480
cacgcgccgg gcaagctgtt cgtcgcgggc gagtacgcgg tcgtggatcc gggcaacccg   3540
gcgatcctgg tagcggtcga ccggcacatc agcgtcaccg tgtccgacgc cgacgcggac   3600
accggggccg ccgacgtcgt gatctcctcc gacctcggtc cgcaggcggt cggctggcgc   3660
tggcacgacg gccggctcgt cgtccgcgac ccggacgacg ggcagcaggc gcgcagcgcc   3720
ctggcccacg tggtgtcggc gatcgagacc gtgggccggc tgctgggcga acgcggacag   3780
aaggtccccg ctctcaccct ctccgtcagc agccgcctgc acgaggacgg ccggaagttc   3840
```

-continued

```
ggcctgggct ccagcggcgc ggtgaccgtg gcgaccgtag ccgccgtcgc cgcgttctgc   3900
ggactcgaac tgtccaccga cgaacggttc cggctggcca tgctcgccac cgcggaactc   3960
gaccccaagg gctccggcgg ggacctcgcc gccagcacct ggggcggctg gatcgcctac   4020
caggcgcccg accgggcctt tgtgctcgac ctggcccggc gcgtgggagt cgaccggaca   4080
ctgaaggcgc cctggccggg gcactcggtg cgccgactgc cggcgcccaa gggcctcacc   4140
ctggaggtcg gctggaccgg agagcccgcc tccaccgcgt ccctggtgtc cgatctgcac   4200
cgccgcacct ggcggggcag cgcctcccac cagaggttcg tcgagaccac gaccgactgt   4260
gtccgctccg cggtcaccgc cctggagtcc ggcgacgaca cgagcctgct gcacgagatc   4320
cgccgggccc gccaggagct ggcccgcctg gacgacgagg tcggcctcgg catcttcaca   4380
cccaagctga cggcgctgtg cgacgccgcc gaagccgtcg gcggcgcggc caagccctcc   4440
ggggcaggcg gcggcgactg cggcatcgcc ctgctggacg ccgaggcgtc gcgggacatc   4500
acacatgtac ggcaacggtg ggagacagcc ggggtgctgc cctgcccct gactcctgcc   4560
ctggaaggga tctaagaatg accagcgccc aacgcaagga cgaccacgta cggctcgcca   4620
tcgagcagca caacgcccac agcggacgca accagttcga cgacgtgtcg ttcgtccacc   4680
acgccctggc cggcatcgac cggccggacg tgtccctggc cacgtccttc gccgggatct   4740
cctggcaggt gccgatctac atcaacgcga tgaccggcgg cagcgagaag accggcctca   4800
tcaaccggga cctggccacc gccgcccgcg agaccggcgt ccccatcgcg tccgggtcca   4860
tgaacgcgta catcaaggac ccctcctgcg ccgacacgtt ccgtgtgctg cgcgacgaga   4920
accccaacgg gttcgtcatc gcgaacatca acgccaccac gacggtcgac aacgcgcagc   4980
gcgcgatcga cctgatcgag gcgaacgccc tgcagatcca catcaacacg gcgcaggaga   5040
cgccgatgcc ggagggcgac cggtcgttcg cgtcctgggt cccgcagatc gagaagatcg   5100
cggcggccgt cgacatcccc gtgatcgtca aggaggtcgg caacggcctg agccggcaga   5160
ccatcctgct gctcgccgac ctcggcgtgc aggcggcgga cgtcagcggc cgcggcggca   5220
cggacttcgc ccgcatcgag aacggccgcc gggagctcgg cgactacgcg ttcctgcacg   5280
gctgggggca gtccaccgcc gcctgcctgc tggacgccca ggacatctcc ctgcccgtcc   5340
tcgcctccgg cggtgtgcgt cacccgctcg acgtggtccg cgccctcgcg ctcggcgccc   5400
gcgccgtcgg ctcctccgcc ggcttcctgc gcaccctgat ggacgacggc gtcgacgcgc   5460
tgatcacgaa gctcacgacc tggctggacc agctggcggc gctgcagacc atgctcggcg   5520
cgcgcacccc ggccgacctc acccgctgcg acgtgctgct ccacggcgag ctgcgtgact   5580
tctgcgccga ccggggcatc gacacgcgcc gcctcgccca gcgctccagc tccatcgagg   5640
ccctccagac gacgggaagc acacgatgac ggaaacgcac gccatagccg gggtcccgat   5700
gaggtgggtg ggaccccttc gtatttccgg gaacgtcgcc gagaccgaga cccaggtccc   5760
gctcgccacg tacgagtcgc cgctgtggcc gtcggtgggc cgcggggcga aggtctcccg   5820
gctgacggag aagggcatcg tcgccaccct cgtcgacgag cggatgaccc gctcggtgat   5880
cgtcgaggcg acggacgcgc agaccgcgta catggccgcg cagaccatcc acgcccgcat   5940
cgacgagctg cgcgaggtgg tgcgcggctg cagccggttc gcccagctga tcaacatcaa   6000
gcacgagatc aacgcgaacc tgctgttcat ccggttcgag ttcaccaccg gtgacgcctc   6060
cggccacaac atggccacgc tcgcctccga tgtgctcctg ggcacctgc tggagacgat    6120
ccctggcatc tcctacggct cgatctccgg caactactgc acggacaaga aggccaccgc   6180
```

-continued

```
gatcaacggc atcctcggcc gcggcaagaa cgtgatcacc gagctgctgg tgccgcggga   6240
cgtcgtcgag aacaacctgc acaccacggc tgccaagatc gtcgagctga acatccgcaa   6300
gaacctgctc ggcaccctgc tcgccggcgg catccgctcg gccaacgccc acttcgcgaa   6360
catgctgctc ggcttctacc tggccaccgg ccaggacgcc gccaacatcg tcgagggctc   6420
gcagggcgtc gtcatggccg aggaccgcga cggcgacctc tacttcgcct gcaccctgcc   6480
gaacctgatc gtcggcacgg tcggcaacgg caagggtctc ggcttcgtgg agacgaacct   6540
cgcccggctc ggctgccgag ccgaccgcga acccggggag aacgcccgcc gcctcgccgt   6600
catcgcggca gcgaccgtgc tgtgcggtga actctcgctg ctcgcggcac agacgaaccc   6660
gggcgaactc atgcgcgcgc acgtccagct ggaacgcgac aacaagaccg caaaggttgg   6720
tgcatagggc atgtccatct ccataggcat tcacgacctg tcgttcgcca caaccgagtt   6780
cgtcctgccg cacacggcgc tcgccgagta caacggcacc gagatcggca agtaccacgt   6840
cggcatcggc cagcagtcga tgagcgtgcc ggccgccgac gaggacatcg tgaccatggc   6900
cgcgaccgcg gcgcggccca tcatcgagcg caacggcaag agccggatcc gcacggtcgt   6960
gttcgccacg gagtcgtcga tcgaccaggc gaaggcgggc ggcgtgtacg tgcactccct   7020
gctggggctg gagtcggcct gccgggtcgt cgagctgaag caggcctgct acggggccac   7080
cgccgccctt cagttcgcca tcggcctggt gcggcgcgac cccgcccagc aggtcctggt   7140
catcgccagt gacgtctcca agtacgagct ggacagcccc ggcgaggcga cccagggcgc   7200
ggccgcggtg gccatgctgg tcggcgccga cccggccctg ctgcgtatcg aggagccgtc   7260
gggcctgttc accgccgacg tcatggactt ctggcggccc aactacctca ccaccgctct   7320
ggtcgacggc caggagtcca tcaacgccta cctgcaggcc gtcgagggcg cctggaagga   7380
ctacgcggag caggacggcc ggtcgctgga ggagttcgcg gcgttcgtct accaccagcc   7440
gttcacgaag atggcctaca aggcgcaccg ccacctgctg aacttcaacg gctacgacac   7500
cgacaaggac gccatcgagg gcgccctcgg ccagacgacg gcgtacaaca acgtcatcgg   7560
caacagctac accgcgtcgg tgtacctggg cctggccgcc ctgctcgacc aggcggacga   7620
cctgacgggc cgttccatcg gcttcctgag ctacggctcg ggcagcgtcg ccgagttctt   7680
ctcgggcacc gtcgtcgccg ggtaccgcga gcgtctgcgc accgaggcga accaggaggc   7740
gatcgcccgg cgcaagagcg tcgactacgc cacctaccgc gagctgcacg agtacacgct   7800
cccgtccgac ggcggcgacc acgccacccc ggtgcagacc accggcccct tccggctggc   7860
cgggatcaac gaccacaagc gcatctacga ggcgcgctag cgacacccct cggcaacggg   7920
gtgcgccact gttcggcgca ccccgtgccg ggctttcgca cagctattca cgaccatttg   7980
aggggcgggc agccgcatga ccgacgtccg attccgcatt atcggtacgg gtgcctacct   8040
agaactagtg gatcccccgg gctgcaggaa ttcgata                            8077
```

<210> SEQ ID NO 64
<211> LENGTH: 8400
<212> TYPE: DNA
<213> ORGANISM: Artificial Sequence
<220> FEATURE:
<223> OTHER INFORMATION: Operon G containing A. thaliana, S. cerevisiae, and S. pombe DNA

<400> SEQUENCE: 64

```
ggccgcagga ggagttcata tgtcagagtt gagagccttc agtgccccag ggaaagcgtt     60
actagctggt ggatatttag ttttagatac aaaatatgaa gcatttgtag tcggattatc    120
```

-continued

```
ggcaagaatg catgctgtag cccatcctta cggttcattg caagggtctg ataagtttga    180
agtgcgtgtg aaaagtaaac aatttaaaga tggggagtgg ctgtaccata taagtcctaa    240
aagtggcttc attcctgttt cgataggcgg atctaagaac cctttcattg aaaaagttat    300
cgctaacgta tttagctact ttaaacctaa catggacgac tactgcaata gaaacttgtt    360
cgttattgat attttctctg atgatgccta ccattctcag gaggatagcg ttaccgaaca    420
tcgtggcaac agaagattga gttttcattc gcacagaatt gaagaagttc ccaaaaacagg   480
gctgggctcc tcggcaggtt tagtcacagt tttaactaca gctttggcct cctttttttgt   540
atcggacctg gaaaataatg tagacaaata tagagaagtt attcataatt tagcacaagt    600
tgctcattgt caagctcagg gtaaaattgg aagcgggttt gatgtagcgg cggcagcata    660
tggatctatc agatatagaa gattcccacc cgcattaatc tctaatttgc cagatattgg    720
aagtgctact tacggcagta aactggcgca tttggttgat gaagaagact ggaatattac    780
gattaaaagt aaccatttac cttcgggatt aactttatgg atgggcgata ttaagaatgg    840
ttcagaaaca gtaaaactgg tccagaaggt aaaaaattgg tatgattcgc atatgccaga    900
aagcttgaaa atatatacag aactcgatca tgcaaattct agatttatgg atggactatc    960
taaactagat cgcttacacg agactcatga cgattacagc gatcagatat ttgagtctct   1020
tgagaggaat gactgtacct gtcaaaagta tcctgaaatc acagaagtta gagatgcagt   1080
tgccacaatt agacgttcct ttagaaaaat aactaaagaa tctggtgccg atatcgaacc   1140
tcccgtacaa actagcttat tggatgattg ccagacctta aaaggagttc ttacttgctt   1200
aatacctggt gctggtggtt atgacgccat tgcagtgatt actaagcaag atgttgatct   1260
tagggctcaa accgctaatg acaaaagatt ttctaaggtt caatggctgg atgtaactca   1320
ggctgactgg ggtgttagga aagaaaaaga tccggaaact tatcttgata aactgcagga   1380
ggagttttaa tgtcattacc gttcttaact tctgcaccgg gaaaggttat tatttttggt   1440
gaacactctg ctgtgtacaa caagcctgcc gtcgctgcta gtgtgtctgc gttgagaacc   1500
tacctgctaa taagcgagtc atctgcacca gatactattg aattggactt cccggacatt   1560
agctttaatc ataagtggtc catcaatgat ttcaatgcca tcaccgagga tcaagtaaac   1620
tcccaaaaat tggccaaggc tcaacaagcc accgatggct tgtctcagga actcgttagt   1680
cttttggatc cgttgttagc tcaactatcc gaatccttcc actaccatgc agcgttttgt   1740
ttcctgtata tgtttgtttg cctatgcccc catgccaaga atattaagtt ttctttaaag   1800
tctactttac ccatcggtgc tgggttgggc tcaagcgcct ctatttctgt atcactggcc   1860
ttagctatgg cctacttggg ggggttaata ggatctaatg acttggaaaa gctgtcagaa   1920
aacgataagc atatagtgaa tcaatgggcc ttcataggtg aaaagtgtat tcacggtacc   1980
ccttcaggaa tagataacgc tgtggccact tatggtaatg ccctgctatt tgaaaaagac   2040
tcacataatg gaacaataaa cacaaacaat tttaagttct tagatgattt cccagccatt   2100
ccaatgatcc taacctatac tagaattcca aggtctacaa aagatcttgt tgctcgcgtt   2160
cgtgtgttgg tcaccgagaa atttcctgaa gttatgaagc caattctaga tgccatgggt   2220
gaatgtgccc tacaaggctt agagatcatg actaagttaa gtaaatgtaa aggcaccgat   2280
gacgaggctg tagaaactaa taatgaactg tatgaacaac tattggaatt gataagaata   2340
aatcatggac tgcttgtctc aatcggtgtt tctcatcctg gattagaact tattaaaaat   2400
ctgagcgatg atttgagaat tggctccaca aaacttaccg gtgctggtgg cggcggttgc   2460
tctttgactt tgttacgaag agacattact caagagcaaa ttgacagctt caaaaagaaa   2520
```

-continued

```
ttgcaagatg attttagtta cgagacattt gaaacagact tgggtgggac tggctgctgt   2580
ttgttaagcg caaaaaattt gaataaagat cttaaaatca aatccctagt attccaatta   2640
tttgaaaata aaactaccac aaagcaacaa attgacgatc tattattgcc aggaaacacg   2700
aatttaccat ggacttcaga cgaggagttt taatgactgt atatactgct agtgtaactg   2760
ctccggtaaa tattgctact cttaagtatt gggggaaaag ggacacgaag ttgaatctgc   2820
ccaccaattc gtccatatca gtgactttat cgcaagatga cctcagaacg ttgacctctg   2880
cggctactgc acctgagttt gaacgcgaca ctttgtggtt aaatggagaa ccacacagca   2940
tcgacaatga aagaactcaa aattgtctgc gcgacctacg ccaattaaga aaggaaatgg   3000
aatcgaagga cgcctcattg cccacattat ctcaatggaa actccacatt gtctccgaaa   3060
ataactttcc tacagcagct ggtttagctt cctccgctgc tggctttgct gcattggtct   3120
ctgcaattgc taagttatac caattaccac agtcaacttc agaaatatct agaatagcaa   3180
gaaaggggtc tggttcagct tgtagatcgt tgtttggcgg atacgtggcc tgggaaatgg   3240
gaaaagctga agatggtcat gattccatgg cagtacaaat cgcagacagc tctgactggc   3300
ctcagatgaa agcttgtgtc ctagttgtca gcgatattaa aaaggatgtg agttccactc   3360
agggtatgca attgaccgtg gcaacctccg aactatttaa agaaagaatt gaacatgtcg   3420
taccaaagag atttgaagtc atgcgtaaag ccattgttga aaaagatttc gccacctttg   3480
caaaggaaac aatgatggat tccaactctt tccatgccac atgtttggac tctttccctc   3540
caatattcta catgaatgac acttccaagc gtatcatcag ttggtgccac accattaatc   3600
agttttacgg agaaacaatc gttgcataca cgtttgatgc aggtccaaat gctgtgttgt   3660
actacttagc tgaaaatgag tcgaaactct ttgcatttat ctataaattg tttggctctg   3720
ttcctggatg ggacaagaaa tttactactg agcagcttga ggctttcaac catcaatttg   3780
aatcatctaa ctttactgca cgtgaattgg atcttgagtt gcaaaaggat gttgccagag   3840
tgattttaac tcaagtcggt tcaggcccac aagaaacaaa cgaatctttg attgacgcaa   3900
agactggtct accaaaggaa gaggagtttt aactcgacgc cggcggaggc acatatgtct   3960
cagaacgttt acattgtatc gactgccaga accccaattg gttcattcca gggttctcta   4020
tcctccaaga cagcagtgga attgggtgct gttgctttaa aaggcgcctt ggctaaggtt   4080
ccagaattgg atgcatccaa ggattttgac gaaattattt ttggtaacgt tctttctgcc   4140
aatttgggcc aagctccggc cagacaagtt gctttggctg ccggtttgag taatcatatc   4200
gttgcaagca cagttaacaa ggtctgtgca tccgctatga aggcaatcat tttgggtgct   4260
caatccatca aatgtggtaa tgctgatgtt gtcgtagctg gtggttgtga atctatgact   4320
aacgcaccat actacatgcc agcagcccgt gcgggtgcca aatttggcca aactgttctt   4380
gttgatggtg tcgaaagaga tgggttgaac gatgcgtacg atggtctagc catgggtgta   4440
cacgcagaaa agtgtgcccg tgattgggat attactagag aacaacaaga caattttgcc   4500
atcgaatcct accaaaaatc tcaaaaatct caaaaggaag gtaaattcga caatgaaatt   4560
gtacctgtta ccattaaggg atttagaggt aagcctgata ctcaagtcac gaaggacgag   4620
gaacctgcta gattacacgt tgaaaaattg agatctgcaa ggactgtttt ccaaaaagaa   4680
aacggtactg ttactgccgc taacgcttct ccaatcaacg atggtgctgc agccgtcatc   4740
ttggtttccg aaaaagtttt gaaggaaaag aatttgaagc ctttggctat tatcaaaggt   4800
tggggtgagg ccgctcatca accagctgat tttacatggg ctccatctct tgcagttcca   4860
```

-continued

```
aaggctttga aacatgctgg catcgaagac atcaattctg ttgattactt tgaattcaat   4920
gaagcctttt cggttgtcgg tttggtgaac actaagattt tgaagctaga cccatctaag   4980
gttaatgtat atggtggtgc tgttgctcta ggtcacccat tgggttgttc tggtgctaga   5040
gtggttgtta cactgctatc catcttacag caagaaggag gtaagatcgg tgttgccgcc   5100
atttgtaatg gtggtggtgg tgcttcctct attgtcattg aaaagatatg aggatcctct   5160
agatgcgcag gaggcacata tggcgaagaa cgttgggatt ttggctatgg atatctattt   5220
ccctcccacc tgtgttcaac aggaagcttt ggaagcacat gatggagcaa gtaaagggaa   5280
atacactatt ggacttggcc aagattgttt agctttttgc actgagcttg aagatgttat   5340
ctctatgagt ttcaatgcgg tgacatcact tttgagaag tataagattg accctaacca    5400
aatcgggcgt cttgaagtag gaagtgagac tgttattgac aaaagcaagt ccatcaagac   5460
cttcttgatg cagctctttg agaaatgtgg aaacactgat gtcgaaggtg ttgactcgac   5520
caatgcttgc tatggtggaa ctgcagcttt gttaaactgt gtcaattggg ttgagagtaa   5580
ctcttgggat ggacgttatg gcctcgtcat ttgtactgac agcgcggttt atgcagaagg   5640
acccgcaagg cccactggag gagctgcagc gattgctatg ttgataggac ctgatgctcc   5700
tatcgttttc gaaagcaaat tgagagcaag ccacatggct catgtctatg acttttacaa   5760
gcccaatctt gctagcgagt acccggttgt tgatggtaag ctttcacaga cttgctacct   5820
catggctctt gactcctgct ataaacattt atgcaacaag ttcgagaaga tcgagggcaa   5880
agagttctcc ataaatgatg ctgattacat tgttttccat tctccataca ataaacttgt   5940
acagaaaagc tttgctcgtc tcttgtacaa cgacttcttg agaaacgcaa gctccattga   6000
cgaggctgcc aaagaaaagt tcacccctta ttcatctttg acccttgacg agagttacca   6060
aagccgtgat cttgaaaagg tgtcacaaca aatttcgaaa ccgttttatg atgctaaagt   6120
gcaaccaacg actttaatac caaaggaagt cggtaacatg tacactgctt ctctctacgc   6180
tgcatttgct tccctcatcc acaataaaca caatgatttg gcgggaaagc gggtggttat   6240
gttctcttat ggaagtggct ccaccgcaac aatgttctca ttacgcctca acgacaataa   6300
gcctcctttc agcatttcaa acattgcatc tgtaatggat gttggcggta aattgaaagc   6360
tagacatgag tatgcacctg agaagtttgt ggagacaatg aagctaatgg aacataggta   6420
tggagcaaag gactttgtga caaccaagga gggtattata gatcttttgg caccgggaac   6480
ttattatctg aaagaggttg attccttgta ccggagattc tatggcaaga aaggtgaaga   6540
tggatctgta gccaatggac actgaggatc cgtcgagcac gtggaggcac atatgcaatg   6600
ctgtgagatg cctgttggat acattcagat tcctgttggg attgctggtc cattgttgct   6660
tgatggttat gagtactctg ttcctatggc tacaaccgaa ggttgtttgg ttgctagcac   6720
taacagaggc tgcaaggcta tgtttatctc tggtggcgcc accagtaccg ttcttaagga   6780
cggtatgacc cgagcacctg ttgttcggtt cgcttcggcg agacgagctt cggagcttaa   6840
gtttttcttg gagaatccag agaactttga tactttggca gtagtcttca acaggtcgag   6900
tagatttgca agactgcaaa gtgttaaatg cacaatcgcg ggaagaatg cttatgtaag    6960
gttctgttgt agtactggtg atgctatggg gatgaatatg gtttctaaag gtgtgcagaa   7020
tgttcttgag tatcttaccg atgatttccc tgacatggat gtgattggaa tctctggtaa   7080
cttctgttcg gacaagaaac ctgctgctgt gaactggatt gagggacgtg gtaaatcagt   7140
tgtttgcgag gctgtaatca gaggagagat cgtgaacaag gtcttgaaaa cgagcgtggc   7200
tgctttagtc gagctcaaca tgctcaagaa cctagctggc tctgctgttg caggctctct   7260
```

```
aggtggattc aacgctcatg ccagtaacat agtgtctgct gtattcatag ctactggcca   7320
agatccagct caaaacgtgg agagttctca atgcatcacc atgatggaag ctattaatga   7380
cggcaaagat atccatatct cagtcactat gccatctatc gaggtgggga cagtgggagg   7440
aggaacacag cttgcatctc aatcagcgtg tttaaacctg ctcggagtta aaggagcaag   7500
cacagagtcg ccgggaatga acgcaaggag gctagcgacg atcgtagccg gagcagtttt   7560
agctggagag ttatctttaa tgtcagcaat tgcagctgga cagcttgtga gaagtcacat   7620
gaaatacaat agatccagcc gagacatctc tggagcaacg acaacgacaa caacaacaac   7680
atgacccgta ggaggcacat atgagttccc aacaagagaa aaaggattat gatgaagaac   7740
aattaaggtt gatggaagaa gtttgtatcg ttgtagatga aaatgatgtc cctttaagat   7800
atggaacgaa aaaggagtgt catttgatgg aaaatataaa taaaggtctt ttgcatagag   7860
cattctctat gttcatcttt gatgagcaaa atcgcctttt acttcagcag cgtgcagaag   7920
agaaaattac atttccatcc ttatggacga atacatgttg ctcccaccca ttggatgttg   7980
ctggtgaacg tggtaatact ttacctgaag ctgttgaagg tgttaagaat gcagctcaac   8040
gcaagctgtt ccatgaattg ggtattcaag ccaagtatat tcccaaagac aaatttcagt   8100
ttcttacacg aatccattac cttgctccta gtactggtgc ttggggagag catgaaattg   8160
actacattct tttcttcaaa ggtaaagttg agctggatat caatcccaat gaagttcaag   8220
cctataagta tgttactatg gaagagttaa aagagatgtt ttccgatcct caatatggat   8280
tcacaccatg gttcaaactt atttgtgagc attttatgtt taaatggtgg caggatgtag   8340
atcatgcgtc aaaattccaa gataccttaa ttcatcgttg ctaaggatcc cccgggatcc   8400
```

```
<210> SEQ ID NO 65
<211> LENGTH: 55
<212> TYPE: DNA
<213> ORGANISM: Artificial Sequence
<220> FEATURE:
<223> OTHER INFORMATION: PCR primer containing R. capsulatus DNA

<400> SEQUENCE: 65

gcgatatcgg atccaggagg accatatgat cgccgaagcg gatatggagg tctgc         55


<210> SEQ ID NO 66
<211> LENGTH: 50
<212> TYPE: DNA
<213> ORGANISM: Artificial Sequence
<220> FEATURE:
<223> OTHER INFORMATION: PCR primer containing R. capsulatus DNA

<400> SEQUENCE: 66

gcgatatcaa gcttggatcc tcaatccatc gccaggccgc ggtcgcgcgc               50


<210> SEQ ID NO 67
<211> LENGTH: 60
<212> TYPE: DNA
<213> ORGANISM: Artificial Sequence
<220> FEATURE:
<223> OTHER INFORMATION: Oligonucleotide containing N. tabacum and R.
      capsulatus DNA

<400> SEQUENCE: 67

ctttcctgaa acataattta taatcagatc caggaggacc atatgatcgc cgaagcggat     60


<210> SEQ ID NO 68
<211> LENGTH: 60
```

-continued

```
<212> TYPE: DNA
<213> ORGANISM: Artificial Sequence
<220> FEATURE:
<223> OTHER INFORMATION: Oligonucleotide containing N. tabacum and R.
      capsulatus DNA

<400> SEQUENCE: 68

cgaccgcggc ctggcgatgg attgaggatc taaacaaacc cggaacagac cgttgggaag     60


<210> SEQ ID NO 69
<211> LENGTH: 60
<212> TYPE: DNA
<213> ORGANISM: Artificial Sequence
<220> FEATURE:
<223> OTHER INFORMATION: Oligonucleotide containing N. tabacum and R.
      capsulatus DNA

<400> SEQUENCE: 69

atttttcatc tcgaattgta ttcccacgaa ggccgcgtcg actacggccg caggaggagt     60


<210> SEQ ID NO 70
<211> LENGTH: 60
<212> TYPE: DNA
<213> ORGANISM: Artificial Sequence
<220> FEATURE:
<223> OTHER INFORMATION: Oligonucleotide containing N. tabacum and R.
      capsulatus DNA

<400> SEQUENCE: 70

ttcggatcga tcctgcgcgg ctgagcggcc ggaatggtga agttgaaaaa cgaatccttc     60


<210> SEQ ID NO 71
<211> LENGTH: 1020
<212> TYPE: DNA
<213> ORGANISM: Rhodobacter capsulatus

<400> SEQUENCE: 71

atgatcgccg aagcggatat ggaggtctgc cgggagctga tccgcaccgg cagctactcc     60

ttccatgcgg cgtccagagt tctgccggcg cgggtccgtg accccgcgct ggcgctttac    120

gccttttgcc gcgtcgccga tgacgaagtc gacgaggttg gcgcgccgcg cgacaaggct    180

gcggcggttt tgaaacttgg cgaccggctg gaggacatct atgccggtcg tccgcgcaat    240

gcgccctcgg atcgggcttt cgcggcggtg gtcgaggaat tcgagatgcc gcgcgaattg    300

cccgaggcgc tgctggaggg cttcgcctgg gatgccgagg ggcggtggta tcacacgctt    360

tcggacgtgc aggcctattc ggcgcgggtg gcggccgccg tcggcgcgat gatgtgcgtg    420

ctgatgcggg tgcgcaaccc cgatgcgctg gcgcgggcct gcgatctcgg tcttgccatg    480

cagatgtcga acatcgcccg cgacgtgggc gaggatgccc gggcggggcg gcttttcctg    540

ccgaccgact ggatggtcga ggaggggatc gatccgcagg cgttcctggc cgatccgcag    600

cccaccaagg gcatccgccg ggtcaccgag cggttgctga accgcgccga ccggctttac    660

tggcgggcgg cgacgggggt gcggcttttg ccctttgact gccgaccggg gatcatggcc    720

gcgggcaaga tctatgccgc gatcggggcc gaggtggcga aggcgaaata cgacaacatc    780

acccggcgtg cccacacgac caagggccgc aagctgtggc tggtggcgaa ttccgcgatg    840

tcggcgacgg cgacctcgat gctgccgctc tcgccgcggg tgcatgccaa gcccgagccc    900

gaagtggcgc atctggtcga tgccgccgcg catcgcaacc tgcatcccga acggtccgag    960

gtgctgatct cggcgctgat ggcgctgaag gcgcgcgacc gcggcctggc gatggattga   1020
```

<210> SEQ ID NO 72
<211> LENGTH: 13917
<212> TYPE: DNA
<213> ORGANISM: Artificial Sequence
<220> FEATURE:
<221> NAME/KEY: misc_feature
<222> LOCATION: ()..()
<223> OTHER INFORMATION: Plastid transformation vector pHK04, containing Operon B, containi

<400> SEQUENCE: 72
gcacttttcg gggaaatgtg cgcggaaccc ctatttgttt atttttctaa atacattcaa 60
atatgtatcc gctcatgaga caataaccct gataaatgct tcaataatat tgaaaaagga 120
agagtatgag tattcaacat ttccgtgtcg cccttattcc cttttttgcg gcattttgcc 180
ttcctgtttt tgctcaccca gaaacgctgg tgaaagtaaa agatgctgaa gatcagttgg 240
gtgcacgagt gggttacatc gaactggatc tcaacagcgg taagatcctt gagagttttc 300
gccccgaaga acgttttcca atgatgagca cttttaaagt tctgctatgt ggcgcggtat 360
tatcccgtat tgacgccggg caagagcaac tcggtcgccg catacactat tctcagaatg 420
acttggttga gtactcacca gtcacagaaa agcatcttac ggatggcatg acagtaagag 480
aattatgcag tgctgccata accatgagtg ataacactgc ggccaactta cttctgacaa 540
cgatcggagg accgaaggag ctaaccgctt ttttgcacaa catgggggat catgtaactc 600
gccttgatcg ttgggaaccg gagctgaatg aagccatacc aaacgacgag cgtgacacca 660
cgatgcctgt agcaatggca acaacgttgc gcaaactatt aactggcgaa ctacttactc 720
tagcttcccg gcaacaatta atagactgga tggaggcgga taaagttgca ggaccacttc 780
tgcgctcggc ccttccggct ggctggttta ttgctgataa atctggagcc ggtgagcgtg 840
ggtctcgcgg tatcattgca gcactggggc cagatggtaa gccctcccgt atcgtagtta 900
tctacacgac ggggagtcag gcaactatgg atgaacgaaa tagacagatc gctgagatag 960
gtgcctcact gattaagcat tggtaactgt cagaccaagt ttactcatat atactttaga 1020
ttgatttaaa acttcatttt taatttaaaa ggatctaggt gaagatcctt tttgataatc 1080
tcatgaccaa aatcccttaa cgtgagtttt cgttccactg agcgtcagac cccgtagaaa 1140
agatcaaagg atcttcttga gatccttttt ttctgcgcgt aatctgctgc ttgcaaacaa 1200
aaaaaccacc gctaccagcg gtggtttgtt tgccggatca agagctacca actctttttc 1260
cgaaggtaac tggcttcagc agagcgcaga taccaaatac tgtccttcta gtgtagccgt 1320
agttaggcca ccacttcaag aactctgtag caccgcctac atacctcgct ctgctaatcc 1380
tgttaccagt ggctgctgcc agtggcgata agtcgtgtct taccgggttg gactcaagac 1440
gatagttacc ggataaggcg cagcggtcgg gctgaacggg gggttcgtgc acacagccca 1500
gcttggagcg aacgacctac accgaactga gatacctaca gcgtgagcta tgagaaagcg 1560
ccacgcttcc cgaagggaga aaggcggaca ggtatccggt aagcggcagg gtcggaacag 1620
gagagcgcac gagggagctt ccagggggaa acgcctggta tctttatagt cctgtcgggt 1680
ttcgccacct ctgacttgag cgtcgatttt tgtgatgctc gtcagggggg cggagcctat 1740
ggaaaaacgc cagcaacgcg gcctttttac ggttcctggc cttttgctgg ccttttgctc 1800
acatgttctt tcctgcgtta tcccctgatt ctgtggataa ccgtattacc gcctttgagt 1860
gagctgatac cgctcgccgc agccgaacga ccgagcgcag cgagtcagtg agcgaggaag 1920
cggaagagcg cccaatacgc aaaccgcctc tccccgcgcg ttggccgatt cattaatgca 1980
gctggcacga caggtttccc gactggaaag cgggcagtga gcgcaacgca attaatgtga 2040

-continued

```
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctccaccgc ggtggcggcc   2220
gctctagaac tagtggatct tcttggctgt tattcaaaag gtccaacaat gtatatatat   2280
tggacatttt gaggcaatta tagatcctgg aaggcaattc tgattggtca ataaaaatcg   2340
atttcaatgc tatttttttt ttgtttttta tgagtttagc caatttatca tgaaaggtaa   2400
aaggggataa aggaaccgtg tgttgattgt cctgtaaata taagttgtct tcctccatat   2460
gtaaaaaggg aataaataaa tcaattaaat ttcgggatgc ttcatgaagt gcttctttcg   2520
gagttaaact tccgtttgtc catatttcga gaaaaagtat ctcttgtttt tcattcccat   2580
tcccataaga atgaatacta tgattcgcgt ttcgaacagg catgaataca gcatctatag   2640
gataacttcc atcttgaaag ttatgtggcg tttttataag atatccacga tttctctcta   2700
tttgtaatcc aatacaaaaa tcaattggtt ccgttaaact ggctatatgt tgtgtattat   2760
caacgatttc tacataaggc ggcaagatga tatcttgggc agttacagat ccaggaccct   2820
tgacacaaat agatgcgtca gaagttccat atagattact tcttaatata atttctttca   2880
aattcattaa aatttcatgt accgattctt gaatgcccgt tatggtagaa tattcatgtg   2940
ggactttctc agattttaca cgtgtgatac atgttccttc tatttctcca agtaaagctc   3000
ttcgcatcgc aatgcctatt gtgtcggctt ggcctttcat aagtggagac agaataaagc   3060
gtccataata aaggcgttta ctgtctgttc ttgattcaac acacttccac tgtagtgtcc   3120
gagtagatac tgttactttc tctcgaacca tagtactatt atttgattag atcatcgaat   3180
cttttatttc tcttgagatt tcttcaatgt tcagttctac acacgtcttt ttttcggagg   3240
tctacagcca ttatgtggca taggagttac atcccgtacg aaagttaata gtataccact   3300
tcgacgaata gctcgtaatg ctgcatctct tccgagaccg ggaccttttta tcatgacttc  3360
tgctcgttgc ataccttgat ccactactgt acggatagcg tttgctgctg cggtttgagc   3420
agcaaacggt gttcctcttc tcgtaccttt gaatccagaa gtaccggcgg aggaccaaga   3480
aactactcga ccccgtacat ctgtaacagt gacaatggta ttattgaaac ttgcttgaac   3540
atgaataact ccctttggta ttctacgtgc acccttacgt gaaccaatac gtccattcct   3600
acgcgaacta attttcggta tagcttttgc catattttat catctcgtaa atatgagtca   3660
gagatatatg gatatatcca tttcatgtca aaacagattc tttatttgta catcggctct   3720
tctggcaagt ctgattatcc ctgtctttgt ttatgtctcg ggttggaaca aattactata   3780
attcgtcccc gcctacggat tagtcgacat ttttcacaaa ttttacgaac ggaagctctt   3840
attttcatat ttctcattcc ttaccttaat tctgaatcta tttcttggaa gaaaataagt   3900
ttcttgaaat ttttcatctc gaattgtatt cccacgaaag gaatggtgaa gttgaaaaac   3960
gaatccttca aatctttgtt gtggagtcga taaattatac gccctttggt tgaatcataa   4020
ggacttactt caattttgac tctatctcct ggcagtatcc gtataaaact atgccggatc   4080
tttcctgaaa cataatttat aatcagatcg gccgcaggag gagttcatat gtcagagttg   4140
agagccttca gtgccccagg gaaagcgtta ctagctggtg gatatttagt tttagataca   4200
aaatatgaag catttgtagt cggattatcg gcaagaatgc atgctgtagc ccatccttac   4260
ggttcattgc aagggtctga taagtttgaa gtgcgtgtga aaagtaaaca atttaaagat   4320
ggggagtggc tgtaccatat aagtcctaaa agtggcttca ttcctgtttc gataggcgga   4380
```

-continued

```
tctaagaacc ctttcattga aaaagttatc gctaacgtat ttagctactt taaacctaac   4440
atggacgact actgcaatag aaacttgttc gttattgata ttttctctga tgatgcctac   4500
cattctcagg aggatagcgt taccgaacat cgtggcaaca gaagattgag ttttcattcg   4560
cacagaattg aagaagttcc caaaaacaggg ctgggctcct cggcaggttt agtcacagtt  4620
ttaactacag ctttggcctc ctttttttgta tcggacctgg aaaataatgt agacaaatat  4680
agagaagtta ttcataattt agcacaagtt gctcattgtc aagctcaggg taaaattgga   4740
agcgggtttg atgtagcggc ggcagcatat ggatctatca gatatagaag attcccaccc   4800
gcattaatct ctaatttgcc agatattgga agtgctactt acggcagtaa actggcgcat   4860
ttggttgatg aagaagactg gaatattacg attaaaagta accatttacc ttcgggatta   4920
actttatgga tgggcgatat taagaatggt tcagaaacag taaaactggt ccagaaggta   4980
aaaaattggt atgattcgca tatgccagaa agcttgaaaa tatatacaga actcgatcat   5040
gcaaattcta gatttatgga tggactatct aaactagatc gcttacacga gactcatgac   5100
gattacagcg atcagatatt tgagtctctt gagaggaatg actgtacctg tcaaaagtat   5160
cctgaaatca cagaagttag agatgcagtt gccacaatta gacgttcctt tagaaaaata   5220
actaaagaat ctggtgccga tatcgaacct cccgtacaaa ctagcttatt ggatgattgc   5280
cagaccttaa aaggagttct tacttgctta atacctggtg ctggtggtta tgacgccatt   5340
gcagtgatta ctaagcaaga tgttgatctt agggctcaaa ccgctaatga caaaagattt   5400
tctaaggttc aatggctgga tgtaactcag gctgactggg gtgttaggaa agaaaaagat   5460
ccggaaactt atcttgataa actgcaggag gagttttaat gtcattaccg ttcttaactt   5520
ctgcaccggg aaaggttatt atttttggtg aacactctgc tgtgtacaac aagcctgccg   5580
tcgctgctag tgtgtctgcg ttgagaacct acctgctaat aagcgagtca tctgcaccag   5640
atactattga attggacttc ccggacatta gctttaatca taagtggtcc atcaatgatt   5700
tcaatgccat caccgaggat caagtaaact cccaaaaatt ggccaaggct caacaagcca   5760
ccgatggctt gtctcaggaa ctcgttagtc ttttggatcc gttgttagct caactatccg   5820
aatccttcca ctaccatgca gcgttttgtt tcctgtatat gtttgtttgc ctatgccccc   5880
atgccaagaa tattaagttt tctttaaagt ctactttacc catcggtgct gggttgggct   5940
caagcgcctc tatttctgta tcactggcct tagctatggc ctacttgggg gggttaatag   6000
gatctaatga cttggaaaag ctgtcagaaa acgataagca tatagtgaat caatgggcct   6060
tcataggtga aaagtgtatt cacggtaccc cttcaggaat agataacgct gtggccactt   6120
atggtaatgc cctgctattt gaaaaagact cacataatgg aacaataaac acaaacaatt   6180
ttaagttctt agatgatttc ccagccattc caatgatcct aacctatact agaattccaa   6240
ggtctacaaa agatcttgtt gctcgcgttc gtgtgttggt caccgagaaa tttcctgaag   6300
ttatgaagcc aattctagat gccatgggtg aatgtgccct acaaggctta gagatcatga   6360
ctaagttaag taaatgtaaa ggcaccgatg acgaggctgt agaaactaat aatgaactgt   6420
atgaacaact attggaattg ataagaataa atcatggact gcttgtctca atcggtgttt   6480
ctcatcctgg attagaactt attaaaaatc tgagcgatga tttgagaatt ggctccacaa   6540
aacttaccgg tgctggtggc ggcggttgct ctttgacttt gttacgaaga gacattactc   6600
aagagcaaat tgacagcttc aaaaagaaat tgcaagatga ttttagttac gagacatttg   6660
aaacagactt gggtgggact ggctgctgtt tgttaagcgc aaaaaatttg aataaagatc   6720
ttaaaatcaa atccctagta ttccaattat ttgaaaataa aactaccaca aagcaacaaa   6780
```

```
ttgacgatct attattgcca ggaaacacga atttaccatg gacttcagac gaggagtttt   6840
aatgactgta tatactgcta gtgtaactgc tccggtaaat attgctactc ttaagtattg   6900
ggggaaaagg gacacgaagt tgaatctgcc caccaattcg tccatatcag tgactttatc   6960
gcaagatgac ctcagaacgt tgacctctgc ggctactgca cctgagtttg aacgcgacac   7020
tttgtggtta aatggagaac cacacagcat cgacaatgaa agaactcaaa attgtctgcg   7080
cgacctacgc caattaagaa aggaaatgga atcgaaggac gcctcattgc ccacattatc   7140
tcaatggaaa ctccacattg tctccgaaaa taactttcct acagcagctg gtttagcttc   7200
ctccgctgct ggctttgctg cattggtctc tgcaattgct aagttatacc aattaccaca   7260
gtcaacttca gaaatatcta gaatagcaag aaaggggtct ggttcagctt gtagatcgtt   7320
gtttggcgga tacgtggcct gggaaatggg aaaagctgaa gatggtcatg attccatggc   7380
agtacaaatc gcagacagct ctgactggcc tcagatgaaa gcttgtgtcc tagttgtcag   7440
cgatattaaa aaggatgtga gttccactca gggtatgcaa ttgaccgtgg caacctccga   7500
actatttaaa gaaagaattg aacatgtcgt accaaagaga tttgaagtca tgcgtaaagc   7560
cattgttgaa aaagatttcg ccacctttgc aaaggaaaca atgatggatt ccaactcttt   7620
ccatgccaca tgtttggact ctttccctcc aatattctac atgaatgaca cttccaagcg   7680
tatcatcagt tggtgccaca ccattaatca gttttacgga gaaacaatcg ttgcatacac   7740
gtttgatgca ggtccaaatg ctgtgttgta ctacttagct gaaaatgagt cgaaactctt   7800
tgcatttatc tataaattgt ttggctctgt tcctggatgg gacaagaaat ttactactga   7860
gcagcttgag gctttcaacc atcaatttga atcatctaac tttactgcac gtgaattgga   7920
tcttgagttg caaaaggatg ttgccagagt gattttaact caagtcggtt caggcccaca   7980
agaaacaaac gaatctttga ttgacgcaaa gactggtcta ccaaaggaag aggagtttta   8040
actcgacgcc ggcggaggca catatgtctc agaacgttta cattgtatcg actgccagaa   8100
ccccaattgg ttcattccag ggttctctat cctccaagac agcagtggaa ttgggtgctg   8160
ttgctttaaa aggcgccttg gctaaggttc cagaattgga tgcatccaag gattttgacg   8220
aaattatttt tggtaacgtt ctttctgcca atttgggcca agctccggcc agacaagttg   8280
ctttggctgc cggtttgagt aatcatatcg ttgcaagcac agttaacaag gtctgtgcat   8340
ccgctatgaa ggcaatcatt ttgggtgctc aatccatcaa atgtggtaat gctgatgttg   8400
tcgtagctgg tggttgtgaa tctatgacta acgcaccata ctacatgcca gcagcccgtg   8460
cgggtgccaa atttggccaa actgttcttg ttgatggtgt cgaaagagat gggttgaacg   8520
atgcgtacga tggtctagcc atgggtgtac acgcagaaaa gtgtgcccgt gattgggata   8580
ttactagaga acaacaagac aattttgcca tcgaatccta ccaaaaatct caaaaatctc   8640
aaaaggaagg taaattcgac aatgaaattg tacctgttac cattaaggga tttagaggta   8700
agcctgatac tcaagtcacg aaggacgagg aacctgctag attacacgtt gaaaaattga   8760
gatctgcaag gactgttttc caaaaagaaa acggtactgt tactgccgct aacgcttctc   8820
caatcaacga tggtgctgca gccgtcatct tggtttccga aaaagttttg aaggaaaaga   8880
atttgaagcc tttggctatt atcaaaggtt ggggtgaggc cgctcatcaa ccagctgatt   8940
ttacatgggc tccatctctt gcagttccaa aggctttgaa acatgctggc atcgaagaca   9000
tcaattctgt tgattacttt gaattcaatg aagccttttc ggttgtcggt ttggtgaaca   9060
ctaagatttt gaagctagac ccatctaagg ttaatgtata tggtggtgct gttgctctag   9120
```

-continued

```
gtcacccatt gggttgttct ggtgctagag tggttgttac actgctatcc atcttacagc   9180
aagaaggagg taagatcggt gttgccgcca tttgtaatgg tggtggtggt gcttcctcta   9240
ttgtcattga aaagatatga ggatcctcta gatgcgcagg aggcacatat ggcgaagaac   9300
gttgggattt tggctatgga tatctatttc cctcccacct gtgttcaaca ggaagctttg   9360
gaagcacatg atggagcaag taaagggaaa tacactattg gacttggcca agattgttta   9420
gctttttgca ctgagcttga agatgttatc tctatgagtt tcaatgcggt gacatcactt   9480
tttgagaagt ataagattga ccctaaccaa atcgggcgtc ttgaagtagg aagtgagact   9540
gttattgaca aaagcaagtc catcaagacc ttcttgatgc agctctttga gaaatgtgga   9600
aacactgatg tcgaaggtgt tgactcgacc aatgcttgct atggtggaac tgcagctttg   9660
ttaaactgtg tcaattgggt tgagagtaac tcttgggatg gacgttatgg cctcgtcatt   9720
tgtactgaca gcgcggttta tgcagaagga cccgcaaggc ccactggagg agctgcagcg   9780
attgctatgt tgataggacc tgatgctcct atcgttttcg aaagcaaatt gagagcaagc   9840
cacatggctc atgtctatga cttttacaag cccaatcttg ctagcgagta cccggttgtt   9900
gatggtaagc tttcacagac ttgctacctc atggctcttg actcctgcta taaacattta   9960
tgcaacaagt tcgagaagat cgagggcaaa gagttctcca taaatgatgc tgattacatt  10020
gttttccatt ctccatacaa taaacttgta cagaaaagct ttgctcgtct cttgtacaac  10080
gacttcttga gaaacgcaag ctccattgac gaggctgcca aagaaaagtt caccccttat  10140
tcatctttga cccttgacga gagttaccaa agccgtgatc ttgaaaaggt gtcacaacaa  10200
atttcgaaac cgttttatga tgctaaagtg caaccaacga ctttaatacc aaaggaagtc  10260
ggtaacatgt acactgcttc tctctacgct gcatttgctt ccctcatcca caataaacac  10320
aatgatttgg cgggaaagcg ggtggttatg ttctcttatg gaagtggctc caccgcaaca  10380
atgttctcat tacgcctcaa cgacaataag cctcctttca gcatttcaaa cattgcatct  10440
gtaatggatg ttggcggtaa attgaaagct agacatgagt atgcacctga gaagtttgtg  10500
gagacaatga agctaatgga acataggtat ggagcaaagg actttgtgac aaccaaggag  10560
ggtattatag atcttttggc accgggaact tattatctga aagaggttga ttccttgtac  10620
cggagattct atggcaagaa aggtgaagat ggatctgtag ccaatggaca ctgaggatcc  10680
gtcgagcacg tggaggcaca tatgcaatgc tgtgagatgc ctgttggata cattcagatt  10740
cctgttggga ttgctggtcc attgttgctt gatggttatg agtactctgt tcctatggct  10800
acaaccgaag gttgtttggt tgctagcact aacagaggct gcaaggctat gtttatctct  10860
ggtggcgcca ccagtaccgt tcttaaggac ggtatgaccc gagcacctgt tgttcggttc  10920
gcttcggcga gacgagcttc ggagcttaag tttttcttgg agaatccaga gaactttgat  10980
actttggcag tagtcttcaa caggtcgagt agatttgcaa gactgcaaag tgttaaatgc  11040
acaatcgcgg ggaagaatgc ttatgtaagg ttctgttgta gtactggtga tgctatgggg  11100
atgaatatgg tttctaaagg tgtgcagaat gttcttgagt atcttaccga tgatttccct  11160
gacatggatg tgattggaat ctctggtaac ttctgttcgg acaagaaacc tgctgctgtg  11220
aactggattg agggacgtgg taaatcagtt gtttgcgagg ctgtaatcag aggagagatc  11280
gtgaacaagg tcttgaaaac gagcgtggct gctttagtcg agctcaacat gctcaagaac  11340
ctagctggct ctgctgttgc aggctctcta ggtggattca acgctcatgc cagtaacata  11400
gtgtctgctg tattcatagc tactggccaa gatccagctc aaaacgtgga gagttctcaa  11460
tgcatcacca tgatggaagc tattaatgac ggcaaagata tccatatctc agtcactatg  11520
```

-continued

```
ccatctatcg aggtggggac agtgggagga ggaacacagc ttgcatctca atcagcgtgt  11580
ttaaacctgc tcggagttaa aggagcaagc acagagtcgc cgggaatgaa cgcaaggagg  11640
ctagcgacga tcgtagccgg agcagtttta gctggagagt tatctttaat gtcagcaatt  11700
gcagctggac agcttgtgag aagtcacatg aaatacaata gatccagccg agacatctct  11760
ggagcaacga caacgacaac aacaacaaca tgacccggga tccggccgat ctaaacaaac  11820
ccggaacaga ccgttgggaa gcgattcagt aattaaagct tcatgactcc tttttggttc  11880
ttaaagtccc tttgaggtat caactaataa gaaagatatt agacaacccc ccttttttct  11940
ttttcacaaa taggaagttt cgaatccaat ttggatatta aaaggattac cagatataac  12000
acaaaatctc tccacctatt ccttctagtc gagcctctcg gtctgtcatt atacctcgag  12060
aagtagaaag aattacaatc cccattccac ctaaaattcg cggaattcgt tgataattag  12120
aatagattcg tagaccaggt cgactgattc gttttaaatt taaaatattt ctatagggtc  12180
ttttcctatt ccttctatgt cgcagggtta aaaccaaaaa atatttgttt ttttctcgat  12240
gttttctcac gttttcgata aaaccttctc gtaaaagtat ttgaacaata ttttcggtaa  12300
tattagtaga tgctattcga accacccttt ttcgatccat atcagcattt cgtatagaag  12360
ttattatctc agcaatagtg tccctaccca tgatgaacta aaattattgg ggcctccaaa  12420
tttgatataa tcaacgtgtt ttttacttat tttttttttg aatatgatat gaattattaa  12480
agatatatgc gtgagacaca atctactaat taatctattt ctttcaaata ccccactaga  12540
aacagatcac aatttcattt tataatacct cgggagctaa tgaaactatt ttagtaaaat  12600
ttaattctct caattcccgg gcgattgcac caaaaattcg agttcctttt gatttccttc  12660
cttcttgatc aataacaact gcagcattgt catcatatcg tattatcatc ccgttgtcac  12720
gtttgagttc tttacaggtc cgcacaatta cagctctgac tacttctgat ctttctaggg  12780
gcatatttgg tacggcttct ttgatcacag caacaataac gtcaccaata tgagcatatc  12840
gacgattgct agctcctatg attcgaatac acatcaattc tcgagccccg ctgttatccg  12900
ctacatttaa atgggtctga ggttgaatca ttttttttaat ccgttctttg aatgcaaagg  12960
gcgaagaaaa aaaagaaata tttttgtcca aaaaaaaaga aacatgcggt ttcgtttcat  13020
atctaagagc cctttccgca tttttttcta ttacattacg aaataatgaa ttgagttcgt  13080
ataggcattt tagatgctgc tagtgaaata gcccttctgg ctatattttc tgttactcca  13140
cccatttcat aaagtattcg acccggttta acaacagcta cccaatattc aggggatccc  13200
ccgggctgca ggaattcgat atcaagctta tcgataccgt cgacctcgag ggggggcccg  13260
gtacccaatt cgccctatag tgagtcgtat tacaattcac tggccgtcgt tttacaacgt  13320
cgtgactggg aaaaccctgg cgttacccaa cttaatcgcc ttgcagcaca tccccctttc  13380
gccagctggc gtaatagcga agaggcccgc accgatcgcc cttcccaaca gttgcgcagc  13440
ctgaatggcg aatgggacgc gccctgtagc ggcgcattaa gcgcggcggg tgtggtggtt  13500
acgcgcagcg tgaccgctac acttgccagc gccctagcgc ccgctccttt cgctttcttc  13560
ccttcctttc tcgccacgtt cgccggcttt ccccgtcaag ctctaaatcg ggggctccct  13620
ttagggttcc gatttagtgc tttacggcac ctcgacccca aaaaacttga ttagggtgat  13680
ggttcacgta gtgggccatc gccctgatag acggtttttc gccctttgac gttggagtcc  13740
acgttcttta atagtggact cttgttccaa actggaacaa cactcaaccc tatctcggtc  13800
tattcttttg atttataagg gattttgccg atttcggcct attggttaaa aaatgagctg  13860
```

atttaacaaa aatttaacgc gaattttaac aaaatattaa cgcttacaat ttaggtg 13917

<210> SEQ ID NO 73
<211> LENGTH: 7252
<212> TYPE: DNA
<213> ORGANISM: Artificial Sequence
<220> FEATURE:
<221> NAME/KEY: misc_feature
<222> LOCATION: ()..()
<223> OTHER INFORMATION: Plastid transformation vector pHK07, containing Operon C, containi

<400> SEQUENCE: 73
gcacttttcg gggaaatgtg cgcggaaccc ctatttgttt atttttctaa atacattcaa 60
atatgtatcc gctcatgaga caataaccct gataaatgct tcaataatat tgaaaaagga 120
agagtatgag tattcaacat ttccgtgtcg cccttattcc cttttttgcg gcattttgcc 180
ttcctgtttt tgctcaccca gaaacgctgg tgaaagtaaa agatgctgaa gatcagttgg 240
gtgcacgagt gggttacatc gaactggatc tcaacagcgg taagatcctt gagagttttc 300
gccccgaaga acgttttcca atgatgagca cttttaaagt tctgctatgt ggcgcggtat 360
tatcccgtat tgacgccggg caagagcaac tcggtcgccg catacactat tctcagaatg 420
acttggttga gtactcacca gtcacagaaa agcatcttac ggatggcatg acagtaagag 480
aattatgcag tgctgccata accatgagtg ataacactgc ggccaactta cttctgacaa 540
cgatcggagg accgaaggag ctaaccgctt ttttgcacaa catgggggat catgtaactc 600
gccttgatcg ttgggaaccg gagctgaatg aagccatacc aaacgacgag cgtgacacca 660
cgatgcctgt agcaatggca acaacgttgc gcaaactatt aactggcgaa ctacttactc 720
tagcttcccg gcaacaatta atagactgga tggaggcgga taaagttgca ggaccacttc 780
tgcgctcggc ccttccggct ggctggttta ttgctgataa atctggagcc ggtgagcgtg 840
ggtctcgcgg tatcattgca gcactggggc cagatggtaa gccctcccgt atcgtagtta 900
tctacacgac ggggagtcag gcaactatgg atgaacgaaa tagacagatc gctgagatag 960
gtgcctcact gattaagcat tggtaactgt cagaccaagt ttactcatat atactttaga 1020
ttgatttaaa acttcatttt taatttaaaa ggatctaggt gaagatcctt tttgataatc 1080
tcatgaccaa aatcccttaa cgtgagtttt cgttccactg agcgtcagac cccgtagaaa 1140
agatcaaagg atcttcttga gatccttttt ttctgcgcgt aatctgctgc ttgcaaacaa 1200
aaaaaccacc gctaccagcg gtggtttgtt tgccggatca agagctacca actctttttc 1260
cgaaggtaac tggcttcagc agagcgcaga taccaaatac tgtccttcta gtgtagccgt 1320
agttaggcca ccacttcaag aactctgtag caccgcctac atacctcgct ctgctaatcc 1380
tgttaccagt ggctgctgcc agtggcgata agtcgtgtct taccgggttg gactcaagac 1440
gatagttacc ggataaggcg cagcggtcgg gctgaacggg gggttcgtgc acacagccca 1500
gcttggagcg aacgacctac accgaactga gatacctaca gcgtgagcta tgagaaagcg 1560
ccacgcttcc cgaagggaga aaggcggaca ggtatccggt aagcggcagg gtcggaacag 1620
gagagcgcac gagggagctt ccagggggaa acgcctggta tctttatagt cctgtcgggt 1680
ttcgccacct ctgacttgag cgtcgatttt tgtgatgctc gtcagggggg cggagcctat 1740
ggaaaaacgc cagcaacgcg gcctttttac ggttcctggc cttttgctgg ccttttgctc 1800
acatgttctt tcctgcgtta tcccctgatt ctgtggataa ccgtattacc gcctttgagt 1860
gagctgatac cgctcgccgc agccgaacga ccgagcgcag cgagtcagtg agcgaggaag 1920

-continued

```
cggaagagcg cccaatacgc aaaccgcctc tccccgcgcg ttggccgatt cattaatgca   1980
gctggcacga caggtttccc gactggaaag cgggcagtga gcgcaacgca attaatgtga   2040
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctccaccgc ggtggcggcc   2220
gctctagaac tagtggatct tcttggctgt tattcaaaag gtccaacaat gtatatatat   2280
tggacatttt gaggcaatta tagatcctgg aaggcaattc tgattggtca ataaaaatcg   2340
atttcaatgc tatttttttt ttgtttttta tgagtttagc caatttatca tgaaaggtaa   2400
aaggggataa aggaaccgtg tgttgattgt cctgtaaata taagttgtct tcctccatat   2460
gtaaaaaggg aataaataaa tcaattaaat ttcgggatgc ttcatgaagt gcttctttcg   2520
gagttaaact tccgtttgtc catatttcga gaaaaagtat ctcttgtttt tcattcccat   2580
tcccataaga atgaatacta tgattcgcgt ttcgaacagg catgaataca gcatctatag   2640
gataacttcc atcttgaaag ttatgtggcg tttttataag atatccacga tttctctcta   2700
tttgtaatcc aatacaaaaa tcaattggtt ccgttaaact ggctatatgt tgtgtattat   2760
caacgatttc tacataaggc ggcaagatga tatcttgggc agttacagat ccaggaccct   2820
tgacacaaat agatgcgtca gaagttccat atagattact tcttaatata atttctttca   2880
aattcattaa aatttcatgt accgattctt gaatgcccgt tatggtagaa tattcatgtg   2940
ggactttctc agattttaca cgtgtgatac atgttccttc tatttctcca agtaaagctc   3000
ttcgcatcgc aatgcctatt gtgtcggctt ggcctttcat aagtggagac agaataaagc   3060
gtccataata aaggcgttta ctgtctgttc ttgattcaac acacttccac tgtagtgtcc   3120
gagtagatac tgttactttc tctcgaacca tagtactatt atttgattag atcatcgaat   3180
cttttatttc tcttgagatt tcttcaatgt tcagttctac acacgtcttt ttttcggagg   3240
tctacagcca ttatgtggca taggagttac atcccgtacg aaagttaata gtataccact   3300
tcgacgaata gctcgtaatg ctgcatctct tccgagaccg ggacctttta tcatgacttc   3360
tgctcgttgc ataccttgat ccactactgt acggatagcg tttgctgctg cggtttgagc   3420
agcaaacggt gttcctcttc tcgtaccttt gaatccagaa gtaccggcgg aggaccaaga   3480
aactactcga ccccgtacat ctgtaacagt gacaatggta ttattgaaac ttgcttgaac   3540
atgaataact ccctttggta ttctacgtgc acccttacgt gaaccaatac gtccattcct   3600
acgcgaacta attttcggta tagcttttgc catattttat catctcgtaa atatgagtca   3660
gagatatatg gatatatcca tttcatgtca aaacagattc tttatttgta catcggctct   3720
tctggcaagt ctgattatcc ctgtctttgt ttatgtctcg ggttggaaca aattactata   3780
attcgtcccc gcctacggat tagtcgacat ttttcacaaa ttttacgaac ggaagctctt   3840
attttcatat ttctcattcc ttaccttaat tctgaatcta tttcttggaa gaaaataagt   3900
ttcttgaaat ttttcatctc gaattgtatt cccacgaaag gaatggtgaa gttgaaaaac   3960
gaatccttca aatctttgtt gtggagtcga taaattatac gccctttggt tgaatcataa   4020
ggacttactt caattttgac tctatctcct ggcagtatcc gtataaaact atgccggatc   4080
tttcctgaaa cataatttat aatcagatcc aggaggacca tatgatcgcc gaagcggata   4140
tggaggtctg ccgggagctg atccgcaccg gcagctactc cttccatgcg gcgtccagag   4200
ttctgccggc gcgggtccgt gaccccgcgc tggcgcttta cgccttttgc cgcgtcgccg   4260
atgacgaagt cgacgaggtt ggcgcgccgc gcgacaaggc tgcggcggtt ttgaaacttg   4320
```

```
gcgaccggct ggaggacatc tatgccggtc gtccgcgcaa tgcgccctcg gatcgggctt   4380
tcgcggcggt ggtcgaggaa ttcgagatgc cgcgcgaatt gcccgaggcg ctgctggagg   4440
gcttcgcctg ggatgccgag gggcggtggt atcacacgct ttcggacgtg caggcctatt   4500
cggcgcgggt ggcggccgcc gtcggcgcga tgatgtgcgt gctgatgcgg gtgcgcaacc   4560
ccgatgcgct ggcgcgggcc tgcgatctcg gtcttgccat gcagatgtcg aacatcgccc   4620
gcgacgtggg cgaggatgcc cgggcggggc ggcttttcct gccgaccgac tggatggtcg   4680
aggaggggat cgatccgcag gcgttcctgg ccgatccgca gcccaccaag ggcatccgcc   4740
gggtcaccga gcggttgctg aaccgcgccg accggcttta ctggcgggcg gcgacggggg   4800
tgcggctttt gccctttgac tgccgaccgg ggatcatggc cgcgggcaag atctatgccg   4860
cgatcggggc cgaggtggcg aaggcgaaat acgacaacat cacccggcgt gcccacacga   4920
ccaagggccg caagctgtgg ctggtggcga attccgcgat gtcggcgacg gcgacctcga   4980
tgctgccgct ctcgccgcgg gtgcatgcca agcccgagcc cgaagtggcg catctggtcg   5040
atgccgccgc gcatcgcaac ctgcatcccg aacggtccga ggtgctgatc tcggcgctga   5100
tggcgctgaa ggcgcgcgac cgcggcctgg cgatggattg aggatctaaa caaacccgga   5160
acagaccgtt gggaagcgat tcagtaatta aagcttcatg actccttttt ggttcttaaa   5220
gtccctttga ggtatcaact aataagaaag atattagaca acccccttt tttcttttc    5280
acaaatagga agtttcgaat ccaatttgga tattaaaagg attaccagat ataacacaaa   5340
atctctccac ctattccttc tagtcgagcc tctcggtctg tcattatacc tcgagaagta   5400
gaaagaatta caatccccat tccacctaaa attcgcggaa ttcgttgata attagaatag   5460
attcgtagac caggtcgact gattcgtttt aaatttaaaa tatttctata gggtcttttc   5520
ctattccttc tatgtcgcag ggttaaaacc aaaaaatatt tgttttttc tcgatgtttt    5580
ctcacgtttt cgataaaacc ttctcgtaaa agtatttgaa caatattttc ggtaatatta   5640
gtagatgcta ttcgaaccac ccttttcga tccatatcag catttcgtat agaagttatt    5700
atctcagcaa tagtgtccct acccatgatg aactaaaatt attggggcct ccaaatttga   5760
tataatcaac gtgtttttta cttatttttt ttttgaatat gatatgaatt attaaagata   5820
tatgcgtgag acacaatcta ctaattaatc tatttcttc aaatacccca ctagaaacag    5880
atcacaattt cattttataa tacctcggga gctaatgaaa ctattttagt aaaatttaat   5940
tctctcaatt cccgggcgat tgcaccaaaa attcgagttc cttttgattt ccttccttct   6000
tgatcaataa caactgcagc attgtcatca tatcgtatta tcatcccgtt gtcacgtttg   6060
agttctttac aggtccgcac aattacagct ctgactactt ctgatctttc taggggcata   6120
tttggtacgg cttctttgat cacagcaaca ataacgtcac caatatgagc atatcgacga   6180
ttgctagctc ctatgattcg aatacacatc aattctcgag ccccgctgtt atccgctaca   6240
tttaaatggg tctgaggttg aatcattttt ttaatccgtt ctttgaatgc aaagggcgaa   6300
gaaaaaaaag aaatattttt gtccaaaaaa aaagaaacat gcggtttcgt ttcatatcta   6360
agagcccttt ccgcattttt ttctattaca ttacgaaata atgaattgag ttcgtatagg   6420
cattttagat gctgctagtg aaatagccct tctggctata ttttctgtta ctccacccat   6480
ttcataaagt attcgacccg gtttaacaac agctacccaa tattcagggg atcccccggg   6540
ctgcaggaat tcgatatcaa gcttatcgat accgtcgacc tcgagggggg gcccggtacc   6600
caattcgccc tatagtgagt cgtattacaa ttcactggcc gtcgttttac aacgtcgtga   6660
```

-continued

```
ctgggaaaac cctggcgtta cccaacttaa tcgccttgca gcacatcccc ctttcgccag   6720

ctggcgtaat agcgaagagg cccgcaccga tcgcccttcc caacagttgc gcagcctgaa   6780

tggcgaatgg gacgcgccct gtagcggcgc attaagcgcg gcgggtgtgg tggttacgcg   6840

cagcgtgacc gctacacttg ccagcgccct agcgcccgct cctttcgctt tcttcccttc   6900

ctttctcgcc acgttcgccg gctttccccg tcaagctcta aatcgggggc tccctttagg   6960

gttccgattt agtgctttac ggcacctcga ccccaaaaaa cttgattagg gtgatggttc   7020

acgtagtggg ccatcgccct gatagacggt ttttcgccct ttgacgttgg agtccacgtt   7080

ctttaatagt ggactcttgt tccaaactgg aacaacactc aaccctatct cggtctattc   7140

ttttgattta taagggattt tgccgatttc ggcctattgg ttaaaaaatg agctgattta   7200

acaaaaattt aacgcgaatt ttaacaaaat attaacgctt acaatttagg tg           7252


<210> SEQ ID NO 74
<211> LENGTH: 14623
<212> TYPE: DNA
<213> ORGANISM: Artificial Sequence
<220> FEATURE:
<221> NAME/KEY: misc_feature
<222> LOCATION: ()..()
<223> OTHER INFORMATION: Plastic transformation vector pHK08, containing
      Operon G, containi

<400> SEQUENCE: 74

cacctaaatt gtaagcgtta atattttgtt aaaattcgcg ttaaattttt gttaaatcag     60

ctcatttttt aaccaatagg ccgaaatcgg caaaatccct tataaatcaa aagaatagac    120

cgagataggg ttgagtgttg ttccagtttg gaacaagagt ccactattaa agaacgtgga    180

ctccaacgtc aaagggcgaa aaaccgtcta tcagggcgat ggcccactac gtgaaccatc    240

accctaatca agttttttgg ggtcgaggtg ccgtaaagca ctaaatcgga accctaaagg    300

gagcccccga tttagagctt gacggggaaa gccggcgaac gtggcgagaa aggaagggaa    360

gaaagcgaaa ggagcgggcg ctagggcgct ggcaagtgta gcggtcacgc tgcgcgtaac    420

caccacaccc gccgcgctta atgcgccgct acagggcgcg tcccattcgc cattcaggct    480

gcgcaactgt tgggaagggc gatcggtgcg ggcctcttcg ctattacgcc agctggcgaa    540

agggggatgt gctgcaaggc gattaagttg ggtaacgcca gggttttccc agtcacgacg    600

ttgtaaaacg acggccagtg aattgtaata cgactcacta tagggcgaat tgggtaccgg    660

gccccccctc gaggtcgacg gtatcgataa gcttgatatc gaattcctgc agcccggggg    720

atcttcttgg ctgttattca aaaggtccaa caatgtatat atattggaca ttttgaggca    780

attatagatc ctggaaggca attctgattg gtcaataaaa atcgatttca atgctatttt    840

tttttgttt tttatgagtt tagccaattt atcatgaaag gtaaaagggg ataaaggaac    900

cgtgtgttga ttgtcctgta aatataagtt gtcttcctcc atatgtaaaa agggaataaa    960

taaatcaatt aaatttcggg atgcttcatg aagtgcttct ttcggagtta aacttccgtt   1020

tgtccatatt tcgagaaaaa gtatctcttg tttttcattc ccattcccat aagaatgaat   1080

actatgattc gcgtttcgaa caggcatgaa tacagcatct ataggataac ttccatcttg   1140

aaagttatgt ggcgttttta taagatatcc acgatttctc tctatttgta atccaataca   1200

aaaatcaatt ggttccgtta aactggctat atgttgtgta ttatcaacga tttctacata   1260

aggcggcaag atgatatctt gggcagttac agatccagga ccccttgacac aaatagatgc   1320

gtcagaagtt ccatatagat tacttcttaa tataatttct ttcaaattca ttaaaatttc   1380
```

-continued

```
atgtaccgat tcttgaatgc ccgttatggt agaatattca tgtgggactt tctcagattt   1440
tacacgtgtg atacatgttc cttctatttc tccaagtaaa gctcttcgca tcgcaatgcc   1500
tattgtgtcg gcttggcctt tcataagtgg agacagaata aagcgtccat aataaaggcg   1560
tttactgtct gttcttgatt caacacactt ccactgtagt gtccgagtag atactgttac   1620
tttctctcga accatagtac tattatttga ttagatcatc gaatctttta tttctcttga   1680
gatttcttca atgttcagtt ctacacacgt ctttttttcg gaggtctaca gccattatgt   1740
ggcataggag ttacatcccg tacgaaagtt aatagtatac cacttcgacg aatagctcgt   1800
aatgctgcat ctcttccgag accgggacct tttatcatga cttctgctcg ttgcatacct   1860
tgatccacta ctgtacggat agcgtttgct gctgcggttt gagcagcaaa cggtgttcct   1920
cttctcgtac ctttgaatcc agaagtaccg gcggaggacc aagaaactac tcgaccccgt   1980
acatctgtaa cagtgacaat ggtattattg aaacttgctt gaacatgaat aactcccttt   2040
ggtattctac gtgcaccctt acgtgaacca atacgtccat tcctacgcga actaattttc   2100
ggtatagctt ttgccatatt ttatcatctc gtaaatatga gtcagagata tatggatata   2160
tccatttcat gtcaaaacag attctttatt tgtacatcgg ctcttctggc aagtctgatt   2220
atccctgtct ttgtttatgt ctcgggttgg aacaaattac tataattcgt ccccgcctac   2280
ggattagtcg acatttttca caaattttac gaacggaagc tcttattttc atatttctca   2340
ttccttacct taattctgaa tctatttctt ggaagaaaat aagtttcttg aaatttttca   2400
tctcgaattg tattcccacg aaaggaatgg tgaagttgaa aaacgaatcc ttcaaatctt   2460
tgttgtggag tcgataaatt atacgccctt tggttgaatc ataaggactt acttcaattt   2520
tgactctatc tcctggcagt atccgtataa aactatgccg gatctttcct gaaacataat   2580
ttataatcag atcggccgca ggaggagttc atatgtcaga gttgagagcc ttcagtgccc   2640
cagggaaagc gttactagct ggtggatatt tagttttaga tacaaaatat gaagcatttg   2700
tagtcggatt atcggcaaga atgcatgctg tagcccatcc ttacggttca ttgcaagggt   2760
ctgataagtt tgaagtgcgt gtgaaaagta aacaatttaa agatggggag tggctgtacc   2820
atataagtcc taaaagtggc ttcattcctg tttcgatagg cggatctaag aaccctttca   2880
ttgaaaaagt tatcgctaac gtatttagct actttaaacc taacatggac gactactgca   2940
atagaaactt gttcgttatt gatattttct ctgatgatgc ctaccattct caggaggata   3000
gcgttaccga acatcgtggc aacagaagat tgagttttca ttcgcacaga attgaagaag   3060
ttcccaaaac agggctgggc tcctcggcag gtttagtcac agttttaact acagctttgg   3120
cctccttttt tgtatcggac ctggaaaata atgtagacaa atatagagaa gttattcata   3180
atttagcaca agttgctcat tgtcaagctc agggtaaaat tggaagcggg tttgatgtag   3240
cggcggcagc atatggatct atcagatata gaagattccc acccgcatta atctctaatt   3300
tgccagatat tggaagtgct acttacggca gtaaactggc gcatttggtt gatgaagaag   3360
actggaatat tacgattaaa agtaaccatt taccttcggg attaacttta tggatgggcg   3420
atattaagaa tggttcagaa acagtaaaac tggtccagaa ggtaaaaaat tggtatgatt   3480
cgcatatgcc agaaagcttg aaaatatata cagaactcga tcatgcaaat tctagattta   3540
tggatggact atctaaacta gatcgcttac acgagactca tgacgattac agcgatcaga   3600
tatttgagtc tcttgagagg aatgactgta cctgtcaaaa gtatcctgaa atcacagaag   3660
ttagagatgc agttgccaca attagacgtt cctttagaaa aataactaaa gaatctggtg   3720
ccgatatcga acctcccgta caaactagct tattggatga ttgccagacc ttaaaaggag   3780
```

```
ttcttacttg cttaatacct ggtgctggtg gttatgacgc cattgcagtg attactaagc   3840
aagatgttga tcttagggct caaaccgcta atgacaaaag attttctaag gttcaatggc   3900
tggatgtaac tcaggctgac tggggtgtta ggaaagaaaa agatccggaa acttatcttg   3960
ataaactgca ggaggagttt taatgtcatt accgttctta acttctgcac cgggaaaggt   4020
tattattttt ggtgaacact ctgctgtgta caacaagcct gccgtcgctg ctagtgtgtc   4080
tgcgttgaga acctacctgc taataagcga gtcatctgca ccagatacta ttgaattgga   4140
cttcccggac attagcttta atcataagtg gtccatcaat gatttcaatg ccatcaccga   4200
ggatcaagta aactcccaaa aattggccaa ggctcaacaa gccaccgatg gcttgtctca   4260
ggaactcgtt agtcttttgg atccgttgtt agctcaacta tccgaatcct tccactacca   4320
tgcagcgttt tgtttcctgt atatgtttgt ttgcctatgc cccccatgcca agaatattaa   4380
gttttcttta aagtctactt tacccatcgg tgctgggttg ggctcaagcg cctctatttc   4440
tgtatcactg gccttagcta tggcctactt ggggggggtta ataggatcta atgacttgga   4500
aaagctgtca gaaaacgata agcatatagt gaatcaatgg gccttcatag gtgaaaagtg   4560
tattcacggt accccttcag gaatagataa cgctgtggcc acttatggta atgccctgct   4620
atttgaaaaa gactcacata atggaacaat aaacacaaac aattttaagt tcttagatga   4680
tttcccagcc attccaatga tcctaaccta tactagaatt ccaaggtcta caaaagatct   4740
tgttgctcgc gttcgtgtgt tggtcaccga gaaatttcct gaagttatga agccaattct   4800
agatgccatg ggtgaatgtg ccctacaagg cttagagatc atgactaagt taagtaaatg   4860
taaaggcacc gatgacgagg ctgtagaaac taataatgaa ctgtatgaac aactattgga   4920
attgataaga ataaatcatg gactgcttgt ctcaatcggt gtttctcatc ctggattaga   4980
acttattaaa aatctgagcg atgatttgag aattggctcc acaaaactta ccggtgctgg   5040
tggcggcggt tgctctttga ctttgttacg aagagacatt actcaagagc aaattgacag   5100
cttcaaaaag aaattgcaag atgattttag ttacgagaca tttgaaacag acttgggtgg   5160
gactggctgc tgtttgttaa gcgcaaaaaa tttgaataaa gatcttaaaa tcaaatccct   5220
agtattccaa ttatttgaaa ataaaactac cacaaagcaa caaattgacg atctattatt   5280
gccaggaaac acgaatttac catggacttc agacgaggag ttttaatgac tgtatatact   5340
gctagtgtaa ctgctccggt aaatattgct actcttaagt attgggggaa aagggacacg   5400
aagttgaatc tgcccaccaa ttcgtccata tcagtgactt tatcgcaaga tgacctcaga   5460
acgttgacct ctgcggctac tgcacctgag tttgaacgcg acactttgtg gttaaatgga   5520
gaaccacaca gcatcgacaa tgaaagaact caaaattgtc tgcgcgacct acgccaatta   5580
agaaaggaaa tggaatcgaa ggacgcctca ttgcccacat tatctcaatg gaaactccac   5640
attgtctccg aaaataactt tcctacagca gctggtttag cttcctccgc tgctggcttt   5700
gctgcattgg tctctgcaat tgctaagtta taccaattac cacagtcaac ttcagaaata   5760
tctagaatag caagaaaggg gtctggttca gcttgtagat cgttgtttgg cggatacgtg   5820
gcctgggaaa tgggaaaagc tgaagatggt catgattcca tggcagtaca aatcgcagac   5880
agctctgact ggcctcagat gaaagcttgt gtcctagttg tcagcgatat taaaaaggat   5940
gtgagttcca ctcagggtat gcaattgacc gtggcaacct ccgaactatt taaagaaaga   6000
attgaacatg tcgtaccaaa gagatttgaa gtcatgcgta aagccattgt tgaaaaagat   6060
ttcgccacct ttgcaaagga aacaatgatg gattccaact ctttccatgc cacatgtttg   6120
```

-continued

```
gactctttcc ctccaatatt ctacatgaat gacacttcca agcgtatcat cagttggtgc   6180
cacaccatta atcagtttta cggagaaaca atcgttgcat acacgtttga tgcaggtcca   6240
aatgctgtgt tgtactactt agctgaaaat gagtcgaaac tctttgcatt tatctataaa   6300
ttgtttggct ctgttcctgg atgggacaag aaatttacta ctgagcagct tgaggctttc   6360
aaccatcaat ttgaatcatc taactttact gcacgtgaat tggatcttga gttgcaaaag   6420
gatgttgcca gagtgatttt aactcaagtc ggttcaggcc cacaagaaac aaacgaatct   6480
ttgattgacg caaagactgg tctaccaaag gaagaggagt tttaactcga cgccggcgga   6540
ggcacatatg tctcagaacg tttacattgt atcgactgcc agaaccccaa ttggttcatt   6600
ccagggttct ctatcctcca agacagcagt ggaattgggt gctgttgctt taaaaggcgc   6660
cttggctaag gttccagaat tggatgcatc caaggatttt gacgaaatta tttttggtaa   6720
cgttctttct gccaatttgg gccaagctcc ggccagacaa gttgctttgg ctgccggttt   6780
gagtaatcat atcgttgcaa gcacagttaa caaggtctgt gcatccgcta tgaaggcaat   6840
cattttgggt gctcaatcca tcaaatgtgg taatgctgat gttgtcgtag ctggtggttg   6900
tgaatctatg actaacgcac catactacat gccagcagcc cgtgcgggtg ccaaatttgg   6960
ccaaactgtt cttgttgatg gtgtcgaaag agatgggttg aacgatgcgt acgatggtct   7020
agccatgggt gtacacgcag aaaagtgtgc ccgtgattgg gatattacta gagaacaaca   7080
agacaatttt gccatcgaat cctaccaaaa atctcaaaaa tctcaaaagg aaggtaaatt   7140
cgacaatgaa attgtacctg ttaccattaa gggatttaga ggtaagcctg atactcaagt   7200
cacgaaggac gaggaacctg ctagattaca cgttgaaaaa ttgagatctg caaggactgt   7260
tttccaaaaa gaaaacggta ctgttactgc cgctaacgct tctccaatca acgatggtgc   7320
tgcagccgtc atcttggttt ccgaaaaagt tttgaaggaa aagaatttga agcctttggc   7380
tattatcaaa ggttggggtg aggccgctca tcaaccagct gattttacat gggctccatc   7440
tcttgcagtt ccaaaggctt tgaaacatgc tggcatcgaa gacatcaatt ctgttgatta   7500
ctttgaattc aatgaagcct tttcggttgt cggtttggtg aacactaaga ttttgaagct   7560
agacccatct aaggttaatg tatatggtgg tgctgttgct ctaggtcacc cattgggttg   7620
ttctggtgct agagtggttg ttacactgct atccatctta cagcaagaag gaggtaagat   7680
cggtgttgcc gccatttgta atggtggtgg tggtgcttcc tctattgtca ttgaaaagat   7740
atgaggatcc tctagatgcg caggaggcac atatggcgaa gaacgttggg attttggcta   7800
tggatatcta tttccctccc acctgtgttc aacaggaagc tttggaagca catgatggag   7860
caagtaaagg gaaatacact attggacttg gccaagattg tttagctttt tgcactgagc   7920
ttgaagatgt tatctctatg agtttcaatg cggtgacatc actttttgag aagtataaga   7980
ttgaccctaa ccaaatcggg cgtcttgaag taggaagtga gactgttatt gacaaaagca   8040
agtccatcaa gaccttcttg atgcagctct ttgagaaatg tggaaacact gatgtcgaag   8100
gtgttgactc gaccaatgct tgctatggtg gaactgcagc tttgttaaac tgtgtcaatt   8160
gggttgagag taactcttgg gatggacgtt atggcctcgt catttgtact gacagcgcgg   8220
tttatgcaga aggacccgca aggcccactg gaggagctgc agcgattgct atgttgatag   8280
gacctgatgc tcctatcgtt ttcgaaagca aattgagagc aagccacatg gctcatgtct   8340
atgactttta caagcccaat cttgctagcg agtacccggt tgttgatggt aagctttcac   8400
agacttgcta cctcatggct cttgactcct gctataaaca tttatgcaac aagttcgaga   8460
agatcgaggg caaagagttc tccataaatg atgctgatta cattgttttc cattctccat   8520
```

-continued

```
acaataaact tgtacagaaa agctttgctc gtctcttgta caacgacttc ttgagaaacg   8580
caagctccat tgacgaggct gccaaagaaa agttcacccc ttattcatct ttgacccttg   8640
acgagagtta ccaaagccgt gatcttgaaa aggtgtcaca acaaatttcg aaaccgtttt   8700
atgatgctaa agtgcaacca acgactttaa taccaaagga agtcggtaac atgtacactg   8760
cttctctcta cgctgcattt gcttccctca tccacaataa acacaatgat ttggcgggaa   8820
agcgggtggt tatgttctct tatggaagtg gctccaccgc aacaatgttc tcattacgcc   8880
tcaacgacaa taagcctcct ttcagcattt caaacattgc atctgtaatg gatgttggcg   8940
gtaaattgaa agctagacat gagtatgcac ctgagaagtt tgtggagaca atgaagctaa   9000
tggaacatag gtatggagca aaggactttg tgacaaccaa ggagggtatt atagatcttt   9060
tggcaccggg aacttattat ctgaaagagg ttgattcctt gtaccggaga ttctatggca   9120
agaaaggtga agatggatct gtagccaatg gacactgagg atccgtcgag cacgtggagg   9180
cacatatgca atgctgtgag atgcctgttg gatacattca gattcctgtt gggattgctg   9240
gtccattgtt gcttgatggt tatgagtact ctgttcctat ggctacaacc gaaggttgtt   9300
tggttgctag cactaacaga ggctgcaagg ctatgtttat ctctggtggc gccaccagta   9360
ccgttcttaa ggacggtatg acccgagcac ctgttgttcg gttcgcttcg gcgagacgag   9420
cttcggagct taagtttttc ttggagaatc cagagaactt tgatactttg gcagtagtct   9480
tcaacaggtc gagtagattt gcaagactgc aaagtgttaa atgcacaatc gcggggaaga   9540
atgcttatgt aaggttctgt tgtagtactg gtgatgctat ggggatgaat atggtttcta   9600
aaggtgtgca gaatgttctt gagtatctta ccgatgattt ccctgacatg gatgtgattg   9660
gaatctctgg taacttctgt tcggacaaga aacctgctgc tgtgaactgg attgagggac   9720
gtggtaaatc agttgtttgc gaggctgtaa tcagaggaga gatcgtgaac aaggtcttga   9780
aaacgagcgt ggctgcttta gtcgagctca acatgctcaa gaacctagct ggctctgctg   9840
ttgcaggctc tctaggtgga ttcaacgctc atgccagtaa catagtgtct gctgtattca   9900
tagctactgg ccaagatcca gctcaaaacg tggagagttc tcaatgcatc accatgatgg   9960
aagctattaa tgacggcaaa gatatccata tctcagtcac tatgccatct atcgaggtgg  10020
ggacagtggg aggaggaaca cagcttgcat ctcaatcagc gtgtttaaac ctgctcggag  10080
ttaaaggagc aagcacagag tcgccgggaa tgaacgcaag gaggctagcg acgatcgtag  10140
ccggagcagt tttagctgga gagttatctt taatgtcagc aattgcagct ggacagcttg  10200
tgagaagtca catgaaatac aatagatcca gccgagacat ctctggagca acgacaacga  10260
caacaacaac aacatgaccc gtaggaggca catatgagtt cccaacaaga gaaaaaggat  10320
tatgatgaag aacaattaag gttgatggaa gaagtttgta tcgttgtaga tgaaaatgat  10380
gtccctttaa gatatggaac gaaaaaggag tgtcatttga tggaaaatat aaataaaggt  10440
cttttgcata gagcattctc tatgttcatc tttgatgagc aaaatcgcct tttacttcag  10500
cagcgtgcag aagagaaaat tacatttcca tccttatgga cgaatacatg ttgctcccac  10560
ccattggatg ttgctggtga acgtggtaat actttacctg aagctgttga aggtgttaag  10620
aatgcagctc aacgcaagct gttccatgaa ttgggtattc aagccaagta tattcccaaa  10680
gacaaatttc agtttcttac acgaatccat taccttgctc ctagtactgg tgcttgggga  10740
gagcatgaaa ttgactacat tcttttcttc aaaggtaaag ttgagctgga tatcaatccc  10800
aatgaagttc aagcctataa gtatgttact atggaagagt taaaagagat gttttccgat  10860
```

-continued

```
cctcaatatg gattcacacc atggttcaaa cttatttgtg agcattttat gtttaaatgg  10920
tggcaggatg tagatcatgc gtcaaaattc caagatacct taattcatcg ttgctaagga  10980
tcccccggga tccggccgat ctaaacaaac ccggaacaga ccgttgggaa gcgattcagt  11040
aattaaagct tcatgactcc tttttggttc ttaaagtccc tttgaggtat caactaataa  11100
gaaagatatt agacaacccc cctttttttct ttttcacaaa taggaagttt cgaatccaat  11160
ttggatatta aaaggattac cagatataac acaaaatctc tccacctatt ccttctagtc  11220
gagcctctcg gtctgtcatt atacctcgag aagtagaaag aattacaatc cccattccac  11280
ctaaaattcg cggaattcgt tgataattag aatagattcg tagaccaggt cgactgattc  11340
gttttaaatt taaaatattt ctatagggtc ttttcctatt ccttctatgt cgcagggtta  11400
aaaccaaaaa atatttgttt ttttctcgat gttttctcac gttttcgata aaaccttctc  11460
gtaaaagtat ttgaacaata ttttcggtaa tattagtaga tgctattcga accacccttt  11520
ttcgatccat atcagcattt cgtatagaag ttattatctc agcaatagtg tccctaccca  11580
tgatgaacta aaattattgg ggcctccaaa tttgatataa tcaacgtgtt ttttacttat  11640
tttttttttg aatatgatat gaattattaa agatatatgc gtgagacaca atctactaat  11700
taatctattt ctttcaaata ccccactaga aacagatcac aatttcattt tataatacct  11760
cgggagctaa tgaaactatt ttagtaaaat ttaattctct caattcccgg gcgattgcac  11820
caaaaattcg agttcctttt gatttccttc cttcttgatc aataacaact gcagcattgt  11880
catcatatcg tattatcatc ccgttgtcac gtttgagttc tttacaggtc cgcacaatta  11940
cagctctgac tacttctgat ctttctaggg gcatatttgg tacggcttct ttgatcacag  12000
caacaataac gtcaccaata tgagcatatc gacgattgct agctcctatg attcgaatac  12060
acatcaattc tcgagccccg ctgttatccg ctacatttaa atgggtctga ggttgaatca  12120
tttttttaat ccgttctttg aatgcaaagg gcgaagaaaa aaaagaaata tttttgtcca  12180
aaaaaaaaga aacatgcggt ttcgtttcat atctaagagc cctttccgca tttttttcta  12240
ttacattacg aaataatgaa ttgagttcgt ataggcattt tagatgctgc tagtgaaata  12300
gcccttctgg ctatattttc tgttactcca cccatttcat aaagtattcg acccggttta  12360
acaacagcta cccaatattc aggggatcca ctagttctag agcggccgcc accgcggtgg  12420
agctccagct tttgttccct ttagtgaggg ttaatttcga gcttggcgta atcatggtca  12480
tagctgtttc ctgtgtgaaa ttgttatccg ctcacaattc cacacaacat acgagccgga  12540
agcataaagt gtaaagcctg gggtgcctaa tgagtgagct aactcacatt aattgcgttg  12600
cgctcactgc ccgctttcca gtcgggaaac ctgtcgtgcc agctgcatta atgaatcggc  12660
caacgcgcgg ggagaggcgg tttgcgtatt gggcgctctt ccgcttcctc gctcactgac  12720
tcgctgcgct cggtcgttcg gctgcggcga gcggtatcag ctcactcaaa ggcggtaata  12780
cggttatcca cagaatcagg ggataacgca ggaaagaaca tgtgagcaaa aggccagcaa  12840
aaggccagga accgtaaaaa ggccgcgttg ctggcgtttt tccataggct ccgcccccct  12900
gacgagcatc acaaaaatcg acgctcaagt cagaggtggc gaaacccgac aggactataa  12960
agataccagg cgtttccccc tggaagctcc ctcgtgcgct ctcctgttcc gaccctgccg  13020
cttaccggat acctgtccgc ctttctccct tcgggaagcg tggcgctttc tcatagctca  13080
cgctgtaggt atctcagttc ggtgtaggtc gttcgctcca agctgggctg tgtgcacgaa  13140
ccccccgttc agcccgaccg ctgcgcctta tccggtaact atcgtcttga gtccaacccg  13200
gtaagacacg acttatcgcc actggcagca gccactggta acaggattag cagagcgagg  13260
```

```
tatgtaggcg gtgctacaga gttcttgaag tggtggccta actacggcta cactagaagg  13320

acagtatttg gtatctgcgc tctgctgaag ccagttacct tcggaaaaag agttggtagc  13380

tcttgatccg gcaaacaaac caccgctggt agcggtggtt tttttgtttg caagcagcag  13440

attacgcgca gaaaaaaagg atctcaagaa gatcctttga tcttttctac ggggtctgac  13500

gctcagtgga acgaaaactc acgttaaggg attttggtca tgagattatc aaaaaggatc  13560

ttcacctaga tccttttaaa ttaaaaatga agttttaaat caatctaaag tatatatgag  13620

taaacttggt ctgacagtta ccaatgctta atcagtgagg cacctatctc agcgatctgt  13680

ctatttcgtt catccatagt tgcctgactc cccgtcgtgt agataactac gatacgggag  13740

ggcttaccat ctggccccag tgctgcaatg ataccgcgag acccacgctc accggctcca  13800

gatttatcag caataaacca gccagccgga agggccgagc gcagaagtgg tcctgcaact  13860

ttatccgcct ccatccagtc tattaattgt tgccgggaag ctagagtaag tagttcgcca  13920

gttaatagtt tgcgcaacgt tgttgccatt gctacaggca tcgtggtgtc acgctcgtcg  13980

tttggtatgg cttcattcag ctccggttcc caacgatcaa ggcgagttac atgatccccc  14040

atgttgtgca aaaaagcggt tagctccttc ggtcctccga tcgttgtcag aagtaagttg  14100

gccgcagtgt tatcactcat ggttatggca gcactgcata attctcttac tgtcatgcca  14160

tccgtaagat gcttttctgt gactggtgag tactcaacca agtcattctg agaatagtgt  14220

atgcggcgac cgagttgctc ttgcccggcg tcaatacggg ataataccgc gccacatagc  14280

agaactttaa aagtgctcat cattggaaaa cgttcttcgg ggcgaaaact ctcaaggatc  14340

ttaccgctgt tgagatccag ttcgatgtaa cccactcgtg cacccaactg atcttcagca  14400

tcttttactt tcaccagcgt ttctgggtga gcaaaaacag gaaggcaaaa tgccgcaaaa  14460

aagggaataa gggcgacacg gaaatgttga atactcatac tcttcctttt tcaatattat  14520

tgaagcattt atcagggtta ttgtctcatg agcggataca tatttgaatg tatttagaaa  14580

aataaacaaa taggggttcc gcgcacattt ccccgaaaag tgc                   14623
```

<210> SEQ ID NO 75
<211> LENGTH: 7252
<212> TYPE: DNA
<213> ORGANISM: Artificial Sequence
<220> FEATURE:
<221> NAME/KEY: misc_feature
<222> LOCATION: ()..()
<223> OTHER INFORMATION: Plastid transformation vector pFHO5 containing R. capsulatus DNA e

<400> SEQUENCE: 75

```
gcacttttcg ggaaatgtg cgcggaaccc ctatttgttt atttttctaa atacattcaa     60

atatgtatcc gctcatgaga caataaccct gataaatgct tcaataatat tgaaaaagga    120

agagtatgag tattcaacat ttccgtgtcg cccttattcc cttttttgcg gcattttgcc    180

ttcctgtttt tgctcaccca gaaacgctgg tgaaagtaaa agatgctgaa gatcagttgg    240

gtgcacgagt gggttacatc gaactggatc tcaacagcgg taagatcctt gagagttttc    300

gccccgaaga acgttttcca atgatgagca cttttaaagt tctgctatgt ggcgcggtat    360

tatcccgtat tgacgccggg caagagcaac tcggtcgccg catacactat tctcagaatg    420

acttggttga gtactcacca gtcacagaaa agcatcttac ggatggcatg acagtaagag    480

aattatgcag tgctgccata accatgagtg ataacactgc ggccaactta cttctgacaa    540

cgatcggagg accgaaggag ctaaccgctt ttttgcacaa catgggggat catgtaactc    600
```

-continued

```
gccttgatcg ttgggaaccg gagctgaatg aagccatacc aaacgacgag cgtgacacca    660
cgatgcctgt agcaatggca acaacgttgc gcaaactatt aactggcgaa ctacttactc    720
tagcttcccg gcaacaatta atagactgga tggaggcgga taaagttgca ggaccacttc    780
tgcgctcggc ccttccggct ggctggttta ttgctgataa atctggagcc ggtgagcgtg    840
ggtctcgcgg tatcattgca gcactggggc cagatggtaa gccctcccgt atcgtagtta    900
tctacacgac ggggagtcag gcaactatgg atgaacgaaa tagacagatc gctgagatag    960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa aatcccttaa cgtgagtttt cgttccactg agcgtcagac cccgtagaaa   1140
agatcaaagg atcttcttga gatccttttt ttctgcgcgt aatctgctgc ttgcaaacaa   1200
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
agttaggcca ccacttcaag aactctgtag caccgcctac atacctcgct ctgctaatcc   1380
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccagggggaa acgcctggta tctttatagt cctgtcgggt   1680
ttcgccacct ctgacttgag cgtcgatttt tgtgatgctc gtcagggggg cggagcctat   1740
ggaaaaacgc cagcaacgcg gcctttttac ggttcctggc cttttgctgg ccttttgctc   1800
acatgttctt tcctgcgtta tcccctgatt ctgtggataa ccgtattacc gcctttgagt   1860
gagctgatac cgctcgccgc agccgaacga ccgagcgcag cgagtcagtg agcgaggaag   1920
cggaagagcg cccaatacgc aaaccgcctc tccccgcgcg ttggccgatt cattaatgca   1980
gctggcacga caggtttccc gactggaaag cgggcagtga gcgcaacgca attaatgtga   2040
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctccaccgc ggtggcggcc   2220
gctctagaac tagtggatct tcttggctgt tattcaaaag gtccaacaat gtatatatat   2280
tggacatttt gaggcaatta tagatcctgg aaggcaattc tgattggtca ataaaaatcg   2340
atttcaatgc tatttttttt ttgtttttta tgagtttagc caatttatca tgaaaggtaa   2400
aaggggataa aggaaccgtg tgttgattgt cctgtaaata taagttgtct tcctccatat   2460
gtaaaaaggg aataaataaa tcaattaaat ttcgggatgc ttcatgaagt gcttctttcg   2520
gagttaaact tccgtttgtc catatttcga gaaaaagtat ctcttgtttt tcattcccat   2580
tcccataaga atgaatacta tgattcgcgt ttcgaacagg catgaataca gcatctatag   2640
gataacttcc atcttgaaag ttatgtggcg tttttataag atatccacga tttctctcta   2700
tttgtaatcc aatacaaaaa tcaattggtt ccgttaaact ggctatatgt tgtgtattat   2760
caacgatttc tacataaggc ggcaagatga tatcttgggc agttacagat ccaggaccct   2820
tgacacaaat agatgcgtca gaagttccat atagattact tcttaatata atttctttca   2880
aattcattaa aatttcatgt accgattctt gaatgcccgt tatggtagaa tattcatgtg   2940
```

-continued

```
ggactttctc agattttaca cgtgtgatac atgttccttc tatttctcca agtaaagctc   3000
ttcgcatcgc aatgcctatt gtgtcggctt ggcctttcat aagtggagac agaataaagc   3060
gtccataata aaggcgttta ctgtctgttc ttgattcaac acacttccac tgtagtgtcc   3120
gagtagatac tgttactttc tctcgaacca tagtactatt atttgattag atcatcgaat   3180
cttttatttc tcttgagatt tcttcaatgt tcagttctac acacgtcttt ttttcggagg   3240
tctacagcca ttatgtggca taggagttac atcccgtacg aaagttaata gtataccact   3300
tcgacgaata gctcgtaatg ctgcatctct tccgagaccg ggacctttta tcatgacttc   3360
tgctcgttgc ataccttgat ccactactgt acggatagcg tttgctgctg cggtttgagc   3420
agcaaacggt gttcctcttc tcgtaccttt gaatccagaa gtaccggcgg aggaccaaga   3480
aactactcga ccccgtacat ctgtaacagt gacaatggta ttattgaaac ttgcttgaac   3540
atgaataact ccctttggta ttctacgtgc acccttacgt gaaccaatac gtccattcct   3600
acgcgaacta attttcggta tagcttttgc catattttat catctcgtaa atatgagtca   3660
gagatatatg gatatatcca tttcatgtca aaacagattc tttatttgta catcggctct   3720
tctggcaagt ctgattatcc ctgtctttgt ttatgtctcg ggttggaaca aattactata   3780
attcgtcccc gcctacggat tagtcgacat ttttcacaaa ttttacgaac ggaagctctt   3840
atttcatat ttctcattcc ttaccttaat tctgaatcta tttcttggaa gaaaataagt   3900
ttcttgaaat ttttcatctc gaattgtatt cccacgaaag gaatggtgaa gttgaaaaac   3960
gaatccttca aatctttgtt gtggagtcga taaattatac gccctttggt tgaatcataa   4020
ggacttactt caattttgac tctatctcct ggcagtatcc gtataaaact atgccggatc   4080
tttcctgaaa cataatttat aatcagatcc aggaggacca tatgatcgcc gaagcggata   4140
tggaggtctg ccgggagctg atccgcaccg gcagctactc cttccatgcg gcgtccagag   4200
ttctgccggc gcgggtccgt gaccccgcgc tggcgcttta cgccttttgc cgcgtcgccg   4260
atgacgaagt cgacgaggtt ggcgcgccgc gcgacaaggc tgcggcggtt ttgaaacttg   4320
gcgaccggct ggaggacatc tatgccggtc gtccgcgcaa tgcgccctcg gatcgggctt   4380
tcgcggcggt ggtcgaggaa ttcgagatgc cgcgcgaatt gcccgaggcg ctgctggagg   4440
gcttcgcctg ggatgccgag gggcggtggt atcacacgct ttcggacgtg caggcctatt   4500
cggcgcgggt ggcggccgcc gtcggcgcga tgatgtgcgt gctgatgcgg gtgcgcaacc   4560
ccgatgcgct ggcgcgggcc tgcgatctcg gtcttgccat gcagatgtcg aacatcgccc   4620
gcgacgtggg cgaggatgcc cgggcggggc ggcttttcct gccgaccgac tggatggtcg   4680
aggaggggat cgatccgcag gcgttcctgg ccgatccgca gcccaccaag ggcatccgcc   4740
gggtcaccga gcggttgctg aaccgcgccg accggcttta ctggcgggcg gcgacggggg   4800
tgcggctttt gccctttgac tgccgaccgg ggatcatggc cgcgggcaag atctatgccg   4860
cgatcggggc cgaggtggcg aaggcgaaat acgacaacat cacccggcgt gcccacacga   4920
ccaagggccg caagctgtgg ctggtggcga attccgcgat gtcggcgacg gcgacctcga   4980
tgctgccgct ctcgccgcgg gtgcatgcca agcccgagcc cgaagtggcg catctggtcg   5040
atgccgccgc gcatcgcaac ctgcatcccg aacggtccga ggtgctgatc tcggcgctga   5100
tggcgctgaa ggcgcgcgac cgcggcctgg cgatggattg aggatctaaa caaacccgga   5160
acagaccgtt gggaagcgat tcagtaatta aagcttcatg actccttttt ggttcttaaa   5220
gtccctttga ggtatcaact aataagaaag atattagaca acccccccttt tttctttttc   5280
acaaatagga agtttcgaat ccaatttgga tattaaaagg attaccagat ataacacaaa   5340
```

-continued

```
atctctccac ctattccttc tagtcgagcc tctcggtctg tcattatacc tcgagaagta   5400
gaaagaatta caatccccat tccacctaaa attcgcggaa ttcgttgata attagaatag   5460
attcgtagac caggtcgact gattcgtttt aaatttaaaa tatttctata gggtcttttc   5520
ctattccttc tatgtcgcag ggttaaaacc aaaaaatatt tgtttttttc tcgatgtttt   5580
ctcacgtttt cgataaaacc ttctcgtaaa agtatttgaa caatattttc ggtaatatta   5640
gtagatgcta ttcgaaccac ccttttttcga tccatatcag catttcgtat agaagttatt   5700
atctcagcaa tagtgtccct acccatgatg aactaaaatt attggggcct ccaaatttga   5760
tataatcaac gtgtttttta cttatttttt ttttgaatat gatatgaatt attaaagata   5820
tatgcgtgag acacaatcta ctaattaatc tatttctttc aaataccccca ctagaaacag   5880
atcacaattt cattttataa tacctcggga gctaatgaaa ctattttagt aaaatttaat   5940
tctctcaatt cccgggcgat tgcaccaaaa attcgagttc cttttgattt ccttccttct   6000
tgatcaataa caactgcagc attgtcatca tatcgtatta tcatcccgtt gtcacgtttg   6060
agttctttac aggtccgcac aattacagct ctgactactt ctgatctttc taggggcata   6120
tttggtacgg cttctttgat cacagcaaca ataacgtcac caatatgagc atatcgacga   6180
ttgctagctc ctatgattcg aatacacatc aattctcgag ccccgctgtt atccgctaca   6240
tttaaatggg tctgaggttg aatcattttt ttaatccgtt ctttgaatgc aaagggcgaa   6300
gaaaaaaaag aaatattttt gtccaaaaaa aaagaaacat gcggtttcgt ttcatatcta   6360
agagcccttt ccgcattttt ttctattaca ttacgaaata atgaattgag ttcgtatagg   6420
cattttagat gctgctagtg aaatagccct tctggctata ttttctgtta ctccacccat   6480
ttcataaagt attcgacccg gtttaacaac agctacccaa tattcagggg atcccccggg   6540
ctgcaggaat tcgatatcaa gcttatcgat accgtcgacc tcgagggggg gcccggtacc   6600
caattcgccc tatagtgagt cgtattacaa ttcactggcc gtcgttttac aacgtcgtga   6660
ctgggaaaac cctggcgtta cccaacttaa tcgccttgca gcacatcccc ctttcgccag   6720
ctggcgtaat agcgaagagg cccgcaccga tcgcccttcc caacagttgc gcagcctgaa   6780
tggcgaatgg gacgcgccct gtagcggcgc attaagcgcg gcgggtgtgg tggttacgcg   6840
cagcgtgacc gctacacttg ccagcgccct agcgcccgct cctttcgctt tcttcccttc   6900
ctttctcgcc acgttcgccg gctttccccg tcaagctcta aatcgggggc tccctttagg   6960
gttccgattt agtgctttac ggcacctcga ccccaaaaaa cttgattagg gtgatggttc   7020
acgtagtggg ccatcgccct gatagacggt ttttcgccct ttgacgttgg agtccacgtt   7080
ctttaatagt ggactcttgt tccaaactgg aacaacactc aaccctatct cggtctattc   7140
ttttgattta taagggattt tgccgatttc ggcctattgg ttaaaaaatg agctgattta   7200
acaaaaattt aacgcgaatt ttaacaaaat attaacgctt acaatttagg tg           7252
```

```
<210> SEQ ID NO 76
<211> LENGTH: 14623
<212> TYPE: DNA
<213> ORGANISM: Artificial Sequence
<220> FEATURE:
<221> NAME/KEY: misc_feature
<222> LOCATION: ()..()
<223> OTHER INFORMATION: Plastid transformation vector pFHO6, containing
      Operon E, containi

<400> SEQUENCE: 76

cacctaaatt gtaagcgtta atattttgtt aaaattcgcg ttaaattttt gttaaatcag     60
```

-continued

```
ctcatttttt aaccaatagg ccgaaatcgg caaaatccct tataaatcaa aagaatagac    120

cgagataggg ttgagtgttg ttccagtttg gaacaagagt ccactattaa agaacgtgga    180

ctccaacgtc aaagggcgaa aaaccgtcta tcagggcgat ggcccactac gtgaaccatc    240

accctaatca agttttttgg ggtcgaggtg ccgtaaagca ctaaatcgga accctaaagg    300

gagcccccga tttagagctt gacggggaaa gccggcgaac gtggcgagaa aggaagggaa    360

gaaagcgaaa ggagcgggcg ctagggcgct ggcaagtgta gcggtcacgc tgcgcgtaac    420

caccacaccc gccgcgctta atgcgccgct acagggcgcg tcccattcgc cattcaggct    480

gcgcaactgt tgggaagggc gatcggtgcg ggcctcttcg ctattacgcc agctggcgaa    540

agggggatgt gctgcaaggc gattaagttg ggtaacgcca gggttttccc agtcacgacg    600

ttgtaaaacg acggccagtg aattgtaata cgactcacta tagggcgaat tgggtaccgg    660

gccccccctc gaggtcgacg gtatcgataa gcttgatatc gaattcctgc agcccggggg    720

atcttcttgg ctgttattca aaaggtccaa caatgtatat atattggaca ttttgaggca    780

attatagatc ctggaaggca attctgattg gtcaataaaa atcgatttca atgctatttt    840

tttttgtttt tttatgagtt tagccaattt atcatgaaag gtaaaagggg ataaaggaac    900

cgtgtgttga ttgtcctgta aatataagtt gtcttcctcc atatgtaaaa agggaataaa    960

taaatcaatt aaatttcggg atgcttcatg aagtgcttct ttcggagtta aacttccgtt   1020

tgtccatatt tcgagaaaaa gtatctcttg tttttcattc ccattcccat aagaatgaat   1080

actatgattc gcgtttcgaa caggcatgaa tacagcatct ataggataac ttccatcttg   1140

aaagttatgt ggcgttttta taagatatcc acgatttctc tctatttgta atccaataca   1200

aaaatcaatt ggttccgtta aactggctat atgttgtgta ttatcaacga tttctacata   1260

aggcggcaag atgatatctt gggcagttac agatccagga cccttgacac aaatagatgc   1320

gtcagaagtt ccatatagat tacttcttaa tataatttct ttcaaattca ttaaaatttc   1380

atgtaccgat tcttgaatgc ccgttatggt agaatattca tgtgggactt tctcagattt   1440

tacacgtgtg atacatgttc cttctatttc tccaagtaaa gctcttcgca tcgcaatgcc   1500

tattgtgtcg gcttggcctt tcataagtgg agacagaata aagcgtccat aataaaggcg   1560

tttactgtct gttcttgatt caacacactt ccactgtagt gtccgagtag atactgttac   1620

tttctctcga accatagtac tattatttga ttagatcatc gaatctttta tttctcttga   1680

gatttcttca atgttcagtt ctacacacgt cttttttteg gaggtctaca gccattatgt   1740

ggcataggag ttacatcccg tacgaaagtt aatagtatac cacttcgacg aatagctcgt   1800

aatgctgcat ctcttccgag accgggacct tttatcatga cttctgctcg ttgcatacct   1860

tgatccacta ctgtacggat agcgtttgct gctgcggttt gagcagcaaa cggtgttcct   1920

cttctcgtac ctttgaatcc agaagtaccg gcggaggacc aagaaactac tcgaccccgt   1980

acatctgtaa cagtgacaat ggtattattg aaacttgctt gaacatgaat aactcccttt   2040

ggtattctac gtgcaccctt acgtgaacca atacgtccat tcctacgcga actaattttc   2100

ggtatagctt ttgccatatt ttatcatctc gtaaatatga gtcagagata tatggatata   2160

tccatttcat gtcaaaacag attctttatt tgtacatcgg ctcttctggc aagtctgatt   2220

atccctgtct ttgtttatgt ctcgggttgg aacaaattac tataattcgt ccccgcctac   2280

ggattagtcg acatttttca caaattttac gaacggaagc tcttattttc atatttctca   2340

ttccttacct taattctgaa tctatttctt ggaagaaaat aagtttcttg aaatttttca   2400
```

-continued

```
tctcgaattg tattcccacg aaaggaatgg tgaagttgaa aaacgaatcc ttcaaatctt   2460
tgttgtggag tcgataaatt atacgccctt tggttgaatc ataaggactt acttcaattt   2520
tgactctatc tcctggcagt atccgtataa aactatgccg gatctttcct gaaacataat   2580
ttataatcag atcggccgca ggaggagttc atatgtcaga gttgagagcc ttcagtgccc   2640
cagggaaagc gttactagct ggtggatatt tagttttaga tacaaaatat gaagcatttg   2700
tagtcggatt atcggcaaga atgcatgctg tagcccatcc ttacggttca ttgcaagggt   2760
ctgataagtt tgaagtgcgt gtgaaaagta aacaatttaa agatggggag tggctgtacc   2820
atataagtcc taaaagtggc ttcattcctg tttcgatagg cggatctaag aaccctttca   2880
ttgaaaaagt tatcgctaac gtatttagct actttaaacc taacatggac gactactgca   2940
atagaaactt gttcgttatt gatattttct ctgatgatgc ctaccattct caggaggata   3000
gcgttaccga acatcgtggc aacagaagat tgagttttca ttcgcacaga attgaagaag   3060
ttcccaaaac agggctgggc tcctcggcag gtttagtcac agttttaact acagctttgg   3120
cctccttttt tgtatcggac ctggaaaata atgtagacaa atatagagaa gttattcata   3180
atttagcaca agttgctcat tgtcaagctc agggtaaaat tggaagcggg tttgatgtag   3240
cggcggcagc atatggatct atcagatata gaagattccc acccgcatta atctctaatt   3300
tgccagatat tggaagtgct acttacggca gtaaactggc gcatttggtt gatgaagaag   3360
actggaatat tacgattaaa agtaaccatt taccttcggg attaacttta tggatgggcg   3420
atattaagaa tggttcagaa acagtaaaac tggtccagaa ggtaaaaaat tggtatgatt   3480
cgcatatgcc agaaagcttg aaaatatata cagaactcga tcatgcaaat tctagattta   3540
tggatggact atctaaacta gatcgcttac acgagactca tgacgattac agcgatcaga   3600
tatttgagtc tcttgagagg aatgactgta cctgtcaaaa gtatcctgaa atcacagaag   3660
ttagagatgc agttgccaca attagacgtt cctttagaaa aataactaaa gaatctggtg   3720
ccgatatcga acctcccgta caaactagct tattggatga ttgccagacc ttaaaaggag   3780
ttcttacttg cttaatacct ggtgctggtg gttatgacgc cattgcagtg attactaagc   3840
aagatgttga tcttagggct caaaccgcta atgacaaaag attttctaag gttcaatggc   3900
tggatgtaac tcaggctgac tggggtgtta ggaaagaaaa agatccggaa acttatcttg   3960
ataaactgca ggaggagttt taatgtcatt accgttctta acttctgcac cgggaaaggt   4020
tattattttt ggtgaacact ctgctgtgta caacaagcct gccgtcgctg ctagtgtgtc   4080
tgcgttgaga acctacctgc taataagcga gtcatctgca ccagatacta ttgaattgga   4140
cttcccggac attagcttta atcataagtg gtccatcaat gatttcaatg ccatcaccga   4200
ggatcaagta aactcccaaa aattggccaa ggctcaacaa gccaccgatg gcttgtctca   4260
ggaactcgtt agtcttttgg atccgttgtt agctcaacta tccgaatcct tccactacca   4320
tgcagcgttt tgtttcctgt atatgtttgt ttgcctatgc cccccatgcca agaatattaa   4380
gttttcttta aagtctactt tacccatcgg tgctgggttg ggctcaagcg cctctatttc   4440
tgtatcactg gccttagcta tggcctactt ggggggggtta ataggatcta atgacttgga   4500
aaagctgtca gaaaacgata agcatatagt gaatcaatgg gccttcatag gtgaaaagtg   4560
tattcacggt accccttcag gaatagataa cgctgtggcc acttatggta atgccctgct   4620
atttgaaaaa gactcacata atggaacaat aaacacaaac aattttaagt tcttagatga   4680
tttcccagcc attccaatga tcctaaccta tactagaatt ccaaggtcta caaaagatct   4740
tgttgctcgc gttcgtgtgt tggtcaccga gaaatttcct gaagttatga agccaattct   4800
```

-continued

```
agatgccatg ggtgaatgtg ccctacaagg cttagagatc atgactaagt taagtaaatg   4860
taaaggcacc gatgacgagg ctgtagaaac taataatgaa ctgtatgaac aactattgga   4920
attgataaga ataaatcatg gactgcttgt ctcaatcggt gtttctcatc ctggattaga   4980
acttattaaa aatctgagcg atgatttgag aattggctcc acaaaactta ccggtgctgg   5040
tggcggcggt tgctctttga ctttgttacg aagagacatt actcaagagc aaattgacag   5100
cttcaaaaag aaattgcaag atgattttag ttacgagaca tttgaaacag acttgggtgg   5160
gactggctgc tgtttgttaa gcgcaaaaaa tttgaataaa gatcttaaaa tcaaatccct   5220
agtattccaa ttatttgaaa ataaaactac cacaaagcaa caaattgacg atctattatt   5280
gccaggaaac acgaatttac catggacttc agacgaggag ttttaatgac tgtatatact   5340
gctagtgtaa ctgctccggt aaatattgct actcttaagt attgggggaa aagggacacg   5400
aagttgaatc tgcccaccaa ttcgtccata tcagtgactt tatcgcaaga tgacctcaga   5460
acgttgacct ctgcggctac tgcacctgag tttgaacgcg acactttgtg gttaaatgga   5520
gaaccacaca gcatcgacaa tgaaagaact caaaattgtc tgcgcgacct acgccaatta   5580
agaaaggaaa tggaatcgaa ggacgcctca ttgcccacat tatctcaatg gaaactccac   5640
attgtctccg aaaataactt tcctacagca gctggtttag cttcctccgc tgctggcttt   5700
gctgcattgg tctctgcaat tgctaagtta taccaattac cacagtcaac ttcagaaata   5760
tctagaatag caagaaaggg gtctggttca gcttgtagat cgttgtttgg cggatacgtg   5820
gcctgggaaa tgggaaaagc tgaagatggt catgattcca tggcagtaca aatcgcagac   5880
agctctgact ggcctcagat gaaagcttgt gtcctagttg tcagcgatat taaaaaggat   5940
gtgagttcca ctcagggtat gcaattgacc gtggcaacct ccgaactatt taaagaaaga   6000
attgaacatg tcgtaccaaa gagatttgaa gtcatgcgta aagccattgt tgaaaaagat   6060
ttcgccacct ttgcaaagga aacaatgatg gattccaact ctttccatgc cacatgtttg   6120
gactctttcc ctccaatatt ctacatgaat gacacttcca agcgtatcat cagttggtgc   6180
cacaccatta atcagtttta cggagaaaca atcgttgcat acacgtttga tgcaggtcca   6240
aatgctgtgt tgtactactt agctgaaaat gagtcgaaac tctttgcatt tatctataaa   6300
ttgtttggct ctgttcctgg atgggacaag aaatttacta ctgagcagct tgaggctttc   6360
aaccatcaat ttgaatcatc taactttact gcacgtgaat tggatcttga gttgcaaaag   6420
gatgttgcca gagtgatttt aactcaagtc ggttcaggcc cacaagaaac aaacgaatct   6480
ttgattgacg caaagactgg tctaccaaag gaagaggagt tttaactcga cgccggcgga   6540
ggcacatatg tctcagaacg tttacattgt atcgactgcc agaaccccaa ttggttcatt   6600
ccagggttct ctatcctcca agacagcagt ggaattgggt gctgttgctt taaaaggcgc   6660
cttggctaag gttccagaat tggatgcatc caaggatttt gacgaaatta tttttggtaa   6720
cgttctttct gccaatttgg gccaagctcc ggccagacaa gttgctttgg ctgccggttt   6780
gagtaatcat atcgttgcaa gcacagttaa caaggtctgt gcatccgcta tgaaggcaat   6840
cattttgggt gctcaatcca tcaaatgtgg taatgctgat gttgtcgtag ctggtggttg   6900
tgaatctatg actaacgcac catactacat gccagcagcc cgtgcgggtg ccaaatttgg   6960
ccaaactgtt cttgttgatg gtgtcgaaag agatgggttg aacgatgcgt acgatggtct   7020
agccatgggt gtacacgcag aaaagtgtgc ccgtgattgg gatattacta gagaacaaca   7080
agacaatttt gccatcgaat cctaccaaaa atctcaaaaa tctcaaaagg aaggtaaatt   7140
```

-continued

```
cgacaatgaa attgtacctg ttaccattaa gggatttaga ggtaagcctg atactcaagt   7200
cacgaaggac gaggaacctg ctagattaca cgttgaaaaa ttgagatctg caaggactgt   7260
tttccaaaaa gaaaacggta ctgttactgc cgctaacgct tctccaatca acgatggtgc   7320
tgcagccgtc atcttggttt ccgaaaaagt tttgaaggaa aagaatttga agcctttggc   7380
tattatcaaa ggttggggtg aggccgctca tcaaccagct gattttacat gggctccatc   7440
tcttgcagtt ccaaaggctt tgaaacatgc tggcatcgaa gacatcaatt ctgttgatta   7500
ctttgaattc aatgaagcct tttcggttgt cggtttggtg aacactaaga ttttgaagct   7560
agacccatct aaggttaatg tatatggtgg tgctgttgct ctaggtcacc cattgggttg   7620
ttctggtgct agagtggttg ttacactgct atccatctta cagcaagaag gaggtaagat   7680
cggtgttgcc gccatttgta atggtggtgg tggtgcttcc tctattgtca ttgaaaagat   7740
atgaggatcc tctagatgcg caggaggcac atatggcgaa gaacgttggg attttggcta   7800
tggatatcta tttccctccc acctgtgttc aacaggaagc tttggaagca catgatggag   7860
caagtaaagg gaaatacact attggacttg gccaagattg tttagctttt tgcactgagc   7920
ttgaagatgt tatctctatg agtttcaatg cggtgacatc actttttgag aagtataaga   7980
ttgaccctaa ccaaatcggg cgtcttgaag taggaagtga gactgttatt gacaaaagca   8040
agtccatcaa gaccttcttg atgcagctct ttgagaaatg tggaaacact gatgtcgaag   8100
gtgttgactc gaccaatgct tgctatggtg gaactgcagc tttgttaaac tgtgtcaatt   8160
gggttgagag taactcttgg gatggacgtt atggcctcgt catttgtact gacagcgcgg   8220
tttatgcaga aggacccgca aggcccactg gaggagctgc agcgattgct atgttgatag   8280
gacctgatgc tcctatcgtt ttcgaaagca aattgagagc aagccacatg gctcatgtct   8340
atgactttta caagcccaat cttgctagcg agtacccggt tgttgatggt aagctttcac   8400
agacttgcta cctcatggct cttgactcct gctataaaca tttatgcaac aagttcgaga   8460
agatcgaggg caaagagttc tccataaatg atgctgatta cattgttttc cattctccat   8520
acaataaact tgtacagaaa agctttgctc gtctcttgta caacgacttc ttgagaaacg   8580
caagctccat tgacgaggct gccaaagaaa agttcacccc ttattcatct ttgacccttg   8640
acgagagtta ccaaagccgt gatcttgaaa aggtgtcaca acaaatttcg aaaccgtttt   8700
atgatgctaa agtgcaacca acgactttaa taccaaagga agtcggtaac atgtacactg   8760
cttctctcta cgctgcattt gcttccctca tccacaataa acacaatgat ttggcgggaa   8820
agcgggtggt tatgttctct tatggaagtg gctccaccgc aacaatgttc tcattacgcc   8880
tcaacgacaa taagcctcct ttcagcattt caaacattgc atctgtaatg gatgttggcg   8940
gtaaattgaa agctagacat gagtatgcac ctgagaagtt tgtggagaca atgaagctaa   9000
tggaacatag gtatggagca aaggactttg tgacaaccaa ggagggtatt atagatcttt   9060
tggcaccggg aacttattat ctgaaagagg ttgattcctt gtaccggaga ttctatggca   9120
agaaaggtga agatggatct gtagccaatg gacactgagg atccgtcgag cacgtggagg   9180
cacatatgca atgctgtgag atgcctgttg gatacattca gattcctgtt gggattgctg   9240
gtccattgtt gcttgatggt tatgagtact ctgttcctat ggctacaacc gaaggttgtt   9300
tggttgctag cactaacaga ggctgcaagg ctatgtttat ctctggtggc gccaccagta   9360
ccgttcttaa ggacggtatg acccgagcac ctgttgttcg gttcgcttcg gcgagacgag   9420
cttcggagct taagtttttc ttggagaatc cagagaactt tgatactttg gcagtagtct   9480
tcaacaggtc gagtagattt gcaagactgc aaagtgttaa atgcacaatc gcggggaaga   9540
```

-continued

```
atgcttatgt aaggttctgt tgtagtactg gtgatgctat ggggatgaat atggtttcta   9600
aaggtgtgca gaatgttctt gagtatctta ccgatgattt ccctgacatg gatgtgattg   9660
gaatctctgg taacttctgt tcggacaaga aacctgctgc tgtgaactgg attgagggac   9720
gtggtaaatc agttgtttgc gaggctgtaa tcagaggaga gatcgtgaac aaggtcttga   9780
aaacgagcgt ggctgcttta gtcgagctca acatgctcaa gaacctagct ggctctgctg   9840
ttgcaggctc tctaggtgga ttcaacgctc atgccagtaa catagtgtct gctgtattca   9900
tagctactgg ccaagatcca gctcaaaacg tggagagttc tcaatgcatc accatgatgg   9960
aagctattaa tgacggcaaa gatatccata tctcagtcac tatgccatct atcgaggtgg  10020
ggacagtggg aggaggaaca cagcttgcat ctcaatcagc gtgtttaaac ctgctcggag  10080
ttaaaggagc aagcacagag tcgccgggaa tgaacgcaag gaggctagcg acgatcgtag  10140
ccggagcagt tttagctgga gagttatctt taatgtcagc aattgcagct ggacagcttg  10200
tgagaagtca catgaaatac aatagatcca gccgagacat ctctggagca acgacaacga  10260
caacaacaac aacatgaccc gtaggaggca catatgagtt cccaacaaga gaaaaaggat  10320
tatgatgaag aacaattaag gttgatggaa gaagtttgta tcgttgtaga tgaaaatgat  10380
gtcccttta a gatatggaac gaaaaaggag tgtcatttga tggaaaatat aaataaaggt  10440
cttttgcata gagcattctc tatgttcatc tttgatgagc aaaatcgcct tttacttcag  10500
cagcgtgcag aagagaaaat tacatttcca tccttatgga cgaatacatg ttgctcccac  10560
ccattggatg ttgctggtga acgtggtaat actttacctg aagctgttga aggtgttaag  10620
aatgcagctc aacgcaagct gttccatgaa ttgggtattc aagccaagta tattcccaaa  10680
gacaaatttc agtttcttac acgaatccat taccttgctc ctagtactgg tgcttgggga  10740
gagcatgaaa ttgactacat tcttttcttc aaaggtaaag ttgagctgga tatcaatccc  10800
aatgaagttc aagcctataa gtatgttact atggaagagt taaaagagat gttttccgat  10860
cctcaatatg gattcacacc atggttcaaa cttatttgtg agcattttat gtttaaatgg  10920
tggcaggatg tagatcatgc gtcaaaattc caagatacct taattcatcg ttgctaagga  10980
tcccccggga tccggccgat ctaaacaaac ccggaacaga ccgttgggaa gcgattcagt  11040
aattaaagct tcatgactcc tttttggttc ttaaagtccc tttgaggtat caactaataa  11100
gaaagatatt agacaacccc cctttttttct ttttcacaaa taggaagttt cgaatccaat  11160
ttggatatta aaaggattac cagatataac acaaaatctc tccacctatt ccttctagtc  11220
gagcctctcg gtctgtcatt atacctcgag aagtagaaag aattacaatc cccattccac  11280
ctaaaattcg cggaattcgt tgataattag aatagattcg tagaccaggt cgactgattc  11340
gttttaaatt taaaatattt ctatagggtc ttttcctatt ccttctatgt cgcagggtta  11400
aaaccaaaaa atatttgttt ttttctcgat gttttctcac gttttcgata aaaccttctc  11460
gtaaaagtat ttgaacaata ttttcggtaa tattagtaga tgctattcga accacccttt  11520
ttcgatccat atcagcattt cgtatagaag ttattatctc agcaatagtg tccctaccca  11580
tgatgaacta aaattattgg ggcctccaaa tttgatataa tcaacgtgtt ttttacttat  11640
tttttttttg aatatgatat gaattattaa agatatatgc gtgagacaca atctactaat  11700
taatctattt ctttcaaata ccccactaga aacagatcac aatttcattt tataatacct  11760
cgggagctaa tgaaactatt ttagtaaaat ttaattctct caattcccgg gcgattgcac  11820
caaaaattcg agttcctttt gatttccttc cttcttgatc aataacaact gcagcattgt  11880
```

-continued

```
catcatatcg tattatcatc ccgttgtcac gtttgagttc tttacaggtc cgcacaatta  11940
cagctctgac tacttctgat ctttctaggg gcatatttgg tacggcttct ttgatcacag  12000
caacaataac gtcaccaata tgagcatatc gacgattgct agctcctatg attcgaatac  12060
acatcaattc tcgagccccg ctgttatccg ctacatttaa atgggtctga ggttgaatca  12120
ttttttaat ccgttctttg aatgcaaagg gcgaagaaaa aaaagaaata tttttgtcca  12180
aaaaaaaaga aacatgcggt ttcgtttcat atctaagagc cctttccgca tttttttcta  12240
ttacattacg aaataatgaa ttgagttcgt ataggcattt tagatgctgc tagtgaaata  12300
gcccttctgg ctatatttc tgttactcca cccatttcat aaagtattcg acccggttta  12360
acaacagcta cccaatattc aggggatcca ctagttctag agcggccgcc accgcggtgg  12420
agctccagct tttgttccct ttagtgaggg ttaatttcga gcttggcgta atcatggtca  12480
tagctgtttc ctgtgtgaaa ttgttatccg ctcacaattc cacacaacat acgagccgga  12540
agcataaagt gtaaagcctg gggtgcctaa tgagtgagct aactcacatt aattgcgttg  12600
cgctcactgc ccgctttcca gtcgggaaac ctgtcgtgcc agctgcatta atgaatcggc  12660
caacgcgcgg ggagaggcgg tttgcgtatt gggcgctctt ccgcttcctc gctcactgac  12720
tcgctgcgct cggtcgttcg gctgcggcga gcggtatcag ctcactcaaa ggcggtaata  12780
cggttatcca cagaatcagg ggataacgca ggaaagaaca tgtgagcaaa aggccagcaa  12840
aaggccagga accgtaaaaa ggccgcgttg ctggcgtttt tccataggct ccgcccccct  12900
gacgagcatc acaaaaatcg acgctcaagt cagaggtggc gaaacccgac aggactataa  12960
agataccagg cgtttccccc tggaagctcc ctcgtgcgct ctcctgttcc gaccctgccg  13020
cttaccggat acctgtccgc ctttctccct tcgggaagcg tggcgctttc tcatagctca  13080
cgctgtaggt atctcagttc ggtgtaggtc gttcgctcca agctgggctg tgtgcacgaa  13140
ccccccgttc agcccgaccg ctgcgcctta tccggtaact atcgtcttga gtccaacccg  13200
gtaagacacg acttatcgcc actggcagca gccactggta acaggattag cagagcgagg  13260
tatgtaggcg gtgctacaga gttcttgaag tggtggccta actacggcta cactagaagg  13320
acagtatttg gtatctgcgc tctgctgaag ccagttacct tcggaaaaag agttggtagc  13380
tcttgatccg gcaaacaaac caccgctggt agcggtggtt tttttgtttg caagcagcag  13440
attacgcgca gaaaaaaagg atctcaagaa gatcctttga tcttttctac ggggtctgac  13500
gctcagtgga acgaaaactc acgttaaggg attttggtca tgagattatc aaaaaggatc  13560
ttcacctaga tccttttaaa ttaaaaatga agttttaaat caatctaaag tatatatgag  13620
taaacttggt ctgacagtta ccaatgctta atcagtgagg cacctatctc agcgatctgt  13680
ctatttcgtt catccatagt tgcctgactc cccgtcgtgt agataactac gatacgggag  13740
ggcttaccat ctggccccag tgctgcaatg ataccgcgag acccacgctc accggctcca  13800
gatttatcag caataaacca gccagccgga agggccgagc gcagaagtgg tcctgcaact  13860
ttatccgcct ccatccagtc tattaattgt tgccgggaag ctagagtaag tagttcgcca  13920
gttaatagtt tgcgcaacgt tgttgccatt gctacaggca tcgtggtgtc acgctcgtcg  13980
tttggtatgg cttcattcag ctccggttcc caacgatcaa ggcgagttac atgatccccc  14040
atgttgtgca aaaaagcggt tagctccttc ggtcctccga tcgttgtcag aagtaagttg  14100
gccgcagtgt tatcactcat ggttatggca gcactgcata attctcttac tgtcatgcca  14160
tccgtaagat gcttttctgt gactggtgag tactcaacca agtcattctg agaatagtgt  14220
atgcggcgac cgagttgctc ttgcccggcg tcaatacggg ataataccgc gccacatagc  14280
```

-continued

```
agaactttaa aagtgctcat cattggaaaa cgttcttcgg ggcgaaaact ctcaaggatc  14340

ttaccgctgt tgagatccag ttcgatgtaa cccactcgtg cacccaactg atcttcagca  14400

tcttttactt tcaccagcgt ttctgggtga gcaaaaacag gaaggcaaaa tgccgcaaaa  14460

aagggaataa gggcgacacg gaaatgttga atactcatac tcttcctttt tcaatattat  14520

tgaagcattt atcagggtta ttgtctcatg agcggataca tatttgaatg tatttagaaa  14580

aataaacaaa taggggttcc gcgcacattt ccccgaaaag tgc                   14623
```